(12) United States Patent
Annis et al.

(10) Patent No.: US 10,059,741 B2
(45) Date of Patent: Aug. 28, 2018

(54) PEPTIDOMIMETIC MACROCYCLES

(71) Applicant: Aileron Therapeutics, Inc., Cambridge, MA (US)

(72) Inventors: David Allen Annis, Cambridge, MA (US); Vincent Guerlavais, Arlington, MA (US)

(73) Assignee: Aileron Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/200,422

(22) Filed: Jul. 1, 2016

(65) Prior Publication Data

US 2017/0002042 A1  Jan. 5, 2017

Related U.S. Application Data

(60) Provisional application No. 62/187,457, filed on Jul. 1, 2015, provisional application No. 62/260,751, filed on Nov. 30, 2015, provisional application No. 62/311,112, filed on Mar. 21, 2016.

(51) Int. Cl.
| | | |
|---|---|---|
| *A01N 37/18* | (2006.01) |
| *A61K 38/00* | (2006.01) |
| *A61P 31/12* | (2006.01) |
| *C07K 7/06* | (2006.01) |
| *C07K 7/56* | (2006.01) |
| *C07K 7/64* | (2006.01) |
| *C07K 14/11* | (2006.01) |

(52) U.S. Cl.
CPC ............ *C07K 7/06* (2013.01); *C07K 7/56* (2013.01); *C07K 7/64* (2013.01); *C07K 14/11* (2013.01); *A61K 38/00* (2013.01)

(58) Field of Classification Search
CPC ......... A61K 38/00; A61K 38/12; A61K 38/10
See application file for complete search history.

(56) References Cited

U.S. PATENT DOCUMENTS

| | | |
|---|---|---|
| 4,000,259 A | 12/1976 | Garsky |
| 4,191,754 A | 3/1980 | Nutt et al. |
| 4,270,537 A | 6/1981 | Romaine |
| 4,438,270 A | 3/1984 | Bey et al. |
| 4,596,556 A | 6/1986 | Morrow et al. |
| 4,730,006 A | 3/1988 | Bohme et al. |
| 4,737,465 A | 4/1988 | Bond et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,120,859 A | 6/1992 | Webb |
| 5,141,496 A | 8/1992 | Dalto et al. |
| 5,190,521 A | 3/1993 | Hubbard et al. |
| 5,245,009 A | 9/1993 | Kornreich et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,364,851 A | 11/1994 | Joran |
| 5,383,851 A | 1/1995 | McKinnon, Jr. et al. |
| 5,417,662 A | 5/1995 | Hjertman et al. |
| 5,446,128 A | 8/1995 | Kahn |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,622,852 A | 4/1997 | Korsmeyer |
| 5,649,912 A | 7/1997 | Peterson |
| 5,650,133 A | 7/1997 | Carvalho et al. |
| 5,663,316 A | 9/1997 | Xudong |
| 5,672,584 A | 9/1997 | Borchardt et al. |
| 5,704,911 A | 1/1998 | Parsons |
| 5,708,136 A | 1/1998 | Burrell et al. |
| 5,710,245 A | 1/1998 | Kahn |
| 5,731,408 A | 3/1998 | Hadley et al. |
| 5,750,767 A | 5/1998 | Carpino et al. |
| 5,811,515 A | 9/1998 | Grubbs et al. |
| 5,817,752 A | 10/1998 | Yu |
| 5,817,789 A | 10/1998 | Heartlein et al. |
| 5,824,483 A | 10/1998 | Houston, Jr. et al. |
| 5,834,209 A | 11/1998 | Korsmeyer |
| 5,837,845 A | 11/1998 | Hosokawa et al. |
| 5,840,833 A | 11/1998 | Kahn |
| 5,846,936 A | 12/1998 | Felix et al. |

(Continued)

FOREIGN PATENT DOCUMENTS

| | | |
|---|---|---|
| AU | 2008232709 A1 | 10/2008 |
| CN | 1252808 A | 5/2000 |

(Continued)

OTHER PUBLICATIONS

Walensky et al., J. Med. Chem. 2014, 57, 6275-6288.*
Peterson, Evans Group Literature Seminar, Apr. 13, 2001.*
Rudinger, Peptide Hormones, JA Parsons, Ed., 1976, 1-7.*
Andrews et al. Forming Stable Helical Peptide Using Natural and Artificial Amino Acids. Tetrahedron. 1999;55:11711-11743.
Angell, et al. Peptidomimetics via copper-catalyzed azide-alkyne cycloadditions. Chem Soc Rev. Oct. 2007;36(10):1674-89.
Angell, et al. Ring closure to beta-turn mimics via copper-catalyzed azide/alkyne cycloadditions. J Org Chem. Nov. 11, 2007;70(23):9595-8.
Annis, et al. A general technique to rank protein-ligand binding affinities and determine allosteric versus direct binding site competition in compound mixtures. J Am Chem Soc. Dec. 1, 2004;126(47):15495-503.

(Continued)

*Primary Examiner* — Hasan S Ahmed
*Assistant Examiner* — Kaipeen E Yang
(74) *Attorney, Agent, or Firm* — Wilson Sonsini Goodrich & Rosati

(57) ABSTRACT

The present invention provides novel peptidomimetic macrocycles and methods of using such macrocycles for the treatment of viral disease.

32 Claims, 3 Drawing Sheets

Specification includes a Sequence Listing.

(56) References Cited

U.S. PATENT DOCUMENTS

| | | |
|---|---|---|
| 5,851,775 A | 12/1998 | Barker et al. |
| 5,856,445 A | 1/1999 | Korsmeyer |
| 5,859,184 A | 1/1999 | Kahn et al. |
| 5,874,529 A | 2/1999 | Gilon et al. |
| 5,893,397 A | 4/1999 | Peterson et al. |
| 5,922,863 A | 7/1999 | Grubbs et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,030,997 A | 2/2000 | Eilat et al. |
| 6,031,072 A | 2/2000 | Blaschuk et al. |
| 6,031,073 A | 2/2000 | Yu |
| 6,043,339 A | 3/2000 | Lin et al. |
| 6,046,289 A | 4/2000 | Komazawa et al. |
| 6,051,554 A | 4/2000 | Hornik et al. |
| 6,054,556 A | 4/2000 | Huby et al. |
| 6,153,391 A | 11/2000 | Picksley et al. |
| 6,169,073 B1 | 1/2001 | Halazonetis et al. |
| 6,177,542 B1 | 1/2001 | Ruoslahti et al. |
| 6,184,344 B1 | 2/2001 | Kent et al. |
| 6,204,361 B1 | 3/2001 | Carpino et al. |
| 6,271,198 B1 | 8/2001 | Braisted et al. |
| 6,287,787 B1 | 9/2001 | Houghten et al. |
| 6,326,354 B1 | 12/2001 | Gross et al. |
| 6,348,558 B1 | 2/2002 | Harris et al. |
| 6,444,425 B1 | 9/2002 | Reed et al. |
| 6,495,674 B1 | 12/2002 | Lemke et al. |
| 6,514,685 B1 | 2/2003 | Moro |
| 6,569,993 B1 | 5/2003 | Sledeski et al. |
| 6,572,856 B1 | 6/2003 | Taylor et al. |
| 6,610,657 B1 | 8/2003 | Goueli |
| 6,613,874 B1 | 9/2003 | Mazur et al. |
| 6,686,148 B1 | 2/2004 | Shen et al. |
| 6,703,382 B2 | 3/2004 | Wang et al. |
| 6,713,280 B1 | 3/2004 | Huang et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,115,372 B2 | 10/2006 | Shen et al. |
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 7,838,711 B2 | 11/2010 | Herweck et al. |
| 7,875,601 B2 | 1/2011 | O'Reilly et al. |
| 7,932,397 B2 | 4/2011 | Hock et al. |
| 7,960,506 B2 | 6/2011 | Nash |
| 7,981,998 B2 | 7/2011 | Nash |
| 7,981,999 B2 | 7/2011 | Nash |
| 8,071,541 B2 | 12/2011 | Arora et al. |
| 8,124,726 B2 | 2/2012 | Robinson et al. |
| 8,198,405 B2 | 6/2012 | Walensky et al. |
| 8,324,428 B2 | 12/2012 | Verdine et al. |
| 8,389,484 B2 | 3/2013 | Shen et al. |
| 8,399,405 B2 | 3/2013 | Nash et al. |
| 8,524,653 B2 | 9/2013 | Nash et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 | 10/2014 | Guerlavais et al. |
| 8,871,899 B2 | 10/2014 | Wang et al. |
| 8,889,632 B2 | 11/2014 | Bernal et al. |
| 8,895,699 B2 | 11/2014 | Verdine et al. |
| 8,927,500 B2 | 1/2015 | Guerlavais et al. |
| 8,957,026 B2 | 2/2015 | Verdine et al. |
| 8,987,414 B2 | 3/2015 | Guerlavais et al. |
| 9,023,988 B2 | 5/2015 | Nash |
| 9,074,009 B2 | 7/2015 | Bradner et al. |
| 9,096,684 B2 | 8/2015 | Kawahata et al. |
| 9,163,330 B2 | 10/2015 | Verdine et al. |
| 9,175,045 B2 | 11/2015 | Huw et al. |
| 9,175,047 B2 | 11/2015 | Nash et al. |
| 9,175,056 B2 | 11/2015 | Nash |
| 9,206,223 B2 | 12/2015 | Nash et al. |
| 9,273,099 B2 | 3/2016 | Walensky et al. |
| 9,394,336 B2 | 7/2016 | Nash et al. |
| 9,458,189 B2 | 10/2016 | Verdine et al. |
| 9,458,202 B2 | 10/2016 | Nash et al. |
| 9,464,115 B2 | 10/2016 | Walensky et al. |
| 9,487,562 B2 | 11/2016 | Moellering et al. |
| 9,493,509 B2 | 11/2016 | Nash et al. |
| 9,505,801 B2 | 11/2016 | Verdine et al. |
| 9,505,804 B2 | 11/2016 | Guerlavais et al. |
| 9,522,947 B2 | 12/2016 | Kawahata et al. |
| 9,527,896 B2 | 12/2016 | Bernal et al. |
| 9,556,227 B2 | 1/2017 | Verdine et al. |
| 9,604,919 B2 | 3/2017 | Darlak et al. |
| 9,617,309 B2 | 4/2017 | Verdine et al. |
| 9,675,661 B2 | 6/2017 | Nash et al. |
| 2003/0166138 A1 | 9/2003 | Kinsella et al. |
| 2004/0023887 A1 | 2/2004 | Pillutla et al. |
| 2004/0038901 A1 | 2/2004 | Basler et al. |
| 2004/0067503 A1 | 4/2004 | Tan et al. |
| 2004/0106159 A1 | 6/2004 | Kern et al. |
| 2004/0106548 A1 | 6/2004 | Schmidt et al. |
| 2004/0115135 A1 | 6/2004 | Quay |
| 2004/0152708 A1 | 8/2004 | Li et al. |
| 2004/0171809 A1 | 9/2004 | Korsmeyer et al. |
| 2004/0235746 A1 | 11/2004 | Hawiger et al. |
| 2005/0119167 A1 | 6/2005 | Abbenante et al. |
| 2005/0222427 A1 | 10/2005 | Sharpless et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2006/0073518 A1 | 4/2006 | Timmerman et al. |
| 2006/0111411 A1 | 5/2006 | Cooper et al. |
| 2006/0148715 A1 | 7/2006 | Tweardy |
| 2006/0293380 A1 | 12/2006 | Nantermet et al. |
| 2007/0020620 A1 | 1/2007 | Finn et al. |
| 2007/0117154 A1 | 5/2007 | Deslongchamps et al. |
| 2007/0161544 A1 | 7/2007 | Wipf et al. |
| 2007/0197772 A1 | 8/2007 | Arora et al. |
| 2007/0203057 A1 | 8/2007 | Doherty et al. |
| 2008/0081831 A1 | 4/2008 | Gour et al. |
| 2008/0213175 A1 | 9/2008 | Kolb et al. |
| 2008/0234183 A1 | 9/2008 | Hallbrink et al. |
| 2008/0250515 A1 | 10/2008 | Reed |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0275519 A1 | 11/2009 | Nash et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0210515 A1 | 8/2010 | Nash et al. |
| 2010/0216688 A1 | 8/2010 | Nash et al. |
| 2010/0234563 A1 | 9/2010 | Arora et al. |
| 2010/0273704 A1 | 10/2010 | Korsmeyer et al. |
| 2010/0291040 A1 | 11/2010 | Lobel et al. |
| 2010/0298201 A1 | 11/2010 | Nash et al. |
| 2011/0028753 A1 | 2/2011 | Verdine et al. |
| 2011/0046043 A1 | 2/2011 | Wang et al. |
| 2011/0065915 A1 | 3/2011 | Malcolmson et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0245175 A1 | 10/2011 | Arora et al. |
| 2011/0245477 A1 | 10/2011 | Hoveyda et al. |
| 2011/0250685 A1 | 10/2011 | Nash |
| 2011/0263815 A1 | 10/2011 | Nash |

(56) References Cited

U.S. PATENT DOCUMENTS

| | | |
|---|---|---|
| 2012/0040889 A1 | 2/2012 | Nash et al. |
| 2012/0082636 A1 | 4/2012 | Walensky et al. |
| 2012/0101047 A1 | 4/2012 | Nash et al. |
| 2012/0115783 A1 | 5/2012 | Nash et al. |
| 2012/0115793 A1 | 5/2012 | Nash et al. |
| 2012/0172311 A1 | 7/2012 | Nash et al. |
| 2012/0178700 A1 | 7/2012 | Nash et al. |
| 2012/0264674 A1 | 10/2012 | Nash et al. |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0072439 A1 | 3/2013 | Nash et al. |
| 2013/0123196 A1 | 5/2013 | Arora et al. |
| 2013/0177979 A1 | 7/2013 | Turkson |
| 2013/0211046 A1 | 8/2013 | Verdine et al. |
| 2014/0005118 A1 | 1/2014 | Verdine et al. |
| 2014/0011979 A1 | 1/2014 | Verdine et al. |
| 2014/0051828 A1 | 2/2014 | Arora et al. |
| 2014/0128581 A1 | 5/2014 | Darlak et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0296160 A1 | 10/2014 | Walensky et al. |
| 2014/0323701 A1 | 10/2014 | Nash et al. |
| 2014/0378390 A1 | 12/2014 | Guerlavais et al. |
| 2015/0038430 A1 | 2/2015 | Nash et al. |
| 2015/0051155 A1 | 2/2015 | Guerlavais et al. |
| 2015/0056612 A1 | 2/2015 | Shen et al. |
| 2015/0119551 A1 | 4/2015 | Bernal et al. |
| 2015/0183825 A1 | 7/2015 | Guerlavais et al. |
| 2015/0225471 A1 | 8/2015 | Liang et al. |
| 2015/0239937 A1 | 8/2015 | Verdine et al. |
| 2015/0284437 A1 | 10/2015 | Verdine et al. |
| 2016/0024153 A1 | 1/2016 | Verdine et al. |
| 2016/0031936 A1 | 2/2016 | Nash |
| 2016/0052970 A1 | 2/2016 | Guerlavais et al. |
| 2016/0068573 A1 | 3/2016 | Nash et al. |
| 2016/0095896 A1 | 4/2016 | Nash |
| 2016/0096873 A1 | 4/2016 | Nash et al. |
| 2016/0101145 A1 | 4/2016 | Annis et al. |
| 2016/0108089 A1 | 4/2016 | Nash et al. |
| 2016/0115204 A1 | 4/2016 | Nash et al. |
| 2016/0122405 A1 | 5/2016 | Palchaudhuri et al. |
| 2016/0137710 A1 | 5/2016 | Kawahata et al. |
| 2016/0193283 A1 | 7/2016 | Chen et al. |
| 2016/0215036 A1 | 7/2016 | Verdine et al. |
| 2016/0244494 A1 | 8/2016 | Verdine et al. |
| 2016/0250278 A1 | 9/2016 | Nash et al. |
| 2016/0251399 A1 | 9/2016 | Nash et al. |
| 2016/0257716 A1 | 9/2016 | Guerlavais et al. |
| 2016/0257725 A1 | 9/2016 | Verdine et al. |
| 2016/0289274 A1 | 10/2016 | Nash |
| 2016/0304564 A1 | 10/2016 | Nash |
| 2016/0333049 A1 | 11/2016 | Chen et al. |
| 2017/0008930 A1 | 1/2017 | Walensky et al. |
| 2017/0015716 A1 | 1/2017 | Walensky et al. |
| 2017/0037086 A1 | 2/2017 | Kawahata et al. |
| 2017/0037105 A1 | 2/2017 | Samant |
| 2017/0066714 A1 | 3/2017 | Darlak et al. |
| 2017/0066799 A1 | 3/2017 | Verdine et al. |
| 2017/0081379 A1 | 3/2017 | Bernal et al. |
| 2017/0088581 A1 | 3/2017 | Verdine et al. |
| 2017/0107252 A1 | 4/2017 | Guerlavais et al. |
| 2017/0114098 A1 | 4/2017 | Aivado et al. |
| 2017/0212125 A1 | 7/2017 | Nash et al. |
| 2017/0226177 A1 | 8/2017 | Kawahata et al. |
| 2017/0266254 A1 | 9/2017 | Nash et al. |
| 2017/0281720 A1 | 10/2017 | Guerlavais et al. |
| 2017/0296620 A1 | 10/2017 | Nash |
| 2017/0298099 A1 | 10/2017 | Nash et al. |

FOREIGN PATENT DOCUMENTS

| | | |
|---|---|---|
| CN | 1583730 A | 2/2005 |
| EP | 0467699 A2 | 1/1992 |
| EP | 0467699 A3 | 2/1993 |
| EP | 0729972 A1 | 9/1996 |
| EP | 1452868 A2 | 9/2004 |
| EP | 1541692 A1 | 6/2005 |
| EP | 1602663 A1 | 12/2005 |
| EP | 1597585 B1 | 6/2011 |
| JP | 2002524391 A | 8/2002 |
| JP | 2010510236 A | 4/2010 |
| WO | WO-8909233 A1 | 10/1989 |
| WO | WO-9213878 A2 | 8/1992 |
| WO | WO-9301203 A1 | 1/1993 |
| WO | WO-9319176 A1 | 9/1993 |
| WO | WO-9425482 A1 | 11/1994 |
| WO | WO-9500534 A1 | 1/1995 |
| WO | WO-9602642 A1 | 2/1996 |
| WO | WO-9620951 A1 | 7/1996 |
| WO | WO-9628449 A1 | 9/1996 |
| WO | WO-9634878 A1 | 11/1996 |
| WO | WO-9700267 A1 | 1/1997 |
| WO | WO-9713537 A1 | 4/1997 |
| WO | WO-9726002 A1 | 7/1997 |
| WO | WO-9730072 A1 | 8/1997 |
| WO | WO-9737705 A1 | 10/1997 |
| WO | WO-9801467 A2 | 1/1998 |
| WO | WO-9846631 A1 | 10/1998 |
| WO | WO-9914259 A1 | 3/1999 |
| WO | WO-9934833 A1 | 7/1999 |
| WO | WO-9934850 A1 | 7/1999 |
| WO | WO-0006187 A2 | 2/2000 |
| WO | WO-0006187 A3 | 5/2000 |
| WO | WO-02064790 A2 | 8/2002 |
| WO | WO-02072597 A2 | 9/2002 |
| WO | WO-02064790 A3 | 5/2003 |
| WO | WO-03059933 A2 | 7/2003 |
| WO | WO-03070892 A2 | 8/2003 |
| WO | WO-03106491 A2 | 12/2003 |
| WO | WO-03059933 A3 | 1/2004 |
| WO | WO-2004026896 A2 | 4/2004 |
| WO | WO-2004041275 A1 | 5/2004 |
| WO | WO-2004058804 A1 | 7/2004 |
| WO | WO-2004077062 A2 | 9/2004 |
| WO | WO-03070892 A3 | 11/2004 |
| WO | WO-03106491 A3 | 12/2004 |
| WO | WO-2004077062 A3 | 1/2005 |
| WO | WO-2005007675 A2 | 1/2005 |
| WO | WO-2004077062 B1 | 2/2005 |
| WO | WO-2005012335 A1 | 2/2005 |
| WO | WO-2005040202 A2 | 5/2005 |
| WO | WO-2005044839 A2 | 5/2005 |
| WO | WO-2005040202 A3 | 6/2005 |
| WO | WO-2005007675 A3 | 7/2005 |
| WO | WO-2005044839 A3 | 7/2005 |
| WO | WO-2005085457 A2 | 9/2005 |
| WO | WO-2005090388 A1 | 9/2005 |
| WO | WO-2005118620 A2 | 12/2005 |
| WO | WO-2005118625 A1 | 12/2005 |
| WO | WO-2005118634 A2 | 12/2005 |
| WO | WO-2006038208 A2 | 4/2006 |
| WO | WO-2005118634 A3 | 5/2006 |
| WO | WO-2006078161 A1 | 7/2006 |
| WO | WO-2006103666 A2 | 10/2006 |
| WO | WO-2006103666 A3 | 3/2007 |
| WO | WO-2006038208 A3 | 5/2007 |
| WO | WO-2007141533 A2 | 12/2007 |
| WO | WO-2007144886 A2 | 12/2007 |
| WO | WO-2008013454 A2 | 1/2008 |
| WO | WO-2008045238 A2 | 4/2008 |
| WO | WO-2008061192 A2 | 5/2008 |
| WO | WO-2008074895 A1 | 6/2008 |
| WO | WO-2008076904 A1 | 6/2008 |
| WO | WO-2008061192 A3 | 7/2008 |
| WO | WO-2008095063 A1 | 8/2008 |
| WO | WO-2008104000 A2 | 8/2008 |
| WO | WO-2008121767 A2 | 10/2008 |
| WO | WO-2008104000 A3 | 11/2008 |
| WO | WO-2008137633 A2 | 11/2008 |
| WO | WO-2008121767 A3 | 1/2009 |
| WO | WO-2009042237 A2 | 4/2009 |
| WO | WO-2009089004 A1 | 7/2009 |

(56) References Cited

FOREIGN PATENT DOCUMENTS

| | | |
|---|---|---|
| WO | WO-2009099677 A2 | 8/2009 |
| WO | WO-2009108261 A2 | 9/2009 |
| WO | WO-2009110952 A2 | 9/2009 |
| WO | WO-2009126292 A2 | 10/2009 |
| WO | WO-2009099677 A3 | 12/2009 |
| WO | WO-2009149214 A2 | 12/2009 |
| WO | WO-2009108261 A3 | 1/2010 |
| WO | WO-2010011313 A2 | 1/2010 |
| WO | WO-2010033879 A2 | 3/2010 |
| WO | WO-2010034026 A1 | 3/2010 |
| WO | WO-2010034028 A1 | 3/2010 |
| WO | WO-2010034029 A1 | 3/2010 |
| WO | WO-2010034031 A1 | 3/2010 |
| WO | WO-2010034032 A2 | 3/2010 |
| WO | WO-2010034034 A1 | 3/2010 |
| WO | WO-2010060112 A1 | 5/2010 |
| WO | WO-2010068684 A2 | 6/2010 |
| WO | WO-2010083347 A2 | 7/2010 |
| WO | WO-2010121288 A1 | 10/2010 |
| WO | WO-2011008260 A2 | 1/2011 |
| WO | WO-2011038049 A1 | 3/2011 |
| WO | WO-2011047215 A1 | 4/2011 |
| WO | WO-2012021874 A1 | 2/2012 |
| WO | WO-2012021875 A1 | 2/2012 |
| WO | WO-2012021876 A2 | 2/2012 |
| WO | WO-2012040459 A2 | 3/2012 |
| WO | WO-2012065181 A2 | 5/2012 |
| WO | WO-2012122059 A1 | 9/2012 |
| WO | WO-2012173846 A2 | 12/2012 |
| WO | WO-2012174423 A1 | 12/2012 |
| WO | WO-2013033645 A1 | 3/2013 |
| WO | WO-2013059525 A1 | 4/2013 |
| WO | WO-2013059530 A2 | 4/2013 |
| WO | WO-2013123266 A1 | 8/2013 |
| WO | WO-2013123267 A1 | 8/2013 |
| WO | WO-2014047673 A1 | 4/2014 |
| WO | WO-2014052647 A2 | 4/2014 |
| WO | WO-2014055564 A1 | 4/2014 |
| WO | WO-2014071241 A1 | 5/2014 |
| WO | WO-2014138429 A2 | 9/2014 |
| WO | WO-2015157508 A1 | 10/2015 |
| WO | WO-2016049355 A1 | 3/2016 |
| WO | WO-2016049359 A1 | 3/2016 |
| WO | WO-2016154058 A1 | 9/2016 |
| WO | WO-2017004548 A1 | 1/2017 |
| WO | WO-2017004591 A2 | 1/2017 |
| WO | WO-2017023933 A2 | 2/2017 |
| WO | WO-2017040990 A1 | 3/2017 |
| WO | WO-2017044633 A1 | 3/2017 |
| WO | WO-2017165299 A2 | 9/2017 |

OTHER PUBLICATIONS

Annis, et al. ALIS: An affinity selection-mass spectrometry system for the discovery and characterization of protein-ligand Interactions. Mass Spectrometry in Medicinal Chemistry: Applications in Drug Discovery (2007): 121-156.
Armstrong et al., X=Y-Zh Systems as potential 1,3-dipoles. 5. Intramolecular cycloadditions of imines of a-amino acid esters. Tetrahedron. 1985;41(17):3547-58.
Arosio, et al. Click chemistry to functionalise peptidomimetics. Tetrahedron Letters. 2006; 47:3697-3700.
Austin et al., "A Template for Stabilization of a Peptide α-Helix: Synthesis and Evaluation of Conformational Effects by Circular Dichroism and NMR," J. Am. Chem. Soc. 119:6461-6472 (1997).
Babine et aL, Molecular Recognition of Proteinminus signLigand Complexes: Applications to Drug Design. Chem Rev. Aug. 5, 1997;97(5):1359-1472.
Baell, J.B. Prospects for Targeting the Bcl-2 Family of Proteins to Develop Novel cytotoxic drugs. Biochem Pharmacol. Sep. 2002;64(5-6):851-63.
Bakhshi, et al. Cloning the chromosomal breakpoint of t(14;18) human lymphomas: clustering around JH on chromosome 14 and near a transcriptional unit on 18. Cell. Jul. 1985;41(3):899-906.

Banerji et al. Synthesis of Cyclic β-Turn Mimics from L-Pro-Phe/Phe-L-Pro Derived Di- and Tripeptides via Ring Closing Metathesis: The Role of Chirality of the Phe Residue During Cyclization. Tetrahedron Lett. 2002; 43:6473-6477.
Bang et al., Total chemical synthesis of crambin. J Am Chem Soc. Feb. 11, 2004;126(5):1377-83.
Barker, et al. Cyclic RGD peptide analogues as antiplatelet antithrombotics. J Med Chem. May 29, 1992;35(11):2040-8. (Abstract only).
Belokon et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon, et al. Improved procedures for the synthesis of (S)-2-[N-(N'-benzylprolyl)amino]benzophenone (BPB) and Ni(II) complexes of Schiff's bases derived from BPB and amino acids. Tetrahedron: Asymmetry, vol. 9, Issue 23, Dec. 11, 1998, pp. 4249-4252.
Berendsen et al. A glimpse of the Holy Grail? Science 282(5389):642-643 (1998).
Berge et al. Pharmaceutical Salts. Journal of Pharmaceutical Sciences 66(1):1-19 (Jan. 1977).
Bernal et al., Reactivation of the p53 tumor suppressor pathway by a stapled p53 peptide. (2007) J. Am Chem Soc. 9129, 2456-2457.
Walensky et al., A stapled BID BH3 helix directly binds and activates BAX. (2006) Mol Cell 24:199-210.
Biagini et al., Cross-metathesis of Unsaturated a-amino Acid Derivatives. J Chem Soc Perkin Trans. 1998;1:2485-99.
Bierzynski et al. A salt bridge stabilizes the helix formed by isolated C-Peptide of RNase A. PNAS USA. 1982;79:2470-2474.
Blackwell, et al. Highly Efficient Synthesis of Covalently Cross-Linked Peptide Helices by Ring-Closing Metathesis. Angewandte Chemie International Edition. 1998; 37(23):3281-3284.
Blackwell, et al. Ring-closing metathesis of olefinic peptides: design, synthesis, and structural characterization of macrocyclic helical peptides. J Org Chem. Aug. 10, 2001;66(16):5291-302.
Boal, et al. Facile and E-selective intramolecular ring-closing metathesis reactions in 3(10)-helical peptides: a 3D structural study. J Am Chem Soc. Jun. 6 2007;129(22):6986-7. Epub May 11, 2007.
von Itzstein et al, "Rational design of potent sialidase-based inhibitors of influenza virus replication," Nature, Jun. 3, 1993, 363: 418-423.
Bock, et al. 1,2,3-Triazoles as peptide bond isosteres: synthesis and biological evaluation of cyclotetrapeptide mimics. Org Biomol Chem. Mar. 21, 2007;5(6):971-5.
Boguslavsky, et al. Effect of peptide conformation on membrane permeability. J Pept Res. Jun. 2003;61(6):287-97.
Bossy-Wetzel et al. Assays for cytochrome c release from mitochondria during apoptosis. Methods Enzymol. 322:235-242 (2000).
Bossy-Wetzel, et al. Detection of apoptosis by annexin V labeling. Methods Enzymol. 2000;322:15-8.
Bracken et al. Synthesis and nuclear magnetic resonance structure determination of an alpha-helical, bicyclic, lactam-bridged hexapeptide. JACS. 1994;116:6431-6432.
Bradley et al. Limits of cooperativity in a structurally modular protein: response of the Notch ankyrin domain to analogous alanine substitutions in each repeat. J Mol Biol. 324(2):373-386 (2002).
Brea, et al. Synthesis of omega-(hetero)arylalkynylated alpha-amino acid by Sonogashira-type reactions in aqueous media. J Org Chem. Sep. 29, 2006;71(20):7870-3.
Brunel, et al. Synthesis of constrained helical peptides by thioether ligation: application to analogs of gp41. Chem Commun (Camb). May 28, 2005;(20):2552-4. Epub Mar. 11, 2005.
Voet D, Voet JG, Biochemistry, Second Edition, John Wiley & Sons, Inc., 1995, pp. 235-241.
Burrage, et al. Biomimetic synthesis of lantibiotics. Chemistry. Apr. 14, 2000;6(8):1455-66.
Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).
Cantel, et al. Synthesis and Conformational Analysis of a Cyclic Peptide Obtained via i to i+4 Intramolecular Side-Chain to Side-Chain Azide-Alkyne 1,3-Dipolar Cycloaddition. JOC Featured Article. Published on the web May 20, 2008.

(56) References Cited

OTHER PUBLICATIONS

Carlson et al., Specificity landscapes of DNA binding molecules elucidate biological function. Proc Natl Acad Sci USA. Mar. 9, 2010;107(10):4544-9. doi: 10.1073/pnas.0914023107. Epub Feb. 22, 2010.
CAS Registry No. 2176-37-6, STN Entry Date Nov. 16, 1984.
CAS Registry No. 2408-85-7, STN Entry Date Nov. 16, 1984.
CAS Registry No. 4727-05-3, STN Entry Date Nov. 16, 1984.
CAS Registry No. 561321-72-0, STN Entry Date Aug. 6, 2003.
CAS Registry No. 721918-14-5, STN Entry Date Aug. 4, 2004.
Chakrabartty et al., "Helix Capping Propensities in Peptides Parallel Those in Proteins," Proc. Nat'l Acad. Sci. USA 90:11332-11336 (1993).
Chapman et al., "A Highly Stable Short $\alpha$-Helix Constrained by a Main-chain Hydrogen-bond Surrogate," J. Am. Chem. Soc. 126:12252-12253 (2004).
Chapman, et al. Optimized synthesis of hydrogen-bond surrogate helices: surprising effects of microwave heating on the activity of Grubbs catalysts. Org Lett. Dec. 7, 2006;8(25):5825-8.
Chen et al., Determination of the helix and beta form of proteins in aqueous solution by circular dichroism. Biochemistry. Jul. 30, 1974;13(16):3350-9.
Chin & Schepartz, "Design and Evolution of a Miniature Bcl-2 Binding Protein," Angew. Chem. Int. Ed. 40(20):3806-3809 (2001).
Chin et al., "Circular Dichroism Spectra of Short, Fixed-nucleus Alanine Helices," Proc. Nat'l Acad. Sci. USA 99(24):15416-15421 (2002).
Chittenden, et al. A conserved domain in Bak, distinct from BH1 and BH2, mediates cell death and protein binding functions. EMBO J. Nov. 15, 1995;14(22):5589-96.
Choi, et al. Application of azide-alkyne cycloaddition 'click chemistry' for the synthesis of Grb2 SH2 domain-binding macrocycles. Bioorg Med Chem Lett. Oct. 15, 2006;16(20):5265-9.
Chu, et al. Peptide-formation on cysteine-containing peptide scaffolds. Orig Life Evol Biosph. Oct. 1999;29(5):441-9.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci U S A. Nov. 1985;82(21):7439-43.
Cline, et al. Effects of As(III) binding on alpha-helical structure. J Am Chem Soc. Mar. 12, 2003;125(10):2923-9.
Colacino, et al. Evaluation of the anti-influenza virus activities of 1,3,4-thiadiazol-2-ylcyanamide (LY217896) and its sodium salt. Antimicrob Agents Chemother. Nov. 1990;34(11):2156-63.
Colaluca et al., NUMB controls p53 tumour suppressor activity. Nature. Jan. 3, 2008;451(7174):76-80. doi: 10.1038/nature06412.
Co-pending U.S. Appl. No. 13/494,846, filed Jun. 12, 2012.
Co-pending U.S. Appl. No. 13/655,442, filed Oct. 18, 2010.
Walker, et al. General method for the synthesis of cyclic peptidomimetic compounds. Tetrahedron Letters. 2001; 42(34):5801-5804.
Wang, et al. BID: a novel BH3 domain-only death agonist. Genes Dev. Nov. 15, 1996;10(22):2859-69.
Wang et al. Cell permeable Bcl-2 binding peptides: a chemical approach to apoptosis induction in tumor cells. Cancer Res. Mar. 15, 2000;60(6):1498-502.
Wang, et al. "Click" synthesis of small molecule probes for activity-based fingerprinting of matrix metalloproteases. Chem Commun (Camb). Sep. 28, 2006;(36):3783-5.
Wang et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.
Wang, et al. Evaluation of biologically relevant short alpha-helices stabilized by a main-chain hydrogen-bond surrogate. J Am Chem Soc. Jul. 19, 2006;128(28):9248-56.
Co-pending U.S. Appl. No. 15/201,235, filed Jul. 1, 2016.

Co-pending U.S. Appl. No. 15/226,059, filed Aug. 2, 2016.
Co-pending U.S. Appl. No. 15/229,517, filed Aug. 5, 2016.
Co-pending U.S. Appl. No.15/233,796, filed Aug. 10, 2016.
Co-pending U.S. Appl. No. 15/240,505, filed Aug. 18, 2016.
Co-pending U.S. Appl. No. 15/256,130, filed Sep. 2, 2016.
Co-pending U.S. Appl. No. 15/257,807, filed Sep. 6, 2016.
Co-pending U.S. Appl. No. 15/259,947, filed Sep. 8, 2016.
Co-pending U.S. Appl. No. 15/278,824, filed Sep. 28, 2016.
Co-pending U.S. Appl. No. 15/332,492, filed Oct. 24, 2016.
Cox et al., Insulin receptor expression by human prostate cancers. Prostate. Jan. 1, 2009;69(1):33- 40. doi: 10.1002/pros.20852.
Cusack et al. 2,4,6-Tri-isopropylbenzenesulphonyl Hydrazide: A convenient source of Di-Imide. Tetrahedron. 1976;32:2157-2162.
Danial, et al. Cell death: critical control points. Cell. 2004; 116:204-219.
Darnell, Transcription factors as targets for cancer therapy. Nat Rev Cancer. Oct. 2002;2(10):740-9.
Definition of Analog from http://cancerweb.ncl.ac.uk/cgi-bin/omd?query=analog. pp. 1-5. Accessed Jul. 7, 2005.
Degterev et al. Identification of Small-molecule Inhibitors of Interaction between the BH3 Domain and Bcl-xL. Nature Cell Biol. 3:173-182 (2001).
Deiters, et al. Adding amino acids with novel reactivity to the genetic code of Saccharomyces cerevisiae. J Am Chem Soc. Oct. 1, 2003;125(39):11782-3.
Deng, et al. Cross-Coupling Reaction of Iodo-1,2,3-triazoles Catalyzed by Palladium. Synthesis 2005(16): 2730-2738.
Designing Custom Peptide. SIGMA Genosys (pp. 1-2) (Accessed Dec. 16, 2004).
Dimartino et al. Solid-phase synthesis of hydrogen-bond surrogate-derived alpha-helices. Org Lett. Jun. 9, 2005;7(12):2389-92.
Duronio, Insulin receptor is phosphorylated in response to treatment of HepG2 cells with insulin-like growth factor I. Biochem J. Aug. 15, 1990;270(1):27-32.
Erez, et al. Induction of apoptosis in cultured endothelial cells by a cadherin antagonist peptide: involvement of fibroblast growth factor receptor-mediated signalling. Exp Cell Res. Apr. 1, 2004;294(2):366-78. Abstract only.
Erlanson, et al. Facile synthesis of cyclic peptides containing di-, tri-, tetra-, and Pentasulfides. Tetrahedron Letters. 1998; 39(38):6799-6802.
European office action dated Aug. 20, 2012 for EP Application No. 09730445.5.
Woodfin, et al. Interaction of the amino-terminus of an influenza virus protein with mitochondria. Arch Biochem Biophys. Nov. 1, 1993;306(2):427-30.
Yang, et al. Calculation of protein conformation from circular dichroism. Methods Enzymol. 1986;130:208-69.
Yang et al. Synthesis and helical structure of lactam bridged BH3 peptides derived from pro-apoptotic Bcl-2 family proteins. Bioorg Med Chem Lett. Mar. 22, 2004;14(6):1403-6.
Yang, et al. Synthesis and helical structure of lactam bridged BH3 peptides derived from pro-apoptotic Bcl-2 family proteins. Bioorganic & medicinal chemistry letters. 2004;14(6):1403-1406.
Yu, et al. Synthesis of macrocyclic natural products by catalyst-controlled stereoselective ring-closing metathesis. Nature. Nov. 2, 2011;479(7371):88-93. doi: 10.1038/nature10563.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. 310 Helix versus alpha-helix: a molecular dynamics study of conformational preferences of Aib and Alanine. J. American Cancer Society. Dec. 1994; 116(26):11915-11921.
Wu, et al. Regiospecific Synthesis of 1,4,5-Trisubstituted-1,2,3-triazole via One-Pot Reaction Promoted by Copper(I) Salt. Synthesis. 2005(8): 1314-1318.
Zhang, et al. Ruthenium-catalyzed cycloaddition of alkynes and organic azides. J Am Chem Soc. Nov. 23, 2005;127(46):15998-9.
Zitzow, et al. Pathogenesis of avian influenza A (H5N1) viruses in ferrets. J Virol. May 2002;76(9):4420-9.

(56) References Cited

OTHER PUBLICATIONS

Wunderlich, et al. Identification of a PA-binding peptide with inhibitory activity against influenza A and B virus replication. PLoS One. Oct. 20, 2009;4(10):e7517. doi: 10.1371/journal.pone. 0007517.

Felix et al., "Synthesis, Biological Activity and Conformational Analysis of Cyclic GRF Analogs," Int. J. Pep. Protein Res. 32:441-454 (1988).

Feng et al. Solid-phase SN2 macrocyclization reactions to form beta-turn mimics. Org Lett. Jul. 15, 1999;1(1):121-4.

Fields, et al. Chapter 3 in Synthetic Peptides: A User's Guide. Grant W.H. Freeman & Co. New York, NY. 1992. p. 77.

Fieser, et al. Fieser and Fieser's Reagents for Organic Synthesis. John Wiley and Sons. 1994.

File Hcaplus on STN. AN No. 1990:532752. Burger et al. Synthesis of a-(trifluoromethyl)-substituted a-amino acids. Part 7. An efficient synthesis for a-trifluoromethyl-substituted w-carboxy a-amino acids. Chemiker-Zeitung (1990), 114(3), 101-4. Abstract only, date Oct. 1990.

Fischer, et al. Apoptosis-based therapies and drug targets. Cell Death and Differentiation. 2005; 12:942-961.

Folkers, et al. Methods and principles in medicinal chemistry. Eds. R. Mannhold, H. Kubinyi, and H. Timmerman. Wiley-VCH, 2001.

Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.

Freedman, et al. Structural basis for recruitment of CBP/p300 by hypoxia-inducible factor-1 alpha. Proc Natl Acad Sci U S A. Apr. 16, 2002;99(8):5367-72.

Fulda, et al. Extrinsic versus intrinsic apoptosis pathways in anti-cancer chemotherapy. Oncogene. Aug. 7, 2006;25(34):4798-811.

Furstner et al., Alkyne Metathesis: Development of a Novel Molybdenum-Based Catalyst System and Its Application to the Total Synthesis of Epothilone A and C. Chem Euro J. 2001;7(24):5299-5317.

Furstner, et al. Mo[N(t-Bu)(AR)]3 Complexes as catalyst precursors: In situ activation and application to metathesis reactions of alkynes and diynes. J Am chem Soc. 1999; 121:9453-54.

Furstner, et al. Nozaki—Hiyama—Kishi reactions catalytic in chromium. J Am Chem Soc. 1996; 118:12349-57.

"Fustero, et al. Asymmetric synthesis of new beta,beta-difluorinated cyclic quaternary alpha-amino acid derivatives. Org Lett. Aug. 31, 2006;8(18):4129-32."

Galande, et al. Thioether side chain cyclization for helical peptide formation: inhibitors of estrogen receptor-coactivator interactions. Journal of Peptide Research. 2004; 63(3): 297-302.

Galande, et al. An effective method of on-resin disulfide bond formation in peptides. J Comb Chem. Mar.-Apr. 2005;7(2):174-7.

Galande, et al. An effective method of on-resin disulfide bond formation in peptides. Journal of combinatorial chemistry. 2005;7(2):174-177.

Gallivan et al., A neutral, water-soluble olefin metathesis catalyst based on an N-heterocyclic carbene ligand. Tetrahedron Letters. 2005;46:2577-80.

Galluzzi, et al. Guidelines for the use and interpretation of assays for monitoring cell death in higher eukaryotes. Cell Death Differ. Aug. 2009;16(8):1093-107. Epub Apr. 17, 2009.

Gante, Peptidomimetics—Tailored Enzyme Inhibitors. J Angew Chem Int Ed Engl. 1994;33:1699-1720.

Ghadiri & Choi, "Secondary Structure Nucleation in Peptides. Transition Metal Ion Stabilized α-Helices," J. Am. Chem. Soc. 112:1630-1632 (1990).

Ghanem, et al. Peptide-mediated interference with influenza A virus polymerase. J Virol. Jul. 2007;81(14):7801-4.

Giannis et aL, Peptidomimetics for Receptor Ligands—Discovery, Development, and Medical Perspectives. Angew Chem Int Ed Engl. 1993;32:1244-67.

Giorello, et al. Inhibition of cancer cell growth and c-Myc transcriptional activity by a c-Myc helix 1-type peptide fused to an internalization sequence. Cancer Res. Aug. 15, 1998;58(16):3654-9.

Goncalves, et al. On-resin cyclization of peptide ligands of the Vascular Endothelial Growth Factor Receptor 1 by copper(I)-catalyzed 1,3-dipolar azide-alkyne cycloaddition. Bioorg Med Chem Lett. Oct. 15, 2007;17(20):5590-4.

Goodson et al., Potential Growth Antagonists. I. Hydantoins and Disubstituted Glycines. J Org Chem. 1960;25:1920-24.

Green, T.W.; Wuts, P.G.M. Protective Groups in Organic Synthesis, 2nd ed. New York; John Wiley and Sons, Inc.; 1991.

Greene, et al. Protective Groups in Organic Synthesis, 2nd Ed. John Wiley and Sons. 1991.

Greenfield et al. Computed circular dichroism spectra for the evaluation of protein conformation. Biochemistry. Oct. 8, 1969;(10):4108-4116.

Greenlee et al., A General Synthesis of a-vinyl-a-amino acids. Tetrahedron Letters. 1978;42:3999-40002.

Grubbs, et al. Ring-Closing Metathesis and Related Processes in Organic Synthesis. Acc. Chem. Res., 1995, 28 (11), pp. 446-452.

Guinn et al., Synthesis and characterization of polyamides containing unnatural amino acids. Biopolymers. May 1995;35(5):503-12.

Gupta et al., Long-term effects of tumor necrosis factor-alpha treatment on insulin signaling GUPTA pathway in HepG2 cells and HepG2 cells overexpressing constitutively active Akt/PKB. J Cell Biochem. Feb. 15, 2007;100(3):593-607.

Hanessian, et al. Structure-based design and synthesis of macroheterocyclic peptidomimetic inhibitors of the aspartic protease beta-site amyloid precursor protein cleaving enzyme (BACE). J Med Chem. Jul. 27, 2006;49(15):4544-67.

Hara, S. et al. 'Synthetic studies on halopeptins, anti-inflammatory cyclodepsipeptides', Peptide Science. 2006 (vol. date 2005), 42nd, pp. 39-42.

Hase; et al., "1,6-Aminosuberic acid analogs of lysine- and arginine-vasopressin and —vasotocin. Synthesis and biological properties. J Am Chem Soc. May 17, 1972;94(10):3590-600."

Wang, et al. Nucleation and stability of hydrogen-bond surrogate-based alpha-helices. Org Biomol Chem. Nov. 21, 2006;4(22):4074-81.

He, X. et al., Crystal structure of the polymerase PAC-PB1N complex from an avian influenza H5N1 virus. Nature, 2008. 454: p. 1123-6.

Hecht, S.M., ed. Bioorganic Chemistry: Peptides and Proteins. Oxford University Press. New York; 1998.

Hein, et al. Copper(I)-Catalyzed Cycloaddition of Organic Azides and 1-Iodoalkynes. Angew Chem Int Ed Engl. 2009;48(43):8018-21.

Wels, et al. Synthesis of a novel potent cyclic peptide MC4-ligand by ring-closing metathesis. Bioorg. Med. Chem. Lett. 2005; 13: 4221-4227.

Hemerka, et al. Detection and characterization of influenza A virus PA-PB2 interaction through a biomolecular fluorescence complementation assay. J Virol. Apr. 2009;83(8):3944-55. Epub Feb. 4, 2009.

Hiroshige, et al. Palladium-mediated macrocyclisations on solid support and its applica-tions to combinatorial synthesis. J. Am. Chem. Soc. 1995; 117:11590-11591.

Horne, et al. Heterocyclic peptide backbone modifications in an alpha-helical coiled coil. J Am Chem Soc. Dec. 1, 2004;126(47):15366-7.

Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).

Hunt, S. The Non-Protein Amino Acids. In: Barrett G.C., ed. Chemistry and Biochemistry of the Amino Acids. New York; Chapman and Hall; 1985.

"Sidwell, R. W. et al., In vitro and in vivo assay systems for study of influenza virus inhibitors. Antiviral Res, 2000. 48(1): p. 1-16".

International Preliminary Report on Patentability for PCT/US2013/062004, dated Apr. 9, 2015.

International Preliminary Report on Patentability for PCT/US2013/062929, dated Apr. 16, 2015.

International Preliminary Report on Patentability for PCT/US2014/025544, dated Sep. 24, 2015.

International search report and written opinion dated Jan. 7, 2011 for PCT Application No. US2010/049892.

(56) References Cited

OTHER PUBLICATIONS

International search report and written opinion dated Feb. 16, 2010 for PCT Application No. US2009/057927.
International search report and written opinion dated Mar. 5, 2010 for PCT Application No. US2009/057928.
International search report and written opinion dated Mar. 8, 2010 for PCT Application No. US09/057925.
International search report and written opinion dated Mar. 10, 2010 for PCT Application No. US2009/057930.
International search report and written opinion dated May 16, 2008 for PCT Application No. US2007/084838.
International search report and written opinion dated Jul. 6, 2010 for PCT Application No. US2010/021091.
International Search Report and Written Opinion for PCT/US2008/052580, dated May 16, 2008.
International Search Report and Written Opinion for PCT/US2014/025544, dated Sep. 10, 2014.
International Search Report and Written Opinion for PCT/US2014/058680, dated Apr. 23, 2015.
International search report dated Nov. 30, 2009 for PCT Application No. US2009/02225.
International search report dated Apr. 28, 2008 for PCT Application No. US2007/87615.
International search report dated May 18, 2005 for PCT Application No. US2004/38403.
International Search Report dated Sep. 10, 2014 for PCT Application No. US2014/025544.
International search report dated Sep. 25, 2008 for PCT Application No. US2008/54922.
Jackson et al. General approach to the synthesis of short alpha-helical peptides. JACS. 1991;113:9391-9392.
Jin, et al. Structure-based design, synthesis, and activity of peptide inhibitors of RGS4 GAP activity. Methods Enzymol. 2004;389:266-77.
Jin, et al. Structure-based design, synthesis, and pharmacologic evaluation of peptide RGS4 inhibitors. J Pept Res. Feb. 2004;63(2):141-6.
Johannesson, et al. Vinyl sulfide cyclized analogues of angiotensin II with high affinity and full agonist activity at the AT(1) receptor. J Med Chem. Apr. 25, 2002;45(9):1767-77.
Kanan et al. Reaction discovery enabled by DNA-templated synthesis and in vitro selection. Nature. Sep. 30, 2004;431(7008):545-9.
Karle, et al. Structural charateristics of alpha-helical peptide molecules containing Aib residues. Biochemistry. Jul. 24, 1990;29(29):6747-56.
Karle. Flexibility in peptide molecules and restraints imposed by hydrogen bonds, the Aib residue, and core inserts. Biopolymers. 1996;40(1):157-80.
Karwoski et al., Lysinonorleucine cross-link formation in alpha amino heptenoic acid-substituted peptide derivatives. Biopolymers. 1978;17(5):1119-27.
Kaul & Balaram, "Stereochemical Control of Peptide Folding," Bioorg. Med. Chem. 7:105-117 (1999).
Kazmaier, Sythesis of Quaternary Amino Acids Containing 13, γ- as well as 7,6-Unsatured Side Chains via Chelate-Enolate Claisen Rearrangement. Tetrahedron Letters. 1996;37(30):5351-4.
Kedrowski, B.L. et al. 'Thiazoline ring formation from 2-methylcysteines and 2-halomethylalanines', Heterocycles. 2002, vol. 58, pp. 601-634.
Kelso et al., "A Cyclic Metallopeptide Induces α Helicity in Short Peptide Fragments of Thermolysin," Angew. Chem. Int. Ed. 42(4):421-424 (2003).
Kelso et al., "α-Turn Mimetics: Short Peptide α-Helices Composed of Cyclic Metallopentapeptide Modules," J. Am. Chem. Soc. 126:4828-4842 (2004).
Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6672-6682 (1991).

Kent. Advanced Biology. Oxford University Press. 2000.
Kilby et al., "Potent Suppression of HIV-1 Replication in Humans by T-20, a Peptide Inhibitor of gp41-Mediated Virus Entry," Nat. Med. 4(11):1302-1307 (1998).
Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.
Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.
Kotha et al., Modification of constrained peptides by ring-closing metathesis reaction. Bioorg Med Chem Lett. Jun. 4, 2001;11(11):1421-3.
Kritzer et al., "Helical β-Peptide Inhibitors of the p53-hDM2 Interaction," J. Am. Chem. Soc. 126:9468-9469 (2004).
Kudaj, et al. An efficient synthesis of optically pure alpha-alkyl-beta-azido- and alpha-alkyl-beta-aminoalanines via ring opening of 3-amino-3-alkyl-2-oxetanones. Tetrahedron Letters. 2007; 48:6794-6797.
Kussie et al, "Structure of the MDM2 Oncoprotein Bound to the p53 Tumor Suppressor Transactivation Domain," Science 274:948-953 (1996).
Kutzki et al., "Development of a Potent Bcl-xL Antagonist Based on α-Helix Mimicry," J. Am. Chem. Soc. 124:11838-11839 (2002).
Kwon, et al. Quantitative comparison of the relative cell permeability of cyclic and linear peptides. Chem Biol. Jun. 2007 Jun;14(6):671-7.
Lacombe et al. Reduction of olefins on solid support using diimide. Tetrahedron Letters. 1998;39:6785-6786.
Wild et al., "Peptides Corresponding to a Predictive α-Helical Domain of Human Immunodeficiency Virus Type 1 gp41 are Potent Inhibitors of Virus Infection," Proc. Nat'l Acad. Sci. USA 91:9770-9774 (1994).
Larock, R.C. Comprehensive Organic Transformations, New York: VCH Publishers; 1989.
Latini, et al. 395 Blocking the interaction between HIF-/alpha and p300 by a 32 amino acid fragment of p35srj inhibits the hypoxia induced transcriptional activity of HIF-1alpha in human U87MG glioma cells. Euro J Canc Suppl. 2004; 2(8):118.
Leduc et al., Helix-stabilized cyclic peptides as selective inhibitors of steroid receptor-coactivator interactions. Proc Natl Acad Sci USA. 2003;100(20):11273-78.
Lee, et al. A novel BH3 ligand that selectively targets Mcl-1 reveals that apoptosis can proceed without Mcl-1 degradation. J Cell Biol. Jan. 28, 2008;180(2):341-355.
Li, et al. A convenient preparation of 5-iodo-1,4-disubstituted-1,2,3-triazole: multicomponent one-pot reaction of azide and alkyne mediated by CuI-NBS. J Org Chem. May 2, 2008;73(9):3630-3. doi: 10.1021/jo800455v. Epub Mar. 22, 2008.
Li, et al. Structure-based design of thioether-bridged cyclic phosphopeptides binding to Grb2-SH2 domain. Bioorg Med Chem Lett. Mar. 10, 2003;13(5):895-9.
Liskamp, et al. Conformationally restricted amino acids and dipeptides, (non)peptidomimetics and secondary structure mimetics. Recl Travl Chim Pays-Bas. 1994; 113:1-19.
Litowski & Hodges, "Designing Heterodimeric Two-stranded α-Helical Coiled-coils: Effects of Hydrophobicity and α-Helical Propensity on Protein Folding, Stability, and Specificity," J. Biol. Chem. 277(40):37272-37279 (2002).
Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.
Lyu, et al. Capping Interactions in Isolated α Helices: Position-dependent Substitution Effects and Structure of a Serine-capped Peptide Helix. Biochemistry. 1993; 32:421-425.
Lyu et al, "α-Helix Stabilization by Natural and Unnatural Amino Acids with Alkyl Side Chains," Proc. Nat'l Acad. Sci. USA 88:5317-5320 (1991).
Mai, et al. A proapoptotic peptide for the treatment of solid tumors. Cancer Research. 2001; 61:7709-7712.

(56) References Cited

OTHER PUBLICATIONS

Mangold, et al. Azidoalanine mutagenicity in *Salmonella*: effect of homologation and alpha-Mutat Res. Feb. 1989;216(1):27-33.methyl substitution.
Mannhold, R et al. Molecular Drug Properties: Measurement and Prediction (Methods and Principles in Medicinal Chemistry). Wiley-VCH; 2007.
Marshall et al., Back to the future: ribonuclease A. Biopolymers. 2008;90(3):259-77.
Martin, et al. Thermal [2+2] intramolecular cycloadditions of fuller-1,6-enynes. Angew Chem Int Ed Engl. Feb. 20, 2006;45(9):1439-42.
McGahon, et al. The end of the (cell) line: methods for the study of apoptosis in vitro. Methods Cell Biol. 1995;46:153-85.
McNamara et al. Peptides constrained by an aliphatic linkage between two C(alpha) sites: design, synthesis, and unexpected conformational properties of an i,(i + 4)-linked peptide. J Org Chem. Jun. 29, 2001;66(13):4585-95.
Miller et al., Application of Ring-Closing Metathesis to the Synthesis of Rigidified Amino Acids and Peptides. J Am Chem Soc. 1996;118(40):9606-9614.
Miller et al., Synthesis of Conformationally Restricted Amino Acids and Peptides Employing Olefin Metathesis. J Am Chem Soc. 1995;117(21):5855-5856.
Moellering et al., Abstract 69. Computational modeling and molecular optimization of stabilized alpha-helical peptides targeting NOTCH-CSL transcriptional complexes. Nov. 2010; 8(7):30. DOI: 10.1016/S1359-6349(10)71774-2. Abstract Only, European Journal of Cancer Supplements, 2010, 8(7).
Mosberg, et al. Dithioeter-containing cyclic peptides. J. Am. Chem. Soc. 1985;107(10):2986-2987.
Mosberg, et al. Dithioether-containing cyclic peptides. Journal of the American Chemical Society. 1985;107(10):2986-2987.
Muchmore, et al. X-ray and NMR structure of human Bcl-xL, an inhibitor of programmed cell death. Nature. May 23, 1996;381(6580):335-41.
Muir, Semisynthesis of proteins by expressed protein ligation. Annu Rev Biochem. 2003;72:249-89. Epub Feb. 27, 2003.
Mulqueen et al. Synthesis of the thiazoline-based siderophore (S)-desferrithiocin. 1993;48(24):5359-5364.
Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi: 10.1016/j.bmcl.2011.10.009. Epub Oct. 12, 2011.
Williams and IM. Asymmetric Synthesis of Nonsubstituted and α,α-Disubstituted α-Amino Acids via Disatereoselective Glycine Enolate Alkylations. JACS. 1991;113:9276-9286.
Mustapa, et al. Synthesis of a cyclic peptide containing norlanthionine: effect of the thioether bridge on peptide conformation. J Org Chem. Oct. 17, 2003;68(21):8193-8.
Myriem, V. One pot iodination click reaction: A Convenient Preparation of 5-Iodo-1,4- disubstituted-1,2,3-triazole. Date unknown.
Nam et al., Structural basis for cooperativity in recruitment of MAML coactivators to Notch transcription complexes. Cell. Mar. 10, 2006;124(5):973-83.
Nelson & Kallenbach, "Persistence of the α-Helix Stop Signal in the S-Peptide in Trifluoroethanol Solutions," Biochemistry 28:5256-5261 (1989).
Ngo et al. Computational complexity, protein structure prediction and the Levinthal Paradox.ln: the Protein Folding Problem and Tertiary Structure Prediction. K.Merz, Jr. and S. LeGrand, eds., 1994, pp. 491-495.
Noah, et al. A cell-based luminescence assay is effective for high-throughput screening of potential influenza antivirals. Antiviral Res. Jan. 2007;73(1):50-9. Epub Jul. 28, 2006.
Notice of allowance dated Jan. 7, 2015 for U.S. Appl. No. 13/370,057.
Notice of allowance dated Jan. 27, 2014 for U.S. Appl. No. 12/233,555.
Notice of allowance dated Mar. 22, 2010 for U.S. Appl. No. 11/148,976.
Notice of allowance dated May 4, 2004 for U.S. Appl. No. 09/574,086.
Notice of allowance dated May 8, 2012 for U.S. Appl. No. 12/182,673.
Notice of allowance dated May 18, 2016 for U.S. Appl. No. 14/070,354.
Notice of allowance dated Jun. 1, 2016 for U.S. Appl. No. 14/070,354.
Notice of allowance dated Jul. 7, 2009 for U.S. Appl. No. 10/981,873.
Notice of allowance dated Jul. 19, 2016 for U.S. Appl. No. 14/068,844.
Notice of allowance dated Jul. 21, 2016 for U.S. Appl. No. 14/677,679.
Notice of allowance dated Jul. 28, 2014 for U.S. Appl. No. 13/680,905.
Notice of allowance dated Aug. 6, 2012 for U.S. Appl. No. 12/796,212.
Notice of allowance dated Oct. 23, 2015 for U.S. Appl. No. 13/252,751.
Wei, et al. tBID, a membrane-targeted death ligand, oligomerizes BAK to release cytochrome c. Genes Dev. Aug. 15, 2000;14(16):2060-71.
Obayashi, et al. The structural basis for an essential subunit interaction in influenza virus RNA polymerse. Nature. Aug. 28, 2008;454(7208):1127-31. Epub Jul. 27, 2008.
Office action dated Jan. 10, 2013 for U.S. Appl. No. 13/120,370.
Office action dated Jan. 26, 2009 for U.S. Appl. No. 11/148,976.
Office action dated Jan. 27, 2014 for U.S. Appl. No. 13/129,118.
Office Action dated Jan. 30, 2008 for U.S. Appl. No. 10/981,873.
Office action dated Feb. 4, 2014 for U.S. Appl. No. 13/370,057.
Office action dated Feb. 5, 2016 for U.S. Appl. No. 14/068,844.
Office action dated Feb. 6, 2014 for U.S. Appl. No. 13/680,905.
Office action dated Feb. 9, 2012 for U.S. Appl. No. 12/420,816.
Office action dated Feb. 17, 2011 for U.S. Appl. No. 12/796,212.
Office action dated Feb. 24, 2015 for U.S. Appl. No. 13/252,751.
Office action dated Mar. 18, 2013 for U.S. Appl. No. 13/097,930.
Office action dated Mar. 18, 2015 for U.S. Appl. No. 14/070,367.
Office action dated Mar. 22, 2013 for U.S. Appl. No. 12/233,555.
Office action dated Mar. 22, 2013 for U.S. Appl. No. 13/120,376.
Office action dated Mar. 26, 2015 for U.S. Appl. No. 14/070,354.
Office action dated Apr. 18, 2011 for U.S. Appl. No. 12/182,673.
Office action dated Apr. 26, 2012 for U.S. Appl. No. 13/097,930.
Office action dated Apr. 28, 2016 for U.S. Appl. No. 14/677,679.
Office action dated May 10, 2010 for U.S. Appl. No. 11/957,325.
Office action dated May 19, 2010 for U.S. Appl. No. 12/140,241.
Office action dated Jun. 18, 2015 for U.S. Appl. No. 14/068,844.
Office action dated Jun. 28, 2012 for U.S. Appl. No. 12/233,555.
Office action dated Jun. 28, 2013 for U.S. Appl. No. 13/370,057.
Office action dated Jul. 15, 2013 for U.S. Appl. No. 13/570,146.
Office action dated Jul. 21, 2014 for U.S. Appl. No. 13/370,057.
Office action dated Jul. 24, 2015 for U.S. Appl. No. 13/252,751.
Office action dated Jul. 30, 2013 for U.S. Appl. No. 13/097,930.
Office action dated Aug. 9, 2010 for U.S. Appl. No. 12/182,673.
Office action dated Aug. 10, 2009 for U.S. Appl. No. 11/957,325.
Office action dated Aug. 11, 2009 for U.S. Appl. No. 12/140,241.
Office action dated Aug. 19, 2010 for U.S. Appl. No. 12/037,041.
Office action dated Sep. 20, 2016 for U.S. Appl. No. 14/852,368.
Office action dated Sep. 23, 2013 for U.S. Appl. No. 13/680,905.
Office action dated Oct. 15, 2012 for U.S. Appl. No. 13/097,930.
Office action dated Oct. 18, 2011 for U.S. Appl. No. 12/796,212.
Office action dated Oct. 24, 2016 for U.S. Appl. No. 14/718,288.
Office action dated Oct. 31, 2014 for U.S. Appl. No. 13/370,057.
Office action dated Nov. 5, 2002 for U.S. Appl. No. 09/574,086.
Office action dated Nov. 8, 2012 for U.S. Appl. No. 13/120,386.
Office action dated Nov. 16, 2015 for U.S. Appl. No. 14/070,354.
Office action dated Nov. 25, 2009 for U.S. Appl. No. 11/148,976.
Office action dated Dec. 5, 2008 for U.S. Appl. No. 10/981,873.
Office action dated Dec. 7, 2015 for U.S. Appl. No. 14/677,679.
Office action dated Dec. 13, 2012 for U.S. Appl. No. 12/690,076.
Office action dated Dec. 19, 2014 for U.S. Appl. No. 14/068,844.

(56) References Cited

OTHER PUBLICATIONS

Office action dated Dec. 29, 2011 for U.S. Appl. No. 12/233,555.
O'Neil & DeGrado, "A Thermodynamic Scale for the Helix-forming Tendencies of the Commonly Occurring Amino Acids," Science 250:646-651(1990).
Or, et al. Cysteine alkylation in unprotected peptides: synthesis of a carbavasopressin analog by intramolecular cysteine alkylation. The Journal of Organic Chemistry. 1991;56(9):3146-3149.
Chang et al. Stapled α-helical peptide drug development: A potent dual inhibitor of MDM2 and MDMX for p53-dependent cancer therapy PNAS 2013 110 (36) E3445-E3454; published ahead of print Aug. 14, 2013, doi:10.1073/pnas.1303002110.
Williams, et al. A novel family of cyclic peptide antagonists suggests that N-cadherin specificity is determined by amino acids that flank the HAV motif. J Biol Chem. Feb. 11, 2000;275(6):4007-12.
Paquette, L.A., ed. Encyclopedia of Reagents for Organic Synthesis. New York; John Wiley & Sons; 1995.
Patgiri et al. An orthosteric inhibitor of the Ras-Sos interaction. Nat Chem Bio 7:585-587 (2011).
Pattenden, et al. Enantioselective synthesis of 2-alkyl substituted cysteines. 1993;49(10):2131-2138.
Pattenden, et al. Naturally occurring linear fused thiazoline-thiazole containing metabolites: total synthesis of (-)-didehydromirabazole A, a cytotoxic alkaloid from blue-green algae. J Chem Soc. 1993;14:1629-1636.
Peryshkov, et al. Z-Selective olefin metathesis reactions promoted by tungsten oxo alkylidene complexes. J Am Chem Soc. Dec. 28, 2011;133(51):20754-7. doi: 10.1021/ja210349m. Epub Nov. 30, 2011.
Phelan, et al. A General Method for Constraining Short Peptides to an α-Helical Conformation. J. Am. Chem. Soc. 1997;119:455-460.
Wu, et al. Studies on New Strategies for the Synthesis of Oligomeric 1,2,3-Triazoles. Synlett 2006(4): 0645-0647.
Punna, et al. Head-to-tail peptide cyclodimerization by copper-catalyzed azide-alkyne cycloaddition. Angew Chem Int Ed Engl. Apr. 8, 2005;44(15):2215-20.
Qiu et al., Convenient, Large-Scale Asymmetric Synthesis of Enantiomerically Pure trans-Cinnamylglycine and -a-Alanine. Tetrahedron. 2000;56:2577-82.
Rankin, et al. The role of hypoxia-inducible factors in tumorigenesis. Cell Death Differ. Apr. 2008;15(4):678-85.
Walensky, et al. Activation of apoptosis in vivo by a hydrocarbon-stapled BH3 helix. Science. Sep. 3, 2004;305(5689):1466-70.
Rasmussen, et al. Ruthenium-catalyzed cycloaddition of aryl azides and alkynes. Org Lett. Dec. 20, 2007;9(26):5337-9. Epub Dec. 1, 2007.
Rich et al., Synthesis of the cytostatic cyclic tetrapeptide, chlamydocin. Tetranderon Letts. 1983;24(48):5305-08.
Rink, et al. Lantibiotic Structures as Guidelines for the Design of Peptides That Can Be Modified by Lantibiotic Enzymes. Biochemistry. 2005; 44:8873-8882.
Robert, A hierarchical "nesting" approach to describe the stability of alpha helices with side-chain interactions. Biopolymers. 1990;30(3-4):335-47.
Roberts, et al. Efficient synthesis of thioether-based cyclic peptide libraries. Tetrahedon Letters. 1998; 39: 8357-8360.
Roberts, et al. Examination of methodology for the synthesis of cyclic thioether peptide libraries derived from linear tripeptides. J Pept Sci. Dec. 2007;13(12):811-21.
Roice, et al. High Capacity Poly(ethylene glycol) Based Amino Polymers for Peptide and Organic Synthesis. QSAR & Combinatorial Science. 2004;23(8):662-673.
Rojo, et al. Macrocyclic peptidomimetic inhibitors of β-secretase (BACE): First X-ray structure of a macrocyclic peptidomimetic-BACE complex. Bioorg. Med. Chem. Lett. 2006; 16:191-195.
Roof, et al. Mechanism of action and structural requirements of constrained peptide inhibitors of RGS proteins. Chem Biol Drug Des. Apr. 2006;67(4):266-74.

Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Ruan et al., "Metal Ion Enhanced Helicity in Synthetic Peptides Containing Unnatural, Metal-ligating Residues," J. Am. Chem. Soc. 112:9403-9404 (1990).
Rudinger J, "Characteristics of the amino acids as components of a peptide hormone sequence," Peptide Hormones, JA Parsons Edition, University Park Press, Jun. 1976, pp. 1-7.
Ruffolo and Shore. BCL-2 Selectively Interacts with the BID-Induced Open Conformer of BAK, Inhibiting BAK Auto-Oligomerization. J. Biol. Chem. 2003;278(27):25039-25045.
Rushe, et al. Structure of a NEMO/IKK-associating domain reveals architecture of the interaction site. Structure. May 2008;16(5):798-808.
Sali et al., Stabilization of protein structure by interaction of alpha-helix dipole with a charged side chain. Nature. Oct 20, 1988;335(6192):740-3.
Sanchez-Garcia, et al. Tumorigenic activity of the BCR-ABL oncogenes is mediated by BCL2. Proc Natl Acad Sci U S A. Jun. 6, 1995;92(12):5287-91.
Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).
Sattler et al. Structure of Bcl-xL-Back peptide complex: recognition between regulators of apoptosis. Science. 275:983-986 (1997).
Schafmeister et al. An all-hydrocarbon crosslinking system for enhancing the helicity and metabolic stability of peptides. J. Am Chem. Soc. 2000;122:5891-5892.
Scheffzek et al. The Ras-RasGAP complex: structural basis for GTPase activation and its loss in oncogenic Ras mutants. Science 277(5324):333-338 (1997).
Schinzel et al., The phosphate recognition site of Escherichia coli maltodextrin phosphorylase. FEBS Lett. Jul. 29, 1991;286(1-2):125-8.
Schmiedeberg et al. Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Scorrano, et al. A distinct pathway remodels mitochondrial cristae and mobilizes cytochrome c during apoptosis. Dev Cell. Jan. 2002;2(1):55-67.
Scott, et al. A Solid-Phase Synthetic Route to Unnatural Amino Acids with Diverse Side-Chain Substitutions. Journal of Organic Chemistry. 2002, vol. 67, No. 9, pp. 2960-2969.
Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.
Seebach, et al. Self-Regeneration of Stereocenters (SRS)—Applications, Limitations, and Abandonment of a Synthetic Principle. Angewandte Chemie International Edition in English. 1996;35(23-24):2708-2748.
Seebeck, et al. Ribosomal synthesis of dehydroalanine-containing peptides. J Am Chem Soc. Jun. 7, 2006;128(22):7150-1.
Shepherd et al., "Single Turn Peptide Alpha Helices with Exceptional Stability in Water," J. Am. Chem. Soc. 127:2974-2983 (2005).
Shi, et al. The role of arsenic-thiol interactions in metalloregulation of the ars operant. J Biol Chem. Apr. 19, 1996;271(16):9291-7.
Sia et al., "Short Constrained Peptides that Inhibit HIV-1 Entry," Proc. Nat'l Acad. Sci. USA 99(23):14664-14669 (2002).
Singh, et al. Efficient asymmetric synthesis of (S)- and (R)-N-Fmoc-S-trityl-alpha-methylcysteine using camphorsultam as a chiral auxiliary . . . J Org Chem. Jun. 25, 2004;69(13):4551-4.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S39.

(56) References Cited

OTHER PUBLICATIONS

Solution phase synthesis from http://www.combichemistry.com/solution_phase_synthesis.html. P.1. Accessed Aug. 6, 2009.
Spierings, et al. Connected to death: the (unexpurgated) mitochondrial pathway of apoptosis. Science. 2005; 310:66-67.
Stewart, et al. Cell-penetrating peptides as delivery vehicles for biology and medicine. Org Biomol Chem. Jul. 7, 2008;6(13):2242-55. doi: 10.1039/b719950c. Epub Apr. 15, 2008.
Sugiyama K, et al. Structural insight into the essential PB1-PB2 subunit contact of the influenza virus RNA polymerase. The EMBO Journal. 2009;28(12):1803-1811. doi:10.1038/emboj.2009.138.
Suzuki, et al. Structure of Bax: coregulation of dimer formation and intracellular localization. Cell. Nov. 10, 2000;103(4):645-54.
International Search Report with Opinion dated Dec. 12, 2016 for PCT/US16/40744.
Szewczuk et al., Synthesis and biological activity of new conformationally restricted analogues of pepstatin. (1992), Int. J. Peptide Protein Res. 40 :233-242.
Tam, et al. Protein prosthesis: 1,5-disubstituted[1,2,3]triazoles as cis-peptide bond surrogates. J Am Chem Soc. Oct. 24, 2007;129(42):12670-1.
Tanaka, Design and synthesis of non-proteinogenic amino acids and secondary structures of their peptides. Yakugaku Zasshi. Oct. 2006:126(10):931-44. Japanese.
Taylor. The synthesis and study of side-chain lactam-bridged peptides. Biopolymers. 2002;66(1):49-75.
Titus, et al. Human K/natural killer cells targeted with hetero-cross-linked antibodies specifically lyse tumor cells in vitro and prevent tumor growth in vivo. J Immunol. Nov. 1, 1987;139(9):3153-8.
Toniolo, Conformationally restricted peptides through short-range cyclizations. Int J Pept Protein Res. Apr. 1990;35(4):287-300.
Williams, et al. Dimeric versions of two short N-cadherin binding motifs (HAVDI and INPISG) function as N-cadherin agonists. J Biol Chem. Feb. 8, 2002;277(6):4361-7.
Tornoe, et al. Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Torres, et al. Peptide tertiary structure nucleation by side-chain crosslinking with metal complexation and double "click" cycloaddition. Chembiochem. Jul. 21, 2008;9(11):1701-5.
Trnka & Grubbs, "The Development of L2X2Ru=CHR Olefin Metathesis Catalysts: An Organometallic Success Story," Acc. Chem. Res. 34:18-29 (2001).
Tsuruzoe et al., Insulin receptor substrate 3 (IRS-3) and IRS-4 impair IRS-1- and IRS-2-mediated signaling. Mol Cell Biol. Jan. 2001;21(1):26-38.
Tugyi, et al. The effect of cyclization on the enzymatic degradation of herpes simplex virus glycoprotein D derived epitope peptide. J Pept Sci. Oct. 2005;11(10):642-9.
Tyndall et al. Macrocycles mimic the extended peptide conformation recognized by aspartic, serine, cysteine and metallo proteases. Curr Med Chem. Jul. 2001;8(8):893-907.
Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.
Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Vaickus et al., Immune markers in hematologic malignancies. Crit Rev Oncol Hematol. Dec. 1991; 11(4):267-97.
Van Maarseveen, et al. Efficient route to C2 symmetric heterocyclic backbone modified cyclic peptides. Org Lett. Sep. 29, 2005;7(20):4503-6.
Verdine et al., Stapled peptides for intracellular drug targets. Methods Enzymol. 2012;503:3-33. doi: 10.1016/B978-0-12-396962-0.00001-X.
Viallet, et al. Tallimustine is inactive in patients with previously treated small cell lung cancer. A phase II trial of the National Cancer Institute of Canada Clinical Trials Group. Lung Cancer. Nov. 1996;15(3):367-73.
Vila-Perello, et al. A minimalist design approach to antimicrobial agents based on a thionin template. J Med Chem. Jan. 26, 2006;49(2):448-51.
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4): 305-318.
Aman et al., cDNA cloning and characterization of the human interleukin 13 receptor alpha chain. J Biol Chem. Nov. 15, 1996;271(46):29265-70.
Andrews et al., Kinetic analysis of the interleukin-13 receptor complex. J Biol Chem. Nov. 29, 2002;277(48):46073-8. Epub Sep. 26, 2002.
Angel & Karin, "The Role of Jun, Fos and the AP-1 Complex in Cell-proliferation and Transformation," Biochim. Biophys. Acta 1072:129-157 (1991).
Arora, "Design, Synthesis, and Properties of the Hydrogen Bond Surrogate-based Artificial Alpha-helices," American Chemical Society Meeting, San Diego (Mar. 2005) (oral).
Arora, "Hydrogen Bond Surrogate Approach for the Synthesis of Short α-Helical Peptides," American Chemical Society Meeting, Philadelphia (Aug. 2004) (abstract of oral presentation).
Artavanis-Tsakonas et al., Notch signaling: cell fate control and signal integration in development. Science. Apr. 30, 1999;284(5415):770-6.
Attisano et al., TGFbeta and Wnt pathway cross-talk. Cancer Metastasis Rev. Jan.-Jun. 2004;23(1-2):53-61.
Babcock, Proteins, radicals, isotopes, and mutants in photosynthetic oxygen evolution. Proc Natl Acad Sci U S A. Dec. 1, 1993;90(23)10893-5.
Badyal, et al. A Simple Method for the Quantitative Analysis of Resin Bound Thiol Groups. Tetrahedron Lett. 2001; 42:8531-33.
Bagnasco, et al. Inhibition of a protein-protein interaction between INI1 and c-Myc by small peptidomimetic molecules inspired by Helix-1 of c-Myc: identification of a new target of potential antineoplastic interest. FASEB J. Apr. 2007;21(4):1256-63. Epub Jan. 10, 2007.
Banerjee et al., Structure of a DNA glycosylase searching for lesions. Science. Feb. 24, 2006 ;311(5764):1153-7.
Banerjee et al., Structure of a repair enzyme interrogating undamaged DNA elucidates recognition of damaged DNA. Nature. Mar. 31, 2005;434(7033):612-8.
Barker et al., Mining the Wnt pathway for cancer therapeutics. Nat Rev Drug Discov. Dec. 2006;5(12):997-1014.
Belokon et al., Improved procedures for the synthesis of (S)-21N-(N'-benzyl-prolypaminolbenzophenone (BPB) and Ni(II) complexes of Schiff's bases derived from BPB and amino acids. Tetrahedron: Asymmetry. 1998;9:4249-52.
Bennett, et al. Regulation of osteoblastogenesis and bone mass by Wnt1 Ob. Proc Natl Acad Sci U S A. Mar. 1, 2005;102(9):3324-9 . . . Epub Feb. 22, 2005.
Blundell et al., Atomic positions in rhombohedral 2-zinc insulin crystals. Nature. Jun. 25, 1971;231(5304):506-11.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al. High bone density due to a mutation in LDL-receptor-related protein 5. N Engl J Med 346(20):1513-1521 (2002).
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Bray, Notch signalling: a simple pathway becomes complex. Nat Rev Mol Cell Biol. Sep. 2006;7(9):678-89.
Brou et al., A novel proteolytic cleavage involved in Notch signaling: the role of the disintegrin-metalloprotease TACE. Mol Cell. Feb. 2000;5(2):207-16.

(56) References Cited

OTHER PUBLICATIONS

Brubaker et al., Solution structure of the interacting domains of the Mad-Sin3 complex: implications for recruitment of a chromatin-modifying complex. Cell. Nov. 10, 2000;103(4):655-65.
Brusselle et al., Allergen-induced airway inflammation and bronchial responsiveness in wild-type and interleukin-4-deficient mice. Am J Respir Cell Mol Biol. Mar. 1995;12(3):254.-9.
Burfield & Smithers, "Desiccant Efficiency in Solvent Drying. 3. Dipolar Aprotic Solvents," J. Org. Chem. 43(20):3966-3968 (1978).
Campbell, et al. N-alkylated oligoamide alpha-helical proteomimetics. Org Biomol Chem. May 21, 2010;8(10):2344-51. doi: 10.1039/c001164a. Epub Mar. 18, 2010.
Caricasole et al., The Wnt pathway, cell-cycle activation and beta-amyloid: novel therapeutic strategies in Alzheimer's disease? Trends Pharmacol Sci. May 2003;24(5):233-8.
Chakrabartty et al., "Helix Propensities of the Amino Acids Measured in Alanine-based Peptides without Helix-stabilizing Side-chain Interactions," Protein Sci. 3:843-852 (1994).
Chapman, et al. Trapping a folding intermediate of the alpha-helix: stabilization of the pi-helix. Biochemistry. Apr. 8, 2008;47(14):4189-95. doi: 10.1021/bi800136m. Epub Mar. 13, 2008.
Chen, et al. Determination of the Secondary Structures of Proteins by Circular Dichroism and Optical Rotatory Dispersion. Biochemistry. 1972; 11(22):4120-4131.
Chen et al., Small molecule-mediated disruption of Wnt-dependent signaling in tissue regeneration and cancer. Nat Chem Biol. Feb. 2009;5(2):100-7. Epub Jan. 4, 2009.
Chen et al., "Structure of the DNA-binding Domains from NFAT, Fos and Jun Bound Specifically to DNA," Nature 392:42-48 (1998).
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Chène et al., "Study of the Cytotoxic Effect of a Peptidic Inhibitor of the p53-hdm2 Interaction in Tumor Cells," FEBS Lett. 529:293-297 (2002).
Chène, P., "Inhibiting the p53-MDM2 Interaction: An Important Target for Cancer Therapy," Nat Rev. Cancer 3:102-109 (2003).
Christodoulides et al., WNT10B mutations in human obesity. Diabetologia. Apr. 2006;49(4):678-84. Epub Feb. 14, 2006.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Th1, cells. J Immunol. Oct. 15, 1998;161(8):3813-6.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Co-pending U.S. Appl. No. 15/349,478, filed Nov. 11, 2016.
Co-pending U.S. Appl. No. 15/463,826, filed Mar. 20, 2017.
Co-pending U.S. Appl. No. 15/493,301, filed Apr. 21, 2017.
Co-pending U.S. Appl. No. 15/592,517, filed May 11, 2017.
Co-pending U.S. Appl. No. 15/625,672, filed Jun. 16, 2017.
Cory et al., "The Bcl-2 Family: Roles in Cell Survival and Oncogenesis," Oncogene 22:8590-8607 (2003).
Cossu et al., Wnt signaling and the activation of myogenesis in mammals EMBO J. Dec. 15, 1999;18(24):6867-72.
Cummings, et al. Disrupting protein-protein interactions with non-peptidic, small molecule alpha-helix mimetics. Curr Opin Chem Biol. Jun. 2010;14(3):341-6. doi: 10.1016/j.cbpa.2010.04.001. Epub Apr. 27, 2010.
Dames, et al. Structural basis for Hif-1 alpha /CBP recognition in the cellular hypoxic response. Proc Natl Acad Sci U S A. Apr. 16, 2002;99(8):5271-6.
Danial et al., Dual role of proapoptotic BAD in insulin secretion and beta cell survival. Nat Med. Feb. 2008;14(2):144-53. doi: 10.1038/nm1717. Epub Jan. 27, 2008.
Daugherty & Gellman, "A Fluorescence Assay for Leucine Zipper Dimerization: Avoiding Unintended Consequences of Fluorophore Attachment," J. Am. Chem. Soc. 121:4325-4333 (1999).
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De La O et al., Notch and Kras reprogram pancreatic acinar cells to ductal intraepithelial neoplasia. Proc Natl Acad Sci U S A. Dec. 2, 2008;105(48):18907-12. doi: 10.1073/pnas.0810111105. Epub Nov. 21, 2008.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
De Strooper et al., A presenilin-1-dependent gamma-secretase-like protease mediates release of Notch intracellular domain. Nature. Apr. 8, 1999;398(6727):518-22.
Debinski et al., Retargeting interleukin 13 for radioimmunodetection and radioimmunotherapy of human high-grade gliomas. Clin Cancer Res. Oct. 1999;5(10 Suppl):3143s-3147s.
Del Bianco et al., Mutational and energetic studies of Notch 1 transcription complexes. J Mol Biol. Feb. 8, 2008;376(1):131-40. Epub Nov. 28, 2007.
Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Dimartino et al, "A General Approach for the Stabilization of Peptide Secondary Structures," American Chemical Society Meeting, New York (Sep. 2003) (poster).
Dombroski et al., Isolation of an active human transposable element. Science. Dec. 20, 1991;254(5039)1 805-8.
Doron, et al. Probiotics: their role in the treatment and prevention of disease. Expert Rev Anti Infect Ther. Apr. 2006;4(2):261-75.
Dovey et al., Functional gamma-secretase inhibitors reduce beta-amyloid peptide levels in brain. J Neurochem. Jan. 2001;76(1):173-81.
Draeger, et al. Interaction of the bHLH-zip domain of c-Myc with H1-type peptides. Characterization of helicity in the H1 peptides by NMR. J Biol Chem. Jan. 21, 1994;269(3):1785-93.
Eckert & Kim, "Mechanisms of Viral Membrane Fusion and Its Inhibition," Annu. Rev. Biochem. 70:777-810 (2001).
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the *Drosophila* notch gene, is broken by chromosomal translocations in T lymphoblastic neoplasms. Cell. Aug. 23, 1991;66(4):649-61.

(56) References Cited

OTHER PUBLICATIONS

Ellman. Tissue sulfhydryl groups. Arch Biochem Biophys. May, 1959;82(1):70-7.
Erlanson et al., The leucine zipper domain controls the orientation of AP-1 in the NFAT.AP-1.DNA complex. Chem Biol. Dec. 1996;3(12):981-91.
European search report and search opinion dated Mar. 22, 2017 for EP Application No. 16190185.5.
Evans et al., The Rise of Azide—Alkyne 1,3-Dipolar 'Click' Cycloaddition and its Application to Polymer Science and Surface Modification. Australian Journal of Chemistry. 2007;60:384-95.
Extended European Search Report for EP 09800675.2, dated Dec. 6, 2012.
Extended European Search Report for EP 10800148.8, dated Oct. 16, 2013.
Extended European Search Report for EP 12159110.1, dated Jul. 20, 2012.
Extended European Search Report (Replacement Copy) for EP 12159110 1, dated Sep. 27, 2012.
Favrin et al., Two-state folding over a weak free-energy barrier. Biophys J. Sep. 2003;85(3):1457-65.
File Hcaplus on STN. AN No. 1986:572318. Armstrong et al. X=Y-ZH systems as potential 1,3—dipoles. 5. Intramolecular imines of α-amino acid esthers. Tetrahedron. 1985; 41(17):3547-58. Abstract only. Abstract date Nov. 1986.
File Hcaplus on STN. AN No. 1979:168009. Greenlee et al. A general synthesis of alpha- vinyl-alpha-amino acids Tetrahedron Letters (1978), (42), 3999-4002. Abstract date 1984.
Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci U S A. Dec. 15, 1992;89(24):11779-83.
Friedmann et al., RAM-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fung et al., Delta-like 4 induces notch signaling in macrophages: implications for inflammation. Circulation. Jun. 12, 2007;115(23):2948-56. Epub May 28, 2007.
García-Echeverría et al., "Discovery of Potent Antagonists of the Interaction between Human Double Minute 2 and Tumor Suppressor p53," J. Med. Chem. 43:3205-3208 (2000).
Garg et al., Mutations in NOTCH1 cause aortic valve disease. Nature. Sep. 8, 2005;437(7056):270-4. Epub Jul. 17, 2005.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Geistlinger & Guy, "An Inhibitor of the Interaction of Thyroid Hormone Receptor β and Glucocorticoid Interacting Protein 1," J. Am. Chem. Soc. 123:1525-1526 (2001).
Gemperli et al., "Paralog-selective Ligands for Bcl-2 Proteins," J. Am. Chem. Soc. 127:1596-1597 (2005).
Gentle et al., Direct production of proteins with N-terminal cysteine for site-specific conjugation. Bioconjug Chem. May-Jun. 2004;15(3):658-63.

Gerber-Lemaire et al., Glycosylation pathways as drug targets for cancer: glycosidase inhibitors. Mini Rev Med Chem. Sep. 2006;6(9):1043-52.
Glover & Harrison, "Crystal Structure of the Heterodimeric bZIP Transcription Factor c-Fos-c-Jun Bound to DNA," Nature 373:257-261 (1995).
Gong et al. LDL receptor-related protein 5 (LRP5) affects bone accrual and eye development. Cell 107:513-523 (Nov. 16, 2001).
Gorlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Grandori, et al. The Myc/Max/Mad network and the transcriptional control of cell behavior. Annu Rev Cell Dev Biol. 2000;16:653-99.
Grossman, et al. Inhibition of oncogenic Wnt signaling through direct targeting of -catenin. Proc. Natl. Acad. Sco. 2012; 109(44):17942-179747.
Grunig et al., Requirement for IL-13 independently of IL-4 in experimental asthma. Science. Dec. 18, 1998;282(5397):2261-3.
Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285. 2010.00951.x.
Harper et al., Efficacy of a bivalent LI virus-like particle vaccine in prevention of infection with human papillomavirus types 16 and 18 in young women: a randomized controlled trial. Lancet. Nov. 13-19, 2004;364(9447):1757-65.
Harris et al., Synthesis of proline-modified analogues of the neuroprotective agent glycyl-l-prolyl-glutamic acid (GPE). Tetrahedron. 2005;61:10018-35.
Harrison, et al. Downsizing human, bacterial, and viral proteins to short water-stable alpha helices that maintain biological potency. Proc Natl Acad Sci U S A. Jun. 29, 2010;107(26):11686-91. doi: 10.1073/pnas.1002498107. Epub Jun. 11, 2010.
Hartmann, A Wnt canon orchestrating osteoblastogenesis. Trends Cell Biol. Mar. 2006;16(3):151-8. Epub Feb. 7, 2006.
Hartmann et al., Dual roles of Wnt signaling during chondrogenesis in the chicken limb. Development. Jul. 2000;127(14):3141-59.
Hellman et al., Electrophoretic mobility shift assay (EMSA) for detecting protein-nucleic acid interactions. Nat Protoc. 2007;2(8):1849-61.
Henchey et al., Contemporary strategies for the stabilization of peptides in the a-helical conformation. Curr Opin Chem Biol. 2008;12:692-97.
Henchey, et al. High specificity in protein recognition by hydrogen-bond-surrogate α-helices: selective inhibition of the p53/MDM2 complex. Chembiochem. Oct. 18, 2010;11(15):2104-7. doi: 10.1002/cbic.201000378.
Henchey, et al. Inhibition of Hypoxia Inducible Factor 1-Transcription Coactivator Interaction by a Hydrogen Bond Surrogate α-Helix. J Am Chem Soc. Jan. 27, 2010;132(3):941-3.
Hewitson, et al. The HIF pathway as a therapeutic target. Drug Discov Today. Aug. 15, 2004;9(16):704-11.
Hilton et al., Notch signaling maintains bone marrow mesenchymal progenitors by suppressing osteoblast differentiation. Nat Med. Mar. 2008;14(3):306-14. doi: 10.1038/nm1716. Epub Feb. 24, 2008.
Hipfner et al., Connecting proliferation and apoptosis in development and disease. Nat Rev Mol Cell Biol. Oct. 2004;5(10):805-15.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Holford et al., Adding 'splice' to protein engineering. Structure. Aug. 15, 1998;6(8):951-6.
Horiguchi, et al. Identification and characterization of the ER/lipid droplet-targeting sequence in 17beta-hydroxysteroid dehydrogenase type 11. Arch Biochem Biophys. Nov. 15, 2008;479(2):121-30. doi: 10.1016/j.abb.2008.08.020. Epub Sep. 10, 2008.
Horne, et al. Foldamers with heterogeneous backbones. Acc Chem Res. Oct. 2008;41(10):1399-408. doi: 10.1021/ar800009n. Epub Jul. 1, 2008.

(56) References Cited

OTHER PUBLICATIONS

Horne, et al. Structural and biological mimicry of protein surface recognition by alpha/beta-peptide foldamers. Proc Natl Acad Sci U S A. Sep. 1, 2009;106(35):14751-6. doi: 10.1073/pnas.0902663106. Epub Aug. 17, 2009.

Huang et al., How insulin binds: the B-chain alpha-helix contacts the LI beta-helix of the insulin receptor. J Mol Biol. Aug. 6, 2004;341(2):529-50.

Huang et al., Tankyrase inhibition stabilizes axin and antagonizes Wnt signalling. Nature. Oct. 1, 2009;461(7264):614-20. Epub Sep. 16, 2009.

International Preliminary Report on Patentability for PCT/US2008/058575 dated Oct. 8, 2009.

International Preliminary Report on Patentability for PCT/US2009/004260 dated Feb. 3, 2011.

International Preliminary Report on Patentability for PCT/US2010/001952 dated Jan. 26, 2012.

International Preliminary Report on Patentability for PCT/US2011/052755, dated Apr. 4, 2013.

International Preliminary Report on Patentability for PCT/US2012/042719, dated Jan. 3, 2014.

International Preliminary Report on Patentability for PCT/US2012/042738, dated Jan. 3, 2014.

International Search Report and Written Opinion for PCT/US2008/058575 dated Nov. 17, 2008.

International Search Report and Written Opinion for PCT/US2009/004260 dated Oct. 15, 2010.

International Search Report and Written Opinion for PCT/US2010/001952 dated Feb. 2, 2011.

International Search Report and Written Opinion for PCT/US2011/052755 dated Apr. 25, 2012.

International Search Report and Written Opinion for PCT/US2012/042719, dated Nov. 1, 2012.

International Search Report and Written Opinion for PCT/US2012/042738, dated Oct. 18, 2012.

International Search Report and Written Opinion for PCT/US2013/062004, dated Apr. 23, 2014.

International Search Report and Written Opinion for PCT/US2013/062929, dated Jan. 30, 2014.

International search report dated May 11, 2006 for PCT Application No. US2005/016894.

Invitation to Pay Additional Fees for PCT/US2009/004260 dated Mar. 19, 2010.

Invitation to Pay Additional Fees for PCT/US2010/001952 dated Oct. 29, 2010.

Invitation to Pay Additional Fees for PCT/US2011/052755 dated Feb. 16, 2012.

Invitation to Pay Additional Fees for PCT/US2013/062004, dated Jan. 2, 2014.

Jamieson et al., Granulocyte-macrophage progenitors as candidate leukemic stem cells in blast-crisis CML. N Engl J Med. Aug. 12, 2004;351(7):657-67.

Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.

Jimi, et al. Selective inhibition of NF-kappa B blocks osteoclastogenesis and prevents inflammatory bone destruction in vivo. Nat Med. Jun. 2004;10(6):617-24. Epub May 23, 2004.

Joerger, et al. Structural biology of the tumor suppressor p53. Annu Rev Biochem. 2008;77:557-82. doi: 10.1146/annurev.biochem.77.060806.091238.

Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.

Joutel et al., Notch3 mutations in CADASIL, a hereditary adult-onset condition causing stroke and dementia. Nature. Oct. 24, 1996;383(6602):707-10.

Junutula et al., Molecular characterization of Rab11 interactions with members of the family of Rab11-interacting proteins. J Biol Chem. Aug. 6, 2004;279(32):33430-7. Epub Jun. 1, 2004.

Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.

Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.

Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.

Kelly-Welch et al, Interleukin-4 and Interleukin-13 Signaling Connections Maps. Science. 2003;300:1527-28.

Kemp et al., "Studies of N-Terminal Templates for α-Helix Formation. Synthesis and Conformational Analysis of Peptide Conjugates of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6683-6697 (1991).

Khalil et al., An efficient and high yield method for the N-tert-butoxycarbonyl protection of sterically hindered amino acids. Tetrahedron Lett. 1996;37(20):3441-44.

Kiessling, et al. Selective inhibition of c-Myc/Max dimerization and DNA binding by small molecules. Chem Biol. Jul. 2006;13(7):745-51.

Kim et al., Stereochemical effects of all-hydrocarbon tethers in i,i+4 stapled peptides. Bioorg Med Chem Lett. May 1, 2009;19(9):2533-6. Epub Mar. 13, 2009.

Kimmerlin et al., '100 years of peptide synthesis': ligation methods for peptide and protein synthesis with applications to beta-peptide assemblies. J Pept Res. Feb. 2005;65(2):229-60.

Kinzler et al., Identification of FAP locus genes from chromosome 5q21. Science. Aug. 9, 1991;253(5020):661-5.

Knackmuss et al., Specific inhibition of interleukin-13 activity by a recombinant human single-chain immunoglobulin domain directed against the IL-13 receptor alpha1 chain. Biol Chem. Mar. 2007;388(3):325-30.

Kohler et al., DNA specificity enhanced by sequential binding of protein monomers. Proc Natl Acad Sci U S A. Oct. 12, 1999;96(21):11735-9.

Kolb et al., Click Chemistry: Diverse Chemical Function from a Few Good Reactions. Angew Chem Int Ed Engl. Jun. 1, 2001;40(11):2004-2021.

Kondo et al., Frizzled 4 gene (FZD4) mutations in patients with familial exudative vitreoretinopathy with variable expressivity. Br J Ophthalmol. Oct. 2003;87(10):1291-5.

Konishi et al Gamma-secretase inhibitor prevents Notch3 activation and reduces proliferation in human lung cancers. Cancer Res. Sep. 1, 2007;67(17):8051-7.

Korcsmaros et al., Uniformly curated signaling pathways reveal tissue-specific cross-talks and support drug target discovery. Bioinformatics. Aug. 15, 2010;26(16):2042-50. Epub Jun. 11, 2010.

Korinek et al. Depletion of epithelial stem-cell compartments in the small intestine of mice lacking Tcf-4. Nat Genet 19(4):379-383 (1998).

Kouzarides, Acetylation: a regulatory modification to rival phosphorylation? EMBO J. Mar. 15, 2000;19(6):1176-9.

Kovall et al., Crystal structure of the nuclear effector of Notch signaling, CSL, bound to DNA. EMBO J. Sep. 1, 2004;23(17):3441-51. Epub Aug. 5, 2004.

Kozlovsky et aL, GSK-3 and the neurodevelopmental hypothesis of schizophrenia. Eur Neuropsychopharmacol. Feb. 2002;12(1):13-25.

Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.

Kristensen et al., Functional reconstitution of insulin receptor binding site from non-binding receptor fragments. J Biol Chem. May 24, 2002;277(21):18340-5. Epub Mar. 18, 2002.

Kurose et al., Cross-linking of a B25 azidophenylalanine insulin derivative to the carboxyl-terminal region of the alpha-subunit of

(56) References Cited

OTHER PUBLICATIONS the insulin receptor. Identification of a new insulin-binding domain in the insulin receptor. J Biol Chem. Nov. 18, 1994;269(46):29190-7.

Kutchukian et al., All-atom model for stabilization of alpha-helical structure in peptides by hydrocarbon staples. J Am Chem Soc. Apr. 8, 2009;131(13):4622-7.

Lammi et al., Mutations in AXIN2 cause familial tooth agenesis and predispose to colorectal cancer. Am J Hum Genet. May 2004;74(5):1043-50. Epub Mar. 23, 2004.

Laporte et al., Molecular and structural basis of cytokine receptor pleiotropy in the interleukin-4/13 system. Cell. Jan. 25, 2008;132(2):259-72.

Le Guezennec et al., Molecular characterization of Sin3 PAH-domain interactor specificity and identification of PAH partners. Nucleic Acids Res. 2006;34(14):3929-37. Epub Aug. 12, 2006.

Le Guezennec et al., Molecular determinants of the interaction of Mad with the PAH2 domain of mSin3. J Biol Chem. Jun. 11, 2004;279(24):25823-9. Epub Mar. 26, 2004.

Lee, et al. Novel pyrrolopyrimidine-based α-helix mimetics: cell-permeable inhibitors of protein-protein interactions. J Am Chem Soc. Feb. 2, 2011;133(4):676-9. doi: 10.1021/ja108230s.

Letai, et al. Distinct BH3 Domains Either Sensitize or Activate Mitochondrial Apoptosis, Serving as Prototype Cancer Therapeutics. Cancer Cell. 2002; 2:183-192.

Lewis et al., Apoptosis in T cell acute lymphoblastic leukemia cells after cell cycle arrest induced by pharmacological inhibition of notch signaling. Chem Biol. Feb. 2007;14(2):209-19.

Li et al., Alagille syndrome is caused by mutations in human Jagged1, which encodes a ligand for Notch1. Nat Genet. Jul. 1997;16(3):243-51.

Li et al., Modulation of Notch signaling by antibodies specific for the extracellular negative regulatory region of NOTCH3. J Biol Chem. Mar. 21, 2008;283(12):8046-54. doi: 10.1074/jbc.M800170200. Epub Jan. 8, 2008.

Li et al., Notch3 signaling promotes the development of pulmonary arterial hypertension. Nat Med. Nov. 2009;15(11):1289-97. doi: 10.1038/nm.2021. Epub Oct. 25, 2009.

Liang et al., Wnt5a inhibits B cell proliferation and functions as a tumor suppressor in hematopoietic tissue. Cancer Cell. Nov. 2003;4(5):349-60.

Lifson & Roig, "On the Theory of Helix-coil Transition in Polypeptides," J. Chem. Phys. 34(6):1963-1974 (1961).

Little et aL, A Mutation in the LDL Receptor-Related Protein 5 Gene Results in the Autosomal Dominant High-Bone-Mass Trait. Am J Hum Genet. 2002;70:11-19.

Liu et al., Chemical Ligation Approach to Form a Peptide Bond between Unprotected Peptide Segments. Concept and Model Study. J Am Chem Soc. 1994;116(10):4149-53.

Liu et al., Targeted degradation of beta-catenin by chimeric F-box fusion proteins. Biochem Biophys Res Commun. Jan. 23, 2004;313(4)1023-9.

Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.

Logan et al., The Wnt signaling pathway in development and disease. Annu Rev Cell Dev Biol. 2004;20:781-810.

Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.

Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.

Loughlin et al., Functional variants within the secreted frizzled-related protein 3 gene are associated with hip osteoarthritis in females. Proc Natl Acad Sci U S A. Jun. 29, 2006;101(26):9757-62. Epub Jun. 21, 2004.

Lubman et al., Quantitative dissection of the Notch:CSL interaction: insights into the Notch-mediated transcriptional switch. J Mol Biol. Jan. 19, 2007;365(3):577-89. Epub Oct. 3, 2006.

Luo et al., Wnt signaling and human diseases: what are the therapeutic implications? Lab Invest. Feb. 2007;87(2):97-103. Epub Jan. 8, 2007.

Luscher et al., The basic region/helix-loop-helix/leucine zipper domain of Myc proto-oncoproteins: function and regulation. Oncogene. May 13, 1999;18(19):2955-66.

Luu et al, Wnt/beta-catenin signaling pathway as a novel cancer drug target. Curr Cancer Drug Targets. Dec. 2004;4(8):653-71.

MacMillan, Evolving strategies for protein synthesis converge on native chemical ligation. Angew Chem Int Ed Engl. Nov. 27, 2006;45(46):7668-72.

Maillard, et al. Mastermind critically regulates Notch-mediated lymphoid cell fate decisions. Blood. Sep. 15, 2004;104(6):1696-702. Epub Jun. 8, 2004.

Marqusee & Baldwin, "Helix Stabilization by Glu- . . . Lys+ Salt Bridges in Short Peptides of De Novo Design," Proc. Nat'l Acad. Sci. USA 84:8898-8902 (1987).

May, et al. Selective inhibition of NF-kappaB activation by a peptide that blocks the interaction of NEMO with the IkappaB kinase complex. Science. Sep. 1, 2000;289(5484):1550-4.

McKern et al., Structure of the insulin receptor ectodomain reveals a folded-over conformation. Nature. Sep. 14, 2006;443(7108):218-21. Epub Sep. 6, 2006.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.

Miller & Scanlan, "oNBS-SPPS: A New Method for Solid-phase Peptide Synthesis," J. Am. Chem. Soc. 120:2690-2691 (1998).

Miloux et al., Cloning of the human IL-13R alpha1 chain and reconstitution with the IL4R alpha of a functional IL-4/IL-13 receptor complex. FEBS Lett. Jan. 20, 1997;401(2-3):163-6.

Miyaoka et al., Increased expression of Wnt-1 in schizophrenic brains. Schizophr Res. Jul. 27, 1999;38(1):1-6.

Moellering et al., Direct inhibition of the NOTCH transcription factor complex. Nature. Nov. 12, 2009;462(7270):182-8. Erratum in: Nature. Jan. 21, 2010;463(7279):384.

Moon et al., WNT and beta-catenin signalling: diseases and therapies. Nat Rev Genet. Sep. 2004;5(9):689-701.

Morin, beta-catenin signaling and cancer. Bioessays. Dec. 1999;21(12):1021-30.

Moy et al., Solution structure of human IL-13 and implication for receptor binding. J Mol Biol. Jun. 29, 2001;310(1):219-30.

Mudher et al., Alzheimer's disease-do tauists and baptists finally shake hands? Trends Neurosci. Jan. 2002;25(1):22-6.

Muir et al., Expressed protein ligation: a general method for protein engineering. Proc Natl Acad Sci U S A. Jun. 9, 1998;95(12):6705-10.

Muller, P. Glossary of terms used in physical organic chemistry. Pure and Applied Chemistry, 1994, vol. 66, pp. 1077-1184.

Murray, et al. Targeting protein-protein interactions: lessons from p53/MDM2. Biopolymers. 2007;88(5):657-86.

Mynarcik et al., Alanine-scanning mutagenesis of a C-terminal ligand binding domain of the insulin receptor alpha subunit. J Biol Chem. Feb. 2, 1996;271(5):2439-42.

Mynarcik et al., Identification of common ligand binding determinants of the insulin and insulin-like growth factor 1 receptors. Insights into mechanisms of ligand binding. J Biol Chem. Jul. 25, 1997;272(30):18650-5.

Myung et al., The ubiquitin-proteasome pathway and proteasome inhibitors. Med Res Rev. Jul. 2001;21(4):245-73.

Nair et al., X-ray structures of Myc-Max and Mad-Max recognizing DNA. Molecular bases of regulation by proto-oncogenic transcription factors. Cell. Jan. 24, 2003;112(2):193-205.

(56) References Cited

OTHER PUBLICATIONS

Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Nam et al., Structural requirements for assembly of the CSL.intracellular Notch1.Mastermind-like 1 transcriptional activation complex. J Biol Chem. Jun. 6, 2003;278(23):21232-9. Epub Mar. 18, 2003.
Nefedova et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.
Ngo et al. Computational complexity, protein structure prediction, and the levinthal paradox. In: The Protein Folding Problem and Tertiary Structure Prediction. K. Merz, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Niranjan et al., The Notch pathway in podocytes plays a role in the development of glomerular disease. Nat Med. Mar. 2008;14(3):290-8. doi: 10.1038/nm1731. Epub Mar. 2, 2008.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Noguera-Troise et al., Blockade of Dll4 inhibits tumour growth by promoting non-productive angiogenesis. Nature. Dec. 21, 2006;444(7122):1032-7.
Notice of allowance dated Feb. 15, 2017 for U.S. Appl. No. 14/852,368.
Notice of allowance dated Mar. 2, 2017 for U.S. Appl. No. 14/852,368.
Notice of allowance dated Mar. 29, 2017 for U.S. Appl. No. 14/852,368.
Notice of Allowance dated Jul. 22, 2015 for U.S. Appl. No. No. 14/070,367.
Office action dated Mar. 18, 2009 for U.S. Appl. No. No. 11/678,836.
Office action dated Apr. 17, 2017 for U.S. Appl. No. No. 15/287,513.
Office action dated May 25, 2017 for U.S. Appl. No. 15/093,373.
Office action dated May 26, 2017 for U.S. Appl. No. 14/853,894.
Office action dated Jun. 14, 2013 for U.S. Appl. No. No. 12/478,504.
Office action dated Sep. 20, 2016 for U.S. Appl. No. No. 14/853,894.
O'Shea et al., "Mechanism of Specificity in the Fos-Jun Oncoprotein Heterodimer," Cell 68:699-708 (1992).
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
O'Neil et al., FBW7 mutations in leukemic cells mediate NOTCH pathway activation and resistance to gamma-secretase inhibitors. J Exp Med. Aug. 6, 2007;204(8):1813-24. Epub Jul. 23, 2007.
Oswald et al., RBP-Jkappa/Sharp recruits CtIP/CtBP corepressors to silence Notch target genes. Mol Cell Biol. Dec. 2005;25(23):10379-90.
Ou, et al. Review of the role of Dl4-Notch signaling parthway in angiogenesis. Basic Medical Sciences and Clinics. 2008; 28(1):98-105 (in Chinese with English abstract).
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palomero et al., Mutational loss of PTEN induces resistance to NOTCH1 inhibition in T-cell leukemia. Nat Med. Oct. 2007;13(10):1203-10. Epub Sep. 16, 2007.
Pangborn et al., "Safe and Convenient Procedure for Solvent Purification," Organometallics 15:1518-1520 (1996).
Park et al., Notch3 gene amplification in ovarian cancer. Cancer Res. Jun. 15, 2006;66(12):6312-8.
Patgiri, et al. A hydrogen bond surrogate approach for stabilization of short peptide sequences in alpha-helical conformation. Acc Chem Res. Oct. 2008;41(10):1289-300. Epub Jul. 17, 2008.
Patgiri, et al. Solid phase synthesis of hydrogen bond surrogate derived alpha-helices: resolving the case of a difficult amide coupling. Org Biomol Chem. Apr. 21, 2010 ;8(8):1773-6.
Pellois et al., Semisynthetic proteins in mechanistic studies: using chemistry to go where nature can't. Curr Opin Chem Biol. Oct. 2006;10(5):487-91. Epub Aug. 28, 2006.
Petros et al., "Rationale for Bcl-xL/Bad Peptide Complex Formation from Structure, Mutagenesis, and Biophysical Studies," Protein Sci. 9:2528-2534 (2000).
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2009.
Polakis, The oncogenic activation of beta-catenin. Curr Opin Genet Dev. Feb. 1999;9(1):15-21.
Qian & Schellman, "Helix-coil Theories: A Comparative Study for Finite Length Polypeptides," J. Phys. Chem. 96:3987-3994 (1992).
Rao et al., Inhibition of NOTCH signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.
Rawlinson et al., CRM1-mediated nuclear export of dengue virus RNA polymerase NS5 modulates interleukin-8 induction and virus production. J Biol Chem. Jun. 5, 2009rt;284(23):15589-97. Epub Mar. 18, 2009.
Reya et al., Wnt signalling in stem cells and cancer. Nature. Apr. 14, 2005;434(7035):843-50.
Riddoch, et al. A solid-phase labeling strategy for the preparation of technetium and rhenium bifunctional chelate complexes and associated peptide conjugates. Bioconjug Chem. Jan.-Feb. 2006;17(1):226-35.
Ridgway et al., Inhibition of Dll4 signalling inhibits tumour growth by deregulating angiogenesis. Nature. Dec. 21, 2006;444(7122):1083-7.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roehrl et al., "A General Framework for Development and Data Analysis of Competitive High-throughput Screens for Small-molecule Inhibitors of Protein-Protein Interactions by Fluorescence Polarization," Biochemistry 43:16056-16066 (2004).
Roehrl et al., "Discovery of Small-molecule Inhibitors of the NFAT-Calcineurin Interaction by Competitive High-throughput Fluorescence Polarization Screening," Biochemistry 43:16067-16075 (2004).
Roos et al., Synthesis of a-Substituted a-Amino Acids via Cationic Intermediates. J Org Chem. 1993;58:3259-68.
Ross et al. Inhibition of adipogenesis by Wnt signaling. Science 289:950-953 (2000).
Rutledge et al., "A View to a Kill: Ligands for Bcl-2 Family Proteins," Curr. Opin. Chem. Biol. 6:479-485 (2002).
Sadot et al., Down-regulation of beta-catenin by activated p53. Mol Cell Biol. Oct. 2001;21(20):6768-81.

(56) References Cited

OTHER PUBLICATIONS

Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Saxon et al., Cell surface engineering by a modified Staudinger reaction. Science. Mar. 17, 2000;287(5460):2007-10.
Schaffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schaffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Seabra et al., Rab GTPases, intracellular traffic and disease. Trends Mol Med. Jan. 2002;8(1):23-30.
Seebach, et al. Beta-peptidic peptidomimetics. Acc Chem Res. Oct. 2008;41(10):1366-75. doi: 10.1021/ar700263g. Epub Jun. 26, 2008.
Seebach, et al. Self-Regeneration of Stereocenters (SRS)—Applications, Limitations, and Abandonment of a Synthetic Principle. Angew. Chem. Int. Ed. Engl. 1996;35:2708-2748.
Seiffert et al., Presenilin-1 and -2 are molecular targets for gamma-secretase inhibitors. J Biol Chem. Nov. 3, 2000;275(44):34086-91.
Shair, A closer view of an oncoprotein-tumor suppressor interaction. Chem Biol. Nov. 1997;4(11):791-4.
Shangary, et al. Targeting the MDM2-p53 interaction for cancer therapy. Clin Cancer Res. Sep. 1, 2008;14(17):5318-24. doi: 10.1158/1078-0432.CCR-07-5136.
Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.
Si et aL, CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Siddle et al., Specificity in ligand binding and intracellular signalling by insulin and insulin-like growth factor receptors. Biochem Soc Trans. Aug. 2001;29(Pt 4):513-25.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Sparey et al., Cyclic sulfamide gamma-secretase inhibitors. Bioorg Med Chem Lett. Oct. 1, 2005;15(19):4212-6.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Still et al., "Rapid Chromatographic Technique for Preparative Separations with Moderate Resolution," J. Org. Chem. 43(14):2923-2925 (1978).
Still et al., Semianalytical Treatment of Solvation for Molecular Mechanics and Dynamics. J Am Chem Soc. 1990;112:6127-29.
Strickland, et al. Use of cell permeable NBD peptides for suppression of inflammation. Ann Rheum Dis. Nov. 2006;65 Suppl 3:iii75-82.
Strnad, et al. IkappaB kinase inhibitors for treating autoimmune and inflammatory disorders: potential and challenges. Trends Pharmacol Sci. Mar. 2007;28(3):142-8. Epub Feb. 6, 2007.
Struhl et al., Presenilin is required for activity and nuclear access of Notch in *Drosophila*. Nature. Apr. 8, 1999;398(6727):522-5.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Su et al., Eradication of pathogenic beta-catenin by Skpl/Cullin/F box ubiquitination machinery. Proc Natl Acad Sci U S A. Oct. 28, 2003;100(22):12729-34. Epub Oct. 16, 2003.
Sugiyama, et al. Structural insight into the essential PB1-PB2 subunit contact of the influenza virus RNA polymerase. EMBO J. Jun. 17, 2009;28(12):1803-11. Epub May 21, 2009.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Takeda et al. Human sebaceous tumors harbor inactivating mutations in LEF I . Nat Med. 12(4):395-397 (2006).
Thompson et al., Mutants of interleukin 13 with altered reactivity toward interleukin 13 receptors. J Biol Chem. Oct. 15, 1999;274(42):29944-50.
Tian et al., Linear non-competitive inhibition of solubilized human gamma-secretase by pepstatin a methylester, L685458, sulfonamides, and benzodiazepines. J Biol Chem. Aug. 30, 2002;277(35):31499-505. Epub Jun. 18, 2002.
Tian et al.; The role of the Wnt-signaling antagonist DKKI in the development of osteolytic lesions in multiple myeloma. N Engl J Med 349:2483-3494 (2003).
Tolbert et al., New methods for proteomic research: preparation of proteins with N-terminal cysteines for labeling and conjugation. Angew Chem Int Ed Engl. Jun. 17, 2002;41(12):2171-4.
Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.
Torrance et al., Combinatorial chemoprevention of intestinal neoplasia. Nat Med. Sep. 2000;6(9):1024-8.
Tsuji et al., Antiproliferative activity of REIC/Dkk-3 and its significant down-regulation in non-small-cell lung carcinomas. Biochem Biophys Res Commun. Nov. 23, 2001;289(1):257-63.
Turner et al., "Mitsunobu Glycosylation of Nitrobenzenesulfonamides: Novel Route to Amadori Rearrangement Products," Tetrahedron Lett. 40:7039-7042 (1999).
Tyndall, et al. Over one hundred peptide-activated G protein-coupled receptors recognize ligands with turn structure. Chem Rev. Mar. 2005;105(3):793-826.
Tyndall et al., "Proteases Universally Recognize Beta Strands in Their Active Sites," Chem. Rev. 105:973-999 (2005).
Uesugi et al., The alpha-helical FXXPhiPhi motif in p53: TAF interaction and discrimination by MDM2. Proc Natl Acad Sci U S A. Dec. 21, 1999;96(26):14801-6.
Ullman et al., Luminescent oxygen channeling immunoassay: measurement of particle binding kinetics by chemiluminescence. Proc Natl Acad Sci U S A. Jun. 7, 1994;91(12):5426-30.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Van Hoof, et al. Identification of cell surface proteins for antibody-based selection of human embryonic stem cell-derived cardiomyocytes. J Proteome Res. Mar. 5, 2010;9(3):1610-8. doi: 10.1021/pr901138a.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.

(56) References Cited

OTHER PUBLICATIONS

Vartak et al., Allosteric Modulation of the Dopamine Receptor by Conformationally Constrained Type VI (3-Turn Peptidomimetics of Pro-Leu-Gly-NH2. J Med Chem. 2007;50(26):6725-6729.

Vassilev, et al. In Vivo Activation of the p53 Pathway by Small-molecule Antagonists of MDM2. Science. 2004; 303:844-848.

Venancio et al., Reconstructing the ubiquitin network: cross-talk with other systems and identification of novel functions. Genome Biol. 2009;10(3):R33. Epub Mar. 30, 2009.

Verdine et al. The challenge of drugging undruggable targets in cancer: lessons learned from targeting BCL-2 family members. Clin Cancer Res. 13(24):7264-7270 (2007).

Verma et al., Small interfering RNAs directed against beta-catenin inhibit the in vitro and in vivo growth of colon cancer cells. Clin Cancer Res. Apr. 2003;9(4):1291-300.

Walensky, et al. A stapled BID BH3 helix directly binds and activates BAX. Mol. Cell. Oct. 20, 2006;24(2):199-210.

Walter et al., Critical role for IL-13 in the development of allergen-induced airway hyperreactivity. J Immunol. Oct. 15, 2001;167(8):4668-75.

Wang, 4-Alkyl-2-trichloromethyloxazolidin-5-ones: Valuable Precursors to Enantiomerically Pure C- and N-Protected a-Alkyl Prolines. Synlett. 1999;1:33-36.

Wang, et al. Inhibition of HIV-1 fusion 1-15 by hydrogen-bond-surrogate-based alpha helices. Angewandte Chemie International Edition. 2008; 47(10):1879-1882.

Wang et al., Inhibition of p53 degradation by Mdm2 acetylation. FEBS Lett. Mar. 12, 2004;561(1-3):195-201.

Wang et al., "Recognition of a Protein Receptor with the Hydrogen Bond Surrogate-based Artificial Alpha-helices," American Chemical Society Meeting, San Diego (Mar. 2005) (poster).

Wang et al., "Recognition of a Protein Receptor with the Hydrogen Bond Surrogate-based Artificial Alpha-helices," Chemical Biology Symposium, Hunter College (Jan. 2005) (poster).

Wei et al., Disorder and structure in the Rabll binding domain of Rabll family interacting protein 2. Biochemistry. Jan. 27, 2009;48(3):549-57. doi: 10.1021/bi8020197.

Weng et al., Activating mutations of NOTCH1 in human T cell acute lymphoblastic leukemia. Science. Oct. 8, 2004;306(5694):269-71.

Weng et al., Growth suppression of pre-T acute lymphoblastic leukemia cells by inhibition of notch signaling. Mol Cell Biol. Jan. 2003;23(2):655-64.

Westhoff et al., Alterations of the Notch pathway in lung cancer. Proc Natl Acad Sci U S A. Dec. 29, 2009;106(52):22293-8. doi: 10.1073/pnas.0907781106. Epub Dec. 10, 2009.

Wilen et al., Strategies in Optical Resolution. Tetrahedron. 1977;33:2725-36.

Williams et al., Asymmetric synthesis of 2,6-diamino-6-(hydroxymethyl)pimelic acid: assignment of stereochemistry. J Am Chem Soc. 1991;113(18):6976-6981.

Wills-Karp et al., Interleukin-13: central mediator of allergic asthma. Science. Dec. 18, 1998;282(5397):2258-61.

Wills-Karp, Interleukin-13 in asthma pathogenesis. Immunol Rev. Dec. 2004;202:175-90.

Wills-Karp, The gene encoding interleukin-13: a susceptibility locus for asthma and related traits. Respir Res. 2000;1(1):19-23. Epub Jul. 17, 2000.

Wilson et al., Crystal structure of the CSL-Notch-Mastermind ternary complex bound to DNA. Cell. Mar. 10, 2006;124(5):985-96.

Wilson et al., The FIP3-Rabll protein complex regulates recycling endosome targeting to the cleavage furrow during late cytokinesis. Mol Biol Cell. Feb. 2005;16(2):849-60. Epub Dec. 15, 2004.

Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.

Wu et al., MAML1, a human homologue of *Drosophila* mastermind, is a transcriptional co- activator for NOTCH receptors. Nat Genet. Dec. 2000;26(4):484-9.

Wu, et al. Modulation of Notch signaling by mastermind-like (MAML) transcriptional co-activators and their involvement in tumorigenesis. Semin Cancer Biol. Oct. 2004;14(5):348-56.

Wu et al., Therapeutic antibody targeting of individual Notch receptors. Nature. Apr. 15, 2010;464(7291):1052-7. doi: 10.1038/nature08878.

Xi et al., Use of DNA and peptide nucleic acid molecular beacons for detection and quantification of rRNA in solution and in whole cells. Appl Environ Microbiol. Sep. 2003;69(9):5673-8.

Xing, et al. Crystal structure of a beta-catenin/axin complex suggests a mechanism for the beta ¬ catenin destruction complex. Genes Dev. Nov. 15, 2003;17(22):2753-64. Epub Nov. 4, 2003.

Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.

Ye et al., Neurogenic phenotypes and altered Notch processing in *Drosophila presenilin* mutants. Nature. Apr. 8, 1999;398(6727):525-9.

Yin et al., "Terphenyl-based Helical Mimetics That Disrupt the p53/HDM2 Interaction," Angew. Chem. Int. Ed. 44:2704-2707 (2005).

Yu et al., The role of Axin2 in calvarial morphogenesis and craniosynostosis. Development. Apr. 2005; 132(8): 1995-2005.

Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.

Zhang, et al. Development of a High-throughput Fluorescence Polarization Assay for Bcl-xL. Anal. Biochem. 2002; 307:70-75.

Zhou, et al. Identification of ubiquitin target proteins using cell-based arrays. J Proteome Res. 2007; 6:4397-4406.

Zhou et al., Lymphoid enhancer factor 1 directs hair follicle patterning and epithelial cell fate. Genes Dev. Mar. 15, 1995;9(6):700-13.

Zhou et aL, Tyrosine kinase inhibitor STI-571/Gleevec down-regulates the beta-catenin signaling activity. Cancer Lett. Apr. 25, 2003;193(2):161-70.

Zimm & Bragg, "Theory of the Phase Transition between Helix and Random Coil in Polypeptide Chains," J. Chem. Phys. 31(2):526-535 (1959).

Zor et aL, Solution structure of the KIX domain of CBP bound to the transactivation domain of c-Myb. J Mol Biol. Mar. 26, 2004;337(3):521-34.

Balthaser et al., Remodelling ofthe natural product fumagillol employing a reaction discovery approach. Nat Chem. Dec. 2011;3(12):969-73.

Blangetti et al., Suzuki-miyaura cross-coupling in acylation reactions, scope and recent developments.Molecules. Jan. 17, 2013;18(1):1188-213.doi:10.3390/molecules18011188.

Co-pending U.S. Appl. No. 15/711,576, filed Sep. 21, 2017.

Co-pending U.S. Appl. No. 15/794,355, filed Oct. 26, 2017.

Friedman-Einat, et al. Target gene identification: target specific transcriptional activation by three murine homeodomain/VP16 hybrid proteins in *Saccharomyces cerevisiae*. J Exp Zool. Feb. 15, 1996;274(3):145-56.

Goudreau, et al. Potent inhibitors of the hepatitis C virus NS3 protease: design and synthesis of macrocyclic substrate-based β-strand mimics. The Journal of organic chemistry 69.19 (2004): 6185-6201.

International Preliminary Report on Patentability dated Apr. 14, 2016 for PCT/US2014/058680.

International Preliminary Report on Patentability dated Dec. 17, 2015 for PCT/US2014/41338.

International Preliminary Report on Patentability dated Dec. 23, 2015 for PCT/US2014/042329.

International Search Report and Written Opinion dated Nov. 10, 2014 for PCT/US2014/41338.

International Search Report and Written Opinion dated Nov. 24, 2014 for PCT/US2014/042329.

Kelekar, et al. Bcl-2-family proteins: the role of the BH3 domain in apoptosis. Trends Cell Biol. Aug. 1998;8(8):324-30.

(56) References Cited

OTHER PUBLICATIONS

Kinage, et al. Highly regio-selective synthesis of beta-amino alcohol by reaction with aniline and propylene carbonate in self solvent systems over large pore zeolite catalyst. Green and Sustainable Chem. Aug. 2011;1: 76-84.
Lindsay et al., Rab coupling protein (RCP), a novel Rab4 and Rab11 effector protein. J Biol Chem. Apr. 5, 2002;277(14):12190-9. Epub Jan. 10, 2002.
Lohmar et al. Synthese symmetrischerf ketone unter verwendung von 2-Phenyl-2-oxazolin-5-on. (α-Aminosäuren als nucleophile Acyláquivalente, IV.) Chemische Berichte. 1980;113(12): 3706-15.
Lu et al., Both Pbxl and E2A-Pbx1 bind the DNA motif ATCAATCAA cooperatively with the products of multiple murine Hox genes, some of which are themselves oncogenes. Mol Cell Biol. Jul. 1995;15(7):3786-95.
Lu et al., Structural determinants within Pbxl that mediate cooperative DNA binding with pentapeptide-containing Hox proteins: proposal for a model of a Pbxl-Hox-DNA complex. Mol Cell Biol. Apr. 1996;16(4):1632-40.
Mellegaard-Waetzig et al., Allylic amination via decarboxylative c—n bond formation Syn Jett. 2005;18:2759-2762.
Moses, et al. The growing applications of click chemistry. Chem Soc Rev. Aug. 2007;36(8):1249-62.
Narhi, et al. Role of native disulfide bonds in the structure and activity of insulin-like growth factor 1: genetic models of protein-folding intermediates. Biochemistry 32.19 (1993): 5214-5221.
Office action dated Jul. 17, 2017 for U.S. Appl. No. 14/853,894.
Office action dated Aug. 30, 2017 for U.S. Appl. No. 15/287,513.
Office action dated Sep. 5, 2017 for U.S. Appl. No. 15/093,869.
Office action dated Sep. 7, 2017 for U.S. Appl. No. 15/093,426.
Office action dated Nov. 15, 2017 for U.S. Appl. No. 15/240,505.
Palchaudhuriet al.,Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
Parrish et al., Perspectives on alkyl carbonates in organic synthesis. Tetrahedron, 2000; 56(42): 8207-8237.
Singhet al.,Iridium(I)-catalyzed regio- and enantioselective allylic amidation.Tet. Lett. 2007;48 (40): 7094-7098.
Thundimadathil, New Reactions with Click Chemistry. An R&D Magazine Webcast. Oct. 10, 2012. Available at http://www.rdmag.com/articles/2012/10/new-reactions-click-chemistry.
Tsuji et al., Synthesis of γ, δ-unsaturated ketones by the intramolecular decarboxylative allylation of allyl β-keto carboxylates and alkenyl allyl carbonates catalyzed by molybdenum, nickel, and rhodium complexes. Chemistry Letters. 1984; 13(10):1721-1724.
Weaver et al., Transition metal-catalyzed decarboxylative allylation and benzylation reactions.Chemical Rev. Mar. 9, 2011;111(3):1846-913.
Zhang, et al. A triazole-templated ring-closing metathesis for constructing novel fused and bridged triazoles. Chem Commun (Camb). Jun. 21, 2007;(23):2420-2.

* cited by examiner

PEPTIDOMIMETIC MACROCYCLES

CROSS REFERENCE

This application claims the benefit of U.S. Provisional Application No. 62/187,457, filed Jul. 1, 2015, U.S. Provisional Application No. 62/260,751, filed Nov. 30, 2015, and U.S. Provisional Application No. 62/311,112, filed Mar. 21, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 1, 2016, is named 35224-807_601_SL.txt and is 30,181 bytes in size.

BACKGROUND

Seasonal influenza infection is a major health concern for first-world and developing nations alike. Each year in the United States, five- to twenty-percent of the population gets the flu, more than 200,000 people are hospitalized from flu complications, and about 36,000 people die from flu. Worldwide, influenza causes tens of millions of respiratory illnesses and 250,000 to 500,000 deaths each year. New strains of avian influenza that are transmissible to humans are a critical concern for global health because these flu strains could yield pandemic disease for which no immunity exists, potentially resulting in millions of fatalities. "Avian flu" refers to a pathogenic avian influenza subtype that is highly contagious among birds and causes high mortality among domestic poultry. Outbreaks of avian flu among poultry and wild birds are ongoing in a number of countries, and at least three subgroups of avian flu viruses have infected humans to date. While avian flu infections of humans are rare, and most cases have been associated with direct poultry contact during outbreaks among livestock, infection in humans is very serious when it does occur: to date, over half of all reported human cases have been fatal. Since first reported in Hong Kong in 1996, the World Health Organization has carefully tracked avian flu and instances of animal-to-human influenza transmission, with confirmed cases reported from China, Indonesia, and Southeast Asia; Pakistan; Iraq; Egypt; and elsewhere, with 385 cases resulting in 243 deaths worldwide. While there is no evidence of sustained human-to-human transmission, instances of human-to-human spread of avian flu may have occurred. Since all influenza viruses have the ability to rapidly mutate, there is considerable concern that avian flu may be able to infect humans more easily and become communicable from one person to another. Also, avian flu virus strains have not infected many humans worldwide, so there is little or no immune protection against these strains in the human population; therefore, an influenza pandemic could easily occur if sustained avian flu virus transmission were to develop.

SUMMARY

In one aspect, provided herein is a peptidomimetic macrocycle or a pharmaceutically-acceptable salt thereof comprising two non-natural amino acids connected by a macrocycle-forming linker and an amino acid sequence with at least about 60%, 65%, 70%, 75%, 80%, 85%, 90%, 95%, 96%, 97%, 98%, 99% or 100% sequence identity to a sequence of Table 1b.

In some embodiments, the macrocycle-forming linker connects amino acids 5 and 9. In some embodiments, the first macrocycle-forming linker connects amino acids 5 and 12.

In one aspect, provided herein is a peptidomimetic macrocycle comprising an amino acid sequence with at least about 60%, 65%, 70%, 75%, 80%, 85%, 90%, 95%, 96%, 97%, 98%, 99% or 100% sequence identity to a sequence of Table 1b and having Formula (I):

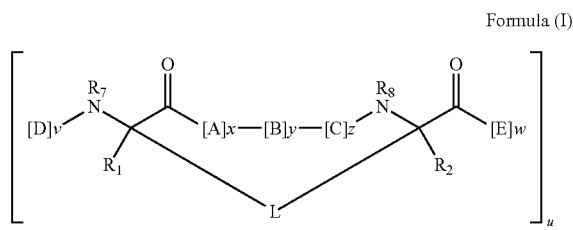

Formula (I)

or a pharmaceutically-acceptable salt thereof, wherein:
each A, C, D, and E is independently an amino acid;
each B is independently an amino acid,

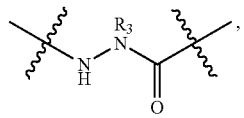

[—NH-$L_3$-CO—], [—NH-$L_3$-$SO_2$—], or [—NH-$L_3$-];
each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-; or at least one of $R_1$ and $R_2$ forms a macrocycle-forming linker L' connected to the α position of one of said D or E amino acids;
each $R_3$ is independently —H, alkyl, alkenyl, alkynyl, arylalkyl, heteroalkyl, cycloalkyl, heterocycloalkyl, cycloalkylalkyl, aryl, or heteroaryl, optionally substituted with $R_5$;
each L and L' is independently a macrocycle-forming linker;
each $L_3$ is independently alkylene, alkenylene, alkynylene, heteroalkylene, cycloalkylene, heterocycloalkylene, arylene, heteroarylene, or [—$R_4$—K—$R_4$—]$_n$, each being optionally substituted with $R_5$;
each $R_4$ is independently alkylene, alkenylene, alkynylene, heteroalkylene, cycloalkylene, heterocycloalkylene, arylene, or heteroarylene;
each K is independently O, S, SO, $SO_2$, CO, $CO_2$ or $CONR_3$,
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with an E residue;

each v and w is independently an integer from 0-1000, for example 0-500, 0-200, 0-100, 0-50, 0-30, 0-20, or 0-10;
u is an integer from 1-10, for example 1-5, 1-3 or 1-2;
each x, y and z is independently an integer from 0-10, for example the sum of x+y+z is 2, 3, 5, 6 or 10; and
each n is independently an integer from 1-5.

In some embodiments, the macrocycle-forming linker connects amino acids 5 and 9. In some embodiments, the macrocycle-forming linker connects amino acids 5 and 12.

In some embodiments, wherein the sum of x+y+z is 2, 3, 5 or 6. In some embodiments, the sum of x+y+z is 3 or 6. In some embodiments, x+y+z=2. In some embodiments, x+y+z=3. In some embodiments, wherein x+y+z=5. In some embodiments, x+y+z=6.

In one aspect, provided herein is peptidomimetic macrocycle having Formula (Ia):

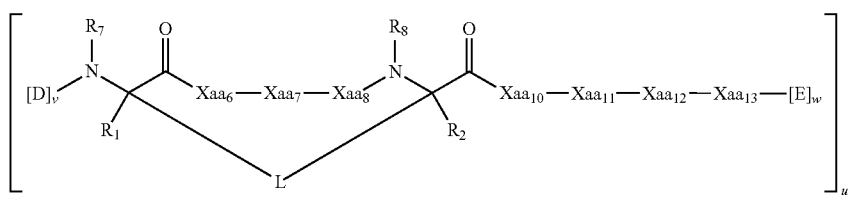

Formula (Ia)

or a pharmaceutically-acceptable salt thereof wherein:

each of $Xaa_6$, $Xaa_7$, $Xaa_8$, $Xaa_{10}$, $Xaa_{11}$, $Xaa_{12}$, and $Xaa_{13}$ is independently an amino acid, wherein at least three, four, five, or each of $Xaa_6$, $Xaa_7$, $Xaa_8$, $Xaa_{10}$, $Xaa_{11}$, and $Xaa_{12}$, are the same amino acid as the amino acid at the corresponding position of the sequence $X_5$-$Thr_6$-$Leu_7$-$Leu_8$-$X_9$-$Leu_{10}$-$Lys_{11}$/$Ala_{11}$-$Val_{12}$/$Ala_{12}$, where each of $X_5$ and $X_9$ is independently an amino acid (SEQ ID NO: 1);

each D and E is independently an amino acid;

each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-; or forms a macrocycle-forming linker L' connected to the α position of one of said D or E amino acids;

each L and L' is independently a macrocycle-forming linker;

each $R_3$ is independently —H, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

each v is independently is an integer from 1-1000;
each w is independently an integer from 1-1000; and
u is an integer from 1-100.

In some embodiments, the peptidomimetic macrocycle of Formula (Ia) is:

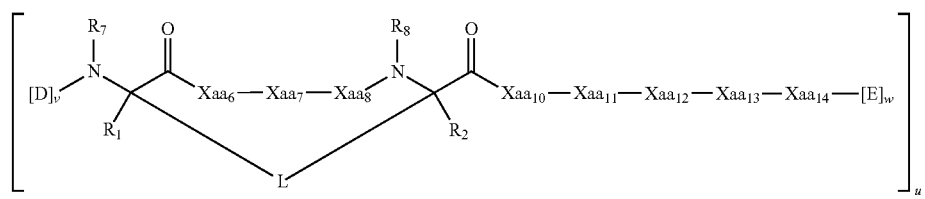

or a pharmaceutically-acceptable salt thereof, wherein each $Xaa_{14}$ is independently an amino acid.

In some embodiments, the peptidomimetic macrocycle of Formula (Ia) is:

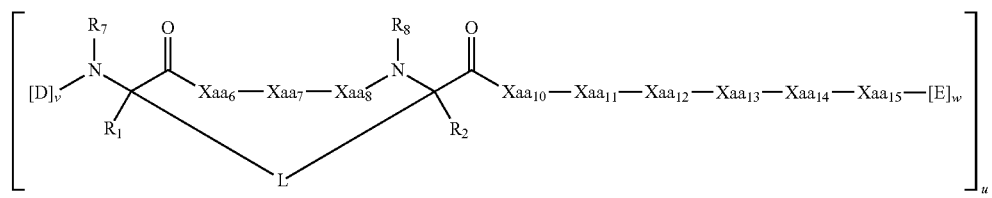

or a pharmaceutically-acceptable salt thereof, wherein each Xaa$_{14}$ and Xaa$_{15}$ is independently an amino acid.

In one aspect, provided herein is a peptidomimetic macrocycle having Formula (Ib):

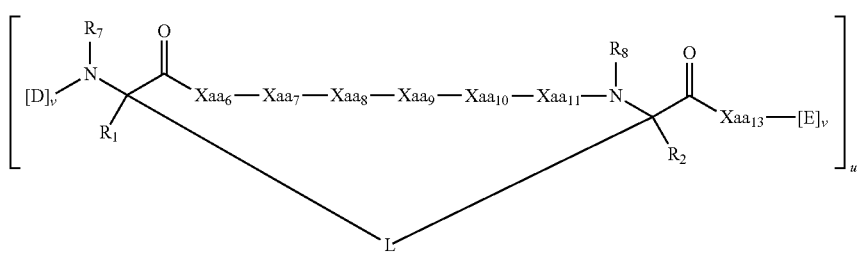

Formula (Ib)

or a pharmaceutically-acceptable salt thereof, wherein:
each of Xaa$_6$, Xaa$_7$, Xaa$_8$, Xaa$_9$, Xaa$_{10}$, Xaa$_{11}$ and Xaa$_{13}$ is independently an amino acid, wherein at least three, four, five, or each of Xaa$_6$, Xaa$_7$, Xaa$_8$, Xaa$_9$, Xaa$_{10}$, and Xaa$_{11}$ are the same amino acid as the amino acid at the corresponding position of the sequence X$_5$-Thr$_6$-Leu$_7$-Leu$_8$-Phe$_9$-Leu$_{10}$-Lys$_{11}$/Ala$_{11}$-X$_{12}$, where each of X$_5$ and X$_{12}$ is independently an amino acid (SEQ ID NO: 2);
each D and E is independently an amino acid;
each R$_1$ and R$_2$ is independently —H, alkyl, alkenyl, alkynyl, arylalkyl, cycloalkyl, cycloalkylalkyl, heteroalkyl, or heterocycloalkyl, unsubstituted or substituted with halo-; or forms a macrocycle-forming linker L' connected to the α position of one of said D or E amino acids;
each L and L' is independently a macrocycle-forming linker;

each R$_3$ is independently —H, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

each R$_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;

each R$_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;

each v is independently is an integer from 1-1000;

each w is independently an integer from 1-1000; and u is an integer from 1-100.

In some embodiments, the peptidomimetic macrocycle of Formula (Ib) is:

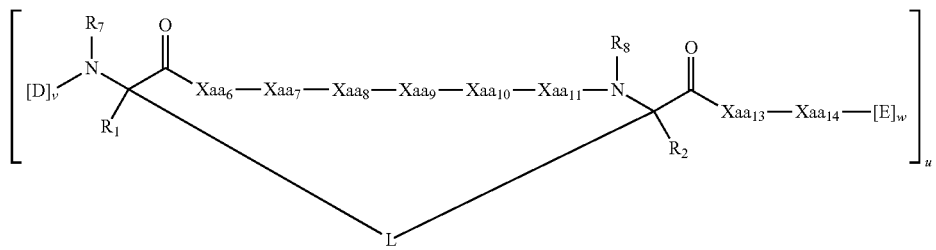

or a pharmaceutically-acceptable salt thereof, wherein each Xaa$_{14}$ is independently an amino acid.

In some embodiments, the peptidomimetic macrocycle of Formula (Ib) is:

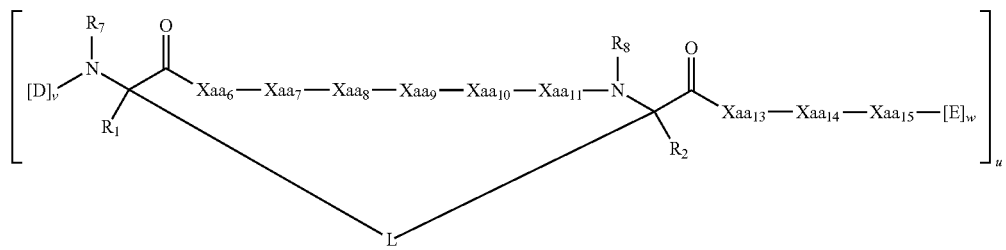

or a pharmaceutically-acceptable salt thereof, wherein each Xaa$_{14}$ and Xaa$_{15}$ is independently an amino acid.

In some embodiments, each L and L' is independently a macrocycle-forming linker of the formula -L$_1$-L$_2$-,

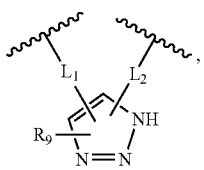

or -L$_1$-S-L$_2$-S-L$_3$-;
each L$_1$, L$_2$ and L$_3$ is independently alkylene, alkenylene, alkynylene, heteroalkylene, cycloalkylene, heterocycloalkylene, arylene, heteroarylene, or [—R$_4$—K—R$_4$-]$_n$, each being optionally substituted with R$_5$; when L is not

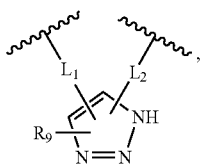

or -L$_1$-S-L$_2$-S-L$_3$-, L$_1$ and L$_2$ are alkylene, alkenylene, alkynylene, heteroalkylene, cycloalkylene, heterocycloalkylene, arylene, or heteroarylene;
each R$_4$ is independently alkylene, alkenylene, alkynylene, heteroalkylene, cycloalkylene, heterocycloalkylene, arylene, or heteroarylene;
each K is independently O, S, SO, SO$_2$, CO, CO$_2$ or CONR$_3$,
each R$_9$ is independently alkyl, alkenyl, alkynyl, aryl, cycloalkyl, cycloalkenyl, heteroaryl, or heterocyclyl group, unsubstituted or optionally substituted with R$_a$ and/or R$_b$;
each R$_a$ and R$_b$ is independently alkyl, OCH$_3$, CF$_3$, NH$_2$, CH$_2$NH$_2$, F, Br, I,

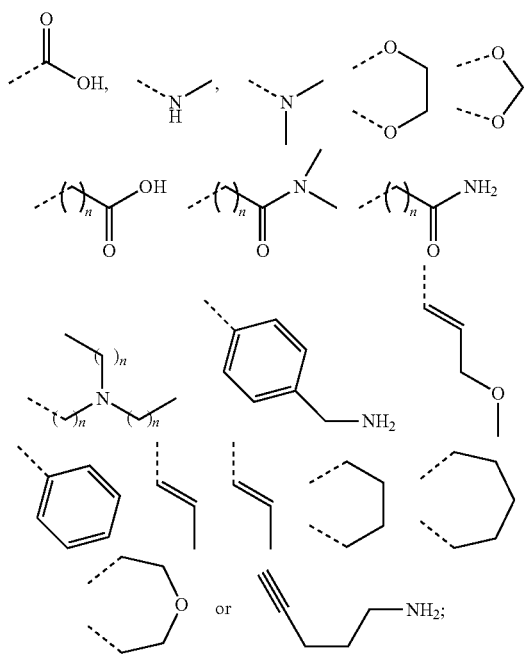

and
each n is independently an integer from 1-5.
In some embodiments, u is 1.
In some embodiments, the peptidomimetic macrocycle comprises an amino acid sequence which is at least about 60%, 65%, 70%, 75%, 80%, 85%, 90%, 95%, 96%, 97%, 98%, or 99% identical to an amino acid sequence of Table 1b.

In some embodiments, each v is independently an integer from 0-200. In some embodiments, each of v is independently an integer from 0-100. In some embodiments, each v is independently an integer from 0-10, 0-15, 0-20, 0-25, or 0-30. In some embodiments, each v is 4.

In some embodiments, [D]$_v$ is -Asn$_4$-Val$_3$-Glu$_2$-[Nle$_1$/Phe$_1$] (SEQ ID NO: 3). In some embodiments, [D]$_v$ is -Asn$_4$-Val$_3$-Glu$_2$-Nle$_1$ (SEQ ID NO: 4). In some embodiments, [D]$_v$ is -Asn$_4$-Val$_3$-Glu$_2$-Phe$_1$ (SEQ ID NO: 5).

In some embodiments, each w is independently an integer from 0-200. In some embodiments, each w is independently an integer from 0-10, 0-15, 0-20, 0-25, or 0-30. In some embodiments, each w is 3-8. In some embodiments, w is 1-3. In some embodiments, each w is 6-8. In some embodiments, each w is 3-6. In some embodiments, each w is 2-4. In some embodiments, each w is 3-5. In some embodiments, each w is 1. In some embodiments, each w is 2. In some embodiments, each w is 3. In some embodiments, each w is 4. In some embodiments, each w is 5. In some embodiments, each w is 6. In some embodiments, each w is 8.

In some embodiments, each of the first two amino acids represented by E comprises an uncharged side chain or a negatively charged side chain. In some embodiments, each of the first three amino acids represented by E comprises an uncharged side chain or a negatively charged side chain. In some embodiments, each of the first four amino acids represented by E comprises an uncharged side chain or a negatively charged side chain. In some embodiments, the first C-terminal amino acid and/or the second C-terminal amino acid represented by E comprise a hydrophobic side chain.

In some embodiments, the first C-terminal amino acid, the second C-terminal amino acid, and/or the third C-terminal amino acid represented by E comprise a hydrophobic side chain.

In some embodiments, the first amino acid represented by E comprises a hydrophobic side chain. In some embodiments, the second amino acid represented by E comprises a hydrophobic side chain. In some embodiments, the third amino acid represented by E comprises a hydrophobic side chain. In some embodiments, the fourth amino acid represented by E comprises a hydrophobic side chain. In some embodiments, the hydrophobic side chain is a small hydrophobic side chain.

In some embodiments, each E is independently an amino acid selected from the group consisting of Ala, D-Ala, Aib, Lys, Leu, Ser, Glu, and Gln. In some embodiments, each E is independently an amino acid selected from the group consisting of Ala, D-Ala, Aib, and Gln. In some embodiments, each E is independently an amino acid selected from the group consisting of Ala, D-Ala, and Aib, and Gln. In some embodiments, each E is independently an amino acid selected from the group consisting of Ala, D-Ala, and Aib. In some embodiments, each E is independently an amino acid selected from the group consisting of Ala, Aib, and Gln. In some embodiments, each E is independently an amino acid selected from the group consisting of Ala, Aib, and Gln. In some embodiments, each E is independently an amino acid selected from the group consisting of Ala and Aib.

In some embodiments, L$_1$ and L$_2$ are independently alkylene, alkenylene, alkynylene, heteroalkylene, cycloalkylene, heterocycloalkylene, cycloarylene, or heterocycloarylene, each being optionally substituted with R$_5$. In some embodiments, L$_1$ and L$_2$ are independently alkylene, alkenylene or alkynylene. In some embodiments, $L_1$ and $L_2$ are independently alkylene or alkenylene. In some embodiments, $L_1$ and $L_2$ are independently $C_3$-$C_{10}$ alkylene or alkenylene. In some embodiments, $L_1$ and $L_2$ are independently $C_3$-$C_6$ alkylene or alkenylene.

In some embodiments, L is alkylene, alkenylene, or alkynylene. In some embodiments, L is alkylene. In some embodiments, L is $C_3$-$C_{16}$ alkylene. In some embodiments, L is $C_{10}$-$C_{14}$ alkylene.

In some embodiments, $R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo. In some embodiments, $R_1$ and $R_2$ are H. In some embodiments, $R_1$ and $R_2$ are independently alkyl. In some embodiments, $R_1$ and $R_2$ are methyl.

In some embodiments, L is

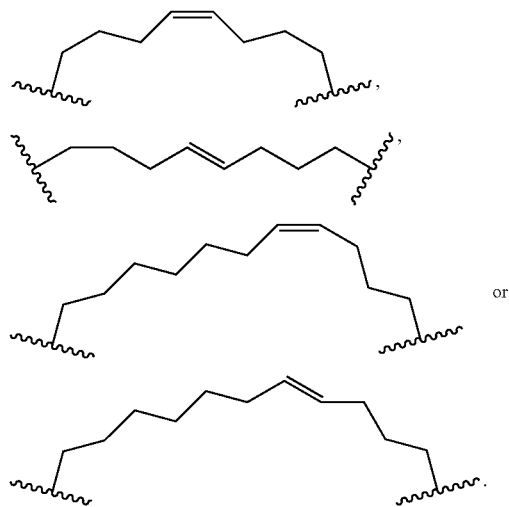

In some embodiments, L is

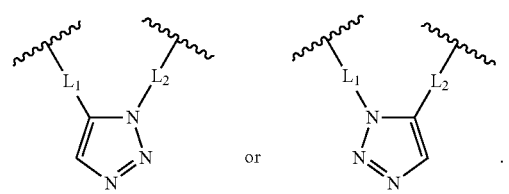

In some embodiments, L is

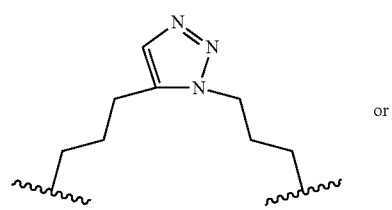

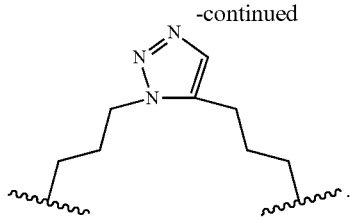

In one aspect, provided herein is peptidomimetic macrocycle comprising an amino acid sequence of formula:

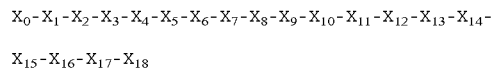

wherein:
$X_0$ is —H or an N-terminal capping group;
$X_{18}$ is —OH, or a C-terminal capping group;
$X_{16}$ and $X_{17}$ are absent or are amino acids; wherein the peptidomimetic macrocycle comprises a macrocycle-forming linker that connects a pair of crosslinked amino acids selected from the group consisting of amino acids $X_5$ and $X_9$, and $X_5$ and $X_{12}$, and wherein $X_1$-$X_{17}$ together with the crosslinked amino acids, form an amino acid sequence with at least about 60%, 65%, 70%, 75%, 80%, 85%, 90%, 95%, 96%, 97%, 98%, 99% or 100% sequence identity to a sequence of Table 1b.

In some embodiments, $X_0$ is —H or an N-terminal capping group, for example acetyl or 5-FAM linked to the N-terminus of residue $X_1$; $X_1$ is Nle or Phe; $X_2$ is Asp; $X_3$ is Val; $X_4$ is Asn; $X_6$ is Thr; $X_7$ is Leu; $X_8$ is Leu; $X_9$ is Phe or a crosslinked amino acid; $X_{10}$ is Leu; $X_{11}$ Lys or Ala; $X_{12}$ is Ala, Val, or a crosslinked amino acid; $X_{13}$ is Aib, Ser, Ala, Glu, Gln, or Pro; $X_{14}$ is Aib or Ala; $X_{15}$ is Gln, Aib or Ala; $X_{16}$ is absent or Aib or Ala; $X_{17}$ is absent or D-Ala or Ala; $X_{18}$ is —OH, or a C-terminal capping group, for example a primary, secondary, or tertiary amino group, an alkyloxy or an aryloxy group, or any combination thereof.

In some embodiments, $Xaa_1$ is Phe. In some embodiments, $Xaa_{16}$ is Ala. In some embodiments, $Xaa_{17}$ is Ala. In some embodiments, $Xaa_{15}$ is Ala. In some embodiments, $Xaa_{13}$ is Ser, Gln, Glu, or Ala. In some embodiments, $Xaa_{12}$ is Ala. In some embodiments, $Xaa_{11}$ is Ala. In some embodiments, $Xaa_9$ is Phe In some embodiments, $X_{16}$ and $X_{17}$ are absent. In some embodiments, $X_{16}$ is Ala or Aib. In some embodiments, $X_{17}$ is Ala or D-Ala.

In some embodiments, the macrocycle-forming linker connects amino acids $X_5$ and $X_9$. In some embodiments, the macrocycle-forming linker connects amino acids $X_5$ and $X_{12}$. In some embodiments, the peptidomimetic macrocycle comprises an α-helix. In some embodiments, the peptidomimetic macrocycle comprises an α,α-disubstituted amino acid. In some embodiments, each amino acid connected by the macrocycle-forming linker is an α,α-disubstituted amino acid.

In some embodiments, the macrocycle-forming linker is a straight chain alkenyl. In some embodiments, the macrocycle-forming linker is a straight chain alkenyl with 6 to 14 carbon atoms. In some embodiments, the at least one macrocycle-forming linker is a straight chain alkenyl with 8 to 12 carbon atoms, for example 8, 9, 10, 11 or 12 carbon atoms In some embodiments, the peptidomimetic macrocycle is capable of binding to a viral polymerase. In some embodiments, the polymerase is a RNA-dependent RNA polymerase.

In some embodiments, the macrocycle is capable of disrupting the assembly of subunits of a viral RNA-dependent RNA polymerase complex. In some embodiments, the virus is influenza virus.

In some embodiments, the peptidomimetic macrocycle is capable of competing with the binding of a peptide of the sequence MDVNPTLLFLKVPAQ (SEQ ID NO: 6) or MERIKELRNLM (SEQ ID NO: 7) to the viral RNA-dependent RNA polymerase.

In one aspect, provided herein is a method of treating influenza infection in a subject comprising administering to the subject a peptidomimetic macrocycle disclosed herein.

In one aspect, provided herein is a method of preventing influenza infection in a subject comprising administering to the subject a peptidomimetic macrocycle disclosed herein.

In one aspect, provided herein is a method of inhibiting the activity of the RNA-dependent RNA polymerase of an influenza virus in a subject comprising administering to the subject a peptidomimetic macrocycle disclosed herein.

In one aspect, provided herein is a pharmaceutical composition comprising a peptidomimetic macrocycle disclosed herein, and a pharmaceutically acceptable excipient.

In one aspect, provided herein is a peptidomimetic macrocycle or pharmaceutical composition disclosed herein, for use in the treatment of an influenza infection.

In one aspect, provided herein is a peptidomimetic macrocycle or pharmaceutical composition disclosed herein, for use in the manufacture of a medicament for treatment of an influenza infection.

In one aspect, provided herein is a use of a peptidomimetic macrocycle or pharmaceutical composition disclosed herein, for the manufacture of a medicament for treatment of an influenza infection.

In one aspect, provided herein is a use of a peptidomimetic macrocycle or pharmaceutical composition disclosed herein, for the treatment of a subject with an influenza infection.

In one aspect, provided herein is a method of preparing a composition comprising a peptidomimetic macrocycle of Formula (IV):

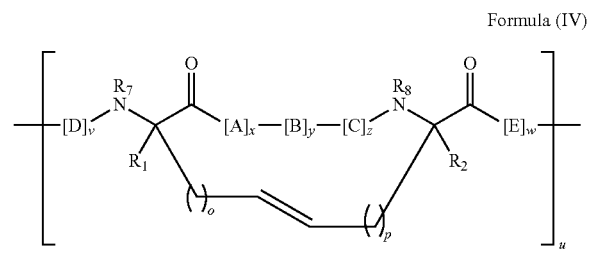

Formula (IV)

comprising an amino acid sequence that has about 60%, 65%, 70%, 75%, 80%, 85%, 90%, 95%, 96%, 97%, 98%, 99% or 100% sequence identity to a sequence of Table 1b, wherein the peptidomimetic macrocycle comprises at least two non-natural amino acids connected by a macrocycle-forming linker, the method comprising treating a compound of Formula (V)

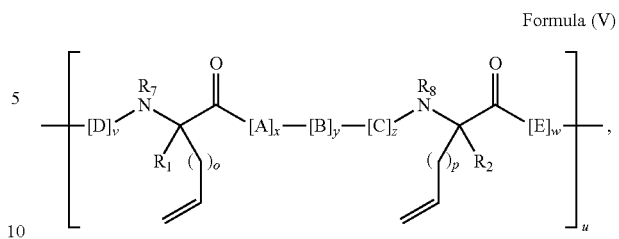

Formula (V)

with a catalyst to result in the compound of Formula (IV) wherein in the compound(s) of Formulae (IV) and (V) each A, C, D, and E is independently an amino acid; each B is independently an amino acid,

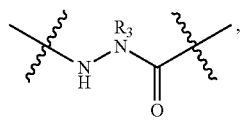

[—NH-$L_3$-CO—], [—NH-$L_3$-$SO_2$—], or [—NH-$L_3$-];
each $R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halogen; or at least one of $R_1$ and $R_2$ forms a macrocycle-forming linker L' connected to the α position of one of the D or E amino acids;
each $R_3$ is independently —H, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$; each L' is independently a macrocycle-forming linker of the formula -$L_1$-$L_2$-;
each $L_1$, $L_2$ and $L_3$ are independently alkylene, alkenylene, alkynylene, heteroalkylene, cycloalkylene, heterocycloalkylene, cycloarylene, heterocycloarylene, or [—$R_4$—K—$R_{4'}$—]$_n$, each being optionally substituted with $R_5$;
each $R_4$ and $R_{4'}$ is independently alkylene, alkenylene, alkynylene, heteroalkylene, cycloalkylene, heterocycloalkylene, arylene, or heteroarylene;
each K is independently O, S, SO, $SO_2$, CO, $CO_2$ or $CONR_3$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;
each v and w is independently an integer from 1-1000;
u is an integer from 1-10;
each x, y and z is independently an integer from 0-10;
each n is independently an integer from 1-5;
each o is independently an integer from 1-15;
each p is independently an integer from 1-15; and In some embodiments, one or more of the amino acids A, C and/or B when B is an amino acid, present in the compounds of Formulae (IV) and (V), has a side chain bearing a protecting group. In some embodiments, the protecting group is a nitrogen atom protecting group. In some embodiments, the protecting group is a Boc group. In some embodiments, the side chain of the amino acid bearing the protecting group comprises a protected indole. In some embodiments, the amino acid bearing the protecting group on its side chain is tryptophan (W) that is protected by the protecting group on its indole nitrogen. In some embodiments, the amino acid bearing the protecting group on its side chain is tryptophan (W) that is protected on its indole nitrogen by a Boc group.

In some embodiments, after the step of contacting the compound of Formula (V) with catalyst the compound of Formula (IV) is

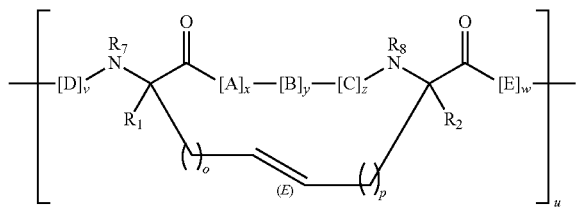

and is obtained in equal or higher amounts than a corresponding compound which is a Z isomer, wherein "(E)" indicates a trans double bond.

In some embodiments, after the step of contacting the compound of Formula (V) with catalyst the compound of Formula (IV) is obtained in a 2, 3, 4, 5, 6, 7, 8, 9, or 10-fold higher amount than the corresponding compound which is a Z isomer. In some embodiments, the catalyst is a ruthenium catalyst. In some embodiments, the method further comprises the step of treating the compounds of Formula (IV) with a reducing agent or an oxidizing agent. In some embodiments, the compound of Formula (V) is attached to a solid support. In some embodiments, the compound of Formula (V) is not attached to a solid support. In some embodiments, the method further comprises removing the protecting group(s) from the compounds of Formula (IV). In some embodiments, the ring closing metathesis is conducted at a temperature ranging from about 20° C. to about 80° C.

Additionally, the invention provides a method of treating influenza virus infection in a subject comprising administering to the subject a peptidomimetic macrocycle. Also provided is a method of preventing infection by an influenza virus in a subject comprising administering to the subject a peptidomimetic macrocycle, or a method of inhibiting the activity of the RNA-dependent RNA polymerase of an influenza virus in a subject comprising administering to the subject such a peptidomimetic macrocycle.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
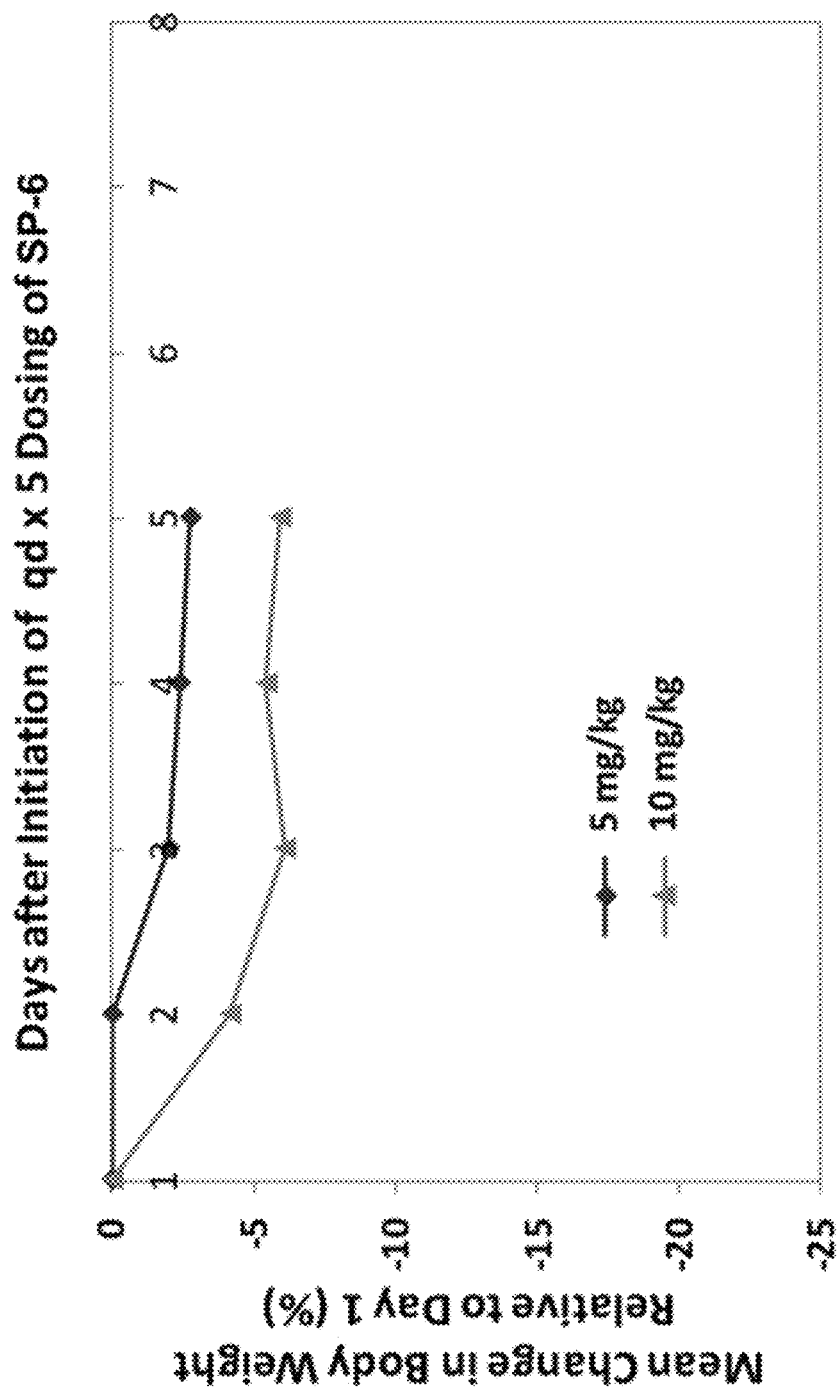
FIG. 1 exemplifies a graph of mean body weight of mice over time after treatment with an exemplary peptidomimetic macrocycle (SP-6) at the indicated doses in replicate experiments.

Three classes of influenza viruses, A, B and C, are responsible for human flu, with influenza A and B viruses causing seasonal epidemics of disease almost every winter. Influenza A viruses are divided into subtypes based on characteristics of two proteins, hemagglutinin (H) and neuraminidase (N), on the surface of the virus. There are 16 different hemagglutinin subtypes and 9 different neuraminidase subtypes, with $H_1N_1$ and H3N2 being the most common subtypes found in humans. The avian flu virus refers to influenza A $H_5N_1$. Influenza A is a negative-sense (3' to 5') single-stranded RNA virus. Its viral genome, which encodes 11 proteins (HA, NA, NP, M1, M2, NS1, NEP, PA, PB1, PB1-F2, PB2) in its RNA, cannot be translated into protein directly; rather, the virus depends on its RNA-dependent RNA polymerase to transcribe its genome to positive-sense RNA prior to translation. RNA-dependent RNA polymerases have no mammalian counterpart, which renders species selectivity less problematic in the development of therapeutics that target this enzyme. Other examples of viral RNA-dependent RNA polymerases include polioviral 3Dpol, vesicular stomatitis virus L, and hepatitis C virus NS5b; the latter is an active target for development of hepatitis C antiviral therapies. Unlike current flu targets (e.g., neuraminidase for Tamiflu), the influenza RNA polymerase is highly conserved and therefore less likely to suffer the resistance issues that current drugs face.

Recently, researchers reported the first atomic-resolution structural details of the influenza protein RNA polymerase, a critical enzyme for viral replication and a novel target for both therapeutic intervention and prophylaxis during influenza outbreaks (He, X., et al., *Nature*, 2008. 454: p. 1123-6; Obayashi, E., et al., *Nature*, 2008. 454: p. 1127-31). The influenza RNA-dependent RNA polymerase is a heterotrimer of three subunits, PA, PB1, and PB2, with the $3_{10}$-helical N-terminal region of PB1 binding between the "jaws" of the PA protein. The PB1 helix is thought to be important for complex formation and nuclear transport and inhibits influenza A viral replication by interfering with polymerase activity. Recently, the PB2 subunit has also been shown to play an essential role in activity of the viral polymerase complex, for instance through contacts with the PB1 subunit. See Sugiyama et al, *EMBO Journal*, 2009, 28, 1803-1811. However, little is known about compounds capable of interfering with the binding and activity of these proteins. In general, there remains a need for therapeutic methods of treating viral diseases in which RNA-dependent RNA polymerases play a role, and for compositions and methods capable of modifying the activity such polymerases.

As used herein, the term "macrocycle" refers to a molecule having a chemical structure including a ring or cycle formed by at least 9 covalently bonded atoms.

As used herein, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycle include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle. A "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, the term "stability" refers to the maintenance of a defined secondary structure in solution by a peptidomimetic macrocycle as measured by circular dichroism, NMR or another biophysical measure, or resistance to proteolytic degradation in vitro or in vivo. Non-limiting examples of secondary structures contemplated herein are α-helices, $3_{10}$ helices, β-turns, and β-pleated sheets.

As used herein, the term "helical stability" refers to the maintenance of helical structure by a peptidomimetic macrocycle as measured by circular dichroism or NMR. For example, in some embodiments, the peptidomimetic macrocycles exhibit at least a 1.25, 1.5, 1.75 or 2-fold increase in helicity as determined by circular dichroism compared to a corresponding uncrosslinked macrocycle.

The term "amino acid" refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration. The abbreviation "b-" prior to an amino acid represents a β configuration for the amino acid.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive (10%) neutral (90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acids" are glycine, alanine, proline, and analogs thereof. "Large hydrophobic amino acids" are valine, leucine, isoleucine, phenylalanine, methionine, tryptophan, tyrosine, and analogs thereof. "Polar amino acids" are serine, threonine, asparagine, glutamine, cysteine, and analogs thereof. "Charged amino acids" include positively charged amino acids and negatively charged amino acids. "Positively charged amino acids" include lysine, arginine, histidine, and analogs thereof. "Negatively charged amino acids" include aspartate, glutamate, and analogs thereof.

The term "amino acid analog" refers to a molecule which is structurally similar to an amino acid and which can be substituted for an amino acid in the formation of a peptidomimetic macrocycle. Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids or amino acid analogs include, without limitation, structures according to the following:

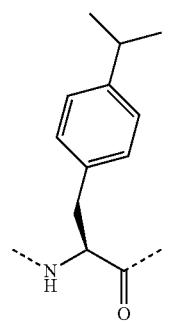
4-t-butylphenylalanine
(F4tBu)
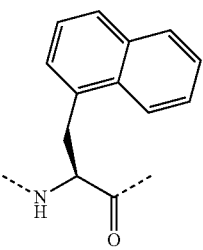
1-Naphthylalanine
(1Nal)
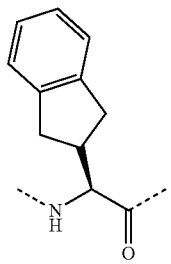
Indanyl glycine
(Igl)
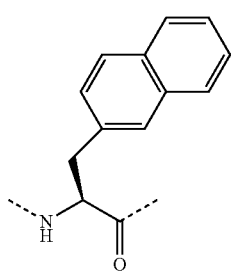
2-Naphthylalanine
(2Nal)
-continued
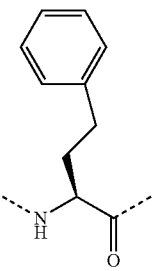
homophenylalanine
(hF)
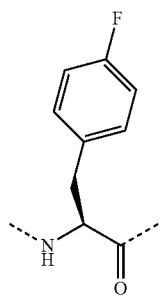
4-fluorophenylalanine
(F4F)
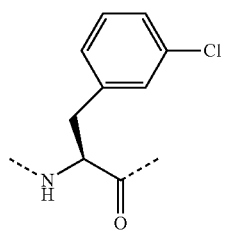
3-chlorohenylalanine
(F3Cl = 3cf)
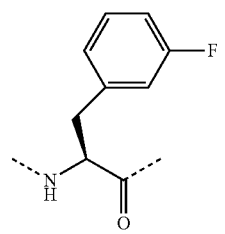
3-fluorophenylalanine
(F3F = 3ff)
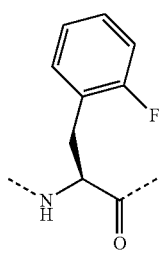
2-fluorophenylalanine
(F2F = 2ff)

-continued
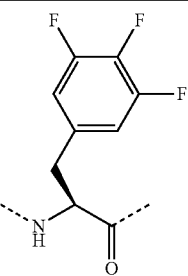
3,4,5-trifluoro
phenylalanine
(F345F3)
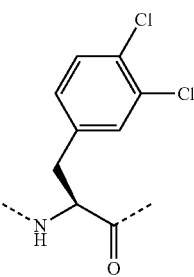
3,4-difluoro
phenylalanine
(F34Cl2)
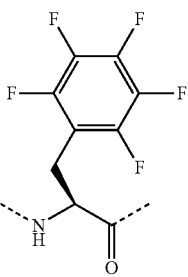
pentafluoro
phenylalanine
(F5F)
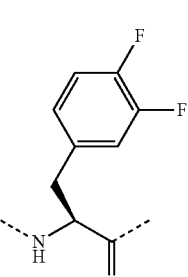
3,4-difluoro
phenylalanine
(F34F2)
-continued
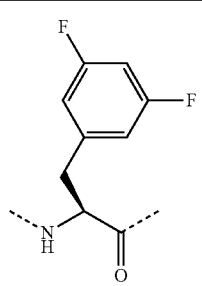
3,5-difluoro
phenylalanine
(F35F2)
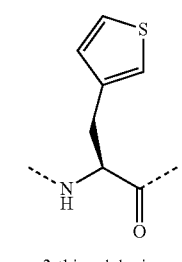
3-thienylalanine
(2Thi)
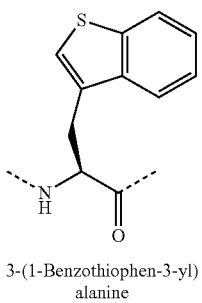
3-(1-Benzothiophen-3-yl)
alanine
(3BthA)
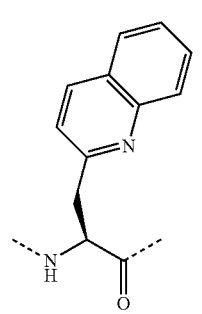
3-(2-quinolyl)
alanine
(2qA)

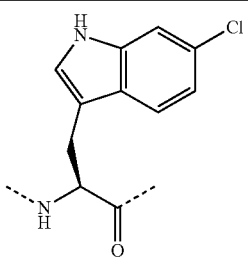
6-chlorotryptophan
(6clW)
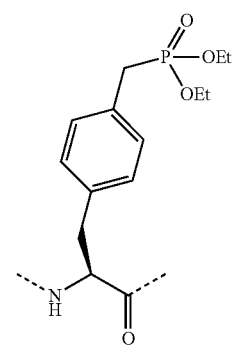
4-[di-(ethyl)phosphono
methyl]phenylalanine
(pmpEt)
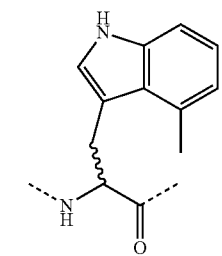
D- or L- 4-methyl
tryptophan
(dl4mW)
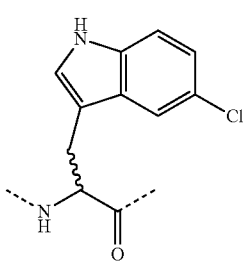
D- or L- 5-chloro
tryptophan
(dl5clW)
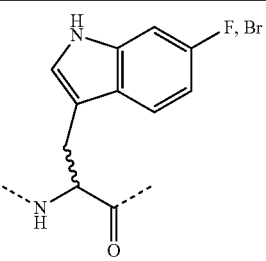
D/L-6-fluorotryptophan &
D/L-6-bromotryptophan
(ddl6fW & dl6brW)
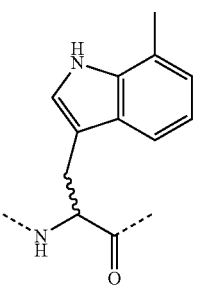
D/L-7-methyl
tryptophan
(dl7mW)
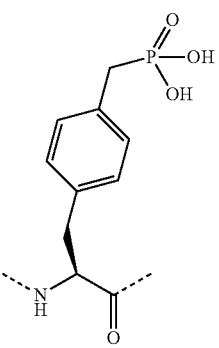
4-(phosphonomethyl)
phenylalanine
(Pmp)
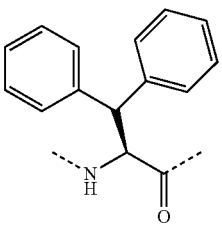
3,3-diphenyl-alanine
(Dip)

-continued
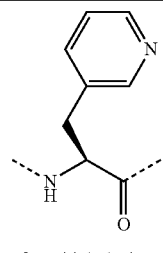
3-pyridyl-alanine
(3Pal)
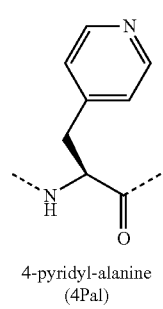
4-pyridyl-alanine
(4Pal)
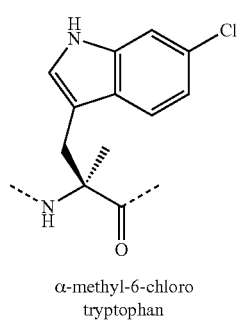
α-methyl-6-chloro
tryptophan
(Me6clW)
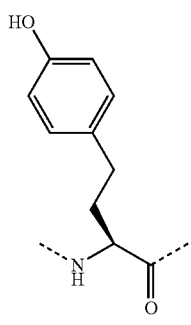
homotyrosine
(hY)
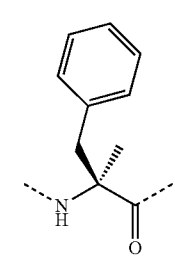
α-methyl-phenylanaline
(Amf)
-continued
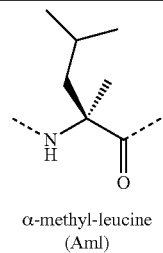
α-methyl-leucine
(Aml)
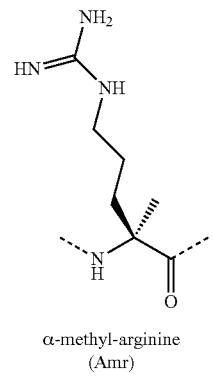
α-methyl-arginine
(Amr)
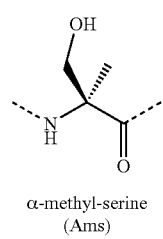
α-methyl-serine
(Ams)
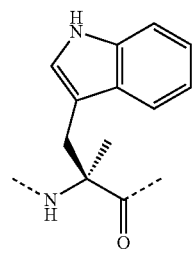
α-methyl-tryptophan
(Amw)
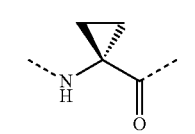
1-amino-cyclopropane-
1-carboxylic acid
(Ac3c)
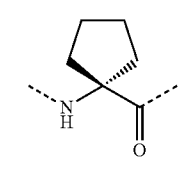
1-amino-cyclopentane-
1-carboxylic acid
(Ac5c)

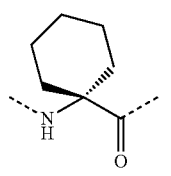
1-amino-cyclohexane-
1-carboxylic acid
(Ac6c)
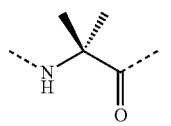
α-amino
isobutyric acid
(Aib)
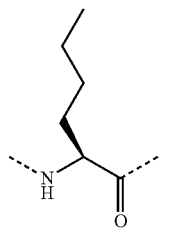
Norleucine
(Nle)
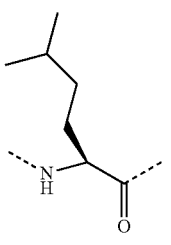
Homoleucine
(hL)
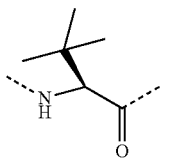
tert-Butyl glycine
(Tle)
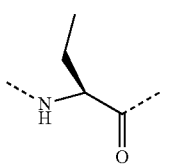
aminobutyric acid
(Abu)
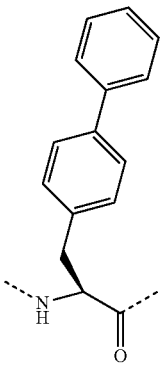
biphenylalanine
(Bip)
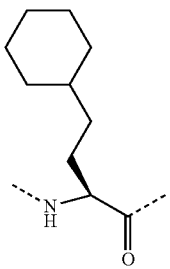
homocyclohexyl
alanine
(hCha)
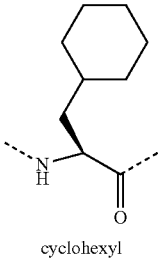
cyclohexyl
alanine
(Cha)
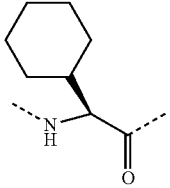
cyclohexyl
glycine
(Chg)
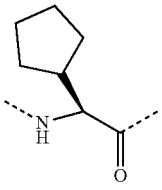
cyclopentyl
glycine
(Cpg)

27
-continued

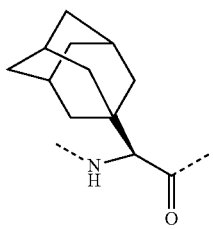

Adamantyl glycine (Adm)

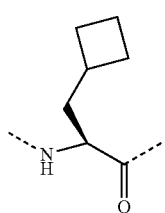

cyclobutyl alanine (Cba)

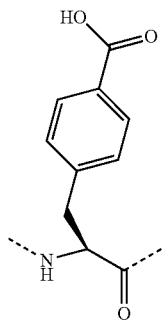

4-carboxyl phenylalanine (F4COOH)

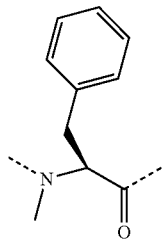

N-methyl phenylalanine (NmF)

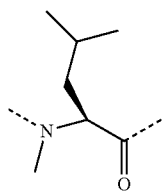

N-methyl leucine (NmL)

28
-continued

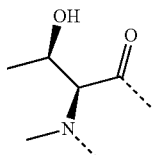

N-methyl threonine (NmT)

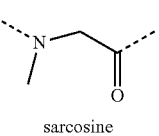

sarcosine (Sar)

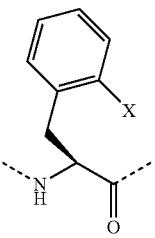

2-chlorophenylalanine (X = Cl),
2-bromophenylalanine (X = Br),
2-trimethylphenylalanine (X = CF3),
2-cyanophenylalanine (X = CN),
2-methylphenylalanine (X = Me),
2-nitrophenylalanine (X = NO2),
(F2X, X = Cl, Br, CF3, CN, Me, NO2)

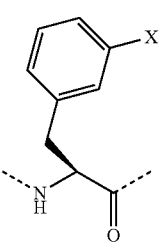

3-chlorophenylalanine (X = Cl),
3-bromophenylalanine (X = Br),
3-trimethylphenylalanine (X = CF3),
3-cyanophenylalanine (X = CN),
3-methylphenylalanine (X = Me),
3-nitrophenylalanine (X = NO2),
(F3X, X = Cl, Br, CF3, CN, Me, NO2)

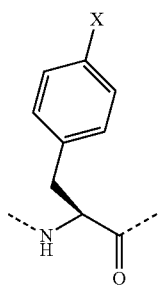
4-chlorophenylalanine (X = Cl),
4-bromophenylalanine (X = Br),
4-trimethylphenylalanine (X = CF3),
4-cyanophenylalanine (X = CN),
4-methylphenylalanine (X = Me),
4-nitrophenylalanine (X = NO2),
(F4X, X = Cl, Br, CF3, CN, Me, NO2)
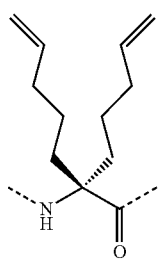
St//
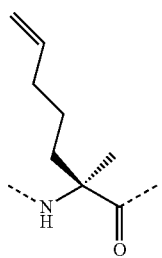
$/
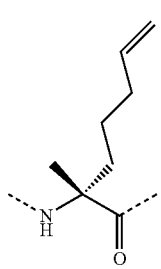
$/r5
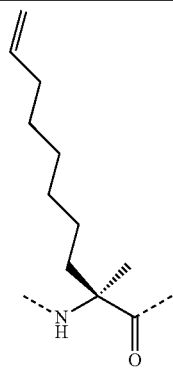
$/s8
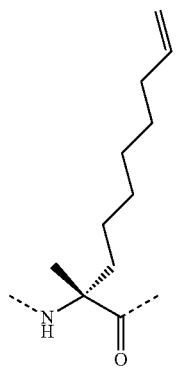
$/r8
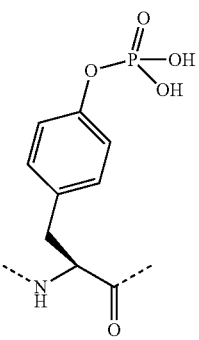
phosphotyrosine
(pY)
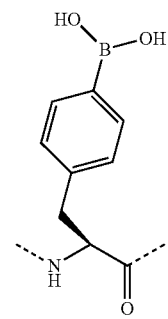
4-borono-
phenylalanine
(F4bOH2)

-continued
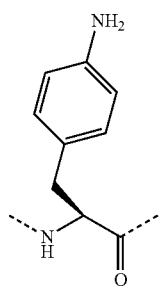
4-amino
phenylalanine
(F4NH2)
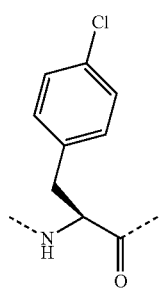
4-chloro
phenylalanine
(F4Cl)
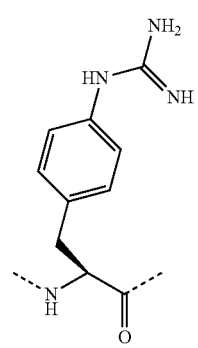
4-guanido
phenylalanine
(F4g)
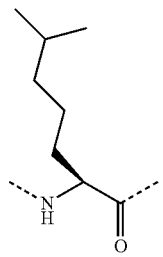
homohomoleucine
(hhL)
-continued
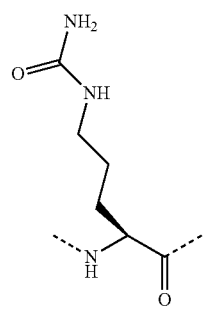
citrulline
(cit)
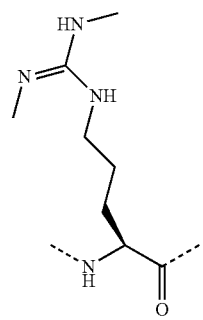
dimethylarginine
(2mR)
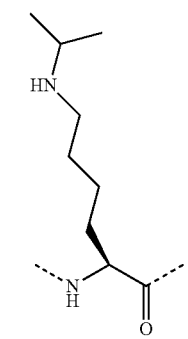
isopropyllysine
(ipK)
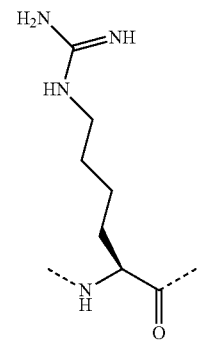
homoarginine
(hR)

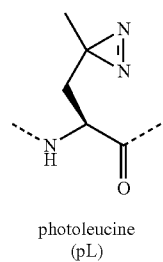
photoleucine
(pL)
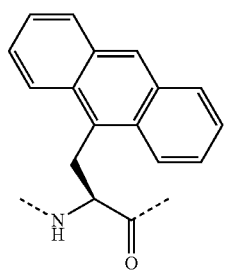
3-(9-anthryl)-
L-alanine
(9Aal)
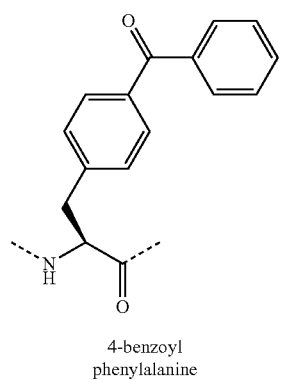
4-benzoyl
phenylalanine
(BPa)
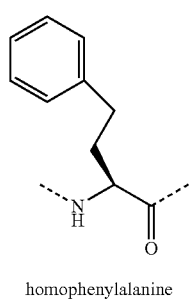
homophenylalanine
(hF)
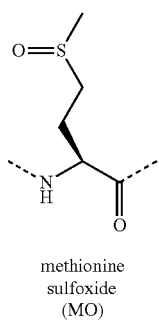
methionine
sulfoxide
(MO)
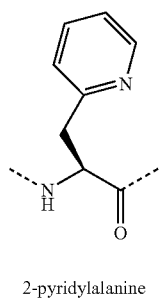
2-pyridylalanine
(2Pal)
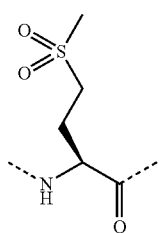
methionine
sulfone
(MO2)
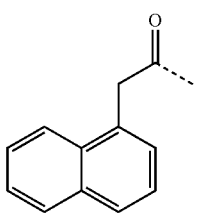
1-Naphthylacetyl
(1-NaAc-)
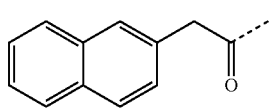
2-Naphthylacetyl
(2-NaAc-)

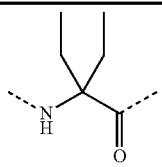

Diethylglycine
(Deg)

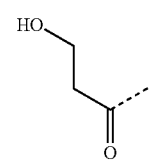

desamino-Ser

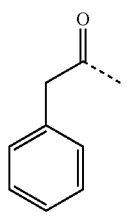

phenylacetyl
(PhAc-)

Amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-iso-quinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl)-butyric acid; (S)-3-amino-4-(4-cyanophenyl)-butyric acid; (S)-3-amino-4-(4-fluorophenyl)-butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysin; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanine; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D- phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine.dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxocyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)$_2$-OH (symmetrical); Lys(ivDde)-OH; Lys(Me)$_2$-OH.HCl; Lys(Me$_3$)-OH chloride; Nω-nitro-D-arginine; and Nω-nitro-L-arginine.

Amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OA11)-OH; L-Asu(OtBu)-OH; and pyroglutamic acid.

Amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichlorophenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2; 4; 5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6- methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs include analogs of tryptophan Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, amino acid analogs are racemic. In some embodiments, the D isomer of the amino acid analog is used. In some embodiments, the L isomer of the amino acid analog is used. In other embodiments, the amino acid analog comprises chiral centers that are in the R or S configuration. In still other embodiments, the amino group (s) of a β-amino acid analog is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analog is protected, e.g., as its ester derivative. In some embodiments the salt of the amino acid analog is used.

A "non-essential" amino acid residue is a residue that can be altered from the wild-type sequence of a polypeptide without abolishing or substantially abolishing its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), β-branched side chains (e.g., T, V, I) and aromatic side chains (e.g., Y, F, W, H). Thus, a predicted nonessential amino acid residue in a polypeptide, e.g., is replaced with another amino acid residue from the same side chain family. Other examples of acceptable substitutions are substitutions based on isosteric considerations (e.g., norleucine for methionine) or other properties (e.g., 2-thienylalanine for phenylalanine, or 6-Cl-tryptophan for tryptophan).

The term "capping group" refers to the chemical moiety occurring at either the carboxy or amino terminus of the polypeptide chain of the subject peptidomimetic macrocycle. The capping group of a carboxy terminus includes an unmodified carboxylic acid (i.e., —COOH) or a carboxylic acid with a substituent. For example, the carboxy terminus can be substituted with an amino group to yield a carboxamide at the C-terminus. Various substituents include but are not limited to primary, secondary, and tertiary amines, including pegylated secondary amines Representative secondary amine capping groups for the C-terminus include:

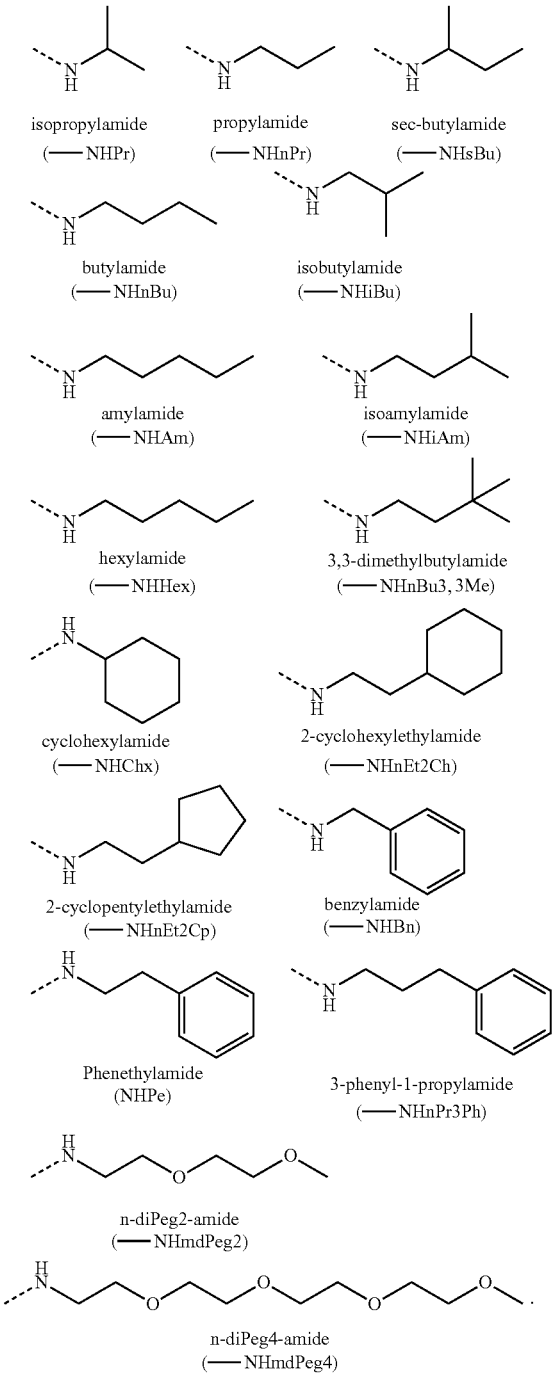

The capping group of an amino terminus includes an unmodified amine (i.e., —NH$_2$) or an amine with a substituent. For example, the amino terminus can be substituted with an acyl group to yield a carboxamide at the N-terminus Various substituents include but are not limited to substituted acyl groups, including $C_1$-$C_6$ carbonyls, $C_7$-$C_{30}$ carbonyls, and pegylated carbamates. Representative capping groups for the N-terminus include, but are not limited to, 4-FBzl (4-fluoro-benzyl) and the following:

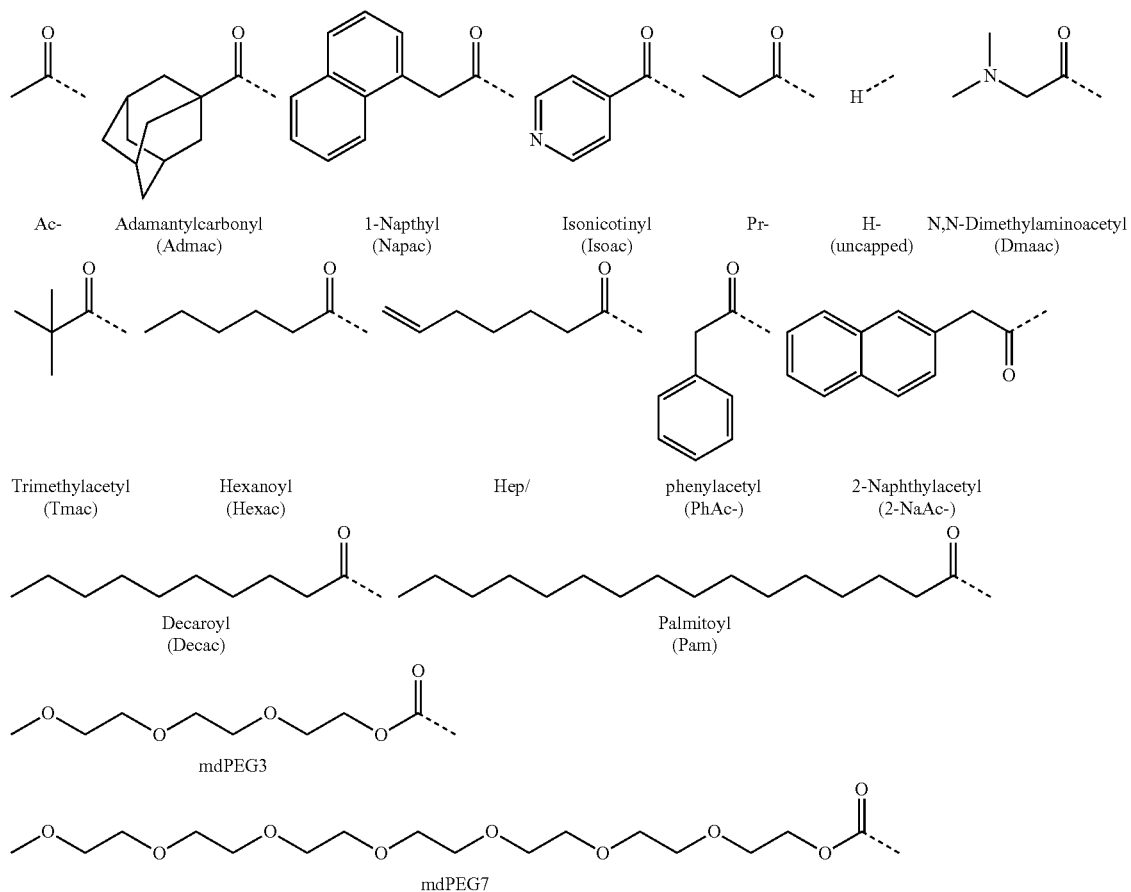

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen (—H) or fluoro substituents or methyl side chains do not participate in forming the macrocycle.

The symbol "⫽" when used as part of a molecular structure refers to a single bond or a trans or cis double bond.

The term "amino acid side chain" refers to a moiety attached to the α-carbon (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, e.g., those that occur in nature (e.g., an amino acid metabolite) or those that are made synthetically (e.g., an α,α di-substituted amino acid).

The term "α,α di-substituted amino acid" refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "first C-terminal amino acid" refers to the amino acid which is closest to the C-terminus. The term "second C-terminal amino acid" refers to the amino acid attached at the N-terminus of the first C-terminal amino acid.

The term "macrocyclization catalyst" or "macrocycle-forming catalyst" as used herein refers to any catalyst which can be used to prepare a peptidomimetic macrocycle by mediating the reaction between two reactive groups. Reactive groups can be, for example, an azide and alkyne, in which case macrocyclization catalysts include, without limitation, Cu catalysts such as catalysts which provide a reactive Cu(I) species, such as CuBr, CuI or CuOTf, as well as Cu(II) salts such as $Cu(CO_2CH_3)_2$, $CuSO_4$, and $CuCl_2$ that can be converted in situ to an active Cu(I) catalyst by the addition of a reducing agent such as ascorbic acid or sodium ascorbate. Macrocyclization catalysts can additionally include, for example, Ru catalysts known in the art such as $Cp*RuCl(PPh_3)_2$, $[Cp*RuCl]_4$ or other Ru catalysts which can provide a reactive Ru(II) species. In other cases, the reactive groups are terminal olefins. In such embodiments, the macrocyclization catalysts or macrocycle-forming catalysts are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. In other examples, catalysts have W or Mo centers. Various catalysts are disclosed in Grubbs et al., "Ring Closing Metathesis and Related Processes in Organic Synthesis" Acc. Chem. Res. 1995, 28, 446-452, U.S. Pat. No. 5,811,515; U.S. Pat. No. 7,932,397; U.S. Application No. 2011/0065915; U.S. Application No. 2011/0245477; Yu et al., "Synthesis of Macrocyclic Natural Products by Catalyst-Controlled Stereoselective Ring-Closing Metathesis," Nature 2011, 479, 88; and Peryshkov et al., "Z-Selective Olefin Metathesis Reactions Promoted by Tungsten Oxo Alkylidene Complexes," J. Am. Chem. Soc. 2011, 133, 20754. In yet other cases, the reactive groups are thiol groups. In such embodiments, the macrocyclization catalyst is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1-10 (inclusive) carbon atoms in it. In the absence of any numerical designation, "alkyl" is a chain (straight or branched) having 1-20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2-10 (inclusive) carbon atoms in it. The term "lower alkenyl" refers to a $C_2$-$C_6$ alkenyl chain. In the absence of any numerical designation, "alkenyl" is a chain (straight or branched) having 2-20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2-10 (inclusive) carbon atoms in it. The term "lower alkynyl" refers to a $C_2$-$C_6$ alkynyl chain. In the absence of any numerical designation, "alkynyl" is a chain (straight or branched) having 2-20 (inclusive) carbon atoms in it.

The term "aryl" refers to a monocyclic or bicyclic aromatic ring system wherein 0, 1, 2, 3, 4, or more atoms of each ring are substituted by a substituent. Exemplary aryls include 6-carbon monocyclic or 10-carbon bicyclic aromatic ring systems. Examples of aryl groups include phenyl, naphthyl and the like. The term "arylalkoxy" refers to an alkoxy substituted with aryl.

"Arylalkyl" refers to an aryl group, as defined above, wherein one of the aryl group's hydrogen atoms has been replaced with an alkyl group (e.g., a $C_1$-$C_5$ alkyl group) as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl, "Alkylheterocycle" refers an alkyl group (e.g., a $C_1$-$C_5$ alkyl group), as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to an alkyl group (e.g., a $C_1$-$C_5$ alkyl group), as defined above, wherein one of the alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—C(O)—CH$_3$, —CH$_2$—CH$_2$—NH—C(O)—CH$_3$—CH3, and —CH$_2$—CH$_2$—NH—C(O)—CH=CH$_2$.

"Alkanol" refers to an alkyl group (e.g., a $C_1$-$C_5$ alkyl group), as defined above, wherein one of the alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to an alkyl group (e.g., a $C_1$-$C_5$ alkyl group), as defined above, wherein one of the alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups wherein the cycloalkyl group additionally is optionally substituted. For example a cycloalkyl can be saturated and partially unsaturated cyclic hydrocarbon groups having 3 to 12 carbons, 3 to 8 carbons, and or 3 to 6 carbons, Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic monocyclic, bicyclic, or tricyclic ring system having 1 or more heteroatoms. For example, a heteroaryl includes an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from 0, N, or S-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of 0, N, or S if monocyclic, bicyclic, or tricyclic, respectively), wherein 0, 1, 2, 3, 4 or more atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylakl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included unless expressly provided otherwise. All crystal forms of the compounds described herein are included unless expressly provided otherwise.

As used herein, the terms "increase" and "decrease" mean, respectively, to cause a statistically significantly (i.e., p<0.1) increase or decrease of at least 5%.

As used herein, the recitation of a numerical range for a variable is intended to convey that the variable is equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values≥0 and ≤2 if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle. Biological activity is, e.g., structural stability, α-helicity, affinity for a target, resistance to proteolytic degradation, cell penetrability, intracellular stability, in vivo stability, or any combination thereof.

The term "binding affinity" refers to the strength of a binding interaction, for example between a peptidomimetic macrocycle and a target. Binding affinity can be expressed, for example, as an equilibrium dissociation constant ("$K_D$"), which is expressed in units which are a measure of concentration (e.g., M, mM, μM, nM, etc.). Numerically, binding affinity and $K_D$ values vary inversely, such that a lower binding affinity corresponds to a higher $K_D$ value, while a higher binding affinity corresponds to a lower $K_D$ value. Where high binding affinity is desirable, "improved" binding affinity refers to higher binding affinity i.e., lower $K_D$ values.

The term "in vitro efficacy" refers to the extent to which a test compound, such as a peptidomimetic macrocycle, produces a beneficial result in an in vitro test system or assay. In vitro efficacy can be measured, for example, as an "$IC_{50}$" or "$EC_{50}$" value, which represents the concentration of the test compound which produces 50% of the maximal effect in the test system.

The term "ratio of in vitro efficacies" or "in vitro efficacy ratio" refers to the ratio of $IC_{50}$ or $EC_{50}$ values from a first assay (the numerator) versus a second assay (the denominator). Consequently, an improved in vitro efficacy ratio for Assay 1 versus Assay 2 refers to a lower value for the ratio expressed as $IC_{50}$(Assay 1)/$IC_{50}$(Assay 2) or alternatively as $EC_{50}$(Assay 1)/$EC_{50}$(Assay 2). This concept can also be characterized as "improved selectivity" in Assay 1 versus Assay 2, which can be due either to a decrease in the $IC_{50}$ or $EC_{50}$ value for Target 1 or an increase in the value for the $IC_{50}$ or $EC_{50}$ value for Target 2.

The details of one or more particular embodiments of the invention are set forth in the accompanying drawings and the description below. Other features, objects, and advantages of the invention will be apparent from the description and drawings, and from the claims.

Peptidomimetic Macrocycles of the Invention

In general, peptidomimetic macrocycles are prepared that target or interact with proteins that a virus needs for infection or replication within a host cell. Such viruses may be, for example, influenza viruses belonging to Orthomyxoviridae family of viruses. This family also includes Thogoto viruses and Dhoriviruses. There are several types and subtypes of influenza viruses known, which infect humans and other species. Influenza type A viruses infect people, birds, pigs, horses, seals and other animals, but wild birds are the natural hosts for these viruses. Influenza type A viruses are divided into subtypes and named on the basis of two proteins on the surface of the virus: hemagglutinin (HA) and neuraminidase (NA). For example, an "$H_7N_2$ virus" designates an influenza A subtype that has an HA 7 protein and an NA 2 protein. Similarly an "$H_5N_1$" virus has an HA 5 protein and an NA 1 protein. There are 16 known HA subtypes and 9 known NA subtypes. Many different combinations of HA and NA proteins are possible. Only some influenza A subtypes (i.e., $H_1H_1$, $H_1N_2$, and $H_3N_2$) are currently in general circulation among people. Other subtypes are found most commonly in other animal species. For example, $H_7N_7$ and $H_3N_8$ viruses cause illness in horses, and $H_3N_8$ also has recently been shown to cause illness in dogs.

Antiviral agents according to the invention can be used to protect high-risk groups (hospital units, institutes caring for elderly, immuno-suppressed individuals), and on a case by case basis. A potential use for antiviral agents is to limit the spread and severity of the future pandemics whether caused by avian $H_5N_1$ or other strains of influenza virus. Avian influenza A viruses of the subtypes $H_5$ and $H_7$, including $H_5N_1$, $H_7N_7$, and $H_7N_3$ viruses, have been associated with high pathogenicity, and human infection with these viruses have ranged from mild ($H_7N_3$, $H_7N_7$) to severe and fatal disease ($H_7N_7$, $H_5N_1$). Human illness due to infection with low pathogenicity viruses has been documented, including very mild symptoms (e.g., conjunctivitis) to influenza-like illness. Examples of low pathogenicity viruses that have infected humans include $H_7N_7$, $H_9N_2$, and $H_7N_2$.

Influenza B viruses are usually found in humans but can also infect seals Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics.

Influenza type C viruses cause mild illness in humans and do not cause epidemics or pandemics. These viruses can also infect dogs and pigs. These viruses are not classified according to subtype.

Influenza viruses differ from each other in respect to cell surface receptor specificity and cell tropism, however they use common entry pathways. Charting these pathways and identification of host cell proteins involved in virus influenza transmission, entry, replication, biosynthesis, assembly, or exit allows the development of general agents against existing and emerging strains of influenza. The agents may also prove useful against unrelated viruses that use similar pathways. For example, the agents may protect airway epithelial cells against a number of different viruses in addition to influenza viruses.

The targeted virus can be an adenovirus. Adenoviruses most commonly cause respiratory illness; symptoms of respiratory illness caused by adenovirus infection range from the common cold syndrome to pneumonia, croup, and bronchitis. Patients with compromised immune systems are especially susceptible to severe complications of adenovirus infection. Acute respiratory disease (ARD), first recognized among military recruits during World War II, can be caused by adenovirus infections during conditions of crowding and stress. Adenoviruses are medium-sized (90-100 nm), nonenveloped icosohedral viruses containing double-stranded DNA. There are 49 immunologically distinct types (6 subgenera: A through F) that can cause human infections. Adenoviruses are unusually stable to chemical or physical agents and adverse pH conditions, allowing for prolonged survival outside of the body. Some adenoviruses, such as AD2 and Ad5 (species C) use clathrin mediated endocytosis and macropinocytosis for infectious entry. Other adenoviruses, such as Ad3 (species B) use dynamin dependent endocytosis and macropinocytosis for infectious entry.

The targeted virus can be a respiratory syncytial virus (RSV). RSV is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems. RSV is a negative-sense, enveloped RNA virus. The virion is variable in shape and size (average diameter of between 120 and 300 nm), is unstable in the environment (surviving only a few hours on environmental surfaces), and is readily inactivated with soap and water and disinfectants.

The targeted virus can be a human parainfluenza virus (HPIV). HPIVs are second to respiratory syncytial virus (RSV) as a common cause of lower respiratory tract disease in young children Similar to RSV, HPIVs can cause repeated infections throughout life, usually manifested by an upper respiratory tract illness (e.g., a cold and/or sore throat). HPIVs can also cause serious lower respiratory tract disease with repeat infection (e.g., pneumonia, bronchitis, and bronchiolitis), especially among the elderly, and among patients with compromised immune systems. Each of the four HPIVs has different clinical and epidemiologic features. The most distinctive clinical feature of HPIV-1 and HPIV-2 is croup (i.e., laryngotracheobronchitis); HPIV-1 is the leading cause of croup in children, whereas HPIV-2 is less frequently detected. Both HPIV-1 and -2 can cause other upper and lower respiratory tract illnesses. HPIV-3 is more often associated with bronchiolitis and pneumonia. HPIV-4 is infrequently detected, possibly because it is less likely to cause severe disease. The incubation period for HPIVs is generally from 1 to 7 days. HPIVs are negative-sense, single-stranded RNA viruses that possess fusion and hemagglutinin-neuraminidase glycoprotein "spikes" on their surface. There are four serotypes types of HPIV (1 through 4) and two subtypes (4a and 4b). The virion varies in size (average diameter between 150 and 300 nm) and shape, is unstable in the environment (surviving a few hours on environmental surfaces), and is readily inactivated with soap and water.

The targeted virus can be a coronavirus. Coronavirus is a genus of animal virus belonging to the family Coronaviridae. Coronaviruses are enveloped viruses with a positive-sense single-stranded RNA genome and a helical symmetry. The genomic size of coronaviruses ranges from approximately 16 to 31 kilobases, extraordinarily large for an RNA virus. The name "coronavirus" is derived from the Latin corona, meaning crown, as the virus envelope appears under electron microscopy to be crowned by a characteristic ring of small bulbous structures. This morphology is actually formed by the viral spike peplomers, which are proteins that populate the surface of the virus and determine host tropism. Coronaviruses are grouped in the order Nidovirales, named for the Latin nidus, meaning nest, as all viruses in this order produce a 3' co-terminal nested set of subgenomic mRNA's during infection. Proteins that contribute to the overall structure of all coronaviruses are the spike, envelope, membrane and nucleocapsid. In the specific case of SARS a defined receptor-binding domain on S mediates the attachment of the virus to its cellular receptor, angiotensin-converting enzyme 2.

The targeted virus can be a rhinovirus. Rhinovirus (from the Greek rhin-, which means "nose") is a genus of the Picornaviridae family of viruses Rhinoviruses are the most common viral infective agents in humans, and a causative agent of the common cold. There are over 105 serologic virus types that cause cold symptoms, and rhinoviruses are responsible for approximately 50% of all cases. Rhinoviruses have single-stranded positive sense RNA genomes of between 7.2 and 8.5 kb in length. At the 5' end of the genome is a virus-encoded protein, and like mammalian mRNA, there is a 3' poly-A tail. Structural proteins are encoded in the 5' region of the genome and nonstructural at the end. This is the same for all picornaviruses. The viral particles themselves are not enveloped and are icosahedral in structure.

Any secondary structure of a viral protein (or of a host cell protein involved in viral infectivity) can form the basis of the methods. For example, a viral protein comprising a secondary structure which is a helix may be used to design peptidomimetic macrocycles based on said helix.

The peptidomimetic macrocycle can be designed based on the PB1 or PB2 sequence of an influenza virus. The PB1 sequence is highly conserved across all known strains of influenza A virus, which may result in less drug resistance should than that observed with the current standard of care. An alignment of the first 25 N-terminal amino acids of PB1 from the NCBI data bank's 2.485 influenza A virus strains (Ghanem. 2007) demonstrates the remarkable sequence conservation in the PA interaction domain of PB1. Therefore, antiviral therapies based on the PB1 sequence may block most, if not all, influenza A virus strains. Additionally, sequence modification of a peptidomimetic macrocycle based on these few variations in PB1 may enable an antiviral cocktail of PB1 inhibitors to eliminate resistance due to escape mutants. The sequence of the first 15 N-terminal amino acids of PB1 is: MDVNPTLLFLKVPAQ (SEQ ID NO: 6). In some embodiments, a peptide of the disclosure is, or is not, Ac-NleDVN$TLL$LKVAibAQ-$NH_2$ ("Aileron peptide 1") (SEQ ID NO: 8). Exemplary sequences suitable for macrocyclization and macrocyclic peptides for use is given below in Table 1:

TABLE 1

| SEQ ID NO: | | | | Table 1a | | | | | | | | | | | | | | | | | |
|---|---|---|---|---|---|---|---|---|---|---|---|---|---|---|---|---|---|---|---|---|---|
| 6 | Ribarivin | | | M | D | V | N | P | T | L | L | F | L | K | V | P | A | Q | | | |
| 8 | AP1 | Ac— | | Nle | D | V | N | $ | T | L | L | $ | L | K | V | Aib | A | Q | | | |
| | Table 1b - Exemplary peptidomimetic macrocycles | | | | | | | | | | | | | | | | | | | | |
| | SP# | | | 1 | 2 | 3 | 4 | 5 | 6 | 7 | 8 | 9 | 10 | 11 | 12 | 13 | 14 | 15 | 16 | 17 | |
| 9 | 1 | Ac— | | Nle | D | V | N | $ | T | L | L | $ | L | K | A | Aib | A | Q | | | —$NH_2$ |
| 10 | 2 | Ac— | | Nle | D | V | N | $ | T | L | L | $ | L | K | V | Aib | A | A | | | —$NH_2$ |
| 11 | 3 | Ac— | | Nle | D | V | N | $ | T | L | L | $ | L | K | V | P | Aib | Q | | | —$NH_2$ |
| 12 | 4 | Ac— | | F | D | V | N | $ | T | L | L | $ | L | K | V | Aib | A | Q | | | —$NH_2$ |
| 13 | 5 | 5-FAM | Ba | Nle | D | V | N | $ | T | L | L | $ | L | A | V | Aib | A | Q | | | —$NH_2$ |
| 14 | 6 | Ac— | | Nle | D | V | N | $ | T | L | L | $ | L | A | V | Aib | A | Q | | | —$NH_2$ |
| 15 | 7 | Ac— | | Nle | D | V | N | $ | T | L | L | $ | L | A | V | Aib | A | Q | A | A | —$NH_2$ |
| 16 | 8 | Ac— | | Nle | D | V | N | $ | T | L | L | $ | L | A | V | A | A | Q | A | A | —$NH_2$ |
| 17 | 9 | Ac— | | Nle | D | V | N | $ | T | L | L | $ | L | A | V | A | A | A | A | A | —$NH_2$ |
| 18 | 10 | Ac— | | Nle | D | V | N | $ | T | L | L | $ | L | A | V | S | A | Q | A | A | —$NH_2$ |
| 19 | 11 | Ac— | | Nle | D | V | N | $ | T | L | L | $ | L | A | V | Q | A | Q | A | A | —$NH_2$ |
| 20 | 12 | Ac— | | Nle | D | V | N | $ | T | L | L | $ | L | A | V | E | A | Q | A | A | —$NH_2$ |
| 21 | 13 | Ac— | | Nle | D | V | N | $ | T | L | L | $ | L | A | V | S | A | A | A | A | —$NH_2$ |
| 22 | 14 | Ac— | | Nle | D | V | N | $ | T | L | L | $ | L | A | V | Q | A | A | A | A | —$NH_2$ |
| 23 | 15 | Ac— | | Nle | D | V | N | $ | T | L | L | $ | L | A | V | E | A | A | A | A | —$NH_2$ |
| 24 | 16 | Ac— | | Nle | D | V | N | $ | T | L | L | $ | L | A | V | Aib | A | Q | A | a | —$NH_2$ |
| 25 | 17 | Ac— | | Nle | D | V | N | $ | T | L | L | $ | L | A | V | Aib | A | Q | A | a | —OH |
| 26 | 18 | Ac— | | Nle | D | V | N | $r8 | T | L | L | F | L | A | $ | A | A | Q | | | —$NH_2$ |
| 27 | 19 | Ac— | | Nle | D | V | N | $ | T | L | L | $ | L | A | V | Q | Aib | Q | A | A | —$NH_2$ |
| 28 | 20 | Ac— | | Nle | D | V | N | $ | T | L | L | $ | L | A | V | Q | A | Q | Aib | A | —$NH_2$ |
| 29 | 21 | Ac— | | Nle | D | V | N | $ | T | L | L | $ | L | A | V | Q | Aib | A | A | A | —$NH_2$ |
| 30 | 22 | Ac— | | Nle | D | V | N | $ | T | L | L | $ | L | A | V | Q | A | A | Aib | A | —$NH_2$ |
| 31 | 23 | Ac— | | Nle | D | V | N | $ | T | L | L | $ | L | A | V | Q | A | Aib | A | A | —$NH_2$ |
| 32 | 24 | Ac— | | Nle | D | V | N | $r8 | T | L | L | F | L | A | $ | A | A | Q | A | A | —$NH_2$ |
| 33 | 25 | Ac— | | Nle | D | V | N | $r8 | T | L | L | F | L | A | $ | A | A | A | A | A | —$NH_2$ |
| 34 | 26 | Ac— | | Nle | D | V | N | $r8 | T | L | L | F | L | A | $ | Q | A | Q | A | A | —$NH_2$ |
| 35 | 27 | Ac— | | Nle | D | V | N | $r8 | T | L | L | F | L | A | $ | Q | A | A | A | A | —$NH_2$ |

AP1—Aileron peptide 1

In the sequences shown above and elsewhere, the following abbreviations are used: "Nle" represents norleucine, "Aib" represents 2-aminoisobutyric acid, "Ac" represents acetyl, and "Pr" represents propionyl. Amino acids represented as "$" are α-Me S5-pentenyl-alanine olefin amino acids connected by an all-carbon crosslinker comprising one double bond. Amino acids represented as "$r5" are α-Me R5-pentenyl-alanine olefin amino acids connected by an all-carbon comprising one double bond. Amino acids represented as "$s8" are α-Me S8-octenyl-alanine olefin amino acids connected by an all-carbon crosslinker comprising one double bond. Amino acids represented as "$r8" are α-Me R8-octenyl-alanine olefin amino acids connected by an all-carbon crosslinker comprising one double bond. "Ahx" represents an aminocyclohexyl linker "%" are α-Me S5-pentenyl-alanine olefin amino acids connected by an all-carbon crosslinker comprising no double bonds (fully saturated alkylene crosslinker). "% r8" are α-Me R8-octenyl-alanine olefin amino acids connected by an all-carbon crosslinker comprising no double bonds (fully saturated alkylene crosslinker). Amino acids represented as "$/" are α-Me S5-pentenyl-alanine olefin amino acids that are not connected by any crosslinker. Amino acids represented as "$/r5" are α-Me R5-pentenyl-alanine olefin amino acids that are not connected by any crosslinker. Amino acids represented as "$/s8" are α-Me S8-octenyl-alanine olefin amino acids that are not connected by any crosslinker. Amino acids represented as "$/r8" are α-Me R8-octenyl-alanine olefin amino acids that are not connected by any crosslinker. Amino acids represented as "Amw" are α-Me tryptophan amino acids. Amino acids represented as "Aml" are α-Me leucine amino acids. Amino acids represented as "Amf" are α-Me phenylalanine amino acids. Amino acids represented as "2ff" are 2-fluoro-phenylalanine amino acids. Amino acids represented as "3ff" are 3-fluoro-phenylalanine amino acids. Amino acids represented as "St" are amino acids comprising two pentenyl-alanine olefin side chains, each of which is crosslinked to another amino acid as indicated. Amino acids represented as "St//" are amino acids comprising two pentenyl-alanine olefin side chains that are not crosslinked. Amino acids represented as "% St" are amino acids comprising two pentenyl-alanine olefin side chains, each of which is crosslinked to another amino acid as indicated via fully saturated hydrocarbon crosslinks. Amino acids represented as "Ba" are β-alanine. The lower-case character "e" or "z" within the designation of a crosslinked amino acid (e.g., "$er8" or "$zr8") represents the configuration of the double bond (E or Z, respectively). In other contexts, lower-case letters such as "a" or "f" represent D amino acids (e.g., D-alanine, or D-phenylalanine, respectively). Amino acids designated as lower case "a" represent D-Alanine. Amino acids designated as "NmW" represent N-methyltryptophan. Amino acids designated as "NmY" represent N-methyltyrosine. Amino acids designated as "NmA" represent N-methylalanine. "Kbio" represents a biotin group attached to the side chain amino group of a lysine residue. Amino acids designated as "Sar" represent sarcosine. Amino acids designated as "Cha" represent cyclohexyl alanine. Amino acids designated as "Cpg" represent cyclopentyl glycine. Amino acids designated as "Chg" represent cyclohexyl glycine. Amino acids designated as "Cba" represent cyclobutyl alanine. Amino acids designated as "F4I" represent 4-iodo phenylalanine. "7L" represents N15 isotopic leucine. Amino acids designated as "F3Cl" represent 3-chloro phenylalanine. Amino acids designated as "F4cooh" represent 4-carboxy phenylalanine. Amino acids designated as "F34F2" represent 3,4-difluoro phenylalanine. Amino acids designated as "6clW" represent 6-chloro tryptophan. Amino acids designated as "$rda6" represent α-Me R6-hexynyl-alanine alkynyl amino acids, crosslinked via a dialkyne bond to a second alkynyl amino acid. Amino acids designated as "$da5" represent α-Me S5-pentynyl-alanine alkynyl amino acids, wherein the alkyne forms one half of a dialkyne bond with a second alkynyl amino acid. Amino acids designated as "$ra9" represent α-Me R9-nonynyl-alanine alkynyl amino acids, crosslinked via an alkyne metathesis reaction with a second alkynyl amino acid. Amino acids designated as "$a6" represent α-Me S6-hexynyl-alanine alkynyl amino acids, crosslinked via an alkyne metathesis reaction with a second alkynyl amino acid. The designation "iso1" or "iso2" indicates that the peptidomimetic macrocycle is a single isomer.

Amino acids designated as "Cit" represent citrulline. Amino acids designated as "Cou4", "Cou6", "Cou7" and "Cou8", respectively, represent the following structures:

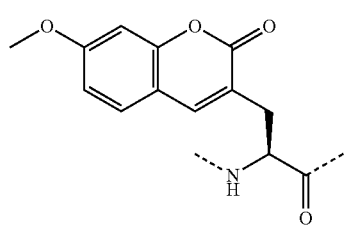
Cou

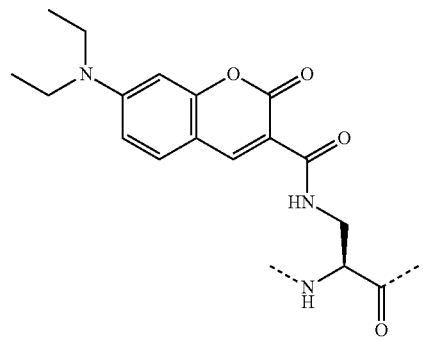
Cou2

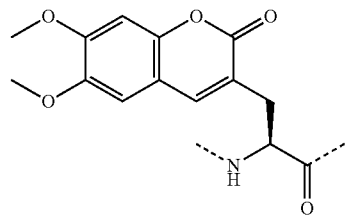
Cou4

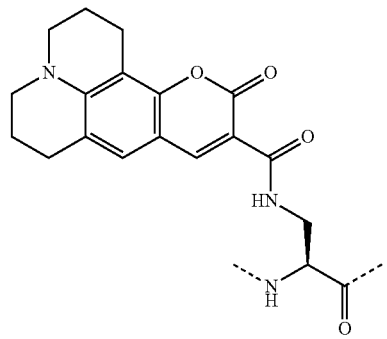
Cou3

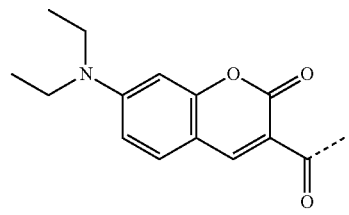
Cou6

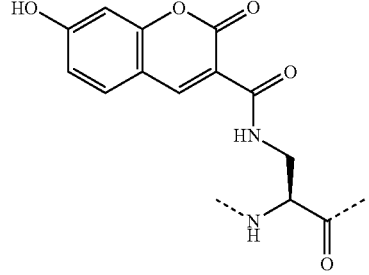
Cou7

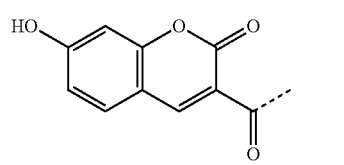
Cou8

In some embodiments, a peptidomimetic macrocycle is obtained in more than one isomer, for example due to the configuration of a double bond within the structure of the crosslinker (E vs Z). Such isomers can or cannot be separable by conventional chromatographic methods. In some embodiments, one isomer has improved biological properties relative to the other isomer. In one embodiment, an E crosslinker olefin isomer of a peptidomimetic macrocycle has better solubility, better target affinity, better in vivo or in vitro efficacy, higher helicity, or improved cell permeability relative to its Z counterpart. In another embodiment, a Z crosslinker olefin isomer of a peptidomimetic macrocycle has better solubility, better target affinity, better in vivo or in vitro efficacy, higher helicity, or improved cell permeability relative to its E counterpart.

In some embodiments, a peptidomimetic macrocycle has the Formula (I):

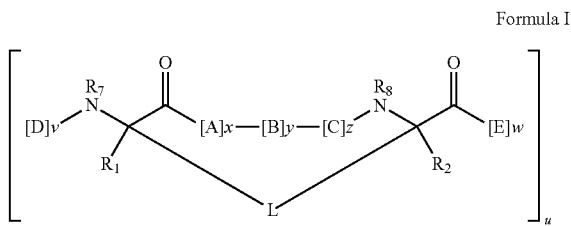

Formula I wherein:
each A, C, D, and E is independently a natural or non-natural amino acid;
B is a natural or non-natural amino acid, amino acid analog,

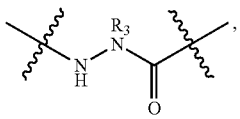

[—NH-$L_3$-CO—], [—NH-$L_3$-$SO_2$—], or [—NH-$L_3$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;
$R_3$ is hydrogen, alkyl, alkenyl, alkynyl, arylalkyl, heteroalkyl, cycloalkyl, heterocycloalkyl, cycloalkylalkyl, aryl, or heteroaryl, optionally substituted with $R_5$;
each L is independently a macrocycle-forming linker;
each $L_3$ is independently alkylene, alkenylene, alkynylene, heteroalkylene, cycloalkylene, heterocycloalkylene, arylene, heteroarylene, or [—$R_4$—K—$R_4$—]$_n$, each being optionally substituted with $R_5$;
each $R_4$ is alkylene, alkenylene, alkynylene, heteroalkylene, cycloalkylene, heterocycloalkylene, arylene, or heteroarylene;
each K is O, S, SO, $SO_2$, CO, $CO_2$, or $CONR_3$;
n is an integer from 1-5;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkyl, cycloalkylalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with an E residue;
each v and w is independently integers from 1-1000, for example 1-500, 1-200, 1-100, 1-50, 1-40, 1-25, 1-20, 1 to 15, or 1 to 10; and
each u, x, y and z is independently integers from 0-10.

In some embodiments, L is a macrocycle-forming linker of the formula -$L_1$-$L_2$-. In some embodiments, $L_1$ and $L_2$ are independently alkylene, alkenylene, alkynylene, heteroalkylene, cycloalkylene, heterocycloalkylene, arylene, heteroarylene, or [—$R_4$—K—$R_4$-]$_n$, each being optionally substituted with $R_5$; each $R_4$ is alkylene, alkenylene, alkynylene, heteroalkylene, cycloalkylene, heterocycloalkylene, arylene, or heteroarylene; each K is O, S, SO, $SO_2$, CO, $CO_2$, or $CONR_3$; and n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments, x+y+z is at least 2. In other embodiments, x+y+z is 1, 2, 3, 4, 5, 6, 7, 8, 9 or 10. Each occurrence of A, B, C, D or E in a macrocycle or macrocycle precursor is independently selected. For example, a sequence represented by the formula [A]$_x$, when x is 3, encompasses embodiments where the amino acids are not identical, e.g., Gln-Asp-Ala as well as embodiments where the amino acids are identical, e.g., Gln-Gln-Gln. This applies for any value of x, y, or z in the indicated ranges. Similarly, when u is greater than 1, each compound may encompass peptidomimetic macrocycles which are the same or different. For example, a compound may comprise peptidomimetic macrocycles comprising different linker lengths or chemical compositions.

In some embodiments, the peptidomimetic macrocycle comprises a secondary structure which is a helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

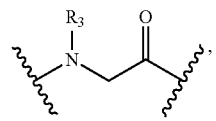

In other embodiments, the length of the macrocycle-forming linker L as measured from a first Cα to a second Cα is selected to stabilize a desired secondary peptide structure, such as a helix formed by residues of the peptidomimetic macrocycle including, but not necessarily limited to, those between the first Cα to a second Cα.

In some embodiments, a peptidomimetic macrocycle of Formula (I) has Formula (Ic):

Formula (Ic)

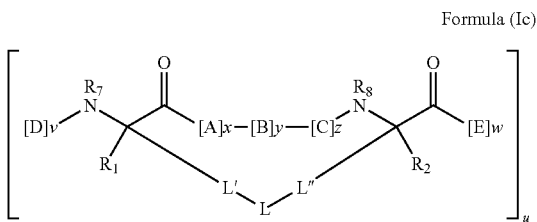

wherein:
each A, C, D, and E is independently a natural or non-natural amino acid;
each B is independently a natural or non-natural amino acid, amino acid analog,

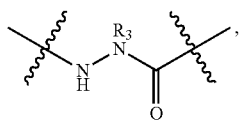

[—NH-$L_3$-CO—], [—NH-$L_3$-$SO_2$—], or [—NH-$L_3$-];
each L is independently a macrocycle-forming linker;
each L' is independently alkylene, alkenylene, alkynylene, heteroalkylene, cycloalkylene, heterocycloalkylene, arylene, or heteroarylene, each being optionally substituted with $R_5$, or a bond, or together with $R_1$ and the atom to which both $R_1$ and L' are bound forms a ring;
each L" is independently alkylene, alkenylene, alkynylene, heteroalkylene, cycloalkylene, heterocycloalkylene, arylene, or heteroarylene, each being optionally substituted with $R_5$, or a bond, or together with $R_2$ and the atom to which both $R_2$ and L" are bound forms a ring;
each $R_1$ is independently —H, alkyl, alkenyl, alkynyl, arylalkyl, cycloalkyl, cycloalkylalkyl, heteroalkyl, or heterocycloalkyl, unsubstituted or substituted with halo-, or together with L' and the atom to which both $R_1$ and L' are bound forms a ring;
each $R_2$ is independently —H, alkyl, alkenyl, alkynyl, arylalkyl, cycloalkyl, cycloalkylalkyl, heteroalkyl, or heterocycloalkyl, unsubstituted or substituted with halo-, or together with L" and the atom to which both $R_2$ and L" are bound forms a ring;
$R_3$ is hydrogen, alkyl, alkenyl, alkynyl, arylalkyl, heteroalkyl, cycloalkyl, heterocycloalkyl, cycloalkylalkyl, aryl, or heteroaryl, optionally substituted with $R_5$;
each $L_3$ is independently alkylene, alkenylene, alkynylene, heteroalkylene, cycloalkylene, heterocycloalkylene, arylene, heteroarylene, or [—$R_4$—K-R4-]$_n$, each being optionally substituted with $R_5$;
each $R_4$ is alkylene, alkenylene, alkynylene, heteroalkylene, cycloalkylene, heterocycloalkylene, arylene, or heteroarylene;
each K is O, S, SO, $SO_2$, CO, $CO_2$, or $CONR_3$;
n is an integer from 1-5;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with an E residue;
each v and w is independently an integer from 1-1000, for example 1-500, 1-200, 1-100, 1-50, 1-40, 1-25, 1-20, 1-15, or 1-10; and
each u, x, y and z is independently an integer from 0-10.

In some embodiments, L is a macrocycle-forming linker of the formula -$L_1$-$L_2$-. In some embodiments, $L_1$ and $L_2$ are independently alkylene, alkenylene, alkynylene, heteroalkylene, cycloalkylene, heterocycloalkylene, arylene, heteroarylene, or [—$R_4$—K—$R_4$—]$_n$, each being optionally substituted with $R_5$; each $R_4$ is alkylene, alkenylene, alkynylene, heteroalkylene, cycloalkylene, heterocycloalkylene, arylene, or heteroarylene; each K is O, S, SO, $SO_2$, CO, $CO_2$, or $CONR_3$; and n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments, x+y+z is at least 2. In other embodiments, x+y+z is 1, 2, 3, 4, 5, 6, 7, 8, 9 or 10. Each occurrence of A, B, C, D or E in a macrocycle or macrocycle precursor is independently selected. For example, a sequence represented by the formula [A]$_x$, when x is 3, encompasses embodiments where the amino acids are not identical, e.g., Gln-Asp-Ala as well as embodiments where the amino acids are identical, e.g., Gln-Gln-Gln. This applies for any value of x, y, or z in the indicated ranges. Similarly, when u is greater than 1, each compound may encompass peptidomimetic macrocycles which are the same or different. For example, a compound may comprise peptidomimetic macrocycles comprising different linker lengths or chemical compositions.

In some embodiments, the peptidomimetic macrocycle comprises a secondary structure which is a helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

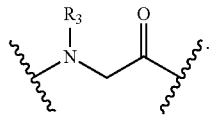

In other embodiments, the length of the macrocycle-forming linker L as measured from a first Cα to a second Cα is selected to stabilize a desired secondary peptide structure, such as a helix formed by residues of the peptidomimetic macrocycle including, but not necessarily limited to, those between the first Cα to a second Cα.

In some embodiments, the peptidomimetic macrocycle of Formula (I) has the Formula:

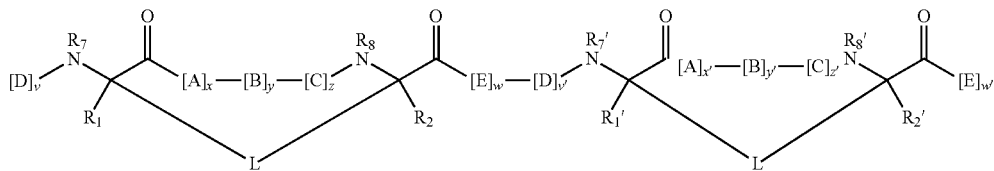

wherein each A, C, D, and E is independently an amino acid; each B is independently an amino acid,

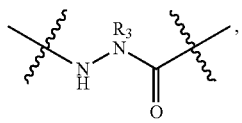

[—NH-L$_3$-CO—], [—NH-L$_3$-SO$_2$—], or [—NH-L$_3$-];

L' is a macrocycle-forming linker of the formula -L$_1$'-L$_2$'-;
and wherein A, B, C, D, and E, taken together with the crosslinked amino acids connected by the macrocycle-forming linkers L and L', form the amino acid sequence of the peptidomimetic macrocycle;

R$_1$' and R$_2$' are independently —H, alkyl, alkenyl, alkynyl, arylalkyl, cycloalkyl, cycloalkylalkyl, heteroalkyl, or heterocycloalkyl, unsubstituted or substituted with halo-;

L$_1$' and L$_2$' and L$_3$ are independently alkylene, alkenylene, alkynylene, heteroalkylene, cycloalkylene, heterocloalkylene, arylene, heteroarylene, or [—R$_4$—K—R$_4$—]$_n$, each being optionally substituted with R$_5$;

each K is independently O, S, SO, SO$_2$, CO, CO$_2$, or CONR$_3$;

R$_7$' is —H, alkyl, alkenyl, alkynyl, arylalkyl, cycloalkyl, heteroalkyl, cycloalkylalkyl, heterocycloalkyl, aryl, or heteroaryl, optionally substituted with R$_5$, or part of a cyclic structure with a D residue;

R$_8$' is —H, alkyl, alkenyl, alkynyl, arylalkyl, cycloalkyl, heteroalkyl, cycloalkylalkyl, heterocycloalkyl, aryl, or heteroaryl, optionally substituted with R$_5$, or part of a cyclic structure with an E residue;

v' and w' are independently integers from 1-1000, for example 1-500, 1-200, 1-100, 1-50, 1-40, 1-25, 1-20, 1 to 15, or 1 to 10;

x', y' and z' are independently integers from 0-10; and n is an integer from 1-5. In some embodiments, the sum of x'+y'+z' is 2, 3 or 6, for example 3 or 6.

In one embodiment, the peptidomimetic macrocycle of Formula (I) is Formula (Ia):

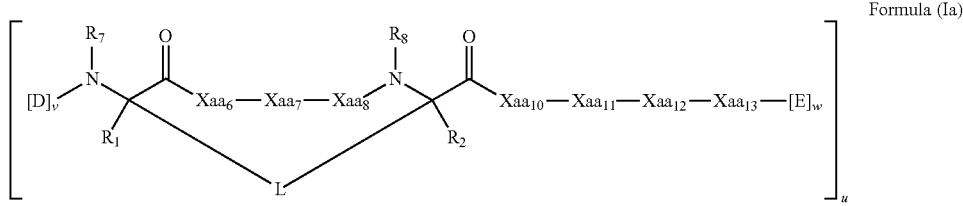

Formula (Ia)

or a pharmaceutically-acceptable salt thereof wherein: each of Xaa$_6$, Xaa$_7$, Xaa$_8$, Xaa$_{10}$, Xaa$_{11}$, Xaa$_{12}$, and Xaa$_{13}$ is independently an amino acid, wherein at least three, four, five, or each of Xaa$_6$, Xaa$_7$, Xaa$_8$, Xaa$_{10}$, Xaa$_{11}$, Xaa$_{12}$, are the same amino acid as the amino acid at the corresponding position of the sequence X$_5$-Thr$_6$-Leu$_7$-Leu$_8$-X$_9$-Lue$_{10}$-Lys$_{11}$/Ala$_{11}$-Val$_{12}$/Ala$_{12}$, where each of X$_5$ and X$_9$ is independently an amino acid (SEQ ID NO: 1).

In some embodiments, the peptidomimetic macrocycle of Formula (Ia) is Formula (Ia-1):

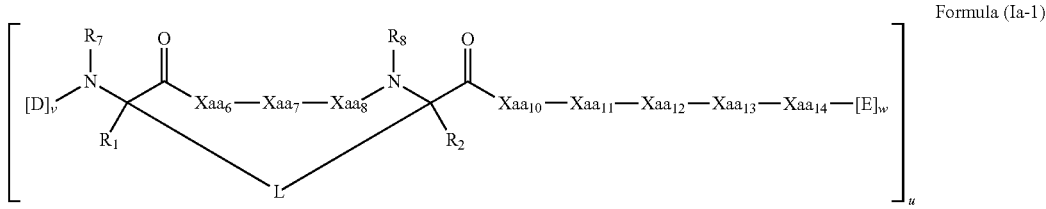

Formula (Ia-1)

or a pharmaceutically-acceptable salt thereof, wherein each $Xaa_{14}$ is independently an amino acid.

In some embodiments, the peptidomimetic macrocycle of Formula (Ia) is Formula (Ia-2):

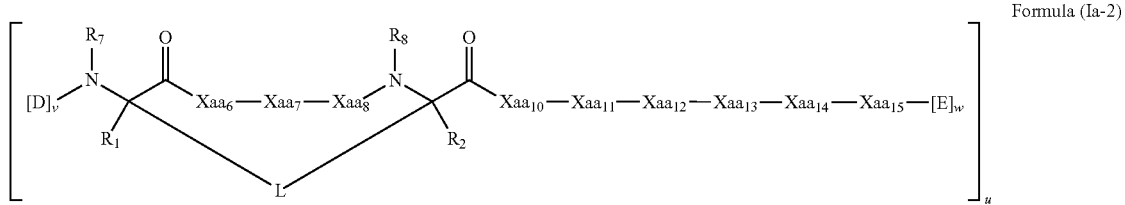

Formula (Ia-2)

or a pharmaceutically-acceptable salt thereof, wherein each $Xaa_{14}$ and $Xaa_{15}$ is independently an amino acid.

In one embodiment, the peptidomimetic macrocycle of Formula (I) is Formula (Ib):

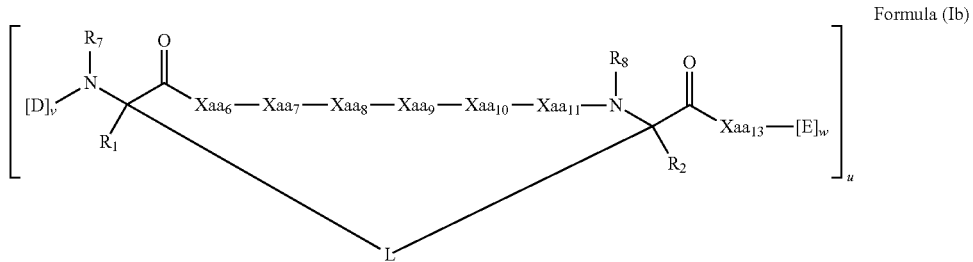

Formula (Ib)

or a pharmaceutically-acceptable salt thereof, wherein: each of $Xaa_6$, $Xaa_7$, $Xaa_8$, $Xaa_9$, $Xaa_{10}$, $Xaa_{11}$ and $Xaa_{13}$ is independently an amino acid, wherein at least three, four, five, or each of $Xaa_6$, $Xaa_7$, $Xaa_8$, $Xaa_9$, $Xaa_{10}$, and $Xaa_{11}$ are the same amino acid as the amino acid at the corresponding position of the sequence $X_5$-$Thr_6$-$Leu_7$-$Leu_8$-$Phe_9$-$Leu_{10}$-$Lys_{11}/Ala_{11}$-$X_{12}$, where each of $X_5$ and $X_{12}$ is independently an amino acid (SEQ ID NO: 2).

In some embodiments, the peptidomimetic macrocycle of Formula (Ib) is Formula (Ib-1):

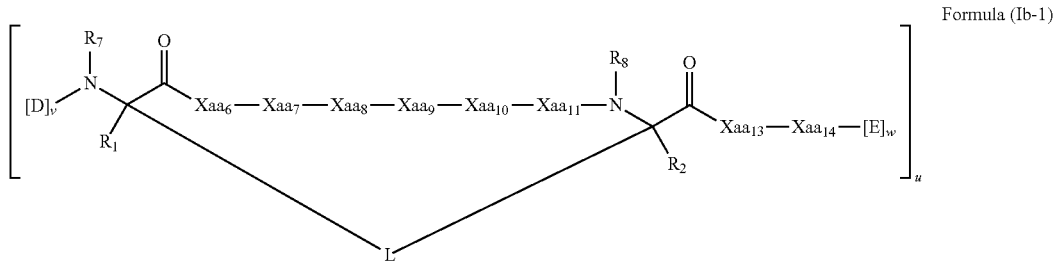

Formula (Ib-1)

or a pharmaceutically-acceptable salt thereof, wherein each $Xaa_{14}$ is independently an amino acid.

In some embodiments, the peptidomimetic macrocycle of Formula (Ib) is Formula (Ib-2):

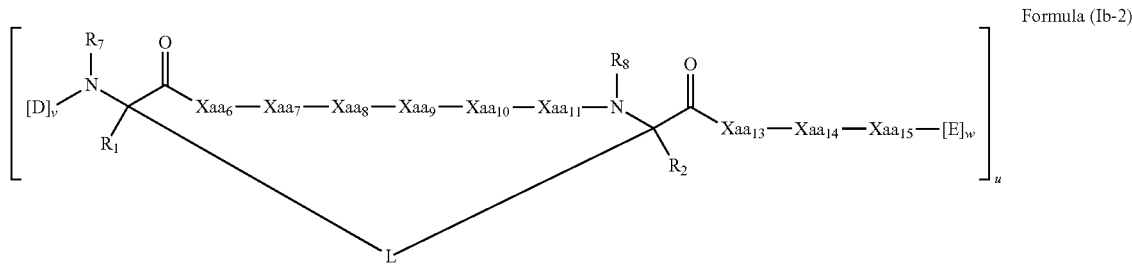

Formula (Ib-2)

or a pharmaceutically-acceptable salt thereof, wherein each $Xaa_{14}$ and $Xaa_{15}$ is independently an amino acid.

In one embodiment, the peptidomimetic macrocycle of Formula (I) is:

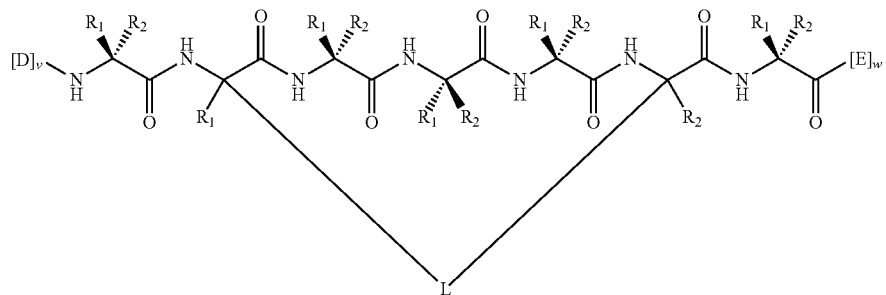

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the peptidomimetic macrocycle comprises a structure of Formula (I) which is:

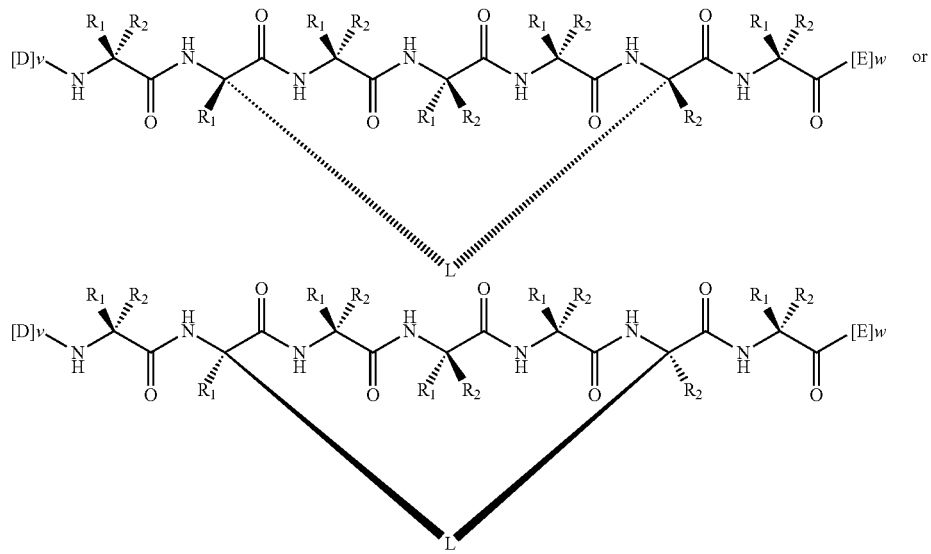

In other embodiments, the peptidomimetic macrocycle of Formula (I) is a compound of any of the formulas shown below:

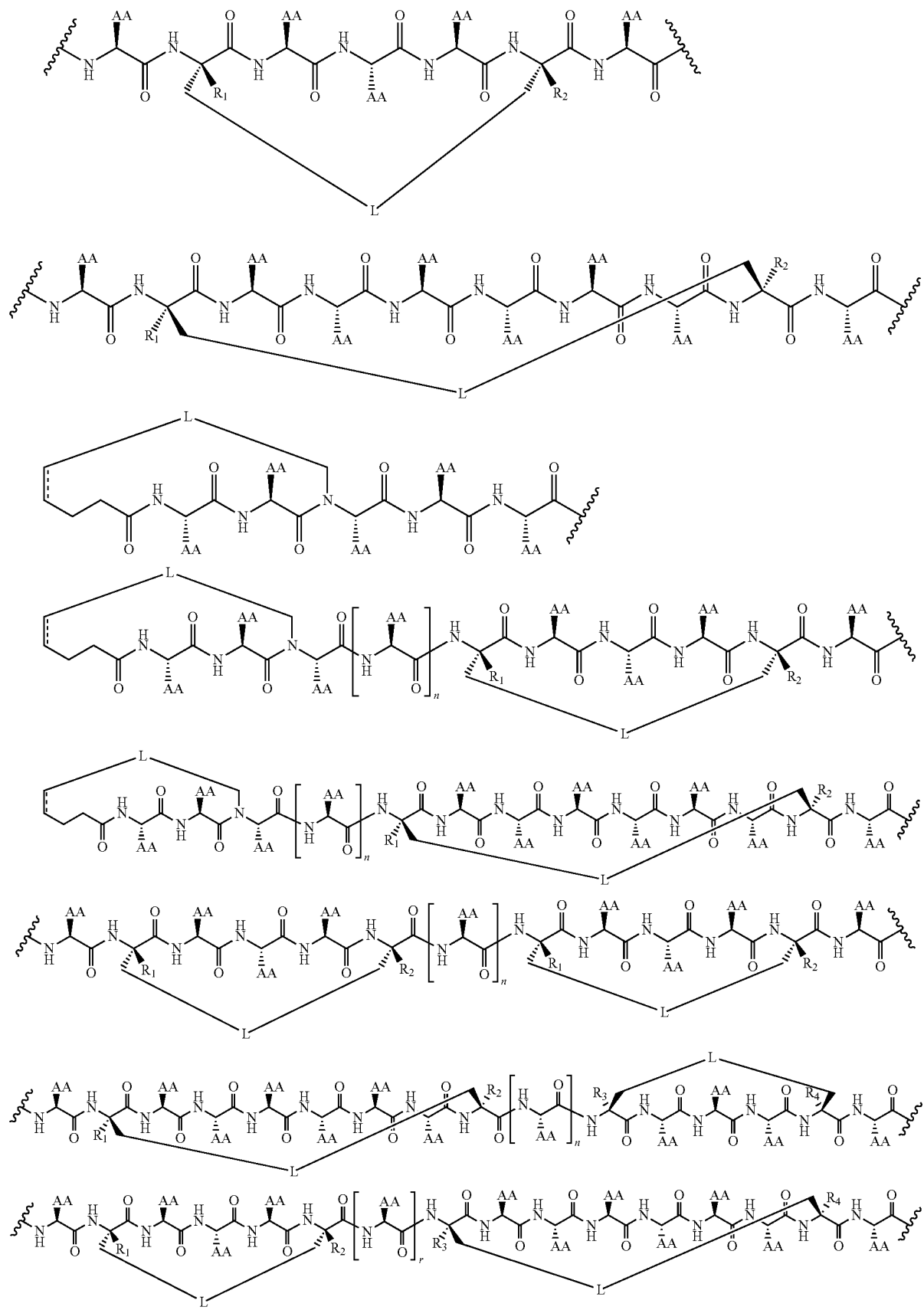

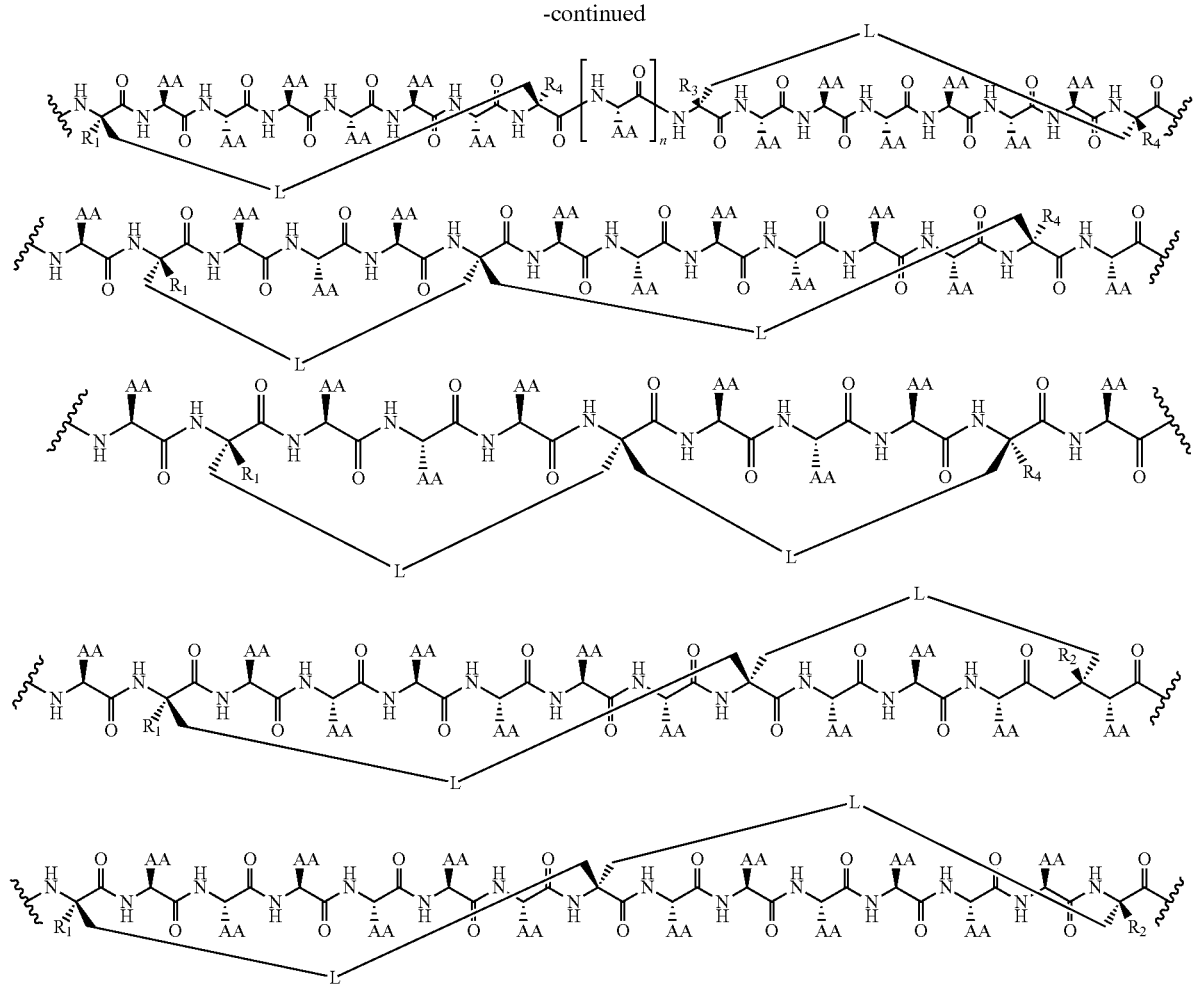

wherein "AA" represents any natural or non-natural amino acid side chain and "⌇" is [D]$_v$, [E]$_w$ as defined above, and n is an integer between 0 and 20, 50, 100, 200, 300, 400 or 500. In some embodiments, the substituent "n" shown in the preceding paragraph is 0. In other embodiments, the substituent "n" shown in the preceding paragraph is less than 50, 40, 30, 20, 10, or 5.

Exemplary embodiments of the macrocycle-forming linker L are shown below.

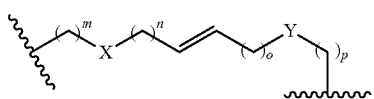

where X, Y = —CH$_2$—, O, S, or NH m, n, o, p = 0-10

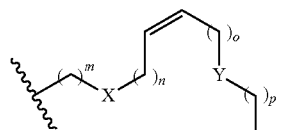

where X, Y = —CH$_2$—, O, S, or NH m, n, o, p = 0-10

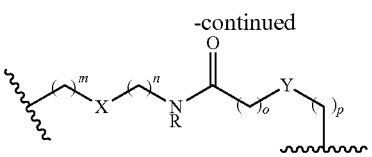

where X, Y = —CH$_2$—, O, S, or NH m, n, o, p = 0-10

R = H, alkyl, other substituent

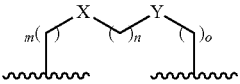

where X, Y = —CH$_2$—, O, S, or NH m, n, o, p = 0-10

In some embodiments, the peptidomimetic macrocycles have the Formula (I):

Formula (I)

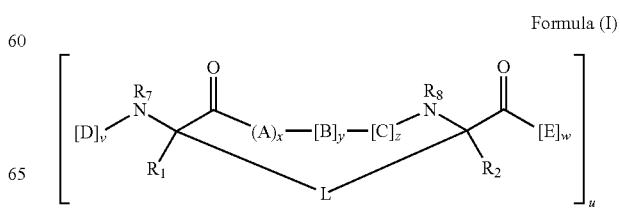

wherein:
each A, C, D, and E is independently a natural or non-natural amino acid;
each B is independently a natural or non-natural amino acid, amino acid analog,

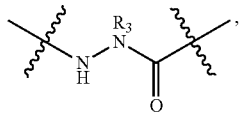

[—NH-L₃-CO—], [—NH-L₃-SO₂—], or [—NH-L₃-];
each R₁ and R₂ is independently —H, alkyl, alkenyl, alkynyl, arylalkyl, cycloalkyl, cycloalkylalkyl, heteroalkyl, or heterocycloalkyl, unsubstituted or substituted with halo-;
each R₃ is independently hydrogen, alkyl, alkenyl, alkynyl, arylalkyl, heteroalkyl, cycloalkyl, heterocycloalkyl, cycloalkylalkyl, aryl, or heteroaryl, optionally substituted with R₅;
each L is independently macrocycle-forming linker of the formula

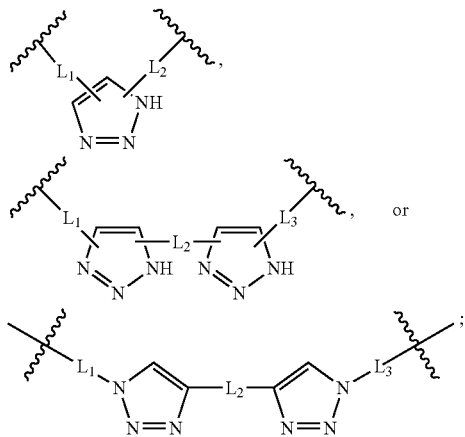

each L₁, L₂ and L₃ is independently alkylene, alkenylene, alkynylene, heteroalkylene, cycloalkylene, heterocycloalkylene, arylene, heteroarylene, or [—R₄—K—R₄—]ₙ, each being optionally substituted with R₅;
each R₄ is alkylene, alkenylene, alkynylene, heteroalkylene, cycloalkylene, heterocycloalkylene, arylene, or heteroarylene;
each K is independently O, S, SO, SO₂, CO, CO₂, or CONR₃;
each R₅ is independently halogen, alkyl, —OR₆, —N(R₆)₂, —SR₆, —SOR₆, —SO₂R₆, —CO₂R₆, a fluorescent moiety, a radioisotope or a therapeutic agent;
each R₆ is independently —H, alkyl, alkenyl, alkynyl, arylalkyl, cycloalkylalkyl, heterocycloalkyl, a fluorescent moiety, a radioisotope or a therapeutic agent;
each R₇ is independently —H, alkyl, alkenyl, alkynyl, arylalkyl, cycloalkyl, heteroalkyl, cycloalkylalkyl, heterocycloalkyl, aryl, or heteroaryl, optionally substituted with R₅, or part of a cyclic structure with a D residue;
each R₈ is independently —H, alkyl, alkenyl, alkynyl, arylalkyl, cycloalkyl, heteroalkyl, cycloalkylalkyl, heterocycloalkyl, aryl, or heteroaryl, optionally substituted with R₅, or part of a cyclic structure with an E residue;
each v and w is independently an integer from 1-1000;
each u, x, y and z is independently integers from 0-10; and
n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments, x+y+z is at least 2. In other embodiments, x+y+z is 1, 2, 3, 4, 5, 6, 7, 8, 9 or 10. Each occurrence of A, B, C, D or E in a macrocycle or macrocycle precursor is independently selected. For example, a sequence represented by the formula $[A]_x$, when x is 3, encompasses embodiments where the amino acids are not identical, e.g., Gln-Asp-Ala as well as embodiments where the amino acids are identical, e.g., Gln-Gln-Gln. This applies for any value of x, y, or z in the indicated ranges.

In some embodiments, each of the first two amino acid represented by E comprises an uncharged side chain or a negatively charged side chain. In some embodiments, each of the first three amino acid represented by E comprises an uncharged side chain or a negatively charged side chain. In some embodiments, each of the first four amino acid represented by E comprises an uncharged side chain or a negatively charged side chain. In some embodiments, one or more or each of the amino acid that is i+1, i+2, i+3, i+4, i+5, and/or i+6 with respect to $Xaa_{13}$ represented by E comprises an uncharged side chain or a negatively charged side chain.

In some embodiments, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some embodiments, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain. In some embodiments, one or more or each of the amino acid that is i+1, i+2, i+3, i+4, i+5, and/or i+6 with respect to $Xaa_{13}$ represented by E comprises an uncharged side chain or a negatively charged side chain.

In some embodiments, w is between 1 and 1000. For example, the first amino acid represented by E comprises a small hydrophobic side chain. In some embodiments, w is between 2 and 1000. For example, the second amino acid represented by E comprises a small hydrophobic side chain. In some embodiments, w is between 3 and 1000. For example, the third amino acid represented by E comprises a small hydrophobic side chain. For example, the third amino acid represented by E comprises a small hydrophobic side chain. In some embodiments, w is between 4 and 1000. In some embodiments, w is between 5 and 1000. In some embodiments, w is between 6 and 1000. In some embodiments, w is between 7 and 1000. In some embodiments, w is between 8 and 1000.

In some embodiments, the peptidomimetic macrocycle comprises a secondary structure which is a helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

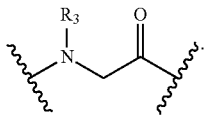

In other embodiments, the length of the macrocycle-forming linker L as measured from a first Cα to a second Cα is selected to stabilize a desired secondary peptide structure, such as a helix formed by residues of the peptidomimetic macrocycle including, but not necessarily limited to, those between the first Cα to a second Cα.

In some embodiments, L is a macrocycle-forming linker of the formula

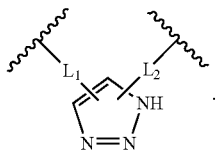

In some embodiments, L is a macrocycle-forming linker of the formula

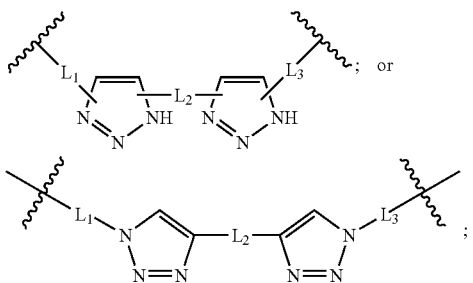

or a tautomer thereof.

Exemplary embodiments of the macrocycle-forming linker L are shown below.

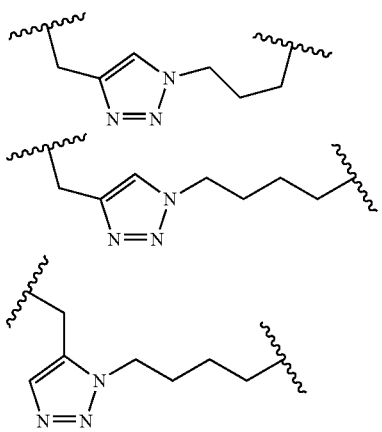

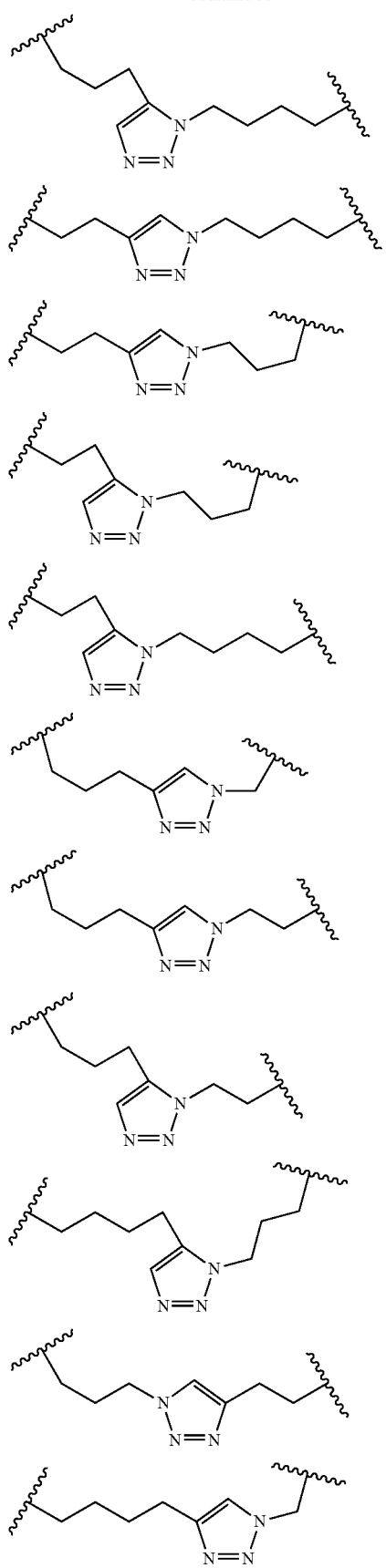

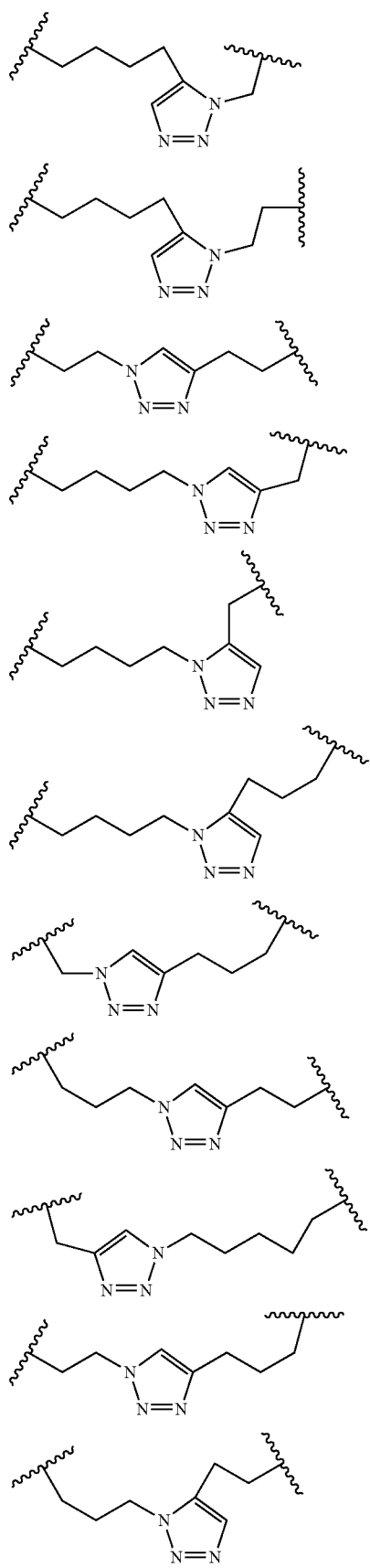
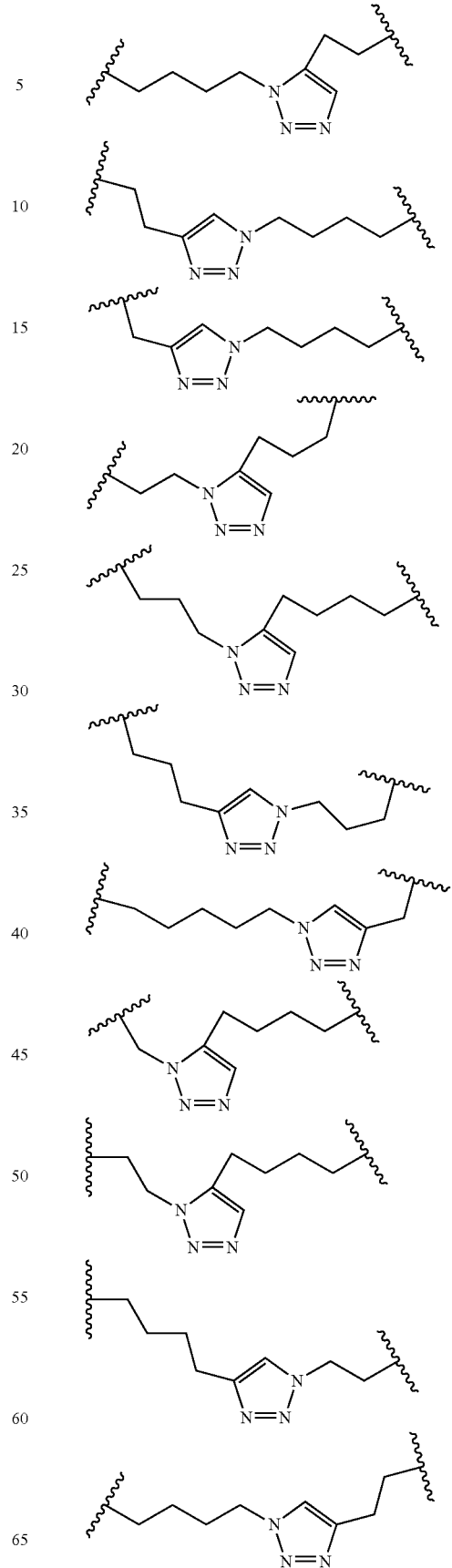

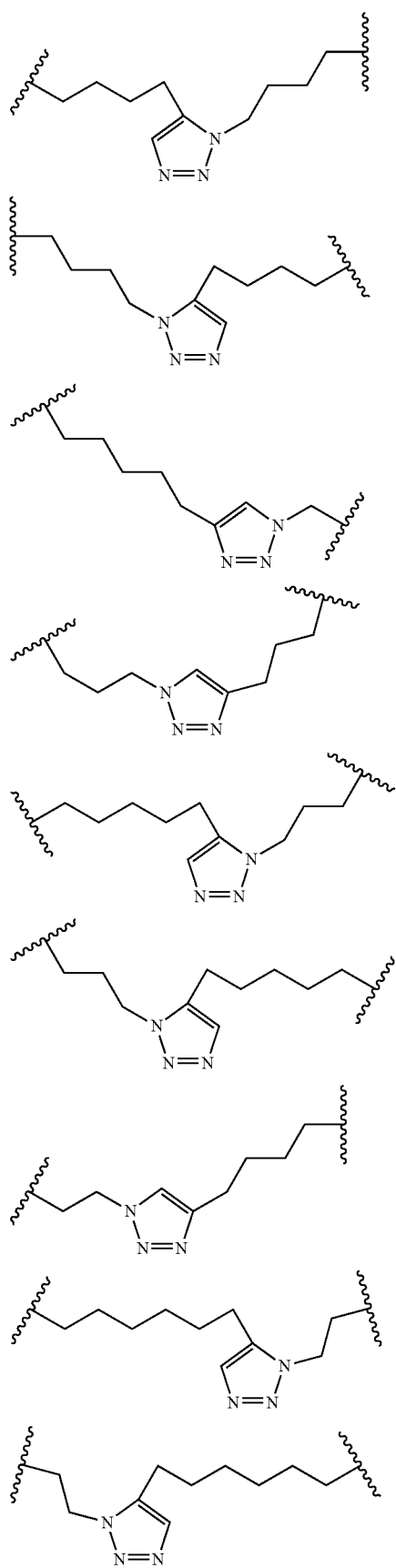
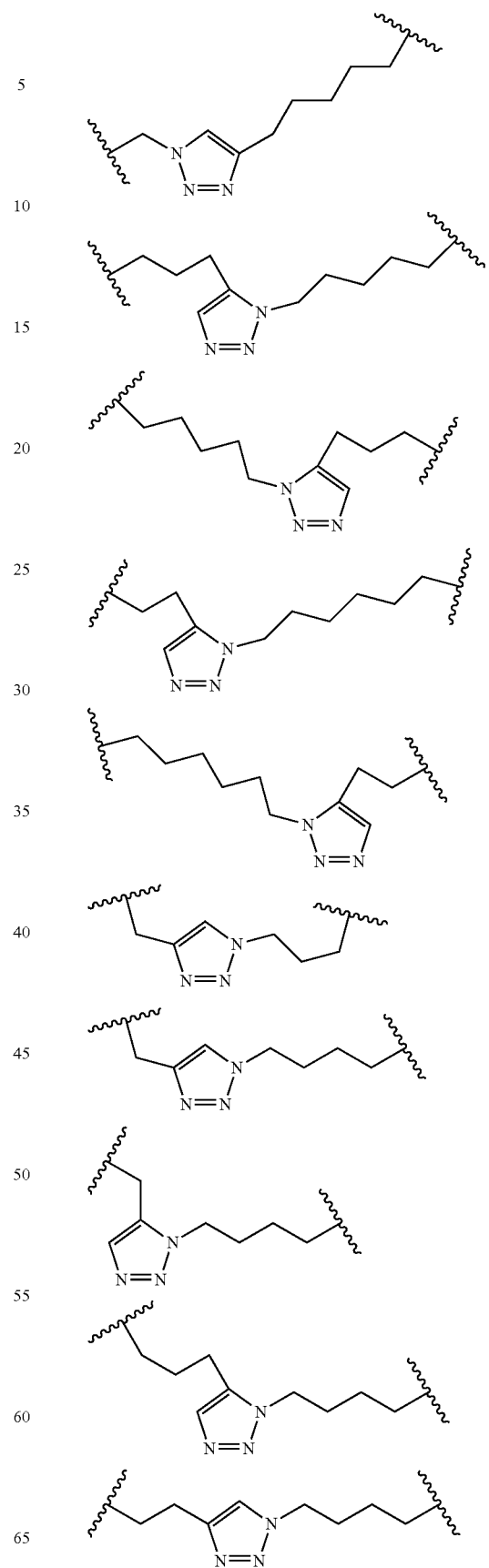

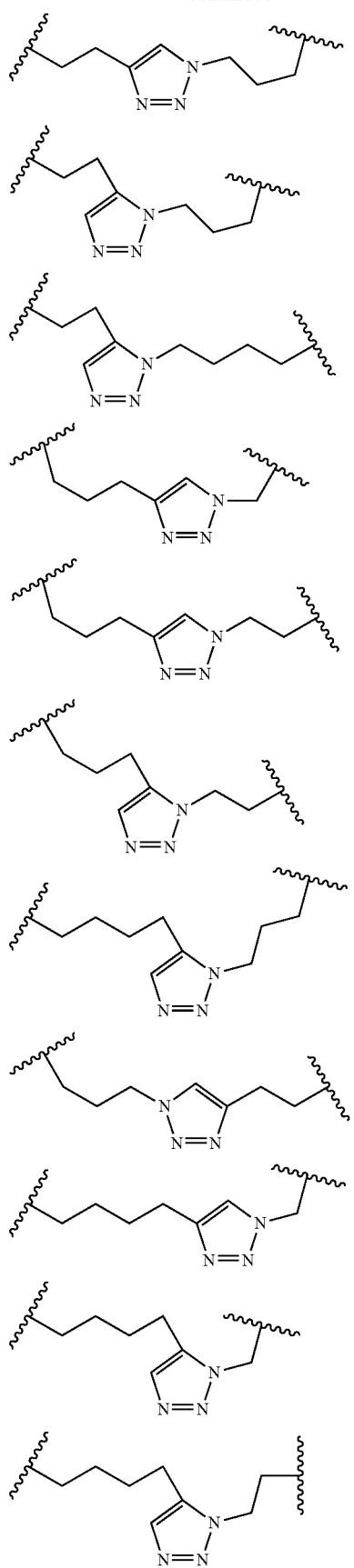
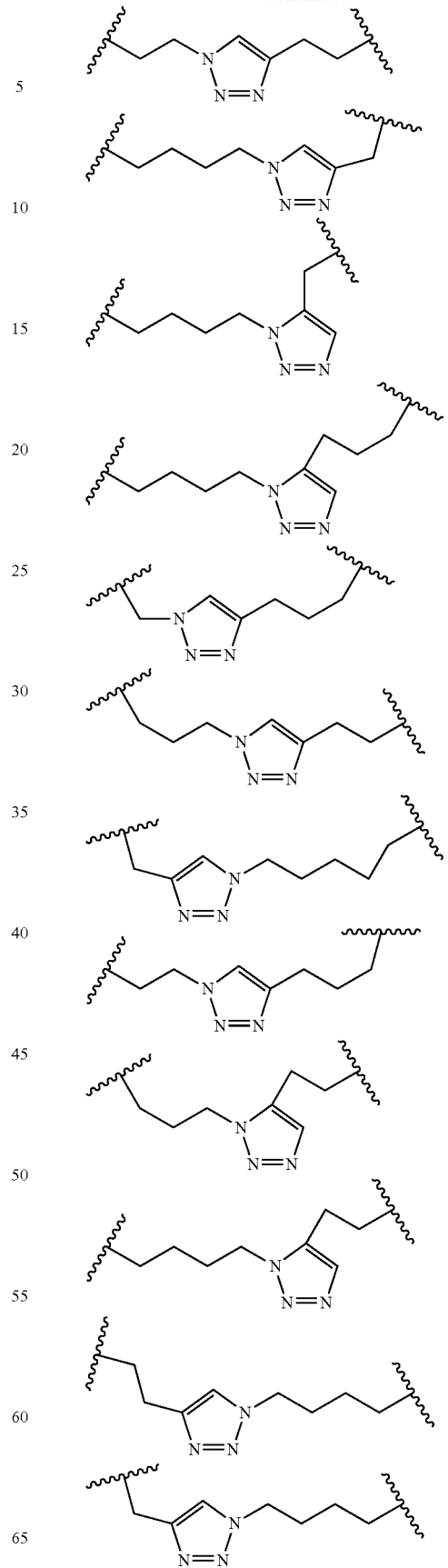

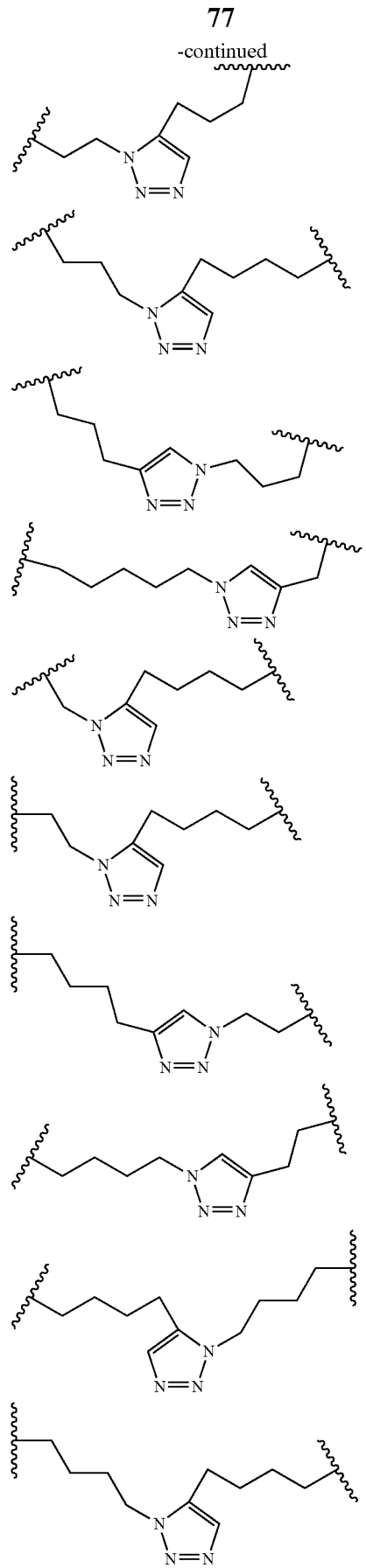
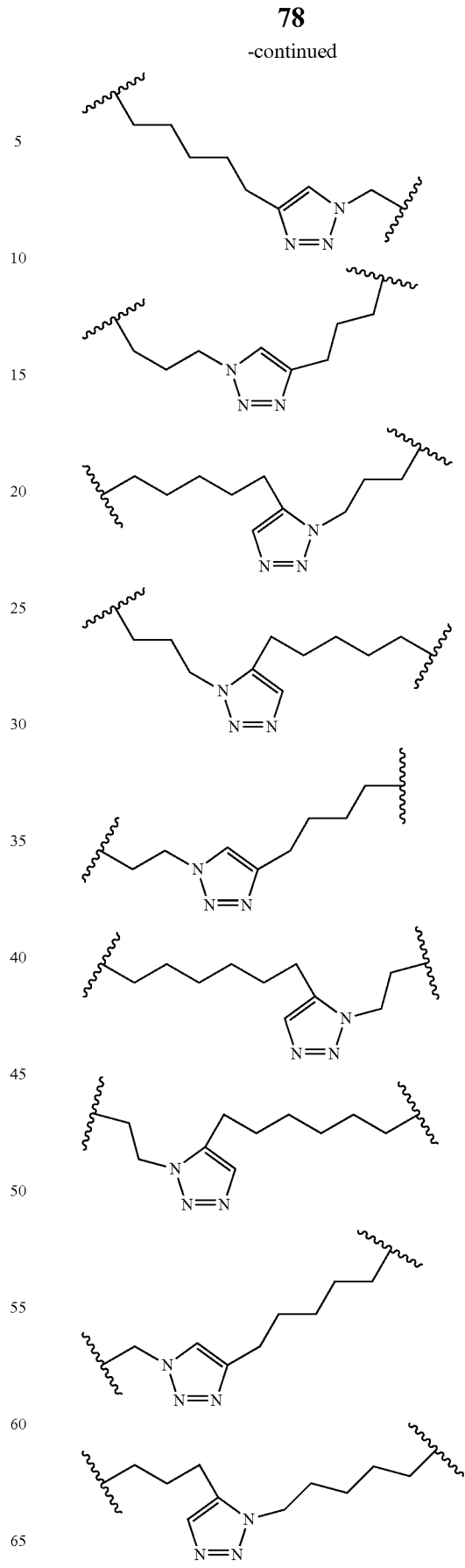

79
-continued
80
-continued
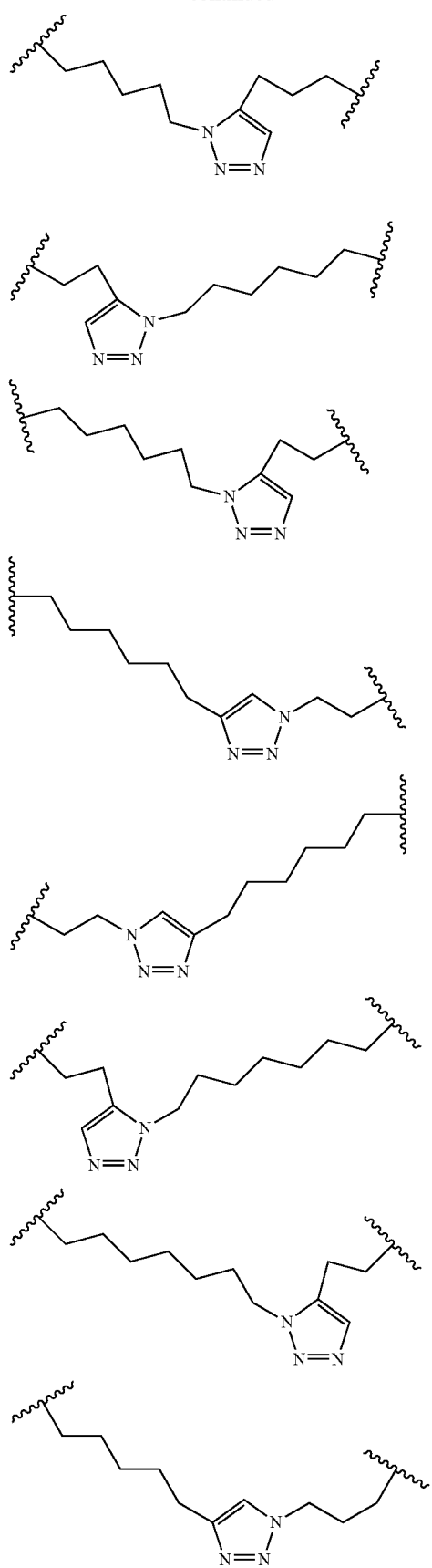
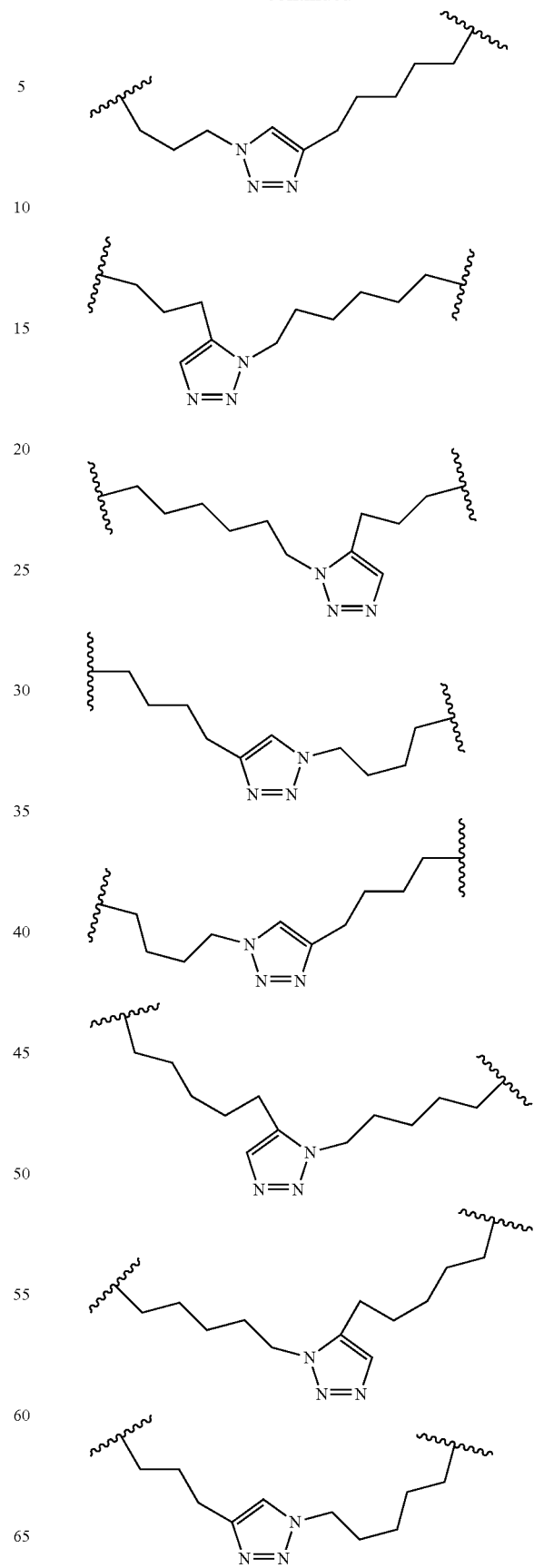

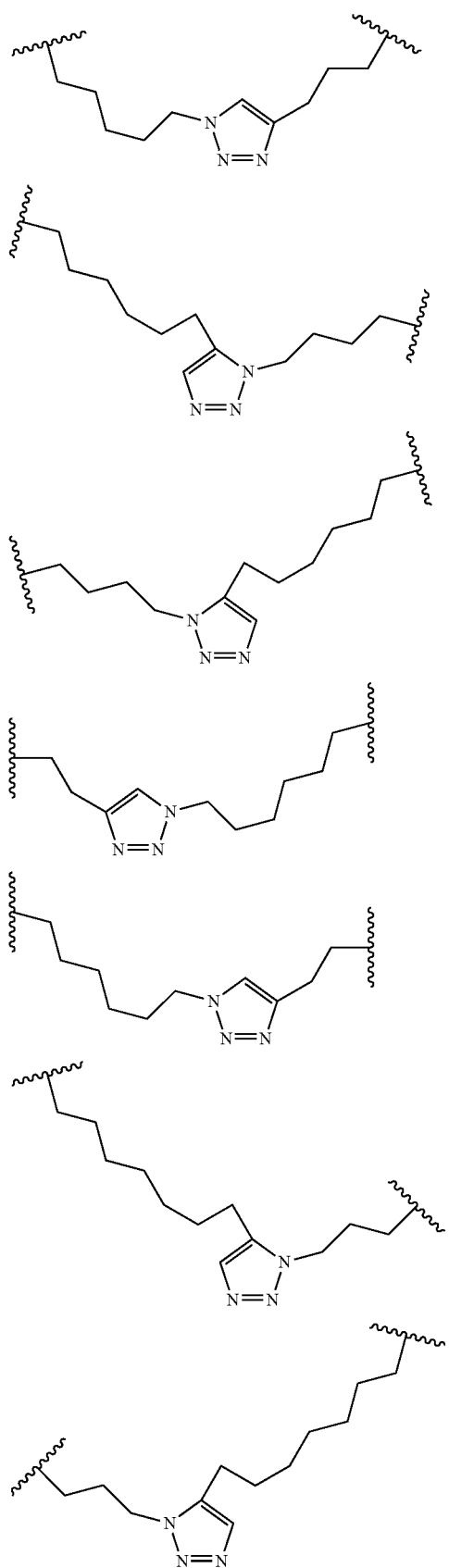
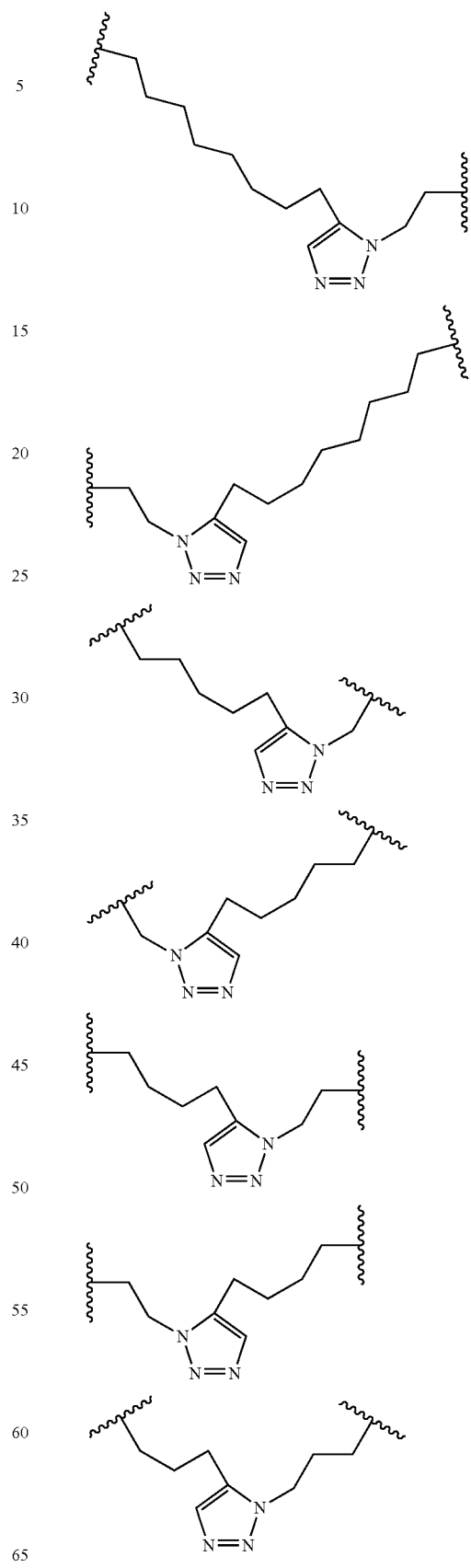

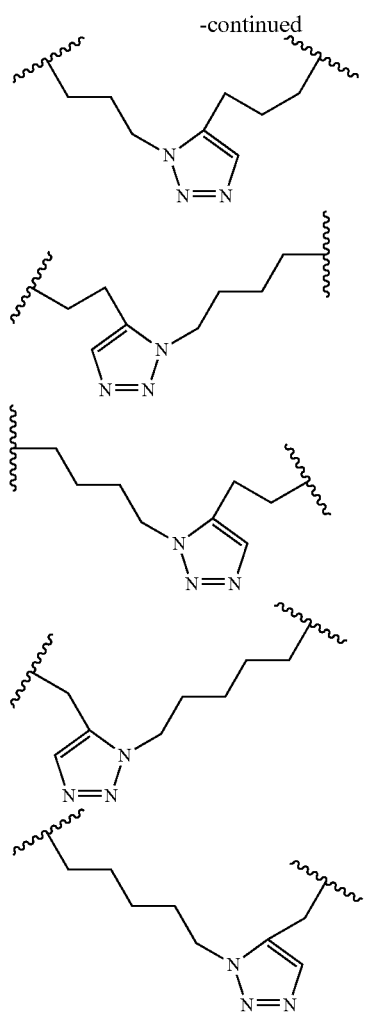

Amino acids which are used in the formation of triazole crosslinkers are represented according to the legend indicated below. Stereochemistry at the α position of each amino acid is S unless otherwise indicated. For azide amino acids, the number of carbon atoms indicated refers to the number of methylene units between the α-carbon and the terminal azide. For alkyne amino acids, the number of carbon atoms indicated is the number of methylene units between the α position and the triazole moiety plus the two carbon atoms within the triazole group derived from the alkyne.

$5a5$ α-Me alkyne 1,5 triazole (5 carbon)
$5n3$ α-Me azide 1,5 triazole (3 carbon)
$4rn6$ α-Me R-azide 1,4 triazole (6 carbon)
$4a5$ α-Me alkyne 1,4 triazole (5 carbon)

In other embodiments, the invention provides peptidomimetic macrocycles of Formula (III):

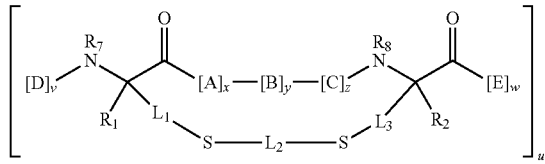

Formula (III)

wherein:
each A, C, D, and E is independently a natural or non-natural amino acid;
each B is independently a natural or non-natural amino acid, amino acid analog,

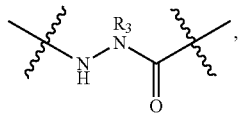

[—NH-L$_4$-CO—], [—NH-L$_4$-SO$_2$—], or [—NH-L$_4$-];
each R$_1$ and R$_2$ is independently —H, alkyl, alkenyl, alkynyl, arylalkyl, cycloalkyl, cycloalkylalkyl, heteroalkyl, or heterocycloalkyl, unsubstituted or substituted with halo-;
each R$_3$ is independently hydrogen, alkyl, alkenyl, alkynyl, arylalkyl, heteroalkyl, cycloalkyl, heterocycloalkyl, cycloalkylalkyl, aryl, or heteroaryl, unsubstituted or substituted with R$_5$;
each L$_1$, L$_2$, L$_3$ and L$_4$ is independently alkylene, alkenylene, alkynylene, heteroalkylene, cycloalkylene, heterocycloalkylene, arylene, heteroarylene or [—R$_4$—K—R$_4$—]$_n$, each being unsubstituted or substituted with R$_5$;
each K is independently O, S, SO, SO$_2$, CO, CO$_2$, or CONR$_3$;
each R$_4$ is independently alkylene, alkenylene, alkynylene, heteroalkylene, cycloalkylene, heterocycloalkylene, arylene, or heteroarylene;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;
each R$_6$ is independently —H, alkyl, alkenyl, alkynyl, arylalkyl, cycloalkylalkyl, heterocycloalkyl, a fluorescent moiety, a radioisotope or a therapeutic agent;
each R$_7$ is independently —H, alkyl, alkenyl, alkynyl, arylalkyl, cycloalkyl, heteroalkyl, cycloalkylalkyl, heterocycloalkyl, aryl, or heteroaryl, unsubstituted or substituted with R$_5$, or part of a cyclic structure with a D residue;
each R$_8$ is independently —H, alkyl, alkenyl, alkynyl, arylalkyl, cycloalkyl, heteroalkyl, cycloalkylalkyl, heterocycloalkyl, aryl, or heteroaryl, unsubstituted or substituted with R$_5$, or part of a cyclic structure with an E residue;
each v and w is independently an integer from 1-1000;
each u, x, y and z is independently an integer from 0-10; and
n is an integer from 1-5.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments, x+y+z is at least 2. In other embodiments, x+y+z is 3, 4, 5, 6, 7, 8, 9 or 10. Each occurrence of A, B, C, D or E in a macrocycle or macrocycle precursor is independently selected. For example, a sequence represented by the formula [A]$_x$, when x is 3, encompasses embodiments where the amino acids are not identical, e.g., Gln-Asp-Ala as well as embodiments where the amino acids are identical, e.g., Gln-Gln-Gln. This applies for any value of x, y, or z in the indicated ranges.

In some embodiments, each of the first two amino acid represented by E comprises an uncharged side chain or a negatively charged side chain. In some embodiments, each of the first three amino acid represented by E comprises an uncharged side chain or a negatively charged side chain. In some embodiments, each of the first four amino acid represented by E comprises an uncharged side chain or a negatively charged side chain.

In some embodiments, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some embodiments, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain.

In some embodiments, w is between 1 and 1000. For example, the first amino acid represented by E comprises a small hydrophobic side chain. In some embodiments, w is between 2 and 1000. For example, the second amino acid represented by E comprises a small hydrophobic side chain. In some embodiments, w is between 3 and 1000. For example, the third amino acid represented by E comprises a small hydrophobic side chain. For example, the third amino acid represented by E comprises a small hydrophobic side chain. In some embodiments, w is between 4 and 1000. In some embodiments, w is between 5 and 1000. In some embodiments, w is between 6 and 1000. In some embodiments, w is between 7 and 1000. In some embodiments, w is between 8 and 1000.

In some embodiments, the peptidomimetic macrocycle comprises a secondary structure which is a helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

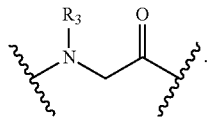

In other embodiments, the length of the macrocycle-forming linker [-L$_1$-S-L$_2$-S-L$_3$-] as measured from a first Cα to a second Cα is selected to stabilize a desired secondary peptide structure, such as a helix (including, but not limited to a $3_{10}$ helix or an α-helix) formed by residues of the peptidomimetic macrocycle including, but not necessarily limited to, those between the first Cα to a second Cα.

Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985. In some embodiments, the thiol moieties are the side chains of the amino acid residues L-cysteine, D-cysteine, α-methyl-L-cysteine, α-methyl-D-cysteine, L-homocysteine, D-homocysteine, α-methyl-L-homocysteine or α-methyl-D-homocysteine. A bis-alkylating reagent is of the general formula X-L$_2$-Y wherein L$_2$ is a linker moiety and X and Y are leaving groups that are displaced by —SH moieties to form bonds with L$_2$. In some embodiments, X and Y are halogens such as I, Br, or Cl.

In other embodiments, D and/or E in the compound of Formula I, II or III are further modified in order to facilitate cellular uptake. In some embodiments, lipidating or PEGylating a peptidomimetic macrocycle facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I, II or III represents a moiety comprising an additional macrocycle-forming linker such that the peptidomimetic macrocycle comprises at least two macrocycle-forming linkers. In a specific embodiment, a peptidomimetic macrocycle comprises two macrocycle-forming linkers.

In the peptidomimetic macrocycles, any of the macrocycle-forming linkers described herein may be used in any combination with any of the sequences shown in Tables 1-4 and also with any of the R-substituents indicated herein.

In some embodiments, the peptidomimetic macrocycle comprises at least one helical motif, such as a $3_{10}$ or an α-helix motif. For example, A, B and/or C in the compound of Formula I, II or III include one or more helices. As a general matter, helices include between 3 and 4 amino acid residues per turn. In some embodiments, the helix of the peptidomimetic macrocycle includes 1 to 5 turns and, therefore, 3 to 20 amino acid residues. In specific embodiments, the helix includes 1 turn, 2 turns, 3 turns, 4 turns, or 5 turns. In some embodiments, the macrocycle-forming linker stabilizes a helix motif included within the peptidomimetic macrocycle. Thus, in some embodiments, the length of the macrocycle-forming linker L from a first Cα to a second Cα is selected to increase the stability of a helix. In some embodiments, the macrocycle-forming linker spans from 1 turn to 5 turns of the helix. In some embodiments, the macrocycle-forming linker spans approximately 1 turn, 2 turns, 3 turns, 4 turns, or 5 turns of the helix. In some embodiments, the length of the macrocycle-forming linker is approximately 5 Å to 9 Å per turn of the helix, or approximately 6 Å to 8 Å per turn of the helix. Where the macrocycle-forming linker spans approximately 1 turn of a helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of a helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of a helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of a helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of a helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of a helix, the linkage contains approximately 4 atoms to 12 atoms, approximately 6 atoms to 10 atoms, or approximately 8 atoms. Where the macrocycle-forming linker spans approximately 2 turns of the helix, the linkage contains approximately 7 atoms to 15 atoms, approximately 9 atoms to 13 atoms, or approximately 11 atoms. Where the macrocycle-forming linker spans approximately 3 turns of the helix, the linkage contains approximately 13 atoms to 21 atoms, approximately 15 atoms to 19 atoms, or approximately 17 atoms. Where the macrocycle-forming linker spans approximately 4 turns of the helix, the linkage contains approximately 19 atoms to 27 atoms, approximately 21 atoms to 25 atoms, or approximately 23 atoms. Where the macrocycle-forming linker spans approximately 5 turns of the helix, the linkage contains approximately 25 atoms to 33 atoms, approximately 27 atoms to 31 atoms, or approximately 29 atoms. Where the macrocycle-forming linker spans approximately 1 turn of the helix, the resulting macrocycle forms a ring containing approximately 17 members to 25 members, approximately 19 members to 23 members, or approximately 21 members. Where the macrocycle-forming linker spans approximately 2 turns of the helix, the resulting macrocycle forms a ring containing approximately 29 members to 37 members, approximately 31 members to 35 members, or approximately 33 members. Where the macrocycle-forming linker spans approximately 3 turns of the helix, the resulting macrocycle forms a ring containing approximately 44 members to 52 members, approximately 46 members to 50 members, or approximately 48 members. Where the macrocycle-forming linker spans approximately 4 turns of the helix, the resulting macrocycle forms a ring containing approximately 59 members to 67 members, approximately 61 members to 65 members, or approximately 63 members. Where the macrocycle-forming linker spans approximately 5 turns of the helix, the resulting macrocycle forms a ring containing approximately 74 members to 82 members, approximately 76 members to 80 members, or approximately 78 members.

In other embodiments, the invention provides peptidomimetic macrocycles of Formula (II) or (IIa):

Formula (II)

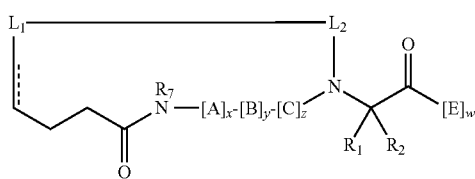

Formula (IIa)

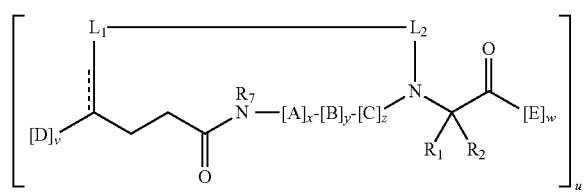

wherein:
each A, C, D, and E is independently a natural or non-natural amino acid;

each B is independently a natural or non-natural amino acid, amino acid analog,

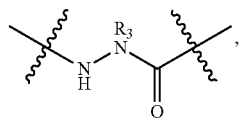

[—NH-$L_3$-CO—], [—NH-$L_3$-$SO_2$—], or [—NH-$L_3$-];
each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;
each $R_3$ is independently hydrogen, alkyl, alkenyl, alkynyl, arylalkyl, heteroalkyl, cycloalkyl, heterocycloalkyl, cycloalkylalkyl, aryl, or heteroaryl, optionally substituted with $R_5$;
each L is independently a macrocycle-forming linker of the formula -$L_1$-$L_2$-;
each $L_1$ and $L_2$ and $L_3$ is independently alkylene, alkenylene, alkynylene, heteroalkylene, cycloalkylene, heterocycloalkylene, arylene, heteroarylene, or [—$R_4$—K—$R_4$—]$_n$, each being optionally substituted with $R_5$;
each $R_4$ is independently alkylene, alkenylene, alkynylene, heteroalkylene, cycloalkylene, heterocycloalkylene, arylene, or heteroarylene;
each K is independently O, S, SO, $SO_2$, CO, $CO_2$, or $CONR_3$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$;
each v and w is independently integers from 1-1000;
u, x, y and z are independently integers from 0-10; and
n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments, x+y+z is at least 1. In other embodiments, x+y+z is at least 2. In other embodiments, x+y+z is 3, 4, 5, 6, 7, 8, 9 or 10. Each occurrence of A, B, C, D or E in a macrocycle or macrocycle precursor is independently selected. For example, a sequence represented by the formula [A]$_x$, when x is 3, encompasses embodiments where the amino acids are not identical, e.g., Gln-Asp-Ala as well as embodiments where the amino acids are identical, e.g., Gln-Gln-Gln. This applies for any value of x, y, or z in the indicated ranges.

In some embodiments, each of the first two amino acid represented by E comprises an uncharged side chain or a negatively charged side chain. In some embodiments, each of the first three amino acid represented by E comprises an uncharged side chain or a negatively charged side chain. In some embodiments, each of the first four amino acid represented by E comprises an uncharged side chain or a negatively charged side chain. In some embodiments, one or more or each of the amino acid that is i+1, i+2, i+3, i+4, i+5, and/or i+6 with respect to $Xaa_{13}$ represented by E comprises an uncharged side chain or a negatively charged side chain.

In some embodiments, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some embodiments, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain. In some embodiments, one or more or each of the amino acid that is i+1, i+2, i+3, i+4, i+5, and/or i+6 with respect to $Xaa_{13}$ represented by E comprises an uncharged side chain or a negatively charged side chain.

In some embodiments, w is between 1 and 1000. For example, the first amino acid represented by E comprises a small hydrophobic side chain. In some embodiments, w is between 2 and 1000. For example, the second amino acid represented by E comprises a small hydrophobic side chain. In some embodiments, w is between 3 and 1000. For example, the third amino acid represented by E comprises a small hydrophobic side chain. For example, the third amino acid represented by E comprises a small hydrophobic side chain. In some embodiments, w is between 4 and 1000. In some embodiments, w is between 5 and 1000. In some embodiments, w is between 6 and 1000. In some embodiments, w is between 7 and 1000. In some embodiments, w is between 8 and 1000.

In some embodiments, the peptidomimetic macrocycle comprises a secondary structure which is a helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

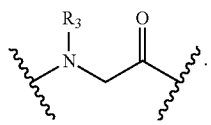

In other embodiments, the length of the macrocycle-forming linker L as measured from a first Cα to a second Cα is selected to stabilize a desired secondary peptide structure, such as a helix (including a $3_{10}$ helix or α-helix) formed by residues of the peptidomimetic macrocycle including, but not necessarily limited to, those between the first Cα to a second Cα.

Exemplary embodiments of the macrocycle-forming linker $-L_1-L_2-$ are shown below.

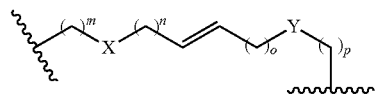

where X, Y = —$CH_2$—, O, S, or NH
m, n, o, p = 0-10

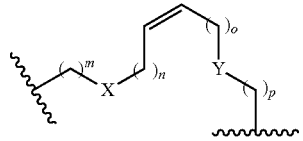

where X, Y = —$CH_2$—, O, S, or NH
m, n, o, p = 0-10

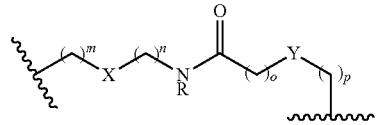

where X, Y = —$CH_2$—, O, S, or NH
m, n, o, p = 0-10
R = H, alkyl, other substituent

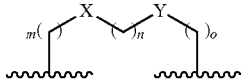

where X, Y = —$CH_2$—, O, S, or NH
m, n, o, p = 0-10

A peptidomimetic macrocycle described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis. Purity can be assessed, for example, by HPLC, MS, LC/MS, melting point, or NMR.

Two or more peptides can share a degree of homology. A pair of peptides can have, for example, up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology. A pair of peptides can have, for example, at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology.

Various methods and software programs can be used to determine the homology between two or more peptides, such as NCBI BLAST, Clustal W, MAFFT, Clustal Omega, AlignMe, Praline, or another suitable method or algorithm.

Preparation of Peptidomimetic Macrocycles

Peptidomimetic macrocycles may be prepared by any of a variety of methods known in the art. For example, any of the residues indicated by "$" or "$r8" in Table 1 may be substituted with a residue capable of forming a crosslinker with a second residue in the same molecule or a precursor of such a residue.

Various methods to effect formation of peptidomimetic macrocycles are known in the art. For example, the preparation of peptidomimetic macrocycles of Formula I is described in Schafmeister et al., J. Am. Chem. Soc. 122: 5891-5892 (2000); Schafmeister & Verdin, J. Am. Chem. Soc. 122:5891 (2005); Walensky et al., Science 305:1466-1470 (2004); and U.S. Pat. No. 7,192,713; and PCT application WO 2008/121767. The α,α-disubstituted amino acids and amino acid precursors disclosed in the cited references may be employed in synthesis of the peptidomimetic macrocycle precursor polypeptides. For example, the "S5-olefin amino acid" is (S)-α-(2'-pentenyl) alanine and the "R8 olefin amino acid" is (R)-α-(2'-octenyl) alanine. Following incorporation of such amino acids into precursor polypeptides, the terminal olefins are reacted with a metathesis catalyst, leading to the formation of the peptidomimetic macrocycle.

In other embodiments, the peptidomimetic macrocycles are of Formula IV or IVa. Methods for the preparation of such macrocycles are described, for example, in U.S. Pat. No. 7,202,332 and PCT application WO 2008/121767.

In some embodiments, the synthesis of these peptidomimetic macrocycles involves a multi-step process that features the synthesis of a peptidomimetic precursor containing an azide moiety and an alkyne moiety; followed by contacting the peptidomimetic precursor with a macrocyclization catalyst to generate a triazole-linked peptidomimetic macrocycle. Such a process is described, for example, in U.S. application Ser. No. 12/037,041, filed on Feb. 25, 2008. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985.

In some embodiments, an azide is linked to the α-carbon of a residue and an alkyne is attached to the α-carbon of another residue. In some embodiments, the azide moieties are azido-analogs of amino acids L-lysine, D-lysine, α-methyl-L-lysine, α-methyl-D-lysine, L-ornithine, D-ornithine, α-methyl-L-ornithine or α-methyl-D-ornithine. In another embodiment, the alkyne moiety is L-propargylglycine. In yet other embodiments, the alkyne moiety is an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid and (R)-2-amino-2-methyl-8-nonynoic acid.

In various embodiments, the following amino acids may be employed in the synthesis of the peptidomimetic macrocycle:

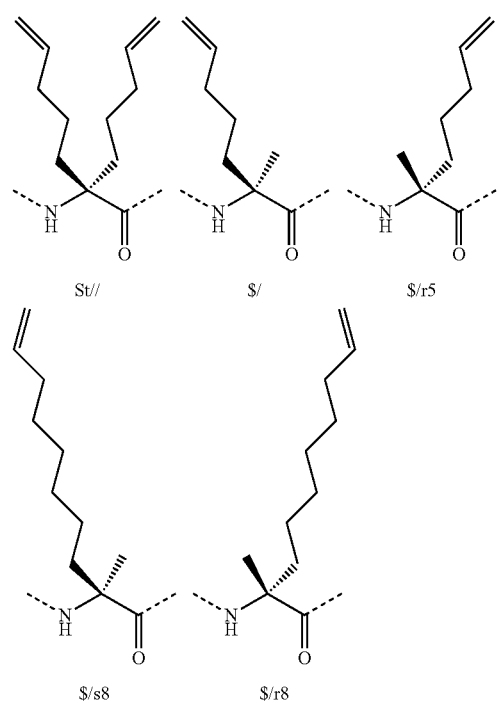

In various embodiments, the following amino acids may be employed in the synthesis of the peptidomimetic macrocycle, wherein L' is an atom (for example, C, O, N, or S); and g is an integer from 1-20, for example, 1, 2, 3, 4, 5, 6, 7, 8, 9, 10, 11, 12, 13, 14, 15, 16, 17, 18, 19, or 20:

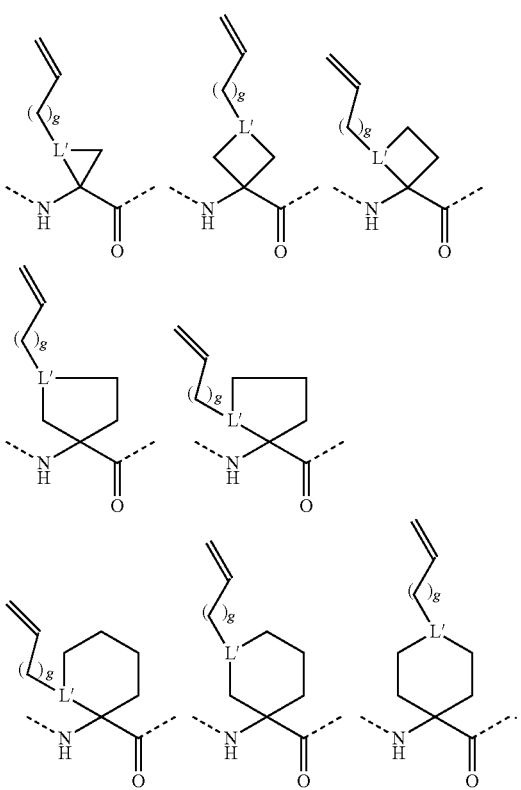

In some embodiments, the invention provides a method for synthesizing a peptidomimetic macrocycle, the method comprising the steps of contacting a peptidomimetic precursor of Formula V or Formula VI:

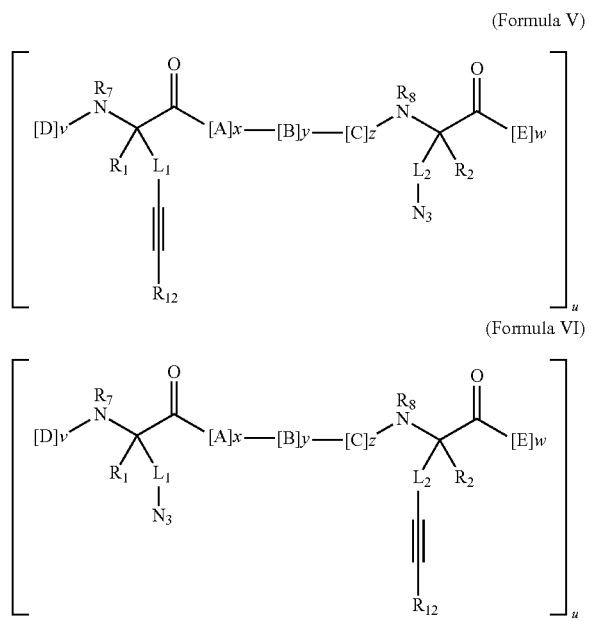

with a macrocyclization catalyst;
wherein v, w, x, y, z, A, B, C, D, E, $R_1$, $R_2$, $R_7$, $R_8$, $L_1$ and $L_2$ are as defined for Formula (II); $R_{12}$ is —H when the macrocyclization catalyst is a Cu catalyst and $R_{12}$ is —H or alkyl when the macrocyclization catalyst is a Ru catalyst, and further wherein said contacting step results in a covalent linkage being formed between the alkyne and azide moiety in Formula III or Formula IV. For example, $R_{12}$ may be methyl when the macrocyclization catalyst t is a Ru catalyst.

In the peptidomimetic macrocycles, at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-. In some embodiments, both $R_1$ and $R_2$ are independently alkyl, alkenyl, alkynyl, arylalkyl, cycloalkyl, cycloalkylalkyl, heteroalkyl, or heterocycloalkyl, unsubstituted or substituted with halo-. In some embodiments, at least one of A, B, C, D or E is an α,α-disubstituted amino acid. In one example, B is an α,α-disubstituted amino acid. For instance, at least one of A, B, C, D or E is 2-aminoisobutyric acid.

For example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl. The macrocyclization catalyst may be a Cu catalyst or a Ru catalyst.

In some embodiments, the peptidomimetic precursor is purified prior to the contacting step. In other embodiments, the peptidomimetic macrocycle is purified after the contacting step. In still other embodiments, the peptidomimetic macrocycle is refolded after the contacting step. The method may be performed in solution, or, alternatively, the method may be performed on a solid support.

Also envisioned herein is performing the method in the presence of a target macromolecule that binds to the peptidomimetic precursor or peptidomimetic macrocycle under conditions that favor said binding. In some embodiments, the method is performed in the presence of a target macromolecule that binds preferentially to the peptidomimetic precursor or peptidomimetic macrocycle under conditions that favor said binding. The method may also be applied to synthesize a library of peptidomimetic macrocycles.

In some embodiments, the alkyne moiety of the peptidomimetic precursor of Formula V or Formula VI is a sidechain of an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid, and (R)-2-amino-2-methyl-8-nonynoic acid. In other embodiments, the azide moiety of the peptidomimetic precursor of Formula V or Formula VI is a sidechain of an amino acid selected from the group consisting of ε-azido-L-lysine, ε-azido-D-lysine, ε-azido-α-methyl-L-lysine, ε-azido-α-methyl-D-lysine, δ-azido-α-methyl-L-ornithine, and δ-azido-α-methyl-D-ornithine.

In some embodiments, x+y+z is 2, and A, B and C are independently natural or non-natural amino acids. In other embodiments, x+y+z is 3 or 6, and A, B and C are independently natural or non-natural amino acids.

In some embodiments, the contacting step is performed in a solvent selected from the group consisting of protic solvent, aqueous solvent, organic solvent, and mixtures thereof. For example, the solvent may be chosen from the group consisting of $H_2O$, THF, THF/$H_2O$, tBuOH/$H_2O$, DMF, DIPEA, CH$_3$CN or CH$_2$Cl$_2$, ClCH$_2$CH$_2$Cl or a mixture thereof. The solvent may be a solvent which favors helix formation.

Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis*, 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The peptidomimetic macrocycles disclosed herein are made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well-known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptidomimetic precursors are made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

The following synthetic schemes are provided solely to illustrate the present invention and are not intended to limit the scope of the invention, as described herein. To simplify the drawings, the illustrative schemes depict azido amino acid analogs ε-azido-α-methyl-L-lysine and ε-azido-α-methyl-D-lysine, and alkyne amino acid analogs L-propargylglycine, (S)-2-amino-2-methyl-4-pentynoic acid, and (S)-2-amino-2-methyl-6-heptynoic acid. Thus, in the following synthetic schemes, each R$_1$, R$_2$, R$_7$ and R$_8$ is —H; each L$_1$ is —(CH$_2$)$_4$—; and each L$_2$ is —(CH$_2$)—. However, as noted throughout the detailed description above, many other amino acid analogs can be employed in which R$_1$, R$_2$, R$_7$, R$_8$, L$_1$ and L$_2$ can be independently selected from the various structures disclosed herein.

Synthetic Scheme 1:

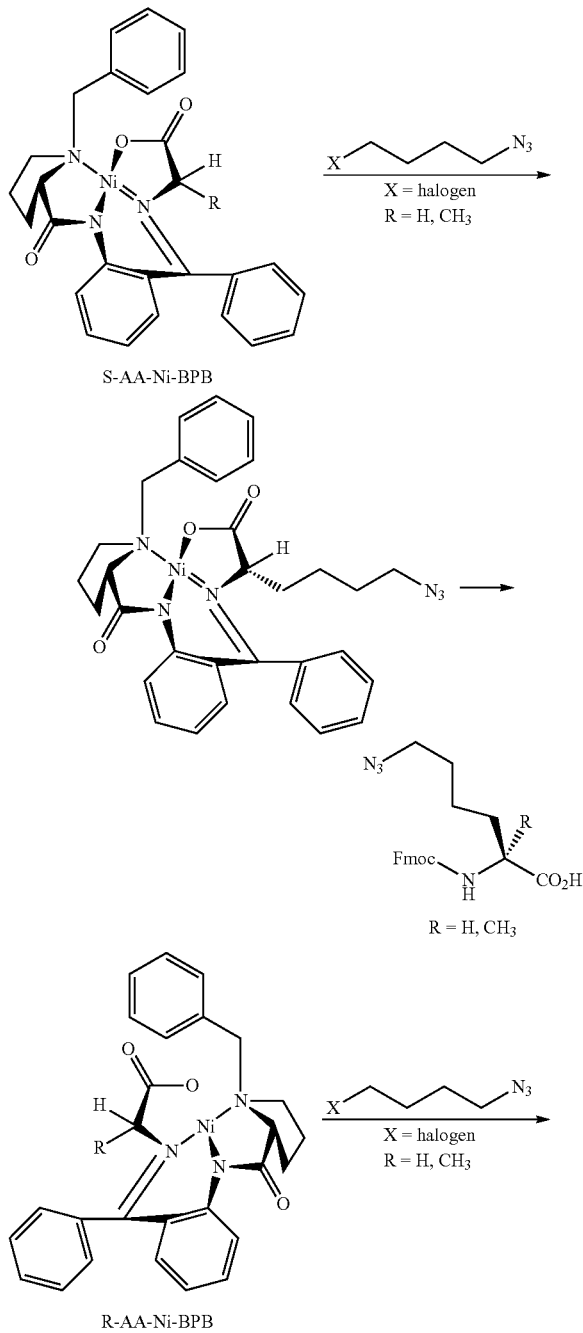

97
-continued

98
-continued

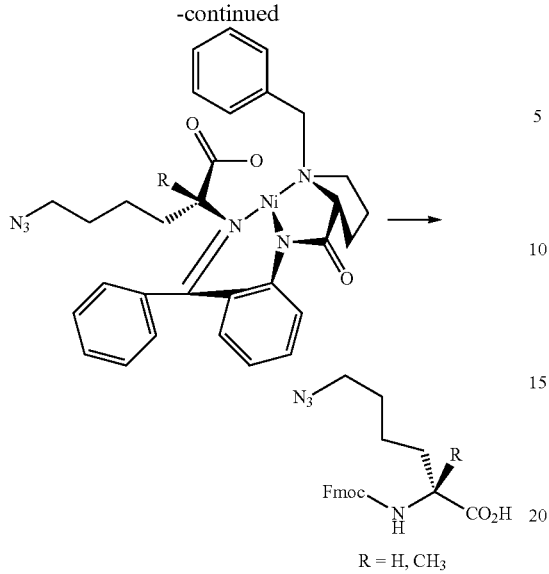

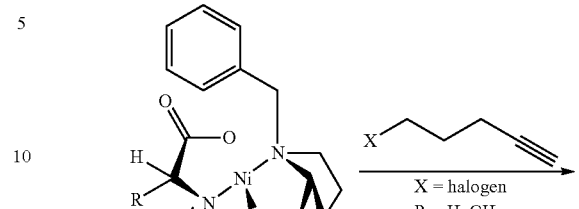

R-AA-Ni-BPB

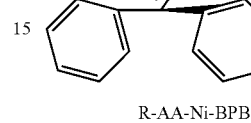

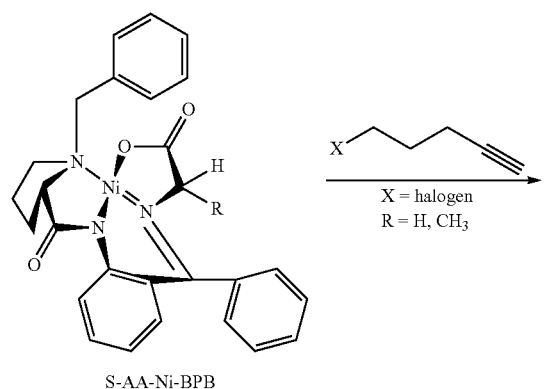

S-AA-Ni-BPB

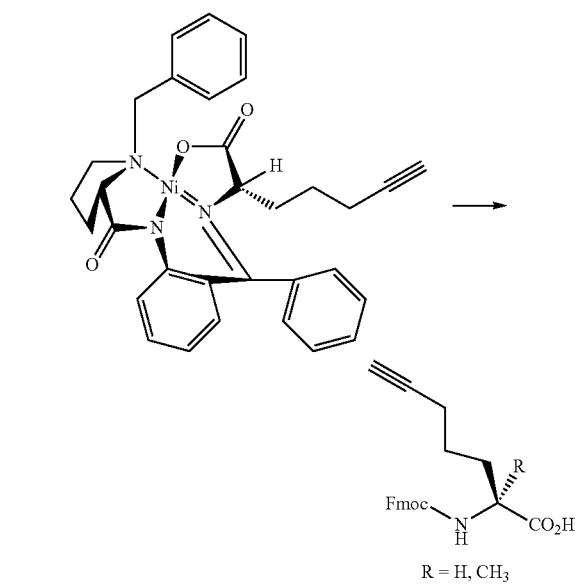

Synthetic Scheme 1 describes the preparation of several compounds of the invention. Ni(II) complexes of Schiff bases derived from the chiral auxiliary (S)-2-[N—(N'-benzylprolyl)amino]benzophenone (BPB) and amino acids such as glycine or alanine are prepared as described in Belokon et al., (1998), *Tetrahedron Asymm.* 9:4249-4252. The resulting complexes are subsequently reacted with alkylating reagents comprising an azido or alkynyl moiety to yield enantiomerically enriched compounds. If desired, the resulting compounds can be protected for use in peptide synthesis.

Synthetic Scheme 2:

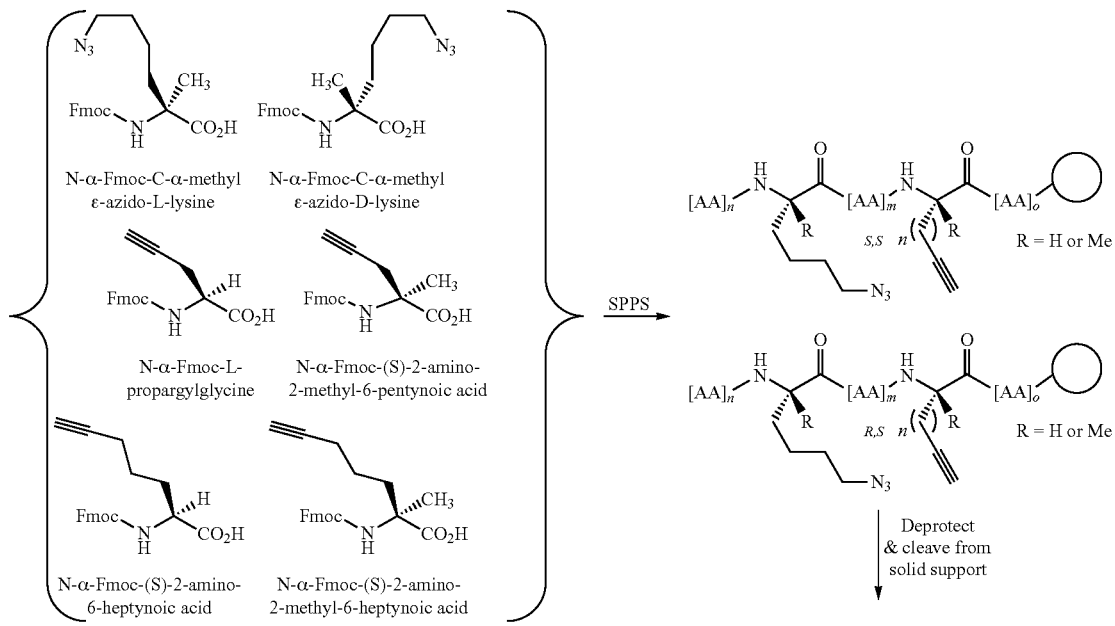

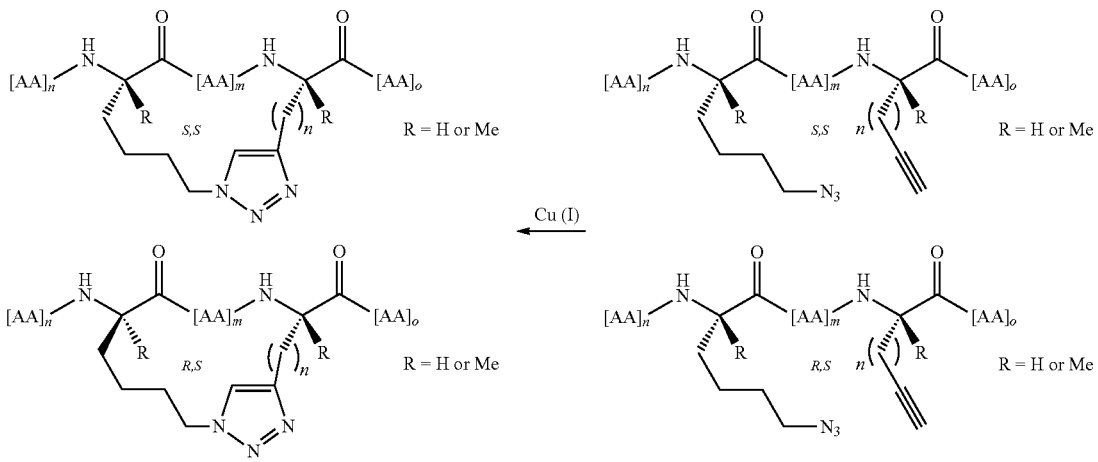

In the general method for the synthesis of peptidomimetic macrocycles shown in Synthetic Scheme 2, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization catalyst such as a Cu(I) in organic or aqueous solutions (Rostovtsev et al., (2002), Angew. Chem. Int. Ed. 41:2596-2599; Tornoe et al., (2002), J. Org. Chem. 67:3057-3064; Deiters et al., (2003), J. Am. Chem. Soc. 125:11782-11783; Punna et al., (2005), Angew. Chem. Int. Ed. 44:2215-2220). In one embodiment, the triazole forming reaction is performed under conditions that favor helix formation. In one embodiment, the macrocyclization step is performed in a solvent chosen from the group consisting of $H_2O$, THF, $CH_3CN$, DMF, DIPEA, tBuOH or a mixture thereof. In another embodiment, the macrocyclization step is performed in DMF. In some embodiments, the macrocyclization step is performed in a buffered aqueous or partially aqueous solvent.

Synthetic Scheme 3:

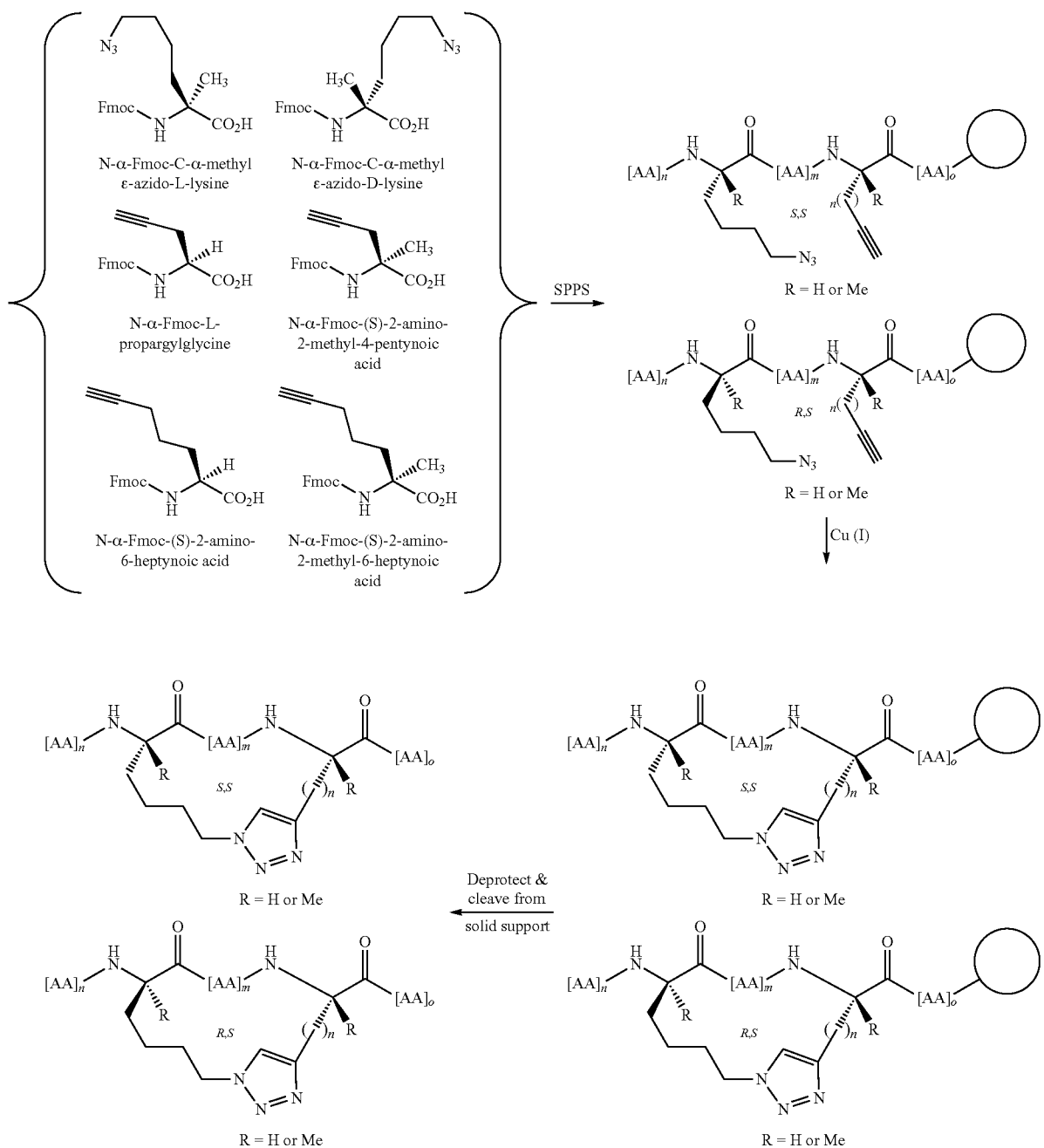

In the general method for the synthesis of peptidomimetic macrocycles shown in Synthetic Scheme 3, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization catalyst such as a Cu(I) catalyst on the resin as a crude mixture (Rostovtsev et al., (2002), Angew. Chem. Int. Ed. 41:2596-2599; Tornoe et al., (2002), J. Org. Chem. 67:3057-3064; Deiters et al., (2003), J. Am. Chem. Soc. 125:11782-11783; Punna et al., (2005), Angew. Chem. Int. Ed. 44:2215-2220). The resultant triazole-containing peptidomimetic macrocycle is then deprotected and cleaved from the solid-phase resin by standard conditions (e.g., strong acid such as 95% TFA). In some embodiments, the macrocyclization step is performed in a solvent chosen from the group consisting of $CH_2Cl_2$, $ClCH_2CH_2Cl$, DMF, THF, NMP, DIPEA, 2,6-lutidine, pyridine, DMSO, $H_2O$ or a mixture thereof. In some embodiments, the macrocyclization step is performed in a buffered aqueous or partially aqueous solvent.

Synthetic Scheme 4:

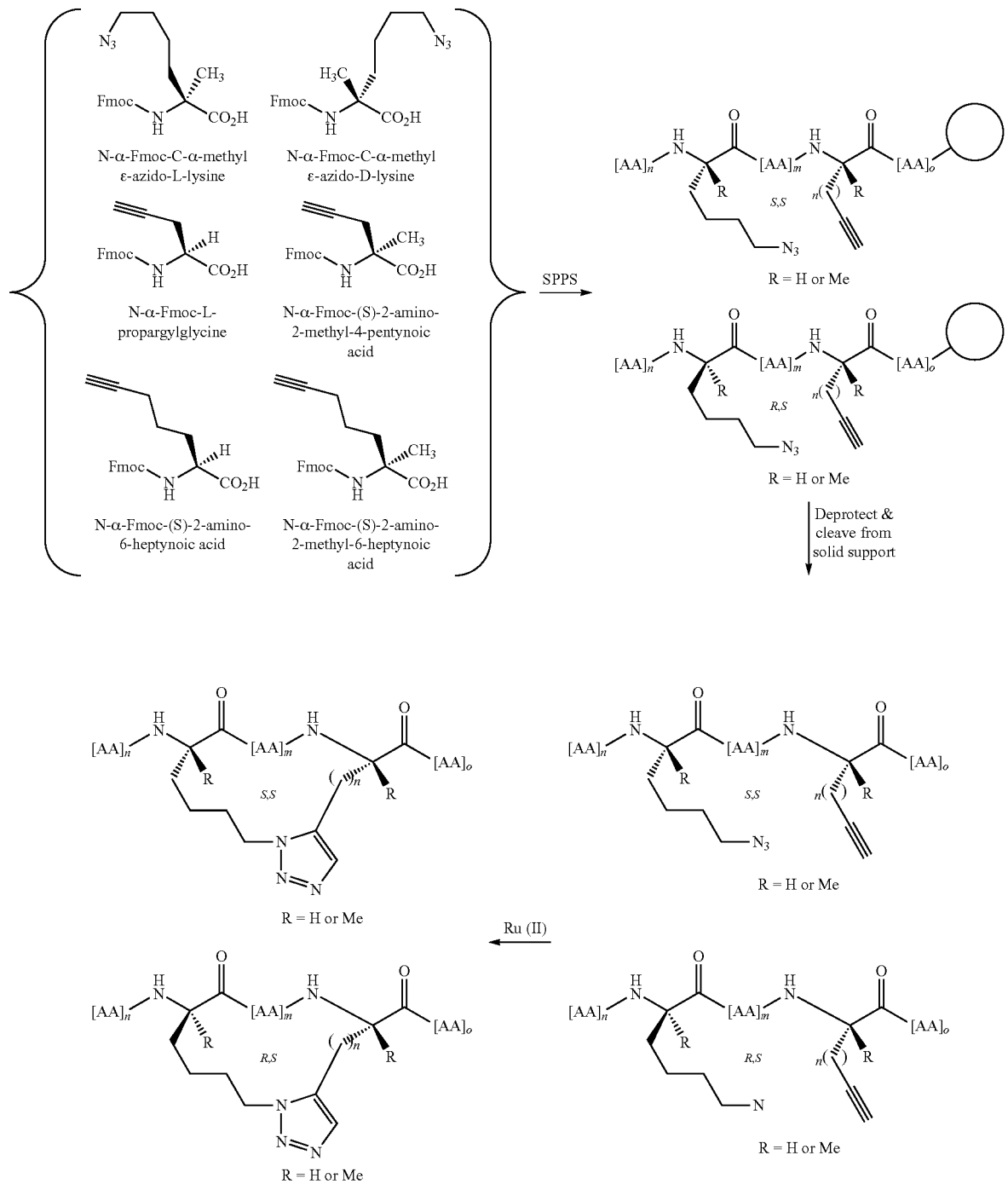

In the general method for the synthesis of peptidomimetic macrocycles shown in Synthetic Scheme 4, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization catalyst such as a Ru(II) catalyst, for example Cp*RuCl(PPh$_3$)$_2$ or [Cp*RuCl]$_4$ (Rasmussen et al., (2007), Org. Lett. 9:5337-5339; Zhang et al., (2005), J. Am. Chem. Soc. 127:15998-15999). In some embodiments, the macrocyclization step is performed in a solvent chosen from the group consisting of DMF, CH$_3$CN and THF.

Synthetic Scheme 5:

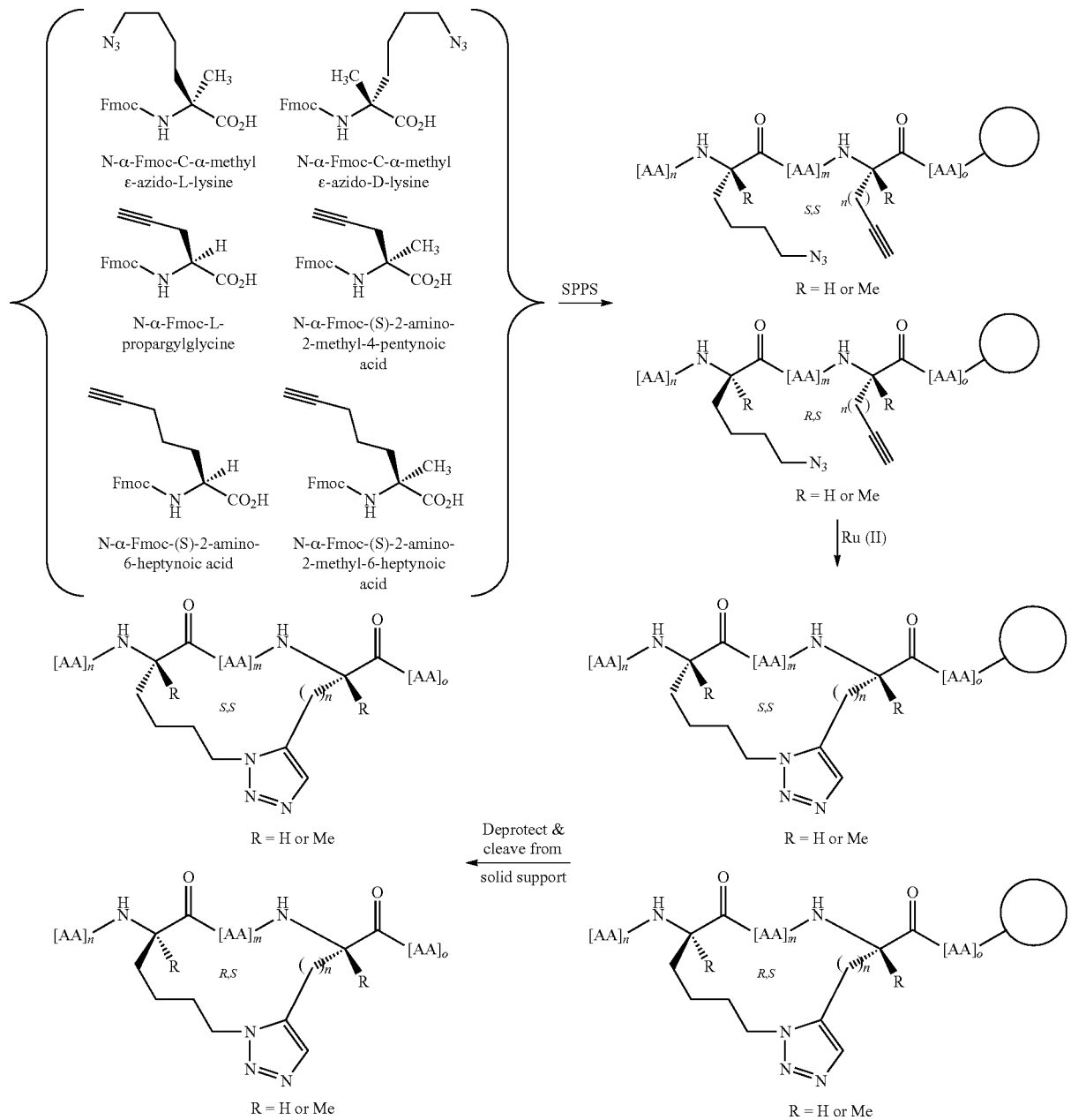

In the general method for the synthesis of peptidomimetic macrocycles shown in Synthetic Scheme 5, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization catalyst such as a Ru(II) catalyst on the resin as a crude mixture. For example, the catalyst can be Cp*RuCl(PPh$_3$)$_2$ or [Cp*RuCl]$_4$ (Rasmussen et al., (2007), *Org. Lett.* 9:5337-5339; Zhang et al., (2005), *J. Am. Chem. Soc.* 127:15998-15999). In some embodiments, the macrocyclization step is performed in a solvent chosen from the group consisting of CH$_2$Cl$_2$, ClCH$_2$CH$_2$Cl, CH$_3$CN, DMF, and THF.

The present invention contemplates the use of non-naturally-occurring amino acids and amino acid analogs in the synthesis of the peptidomimetic macrocycles described herein. Any amino acid or amino acid analog amenable to the synthetic methods employed for the synthesis of stable triazole containing peptidomimetic macrocycles can be used. For example, L-propargylglycine is contemplated as a useful amino acid. However, other alkyne-containing amino acids that contain a different amino acid side chain are also useful in the invention. For example, L-propargylglycine contains one methylene unit between the α-carbon of the amino acid and the alkyne of the amino acid side chain. The invention also contemplates the use of amino acids with multiple methylene units between the α-carbon and the alkyne. Also, the azido-analogs of amino acids L-lysine, D-lysine, α-methyl-L-lysine, and α-methyl-D-lysine are contemplated as useful amino acids. However, other terminal azide amino acids that contain a different amino acid side chain are also useful in the invention. For example, the azido-analog of L-lysine contains four methylene units between the α-carbon of the amino acid and the terminal azide of the amino acid side chain. The invention also contemplates the use of amino acids with fewer than or greater than four methylene units between the α-carbon and the terminal azide. Table 2 shows some amino acids useful in the preparation of peptidomimetic macrocycles.

TABLE 2

Exemplary amino acids useful in the preparation of peptidomimetic macrocycles

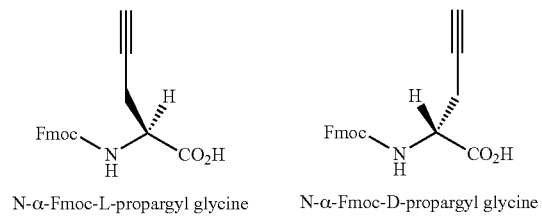

TABLE 2-continued

Exemplary amino acids useful in the preparation of peptidomimetic macrocycles

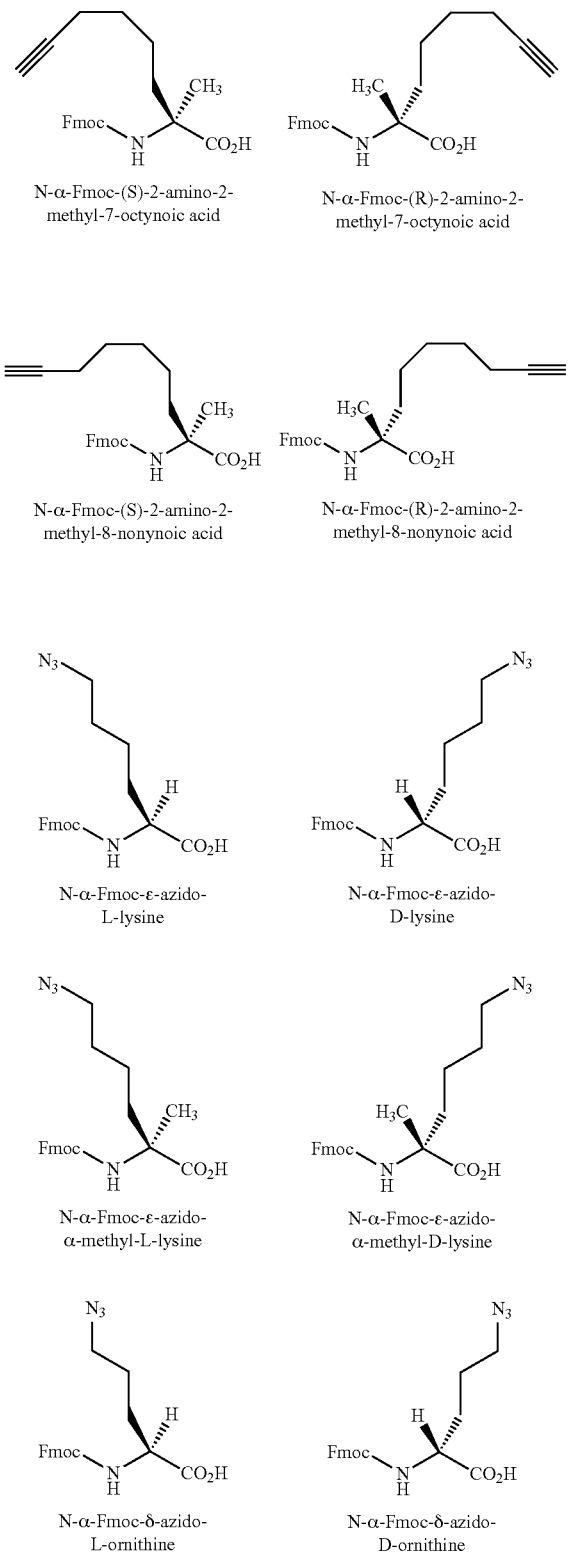

TABLE 2-continued

Exemplary amino acids useful in the preparation of peptidomimetic macrocycles

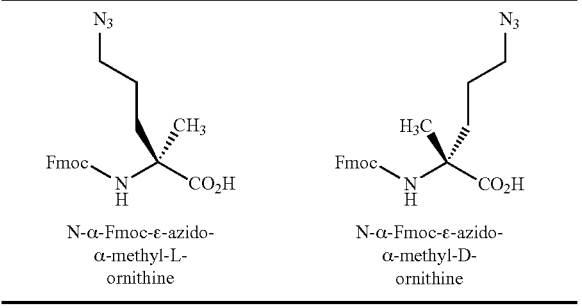

N-α-Fmoc-ε-azido-α-methyl-L-ornithine

N-α-Fmoc-ε-azido-α-methyl-D-ornithine

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargylglycine, α-methyl-D-propargylglycine, ε-azido-α-methyl-L-lysine, and ε-azido-α-methyl-D-lysine. In some embodiments the amino acid analogs are N-alkylated, e.g., N-methyl-L-propargylglycine, N-methyl-D-propargylglycine, N-methyl-ε-azido-L-lysine, and N-methyl-ε-azido-D-lysine.

In some embodiments, the —NH moiety of the amino acid is protected using a protecting group, including without limitation -Fmoc and -Boc. In other embodiments, the amino acid is not protected prior to synthesis of the peptidomimetic macrocycle.

In other embodiments, peptidomimetic macrocycles of Formula III are synthesized. The preparation of such macrocycles is described, for example, in U.S. application Ser. No. 11/957,325, filed on Dec. 17, 2007. The following synthetic schemes describe the preparation of such compounds. To simplify the drawings, the illustrative schemes depict amino acid analogs derived from L- or D-cysteine, in which $L_1$ and $L_3$ are both —($CH_2$)—. However, as noted throughout the detailed description above, many other amino acid analogs can be employed in which $L_1$ and $L_3$ can be independently selected from the various structures disclosed herein. The symbols "$[AA]_m$", "$[AA]_n$", "$[AA]_o$" represent a sequence of amide bond-linked moieties such as natural or unnatural amino acids. As described previously, each occurrence of "AA" is independent of any other occurrence of "AA", and a formula such as "$[A]_m$" encompasses, for example, sequences of non-identical amino acids as well as sequences of identical amino acids.

Synthetic Scheme 6:

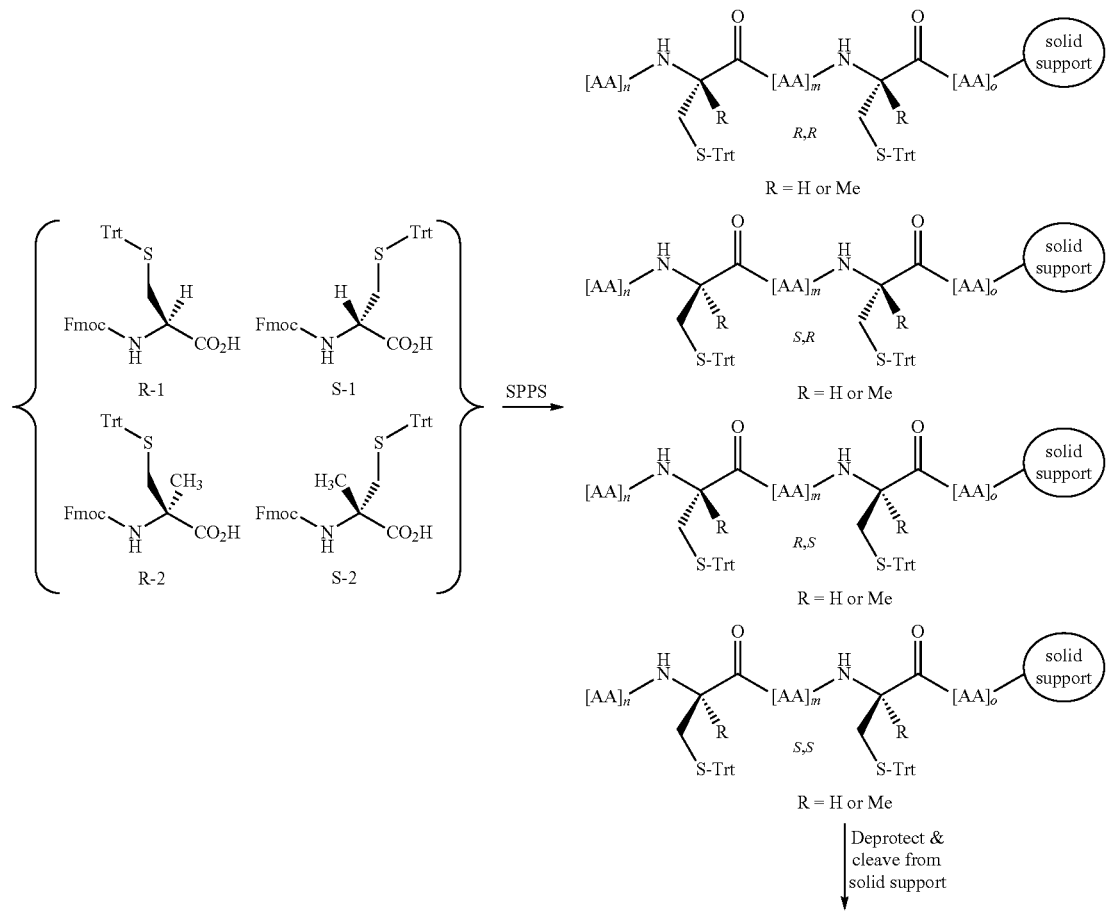

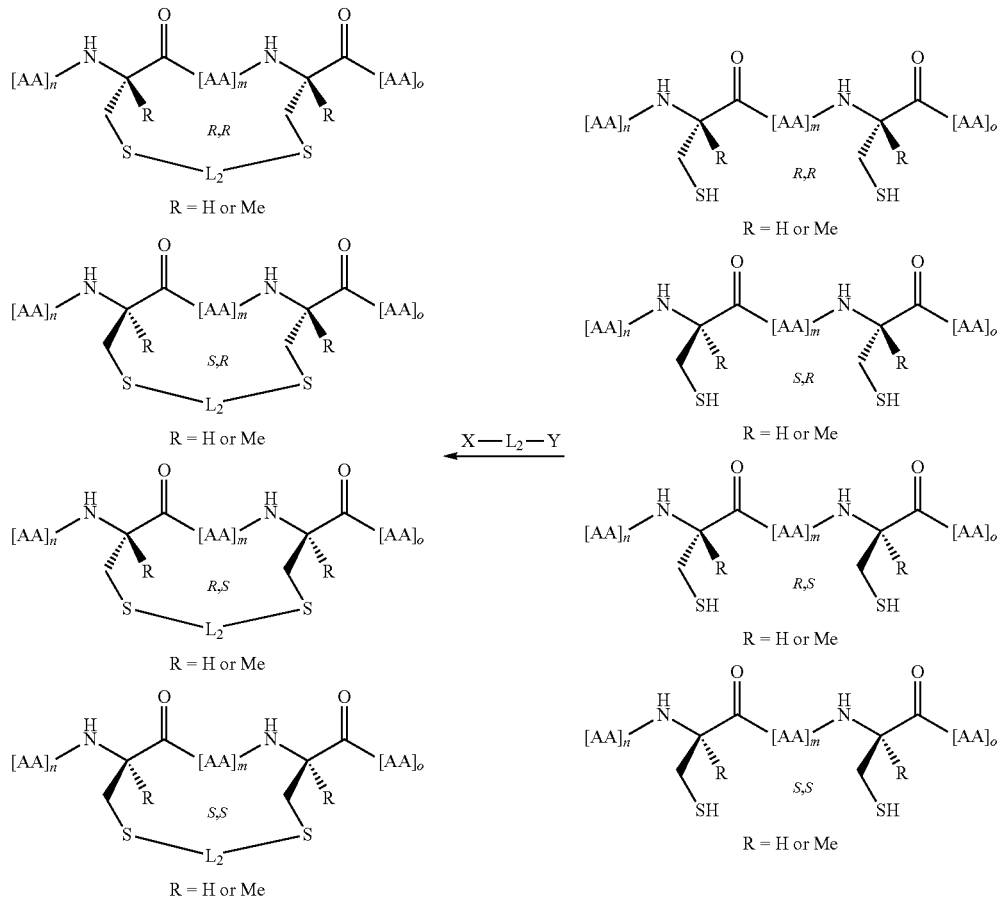

In Scheme 6, the peptidomimetic precursor contains two —SH moieties and is synthesized by solid-phase peptide synthesis (SPPS) using commercially available N-α-Fmoc amino acids such as N-α-Fmoc-S-trityl-L-cysteine or N-α-Fmoc-S-trityl-D-cysteine. α-methylated versions of D-cysteine or L-cysteine are generated by known methods (Seebach et al., (1996), *Angew. Chem. Int. Ed. Engl.* 35:2708-2748, and references therein) and then converted to the appropriately protected N-α-Fmoc-S-trityl monomers by known methods (*Bioorganic Chemistry: Peptides and Proteins*, Oxford University Press, New York: 1998, the entire contents of which are incorporated herein by reference). The precursor peptidomimetic is then deprotected and cleaved from the solid-phase resin by standard conditions (e.g., strong acid such as 95% TFA). The precursor peptidomimetic is reacted as a crude mixture or is purified prior to reaction with X-L$_2$-Y in organic or aqueous solutions. In some embodiments the alkylation reaction is performed under dilute conditions (i.e., 0.15 mmol/L) to favor macrocyclization and to avoid polymerization. In some embodiments, the alkylation reaction is performed in organic solutions such as liquid NH$_3$ (Mosberg et al., (1985), *J. Am. Chem. Soc.* 107:2986-2987; Szewczuk et al., (1992), *Int. J. Peptide Protein Res.* 40:233-242), NH$_3$/MeOH, or NH$_3$/DMF (Or et al., (1991), *J. Org. Chem.* 56:3146-3149). In other embodiments, the alkylation is performed in an aqueous solution such as 6 M guanidinium HCl, pH 8 (Brunel et al., (2005), *Chem. Commun* (20):2552-2554). In other embodiments, the solvent used for the alkylation reaction is DMF or dichloroethane.

Synthetic Scheme 7:

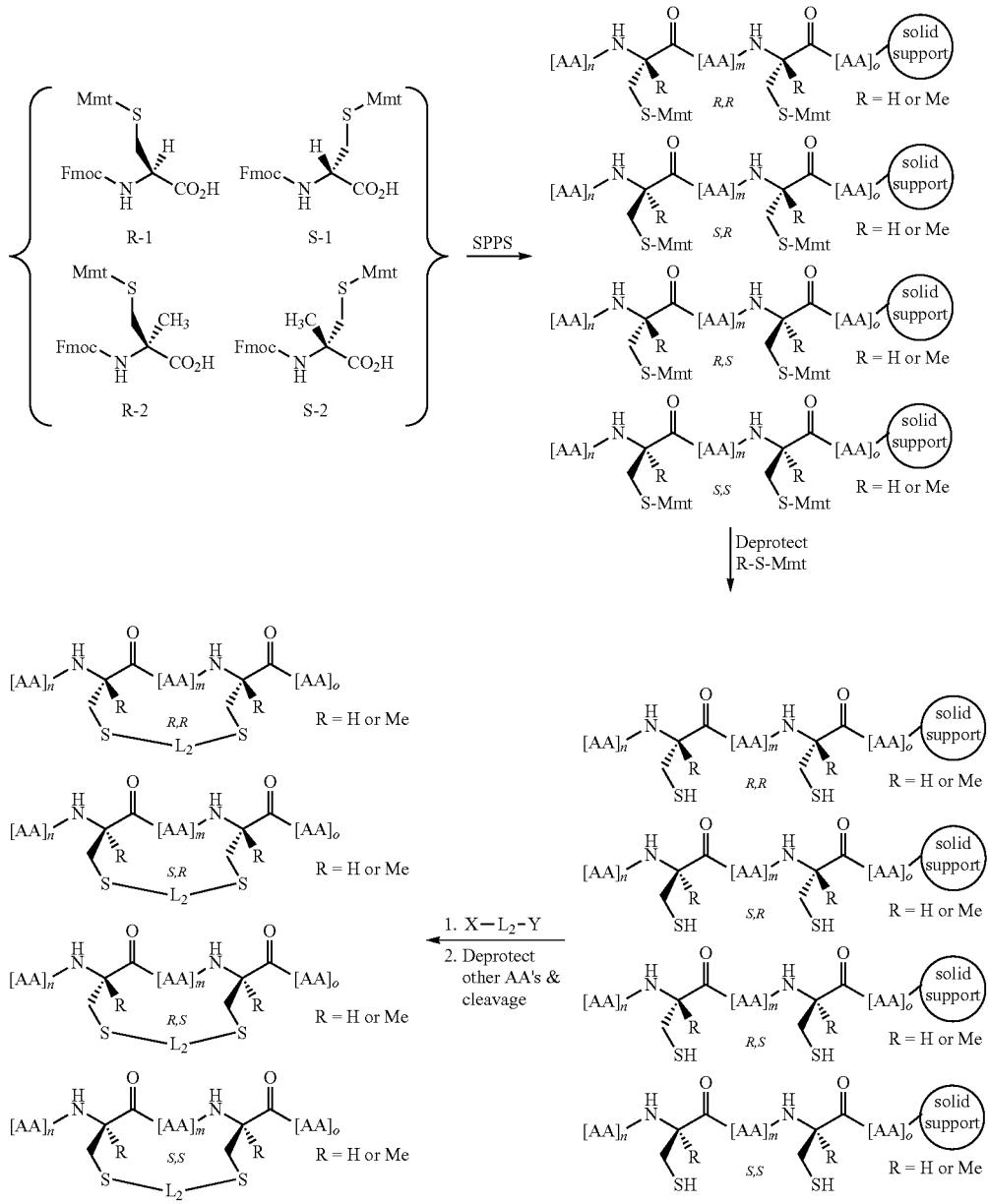

In Scheme 7, the precursor peptidomimetic contains two or more —SH moieties, of which two are specially protected to allow their selective deprotection and subsequent alkylation for macrocycle formation. The precursor peptidomimetic is synthesized by solid-phase peptide synthesis (SPPS) using commercially available N-α-Fmoc amino acids such as N-α-Fmoc-S-p-methoxytrityl-L-cysteine or N-α-Fmoc-S-p-methoxytrityl-D-cysteine. α-methylated versions of D-cysteine or L-cysteine are generated by known methods (Seebach et al., (1996), Angew. Chem. Int. Ed. Engl. 35:2708-2748, and references therein) and then converted to the appropriately protected N-α-Fmoc-S-p-methoxytrityl monomers by known methods (Bioorganic Chemistry: Peptides and Proteins, Oxford University Press, New York: 1998, the entire contents of which are incorporated herein by reference). The Mmt protecting groups of the peptidomimetic precursor are then selectively cleaved by standard conditions (e.g., mild acid such as 1% TFA in DCM). The precursor peptidomimetic is then reacted on the resin with X-L$_2$-Y in an organic solution. For example, the reaction takes place in the presence of a hindered base such as diisopropylethylamine. In some embodiments, the alkylation reaction is performed in organic solutions such as liquid NH$_3$ (Mosberg et al., (1985), J. Am. Chem. Soc. 107:2986-2987; Szewczuk et al., (1992), Int. J. Peptide Protein Res. 40:233-242), NH$_3$/MeOH or NH$_3$/DMF (Or et al., (1991), J. Org. Chem. 56:3146-3149). In other embodiments, the alkylation reaction is performed in DMF or dichloroethane. The peptidomimetic macrocycle is then deprotected and cleaved from the solid-phase resin by standard conditions (e.g., strong acid such as 95% TFA).

Synthetic Scheme 8:

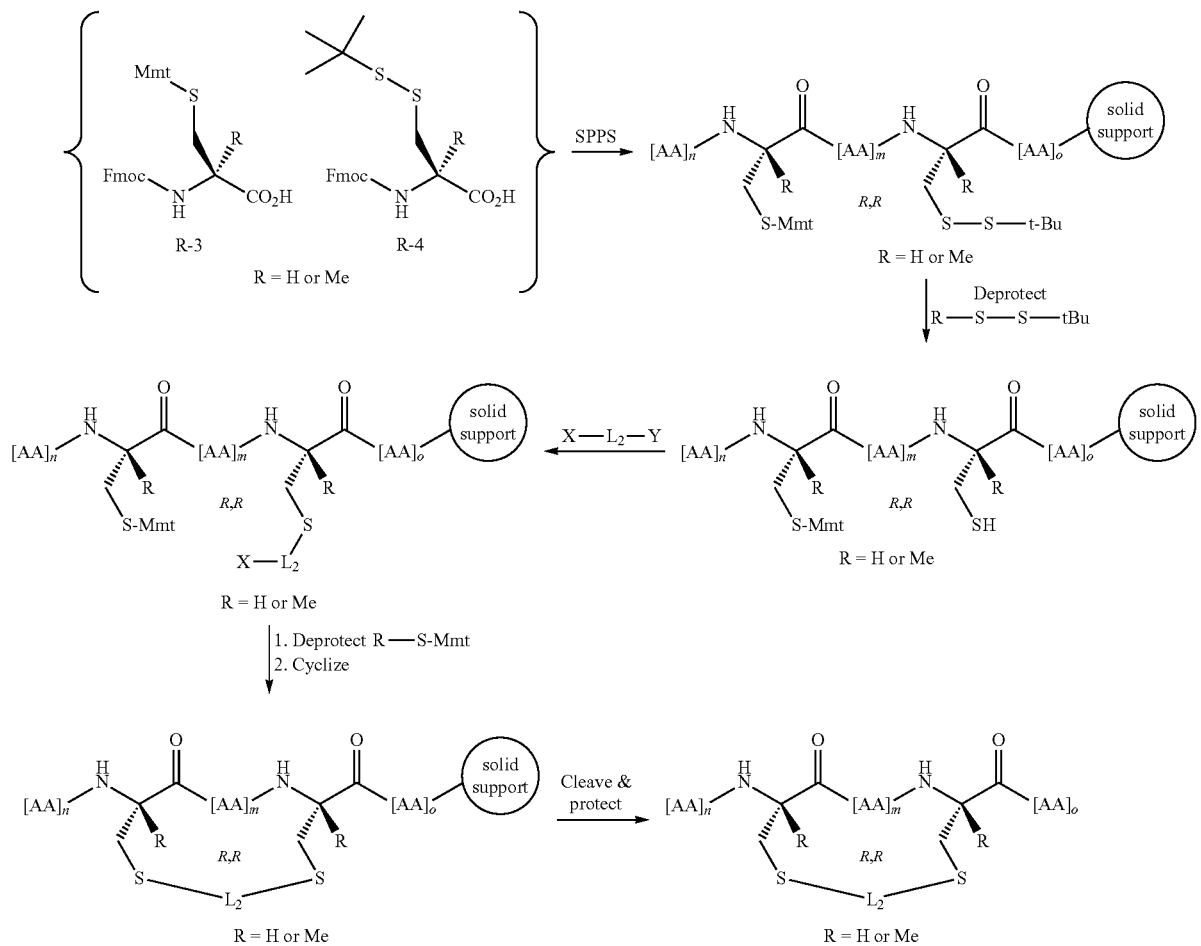

In Scheme 8, the peptidomimetic precursor contains two or more —SH moieties, of which two are specially protected to allow their selective deprotection and subsequent alkylation for macrocycle formation. The peptidomimetic precursor is synthesized by solid-phase peptide synthesis (SPPS) using commercially available N-α-Fmoc amino acids such as N-α-Fmoc-S-p-methoxytrityl-L-cysteine, N-α-Fmoc-S-p-methoxytrityl-D-cysteine, N-α-Fmoc-S—S-t-butyl-L-cysteine, and N-α-Fmoc-S—S-t-butyl-D-cysteine. α-methylated versions of D-cysteine or L-cysteine are generated by known methods (Seebach et al., (1996), *Angew. Chem. Int. Ed. Engl.* 35:2708-2748, and references therein) and then converted to the appropriately protected N-α-Fmoc-S-p-methoxytrityl or N-α-Fmoc-S—S-t-butyl monomers by known methods (*Bioorganic Chemistry: Peptides and Proteins*, Oxford University Press, New York: 1998, the entire contents of which are incorporated herein by reference). The S—S-tButyl protecting group of the peptidomimetic precursor is selectively cleaved by known conditions (e.g., 20% 2-mercaptoethanol in DMF, reference: Galande et al., (2005), *J. Comb. Chem.* 7:174-177). The precursor peptidomimetic is then reacted on the resin with a molar excess of X-$L_2$-Y in an organic solution. For example, the reaction takes place in the presence of a hindered base such as diisopropylethylamine. The Mmt protecting group of the peptidomimetic precursor is then selectively cleaved by standard conditions (e.g., mild acid such as 1% TFA in DCM). The peptidomimetic precursor is then cyclized on the resin by treatment with a hindered base in organic solutions. In some embodiments, the alkylation reaction is performed in organic solutions such as $NH_3$/MeOH or $NH_3$/DMF (Or et al., (1991), *J. Org. Chem.* 56:3146-3149). The peptidomimetic macrocycle is then deprotected and cleaved from the solid-phase resin by standard conditions (e.g., strong acid such as 95% TFA).

Synthetic Scheme 9:

1. Biological synthesis of peptide
2. Purification of peptide

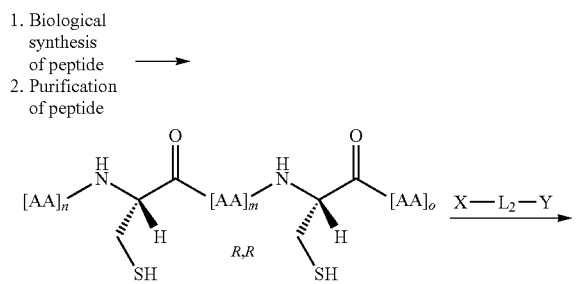

-continued

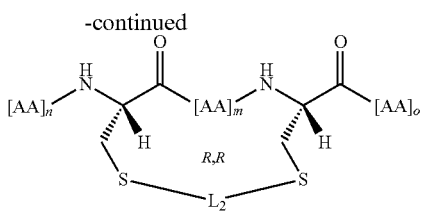

In Scheme 9, the peptidomimetic precursor contains two L-cysteine moieties. The peptidomimetic precursor is synthesized by known biological expression systems in living cells or by known in vitro, cell-free, expression methods. The precursor peptidomimetic is reacted as a crude mixture or is purified prior to reaction with X-L2-Y in organic or aqueous solutions. In some embodiments the alkylation reaction is performed under dilute conditions (i.e., 0.15 mmol/L) to favor macrocyclization and to avoid polymerization. In some embodiments, the alkylation reaction is performed in organic solutions such as liquid $NH_3$ (Mosberg et al., (1985), J. Am. Chem. Soc. 107:2986-2987; Szewczuk et al., (1992), Int. J. Peptide Protein Res. 40:233-242), $NH_3$/MeOH, or $NH_3$/DMF (Or et al., (1991), J. Org. Chem. 56:3146-3149). In other embodiments, the alkylation is performed in an aqueous solution such as 6 M guanidinium HCl, pH 8 (Brunel et al., (2005), Chem. Commun (20): 2552-2554). In other embodiments, the alkylation is performed in DMF or dichloroethane. In another embodiment, the alkylation is performed in non-denaturing aqueous solutions, and in yet another embodiment the alkylation is performed under conditions that favor helical structure formation. In yet another embodiment, the alkylation is performed under conditions that favor the binding of the precursor peptidomimetic to another protein, so as to induce the formation of the bound helical conformation during the alkylation.

Various embodiments for X and Y are envisioned which are suitable for reacting with thiol groups. In general, each X or Y is independently be selected from the general category shown in Table 3. For example, X and Y are halides such as —Cl, —Br or —I. Any of the macrocycle-forming linkers described herein may be used in any combination with any of the sequences shown in Tables 1-4 and also with any of the R— substituents indicated herein.

TABLE 3

Examples of Reactive Groups Capable of Reacting with Thiol Groups and Resulting Linkages

| X or Y | Resulting Covalent Linkage |
|---|---|
| acrylamide | Thioether |
| halide (e.g., alkyl or aryl halide) | Thioether |
| sulfonate | Thioether |
| aziridine | Thioether |
| epoxide | Thioether |
| haloacetamide | Thioether |
| maleimide | Thioether |
| sulfonate ester | Thioether |

The present invention contemplates the use of both naturally-occurring and non-naturally-occurring amino acids and amino acid analogs in the synthesis of the peptidomimetic macrocycles of Formula (III). Any amino acid or amino acid analog amenable to the synthetic methods employed for the synthesis of stable bis-sulfhydryl containing peptidomimetic macrocycles can be used. For example, cysteine is contemplated as a useful amino acid. However, sulfur containing amino acids other than cysteine that contain a different amino acid side chain are also useful. For example, cysteine contains one methylene unit between the α-carbon of the amino acid and the terminal —SH of the amino acid side chain. The invention also contemplates the use of amino acids with multiple methylene units between the α-carbon and the terminal —SH. Non-limiting examples include α-methyl-L-homocysteine and α-methyl-D-homocysteine. In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-cysteine and α-methyl-D-cysteine.

The invention includes macrocycles in which macrocycle-forming linkers are used to link two or more —SH moieties in the peptidomimetic precursors to form the peptidomimetic macrocycles. As described above, the macrocycle-forming linkers impart conformational rigidity, increased metabolic stability and/or increased cell penetrability. Furthermore, in some embodiments, the macrocycle-forming linkages stabilize a helical secondary structure of the peptidomimetic macrocycles. The macrocycle-forming linkers are of the formula $X-L_2-Y$, wherein both X and Y are the same or different moieties, as defined above. Both X and Y have the chemical characteristics that allow one macrocycle-forming linker -$L_2$- to bis alkylate the bis-sulfhydryl containing peptidomimetic precursor. As defined above, the linker -$L_2$- includes alkylene, alkenylene, alkynylene, heteroalkylene, cycloalkylene, heterocycloalkylene, arylene, or heteroarylene, or —$R_4$—K—$R_4$—, all of which can be optionally substituted with an $R_5$ group, as defined above. Furthermore, one to three carbon atoms within the macrocycle-forming linkers -$L_2$-, other than the carbons attached to the —SH of the sulfhydryl containing amino acid, are optionally substituted with a heteroatom such as N, S or O.

The $L_2$ component of the macrocycle-forming linker $X-L_2-Y$ may be varied in length depending on, among other things, the distance between the positions of the two amino acid analogs used to form the peptidomimetic macrocycle. Furthermore, as the lengths of $L_1$ and/or $L_3$ components of the macrocycle-forming linker are varied, the length of $L_2$ can also be varied in order to create a linker of appropriate overall length for forming a stable peptidomimetic macrocycle. For example, if the amino acid analogs used are varied by adding an additional methylene unit to each of $L_1$ and $L_3$, the length of $L_2$ are decreased in length by the equivalent of approximately two methylene units to compensate for the increased lengths of $L_1$ and $L_3$.

In some embodiments, $L_2$ is an alkylene group of the formula —$(CH_2)_n$—, where n is an integer between about 1 and about 15. For example, n is 1, 2, 3, 4, 5, 6, 7, 8, 9 or 10. In other embodiments, $L_2$ is an alkenylene group. In still other embodiments, $L_2$ is an aryl group.

Table 4 shows additional embodiments of $X-L_2-Y$ groups.

TABLE 4

Exemplary X-L2-Y groups of the invention

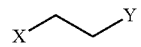

TABLE 4-continued

Exemplary X-L2-Y groups of the invention

TABLE 4-continued

Exemplary X-L2-Y groups of the invention

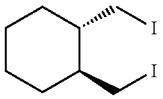

Each X and Y in this table, is, for example, independently Cl—, Br— or I—.

Additional methods of forming peptidomimetic macrocycles which are envisioned as suitable to perform the present invention include those disclosed by Mustapa, M. Firouz Mohd et al., J. Org. Chem (2003), 68, pp. 8193-8198; Yang, Bin et al., Bioorg Med. Chem. Lett. (2004), 14, pp. 1403-1406; U.S. Pat. No. 5,364,851; U.S. Pat. No. 5,446,128; U.S. Pat. No. 5,824,483; U.S. Pat. No. 6,713,280; and U.S. Pat. No. 7,202,332. In such embodiments, amino acid precursors are used containing an additional substituent R— at the α position. Such amino acids are incorporated into the macrocycle precursor at the desired positions, which may be at the positions where the crosslinker is substituted or, alternatively, elsewhere in the sequence of the macrocycle precursor. Cyclization of the precursor is then effected according to the indicated method.

For example, a peptidomimetic macrocycle of Formula (II) is prepared as indicated:

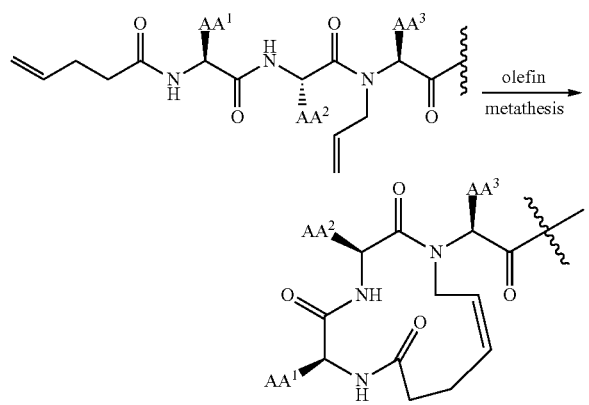

wherein each $AA_1$, $AA_2$, $AA_3$ is independently an amino acid side chain.

In other embodiments, a peptidomimetic macrocycle of Formula (II) is prepared as indicated:

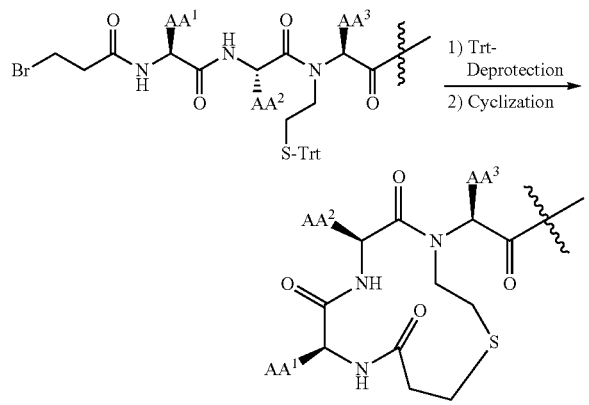

wherein each $AA_1$, $AA_2$, $AA_3$ is independently an amino acid side chain.

In some embodiments, a peptidomimetic macrocycle is obtained in more than one isomer, for example due to the configuration of a double bond within the structure of the crosslinker (E vs Z). Such isomers can or cannot be separable by conventional chromatographic methods. In some embodiments, one isomer has improved biological properties relative to the other isomer. In one embodiment, an E crosslinker olefin isomer of a peptidomimetic macrocycle has better solubility, better target affinity, better in vivo or in vitro efficacy, higher helicity, or improved cell permeability relative to its Z counterpart. In another embodiment, a Z crosslinker olefin isomer of a peptidomimetic macrocycle has better solubility, better target affinity, better in vivo or in vitro efficacy, higher helicity, or improved cell permeability relative to its E counterpart In some embodiments, it is desirable to modify the configuration of the resulting peptidomimetic macrocycle. For instance, when a $3_{10}$ helical configuration is more desirable, additional substitutions or modifications to the macrocycle can be made to induce or bias such conformations, such as substituting 2-aminoisobutyric acid (Aib) for one or more amino acids in the sequence. See, for example, Boal et al., J. Am. Chem. Soc. 2007, 129, 6986-6987. In one embodiment, the helical macrocycle comprises at least 1, 2, 3, 4, 5, 6, 7, 8, 9, 10, or more Aib substitutions.

Assays

The properties of the peptidomimetic macrocycles are assayed, for example, by using the methods described below. In some embodiments, a peptidomimetic macrocycle has improved biological properties relative to a corresponding polypeptide lacking the substituents described herein Assay to Determine Helicity.

In solution, the secondary structure of polypeptides with helical domains will reach a dynamic equilibrium between random coil structures and helical structures, often expressed as a "percent helicity". Thus, for example, unmodified helical domains may be predominantly random coils in solution, with helical content usually under 25%. Peptidomimetic macrocycles with optimized linkers, on the other hand, possess, for example, a helicity that is at least two-fold greater than that of a corresponding uncrosslinked polypeptide. In some embodiments, macrocycles will possess a helicity of greater than 50%. To assay the helicity of peptidomimetic macrocycles, the compounds are dissolved in an aqueous solution (e.g., 50 mM potassium phosphate solution at pH 7, or distilled $H_2O$, to concentrations of 25-50 µM). Circular dichroism (CD) spectra are obtained on a spectropolarimeter (e.g., Jasco J-710) using standard measurement parameters (e.g., temperature, 20° C.; wavelength, 190-260 nm; step resolution, 0.5 nm; speed, 20 nm/sec; accumulations, 10; response, 1 sec; bandwidth, 1 nm; path length, 0.1 cm). The helical content of each peptide is calculated by dividing the mean residue ellipticity (e.g., [Φ]222 obs) by the reported value for a model helical decapeptide (Yang et al., (1986), Methods Enzymol. 130: 208)).

Assay to Determine Melting Temperature (Tm).

A peptidomimetic macrocycle comprising a secondary structure such as a helix exhibits, for example, a higher melting temperature than a corresponding uncrosslinked polypeptide. Typically peptidomimetic macrocycles exhibit Tm of >60° C. representing a highly stable structure in aqueous solutions. To assay the effect of macrocycle formation on melting temperature, peptidomimetic macrocycles or unmodified peptides are dissolved in distilled $H_2O$ (e.g., at a final concentration of 50 μM) and the Tm is determined by measuring the change in ellipticity over a temperature range (e.g., 4 to 95° C.) on a spectropolarimeter (e.g., Jasco J-710) using standard parameters (e.g., wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time (k=−1×slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and a corresponding uncrosslinked polypeptide (2 mcg) are incubated with fresh mouse, rat and/or human serum (2 mL) at 37° C. for 0, 1, 2, 4, 8, and 24 hours. To determine the level of intact compound, the following procedure may be used: The samples are extracted by transferring 100 μL of sera to 2 ml centrifuge tubes followed by the addition of 10 μL of 50% formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis.

In Vitro Binding Assays.

To assess the binding and affinity of peptidomimetic macrocycles and peptidomimetic precursors to acceptor proteins, a fluorescence polarization assay (FPA) is used, for example. The FPA technique measures the molecular orientation and mobility using polarized light and fluorescent tracer. When excited with polarized light, fluorescent tracers (e.g., FITC) attached to molecules with high apparent molecular weights (e.g., FITC-labeled peptides bound to a large protein) emit higher levels of polarized fluorescence due to their slower rates of rotation as compared to fluorescent tracers attached to smaller molecules (e.g., FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCl, pH 7.4) for 30 minutes at room temperature. Binding activity is measured, for example, by fluorescence polarization on a luminescence spectrophotometer (e.g., Perkin-Elmer LS50B). $K_D$ values may be determined by nonlinear regression analysis using, for example, Graphpad Prism software (GraphPad Software, Inc., San Diego, Calif.). A peptidomimetic macrocycle shows, in some instances, similar or lower $K_D$ than a corresponding uncrosslinked polypeptide.

In Vitro Displacement Assays to Characterize Antagonists of Peptide-Protein Interactions.

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g., FITC-labeled peptides bound to a large protein) emit higher levels of polarized fluorescence due to their slower rates of rotation as compared to fluorescent tracers attached to smaller molecules (e.g., FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCl, pH 7.4) for 30 minutes at room temperature. Antagonist binding activity is measured, for example, by fluorescence polarization on a luminescence spectrophotometer (e.g., Perkin-Elmer LS50B). $K_D$ values may be determined by nonlinear regression analysis using, for example, GraphPad Prism software (GraphPad Software, Inc., San Diego, Calif.).

Any class of molecule, such as small organic molecules, peptides, oligonucleotides or proteins can be examined as putative antagonists in this assay.

Assay for Protein-Ligand Binding by Affinity Selection-Mass Spectrometry

To assess the binding and affinity of test compounds for proteins, an affinity-selection mass spectrometry assay is used, for example Protein-ligand binding experiments are conducted according to the following representative procedure outlined for a system-wide control experiment using 1 μM peptidomimetic macrocycle plus 5 μM target protein. A 1 μL DMSO aliquot of a 40 μM stock solution of peptidomimetic macrocycle is dissolved in 19 μL of PBS (Phosphate-buffered saline: 50 mM, pH 7.5 Phosphate buffer containing 150 mM NaCl). The resulting solution is mixed by repeated pipetting and clarified by centrifugation at 10 000 g for 10 min. To a 4 μL aliquot of the resulting supernatant is added 4 μL of 10 μM target protein in PBS. Each 8.0 μL experimental sample thus contains 40 pmol (1.5 μg) of protein at 5.0 μM concentration in PBS plus 1 μM peptidomimetic macrocycle and 2.5% DMSO. Duplicate samples thus prepared for each concentration point are incubated for 60 min at room temperature, and then chilled to 4° C. prior to size-exclusion chromatography-LC-MS analysis of 5.0 μL injections. Samples containing a target protein, protein-ligand complexes, and unbound compounds are injected onto an SEC column, where the complexes are separated from non-binding component by a rapid SEC step. The SEC column eluate is monitored using UV detectors to confirm that the early-eluting protein fraction, which elutes in the void volume of the SEC column, is well resolved from unbound components that are retained on the column. After the peak containing the protein and protein-ligand complexes elutes from the primary UV detector, it enters a sample loop where it is excised from the flow stream of the SEC stage and transferred directly to the LC-MS via a valving mechanism. The $(M+3H)^{3+}$ ion of the peptidomimetic macrocycle is observed by ESI-MS at the expected m/z, confirming the detection of the protein-ligand complex.

Assay for Protein-Ligand $K_D$ Titration Experiments.

To assess the binding and affinity of test compounds for proteins, a protein-ligand $K_D$ titration experiment is performed, for example Protein-ligand $K_D$ titrations experiments are conducted as follows: 2 μL DMSO aliquots of a serially diluted stock solution of titrant peptidomimetic macrocycle (5, 2.5, . . . , 0.098 mM) are prepared then dissolved in 38 μL of PBS. The resulting solutions are mixed by repeated pipetting and clarified by centrifugation at 10 000 g for 10 min. To 4.0 μL aliquots of the resulting supernatants is added 4.0 μL of 10 μM target protein in PBS. Each 8.0 μL experimental sample thus contains 40 pmol (1.5 μg) of protein at 5.0 μM concentration in PBS, varying concentrations (125, 62.5, . . . , 0.24 μM) of the titrant peptide, and 2.5% DMSO. Duplicate samples thus prepared for each concentration point are incubated at room temperature for 30 min, then chilled to 4° C. prior to SEC-LC-MS analysis of 2.0 μL injections. The $(M+H)^{1+}$, $(M+2H)^{2+}$, $(M+3H)^{3+}$, and/or $(M+Na)^{1+}$ ion is observed by ESI-MS; extracted ion chromatograms are quantified, then fit to equations to derive the binding affinity $K_D$ as described in Annis, D. A.; Nazef, N.; Chuang, C. C.; Scott, M. P.; Nash, H. M. *J. Am. Chem. Soc.* 2004, 126, 15495-15503; also in D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Assay for Competitive Binding Experiments by Affinity Selection-Mass Spectrometry To determine the ability of test compounds to bind competitively to proteins, an affinity selection mass spectrometry assay is performed, for example. A mixture of ligands at 40 μM per component is prepared by combining 2 μL aliquots of 400 μM stocks of each of the three compounds with 14 μL of DMSO. Then, 1 μL aliquots of this 40 μM per component mixture are combined with 1 μL DMSO aliquots of a serially diluted stock solution of titrant peptidomimetic macrocycle (10, 5, 2.5, . . . , 0.078 mM). These 2 μL samples are dissolved in 38 μL of PBS. The resulting solutions were mixed by repeated pipetting and clarified by centrifugation at 10 000 g for 10 min. To 4.0 μL aliquots of the resulting supernatants is added 4.0 μL of 10 μM target protein in PBS. Each 8.0 μL experimental sample thus contains 40 pmol (1.5 μg) of protein at 5.0 μM concentration in PBS plus 0.5 μM ligand, 2.5% DMSO, and varying concentrations (125, 62.5, . . . , 0.98 μM) of the titrant peptidomimetic macrocycle. Duplicate samples thus prepared for each concentration point are incubated at room temperature for 60 min, then chilled to 4° C. prior to SEC-LC-MS analysis of 2.0 μL injections. Additional details on these and other methods are provided in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Hofner G: Wiley-VCH; 2007:121-184. Mannhold R, Kubinyi H, Folkers G (Series Editors): Methods and Principles in Medicinal Chemistry Binding Assays in Intact Cells.

It is possible to measure binding of peptides or peptidomimetic macrocycles to their natural acceptors in intact cells by immunoprecipitation experiments. For example, intact cells are incubated with fluoresceinated (FITC-labeled) compounds for 4 hours in the absence of serum, followed by serum replacement and further incubation that ranges from 4-18 hours. Cells are then pelleted and incubated in lysis buffer (50 mM Tris, pH 7.6, 150 mM NaCl, 1% CHAPS and protease inhibitor cocktail) for 10 minutes at 4° C. Extracts are centrifuged at 14,000 rpm for 15 minutes and supernatants collected and incubated with 10 μL goat anti-FITC antibody for 2 hours, rotating at 4° C. followed by further 2 hours incubation at 4° C. with protein A/G Sepharose (50 μL of 50% bead slurry). After quick centrifugation, the pellets are washed in lysis buffer containing increasing salt concentration (e.g., 150, 300, 500 mM). The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the peptidomimetic macrocycle.

Cellular Penetrability Assays.

A peptidomimetic macrocycle is, for example, more cell penetrable compared to a corresponding uncrosslinked macrocycle. Peptidomimetic macrocycles with optimized linkers possess, for example, cell penetrability that is at least two-fold greater than a corresponding uncrosslinked macrocycle, and often 20% or more of the applied peptidomimetic macrocycle will be observed to have penetrated the cell after 4 hours. To measure the cell penetrability of peptidomimetic macrocycles and corresponding uncrosslinked macrocycle, intact cells are incubated with fluoresceinated peptidomimetic macrocycles or corresponding uncrosslinked macrocycle (10 μM) for 4 hours in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

In Vivo Stability Assay.

To investigate the in vivo stability of the peptidomimetic macrocycles, the compounds are, for example, administered to mice and/or rats by IV, IP, PO or inhalation routes at concentrations ranging from 0.1 to 50 mg/kg and blood specimens withdrawn at 0', 5', 15', 30', 1 hour, 4 hours, 8 hours and 24 hours post-injection. Levels of intact compound in 25 μL of fresh serum are then measured by LC-MS/MS as above.

In Vitro Testing for Inhibition of Influenza Replication

This influenza antiviral evaluation assay examines the effects of compounds at designated dose-response concentrations. See also Noah, J. W., W. Severson, D. L. Noah, L. Rasmussen, E. L. White, and C. B. Jonsson, *Antiviral Res*, 2007. 73(1): p. 50-9. Madin Darby canine kidney (MDCK) cells are used in the assay to test the efficacy of the compounds in preventing the cytopathic effect (CPE) induced by influenza infection. Either Ribavirin or Tamiflu is included in each run as a positive control compound. Subconfluent cultures of MDCK cells are plated into 96-well plates for the analysis of cell viability (cytotoxicity) and antiviral activity (CPE). Drugs are added to the cells 24 hours later. At a designated time, the CPE wells also receive 100 tissue culture infectious doses (100 TCID$_{50}$s) of titered influenza virus. 72 hours later the cell viability is determined. The effective compound concentrations which reduce viral-induced CPE by 25% (IC$_{25}$), 50% (IC$_{50}$), and 90% (IC$_{90}$) are calculated by regression analysis with semi-log curve fitting. Cell viability is assessed using CellTiter-Glo (Promega). The toxic concentration of drug that reduces cell numbers by 50% and 90% (TC$_{50}$ and TC$_{90}$, respectively) are calculated as well. Selectivity (therapeutic) indices (SI=TC/IC) are also calculated.

In Vivo Testing for Inhibition of Influenza Replication

In vivo testing of compounds can be performed, including testing on mammals such as rats or ferrets. Because ferrets (*Mustela putorius furo*) are naturally susceptible to infection with human influenza A and B viruses and their disease resembles that of human influenza, these animals have been widely used as a model for influenza virus pathogenesis and immunity studies. See Sidwell, R. W. and D. F. Smee, *Antiviral Res*, 2000. 48(1): p. 1-16; and Colacino, J. M., D. C. DeLong, J. R. Nelson, W. A. Spitzer, J. Tang, F. Victor, and C. Y. Wu, *Antimicrob Agents Chemother*, 1990. 34(11): p. 2156-63. Ferrets are also the model of choice for the study of avian influenza virus H5N1 pathogenesis in mammals. See also Zitzow, L. A., T. Rowe, T. Morken, W.-J. Shieh, S. Zaki, and J. M. Katz, *Pathogenesis of Avian Influenza A (H5N1) Viruses in Ferrets*. 2002. p. 4420-4429. The activities of the PB1 Stapled Peptides can be compared to Ribavirin or Oseltamivir as a positive control.

Briefly, young adult male or female ferrets (five ferrets for each treatment group) that are serologically negative by hemagglutination inhibition assay for currently circulating human influenza A or B viruses are quarantined at least 4 days prior to infection in a BSL-3+ animal holding area, where they are housed in cages contained in bioclean portable laminar flow clean room enclosures (Lab Products, Seaford, Del.). Prior to infection, baseline temperatures are measured twice daily for at least 3 days. Ferrets are anesthetized with ketamine (25 mg/kg), xylazine (2 mg/kg), and atropine (0.05 mg/kg) by the intramuscular route and infected intranasally (i.n.) with virus/ml in phosphate-buffered saline (PBS) delivered to the nostrils. Control animals are mock-infected with an equivalent dilution (1:30) of noninfectious allantoic fluid. Stapled Peptides are administered i.v. or i.p. one hour after virus infection. Temperatures are measured twice daily using either a rectal thermometer or a subcutaneous implantable temperature transponder (BioMedic Data Systems, Inc., Seaford, Del.) with pre-infection values averaged to obtain a baseline temperature for each ferret. The change in temperature (in degrees Celsius) is calculated at each time point for each animal Clinical signs of sneezing (before anesthesia), inappetence, dyspnea, and level of activity are assessed. A scoring system is also used to assess the activity level, and based on the daily scores for each animal in a group a relative inactivity index will be calculated. Rectal temperature and activity scores are used to assess the severity of influenza infection and the ability of Stapled Peptides to prevent flu symptoms Assaying Inhibition of Viral Polymerase Complex Assembly and Activity.

The technique of Bimolecular Fluorescence Complementation ("BiFC") may be used to assay the compounds. In this technique, N- and C-terminal fragments of fluorescent proteins (e.g., GFP or its derivatives) are fused to interacting proteins. The two non-functional halves of the fluorophore, following the expression in cells, are brought into close proximity as a result of the specific protein interactions, which initiates folding of the fragments into an active protein and results in a detectable fluorescent signal at the site of the protein-protein complex. Thus, through BiFC, the specific interaction between PB1 and PA subunits can be visualized, quantified and localized within live cells. By disrupting PB1-PA interaction with a compound, the BiFC signal will be reduced, indicative of the presence of potential inhibitors targeting the assembly of PB1-PA complex. See Hemerka et al., *J. Virol.* 2009, 3944-3955.

Pharmaceutical Compositions and Routes of Administration

The peptidomimetic macrocycles also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature. See, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

In some embodiments, the compositions are present as unit dosage forms that can deliver, for example, from about 0.0001 mg to about 1,000 mg of the peptidomimetic macrocycles, salts thereof, prodrugs thereof, derivatives thereof, or any combination of these. Thus, the unit dosage forms can deliver, for example, in some embodiments, from about 1 mg to about 900 mg, from about 1 mg to about 800 mg, from about 1 mg to about 700 mg, from about 1 mg to about 600 mg, from about 1 mg to about 500 mg, from about 1 mg to about 400 mg, from about 1 mg to about 300 mg, from about 1 mg to about 200 mg, from about 1 mg to about 100 mg, from about 1 mg to about 10 mg, from about 1 mg to about 5 mg, from about 0.1 mg to about 10 mg, from about 0.1 mg to about 5 mg, from about 10 mg to about 1,000 mg, from about 50 mg to about 1,000 mg, from about 100 mg to about 1,000 mg, from about 200 mg to about 1,000 mg, from about 300 mg to about 1,000 mg, from about 400 mg to about 1,000 mg, from about 500 mg to about 1,000 mg, from about 600 mg to about 1,000 mg, from about 700 mg to about 1,000 mg, from about 800 mg to about 1,000 mg, from about 900 mg to about 1,000 mg, from about 10 mg to about 900 mg, from about 100 mg to about 800 mg, from about 200 mg to about 700 mg, or from about 300 mg to about 600 mg of the peptidomimetic macrocycles, salts thereof, prodrugs thereof, derivatives thereof, or any combination of these.

In some embodiments, the compositions are present as unit dosage forms that can deliver, for example, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 500 mg, about 600 mg, about 700 mg, about 800 mg, or about 800 mg of peptidomimetic macrocycles, salts thereof, prodrugs thereof, derivatives thereof, or any combination of these.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition as described herein is administered in a local rather than systemic manner, for example, via injection of the compound directly into an organ. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In another embodiment, compositions described herein are formulated for oral administration. Compositions described herein are formulated by combining a peptidomimetic macrocycle with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the peptidomimetic macrocycles described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the peptidomimetic macrocycles described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the peptidomimetic macrocycles described herein are formulated for buccal or sublingual administration. Formulations suitable for buccal or sublingual administration include, by way of example only, tablets, lozenges, or gels. In still other embodiments, the peptidomimetic macrocycles described herein are formulated for parenteral injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, pharmaceutical compositions are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions herein can be administered, for example, once or twice or three or four or five or six times per day, or once or twice or three or four or five or six times per week, and can be administered, for example, for a day, a week, a month, 3 months, six months, a year, five years, or for example ten years.

Methods of Use

Generally, the invention discloses peptidomimetic macrocycles useful in the treatment of viral disorders. For example, peptidomimetic macrocycles derived from the PB1 helix sequence, or peptidomimetic macrocycles that bind selectively to the PB1 peptide binding site of the PA protein, may selectively inhibit influenza RNA-dependent RNA polymerases. Peptidomimetic macrocycles derived from the PB2 helix sequence, or peptidomimetic macrocycles that bind selectively to the PB2 peptide binding site of the PB1 protein, may selectively inhibit influenza RNA-dependent RNA polymerases. When administered within a therapeutic window after infection, such peptidomimetic macrocycles may reduce the severity or duration of an influenza infection. When administered prophylactically, such peptidomimetic macrocycles may prevent infection by influenza viruses and thereby decrease the spread of influenza and reduce large-scale epidemics.

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the PB1/PA system, labeled peptidomimetic macrocycles based on PB1 can be used in a PA binding assay along with small molecules that competitively bind to PA. Competitive binding studies allow for rapid in vitro evaluation and determination of drug candidates specific for the PB1/PA system. Such binding studies may be performed with any of the peptidomimetic macrocycles disclosed herein and their binding partners.

In other aspects, the present invention provides for both prophylactic and therapeutic methods of treating a subject infected with, at risk of, or susceptible to an influenza virus. These methods comprise administering an effective amount of a compound to a warm blooded animal, including a human. In some embodiments, the administration of the compounds of the present invention prevents the proliferation or transmission of an influenza virus.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, peptidomimetic macrocycles are used to treat diseases induced by influenza viruses. Like other viruses, the replication of influenza virus involves six phases; transmission, entry, replication, biosynthesis, assembly, and exit. Entry occurs by endocytosis, replication and vRNP assembly takes place in the nucleus, and the virus buds from the plasma membrane. In the infected patient, the virus targets airway epithelial cells.

The methods described herein are also useful for development and/or identification of agents for the treatment of infections caused by viruses such as Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Borna disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus. In one embodiment an infectome will be produced for each virus that includes an inventory of the host cellular genes involved in virus infection during a specific phase of viral infection, such cellular entry or the replication cycle.

For some viruses a great deal of progress has been made in the elucidation of the steps involved during infection of host cells, and any of these steps may be targeted using peptidomimetic macrocycles. For example, experiments initiated in the early 1980s showed that influenza virus follows a stepwise, endocytic entry program with elements shared with other viruses such as alpha- and rhabdoviruses (Marsh and Helenius 1989; Whittaker 2006). The steps include: 1) Initial attachment to sialic acid containing glycoconjugates receptors on the cell surface; 2) signaling induced by the virus particle; 3) endocytosis by clathrin-dependent and clathrin-independent cellular mechanism; 4) acid-induced, hemaglutinin (HA)-mediated penetration from late endosomes; 5) acid-activated, M2 and matrix protein (M1) dependent uncoating of the capsid; and, 6) intra-cytosolic transport and nuclear import of vRNPs. These steps depend on assistance from the host cell in the form of sorting receptors, vesicle formation machinery, kinase-mediated regulation, organelle acidification, and, most likely, activities of the cytoskeleton.

Influenza attachment to the cells surface occurs via binding of the HA1 subunit to cell surface glycoproteins and glycolipids that carry oligosaccharide moieties with terminal sialic acid residues (Skehel and Wiley 2000). The linkage by which the sialic acid is connected to the next saccharide contributes to species specificity. Avian strains including H5N1 prefer an a-(2,3)-link and human strains a-(2,6)-link (Matrosovich 2006). In epithelial cells, binding occurs preferentially to microvilli on the apical surface, and endocytosis occurs at base of these extensions (Matlin 1982). Whether receptor binding induces signals that prepare the cell for the invasion is not yet known, but it is likely because activation of protein kinase C and synthesis of phopshatidylinositol-3-phosphate (PI3P) are required for efficient entry (Sieczkarski et al., 2003; Whittaker 2006).

Endocytic internalization occurs within a few minutes after binding (Matlin 1982; Yoshimura and Ohnishi 1984). In tissue culture cells influenza virus makes use of three different types of cellular processes; 1) preexisting clathrin coated pits, 2) virus-induced clathrin coated pits, and 3) endocytosis in vesicles without visible coat (Matlin 1982;

Sieczkarski and Whittaker 2002; Rust et al., 2004). Video microscopy using fluorescent viruses showed the virus particles undergoing actin-mediated rapid motion in the cell periphery followed by minus end-directed, microtubule-mediated transport to the perinuclear area of the cell. Live cell imaging indicated that the virus particles first entered a subpopulation of mobile, peripheral early endosomes that carry them deeper into the cytoplasm before penetration takes place (Lakadamyali et al., 2003; Rust et al., 2004). The endocytotic process is regulated by protein and lipid kinases, the proteasome, as well as by Rabs and ubiquitin-dependent sorting factors (Khor et al., 2003; Whittaker 2006).

The membrane penetration step is mediated by low pH-mediated activation of the trimeric, metastable HA, and the conversion of this Type I viral fusion protein to a membrane fusion competent conformation (Maeda et al., 1981; White et al., 1982). This occurs about 16 min after internalization, and the pH threshold varies between strains in the 5.0-5.6 range. The target membrane is the limiting membrane of intermediate or late endosomes. The mechanism of fusion has been extensively studied (Kielian and Rey 2006). Further it was observed that fusion itself does not seem to require any host cell components except a lipid bilayer membrane and a functional acidification system (Maeda et al., 1981; White et al., 1982). The penetration step is inhibited by agents such as lysosomotropic weak bases, carboxylic ionophores, and proton pump inhibitors (Matlin 1982; Whittaker 2006).

To allow nuclear import of the incoming vRNPs, the capsid has to be disassembled. This step involves acidification of the viral interior through the amantadine-sensitive M2-channels causes dissociation of M1 from the vRNPs (Bukrinskaya et al., 1982; Martin and Helenius 1991; Pinto et al., 1992). Transport of the individual vRNPs to the nuclear pore complexes and transfer into the nucleus depends on cellular nuclear transport receptors (O'Neill et al., 1995; Cros et al., 2005). Replication of the viral RNAs (synthesis of positive and negative strands), and transcription occurs in complexes tightly associated with the chromatin in the nucleus. It is evident that, although many of the steps are catalyzed by the viral polymerase, cellular factors are involved including RNA polymerase activating factors, a chaperone HSP90, hCLE, and a human splicing factor UAP56. Viral gene expression is subject to complex cellular control at the transcriptional level, a control system dependent on cellular kinases (Whittaker 2006).

The final assembly of an influenza particle occurs during a budding process at the plasma membrane. In epithelial cells, budding occurs at the apical membrane domain only (Rodriguez-Boulan 1983). First, the progeny vRNPs are transported within the nucleoplasm to the nuclear envelope, then from the nucleus to the cytoplasm, and finally they accumulate in the cell periphery. Exit from the nucleus is dependent on viral protein NEP and M1, and a variety of cellular proteins including CRM1 (a nuclear export receptor), caspases, and possibly some nuclear protein chaperones. Phosphorylation plays a role in nuclear export by regulating M1 and NEP synthesis, and also through the MAPK/ERK system (Bui et al., 1996; Ludwig 2006). G protein and protein kinase signaling is involved in influenza virus budding from infected host cells (Hui E. and Nayak D, 2002).

The three membrane proteins of the virus are synthesized, folded and assembled into oligomers in the ER (Doms et al., 1993). They pass through the Golgi complex; undergo maturation through modification of their carbohydrate moieties and proteolytic cleavage. After reaching the plasma membrane they associate with M1 and the vRNPs in a budding process that results in the inclusion of all eight vRNPs and exclusion of most host cell components except lipids.

Influenza infection is associated with activation of several signaling cascades including the MAPK pathway (ERK, JNK, p38 and BMK-1/ERK5), the IkB/NF-kB signaling module, the Raf/MEK/ERK cascade, and programmed cell death (Ludwig 2006). These result in a variety of effects that limit the progress of infection such as transcriptional activation of IFNb, apoptotic cell death, and a block in virus escape of from late endosomes (Ludwig 2006).

EXAMPLES

Example 1

Peptidomimetic macrocycles were synthesized, purified and analyzed as previously described (Walensky et al., (2004) Science 305:1466-70; Walensky et al., (2006) Mol Cell 24:199-210; Bernal et al., (2007) J. Am Chem Soc. 9129, 2456-2457) and as indicated below. The macrocycles used in this study are shown in Table 1. The corresponding uncrosslinked polypeptides represent the natural counterparts of the peptidomimetic macrocycles.

α,α-disubstituted non-natural amino acids containing olefinic side chains were synthesized according to Williams et al., (1991) J. Am. Chem. Soc. 113:9276; Schafmeister et al., (2000) J. Am. Chem Soc. 122:5891 and Verdine et al., PCT WO 2008/121767. Peptidomimetic macrocycles were designed by replacing two or more naturally occurring amino acids with the corresponding synthetic amino acids. Substitutions were made at the i and i+3, i and i+4, i and i+6, and i and i+7 positions. Macrocycles were generated by solid phase peptide synthesis followed by olefin metathesis-based crosslinking of the synthetic amino acids via their olefin-containing side chains.

The non-natural amino acids (R and S enantiomers of the 5-carbon olefinic amino acid and the S enantiomer of the 8-carbon olefinic amino acid) were characterized by nuclear magnetic resonance (NMR) spectroscopy (Varian Mercury 400) and mass spectrometry (Micromass LCT). Peptide synthesis was performed manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. Olefin metathesis was performed in the solid phase using 10 mM Grubbs catalyst (Blackewell et al., 1994) (Strem Chemicals) dissolved in degassed dichloromethane and reacted for 2 hours at room temperature. Isolation of metathesized compounds was achieved by trifluoroacetic acid-mediated deprotection and cleavage, ether precipitation to yield the crude product, and high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

The synthesized peptides include a norleucine replacement for methionine to avoid issues with unwanted thioether oxidation. In several peptides, the proline residue is replaced with a 2-aminoisobutyric acid residue (Aib) to increase helicity, and the effect of Glu-to-Arg substitution on cell penetrability was also explored. The N-termini of the exemplary synthetic peptides were acetylated, while the C-termini were amidated. Table 1 shows non-limiting list of peptidomimetic macrocycles prepared.

Example 2: Manufacture of Peptidomimetic Macrocycle

Synthesis of Peptide on Resin

The initial amino acid of the C-terminus was attached to a polyethylene glycol-grafted polystyrene-based Fmoc-Rink resin (Amphispheres 40 RAM), which was prepared for coupling with the first amino acid by treatment with piperidine in DMF. The subsequent amino acids were coupled individually until the full linear sequence was elaborated. The α-amino group of each amino acid was protected by a 9H-fluoren-9-ylmethoxycarbonyl group (Fmoc) during the coupling of the carboxylic acid of the amino acid with the free amino terminus of the peptide attached to the resin. To avoid any side reactions during the coupling steps performed in DMF, the reactive side-chains of amino acids also carry acid-labile protecting groups that effectively mask the reactive groups until treatment of the resin with acid during the cleavage of the peptide from the solid support. After completion of each coupling step the Fmoc group of the just-attached amino acid was removed with piperidine and the resin was thoroughly washed to prepare for the coupling of the subsequent Fmoc-amino acid derivative. Diisopropyl-carbodiimide (DIC) with 1-hydroxybenzotriazole (HOBt) or (7-azabenzotriazol-1-yloxy) tripyrrolidino-phosphonium hexafluorophosphate (PyAOP) were used as coupling agents to create the amide bond between the free amino terminus of the resin-bound protected peptide and the carboxylic acid of the Fmoc-amino acid.

The presence or absence of available amino groups was tested with the Kaiser Ninhydrin Test. After each piperidine treatment a small sample of the resin-bound peptide was removed to verify the availability of free amino groups. Additionally, a small sample of the resin-bound peptide was also removed after each Fmoc-amino acid coupling step to verify that no amino groups were still available to react with the next amino acid. In case of a positive test result after coupling (presence of free amino groups), the coupling reaction was repeated. If there were still available amino groups after repeat coupling, the resin-bound peptide was treated with acetic anhydride in the presence of DIPEA in DMF to block the remaining free amine from further reaction with subsequent Fmoc-amino acids. After release from the resin, the shorter blocked peptides were more readily removed from the complete peptide than a peptide containing a deletion.

Cyclization (Metathesis)

Cyclization was carried out in Toluene with the peptide on the resin resulting in a cross-link of terminal olefin moieties with the application of Hoveyda-Grubbs' $2^{nd}$ generation catalyst. This cyclization was performed at room temperature with stepwise addition of catalyst (5-10% total amount) over period of 5-7 days. Progress of the cyclization was monitored by TFA cleavage of small sample of peptide resin and LC-MS analysis of cleaved peptide. After cyclization was completed resin was washed extensively and treated with DMSO/DCM mixture (1:1, v/v) for 16 hours. Following extensive washes resin was dried under vacuum before TFA cleavage. Treatment of the resin with trifluoroacetic acid (TFA) removes side chain protecting groups and releases the peptide from the resin as the C-terminal primary amide. Water and triisopropylsilane were added to the TFA cleavage solution to quench reactive side products that result from the removal of side chain protecting groups.

Purification

Purification was performed by preparative reversed-phase high performance liquid chromatography (RP-HPLC) in three sequential steps on phenyl-hexyl-derivatized silica as purification media. In the first step, the peptide was eluted from the column using a gradient of acetonitrile in 0.1% TFA in water; in the second step, an acetonitrile gradient of acetonitrile in 0.1 M triethylamine/phosphoric acid in water was used.

Fractions from each step were tested for peptide purity using an in-process analytical HPLC method. Pooled fractions were lyophilized and stored until the entire batch has been purified.

Desalting, Reconstitution and Lyophilization

The purified product from the second reverse-phase HPLC purification step was converted to the free carboxylic acid (side chain of Glu) on phenyl-hexyl-derivatized silica and eluted using an acetonitrile gradient in 0.1% aqueous TFA. The eluate was clarified by filtration through a 0.2 µm membrane filter and then lyophilized to homogeneity.

Packaging

Following lyophilization final peptide was packaged into Type III amber glass bottles in a HEPA-filtered environment. The bottles were sealed with Teflon®-lined polypropylene screw caps. To ensure that no moisture can enter the containers, the screw cap bottle interface was additionally wrapped with PTFE tape.

Example 3: Pd-Catalyzed Cross Coupling of Terminal Alkynes to Diynes

The fully protected resin-bound peptides were synthesized on a PEG-PS resin (loading 0.4 mmol/g) on a 0.2 mmol scale. Deprotection of the temporary Fmoc group was achieved by 3×10 min treatments of the resin bound peptide with 20% (v/v) piperidine in DMF. After washing with NMP (3×), dichloromethane (3×) and NMP (3×), coupling of each successive amino acid was achieved with 1×120 min incubation with the appropriate preactivated Fmoc-amino acid derivative. All protected amino acids (0.8 mmol) were dissolved in NMP and activated with HCTU (0.8 mmol) and DIEA (1.6 mmol) prior to transfer of the coupling solution to the deprotected resin-bound peptide. α-methylated amino acids and amino acids immediately followed α-methylated ones were coupled in the similar way with the use of PyAOP instead HCTU as a coupling agent. After all couplings were completed, the resin was washed in preparation for the next deprotection/coupling cycle. Acetylation of the amino terminus was carried out in the presence of acetic anhydride/DIEA in NMP. The LC-MS analysis of a cleaved and deprotected sample obtained from an aliquot of the fully assembled resin-bound peptide was accomplished in order to verifying the completion of each coupling.

In a typical example, 1,2-dichloroethane (6 ml) and triethylamine (3 ml) were added to the peptide resin (0.2 mmol) in a 40 mL glass vial and shaken for 60 minutes. Copper iodide (0.008 g, 0.04 mmol) was added to the resin slurry followed by 10 min later with Pd(PPh$_3$)$_2$Cl$_2$ (0.028 g, 0.04 mmol) and triphenylphosphine (0.031 g, 0.12 mmol). The resulting reaction mixture was mechanically shaken 16 hours at 50° C. while open to atmosphere. The diyne-cyclized resin-bound peptides were deprotected and cleaved from the solid support by treatment with TFA/H$_2$O/TIS (95/5/5 v/v) for 2.5 hours at room temperature. After filtration of the resin the TFA solution was precipitated in cold diethyl ether and centrifuged to yield the desired product as a solid. The crude product was purified by preparative HPLC.

Example 4: Stability

The ex vivo serum stability of several peptidomimetic macrocycles will be tested by incubating them at 5000 ng/mL (2 µM at MW=2500) with fresh human serum at 37° C. and taking samples at 0, 0.5, 1, 2, 4, 6 and 24 hours. At each time point the samples will be flash-frozen until analysis in duplicate, then extracted by transferring 100 µL of sera to 2 ml centrifuge tubes followed by the addition of 10 µL of 50% formic acid and 500 µL acetonitrile and centrifugation at 14,000 RPM for 10 min at 4±2° C. After protein precipitation, the supernatants will be transferred to fresh 2 ml tubes and evaporated on Turbovap under $N_2$ at <10 psi, 37° C. The samples will be reconstituted in 100 µL of 50:50 acetonitrile/water and quantified by LC-MS/MS analysis. The response for each compound will be normalized to estimate a percent decrease in concentration versus time.

Example 5: PK Properties

Several peptidomimetic macrocycles will be tested for PK properties in single IV dose in rats. The in-life portion of the study will be conducted at ViviSource Laboratories (Waltham, Mass.). A single intravenous dose of 3 mg/kg Stapled Peptide formulated in water continuing 5% PEG-400 and 2% Dextrose will be administered to a pair of jugular vein-cannulated male Sprague-Dawley rats. The IV dose that is mostly well-tolerated and whether animals appear healthy within the study duration will be determined Blood samples will be collected over thirteen sampling times up to 24 hours and the plasma samples will be shipped on dry ice to Tandem Bioanalytical Facilities, Inc. (Woburn, Mass.) for the analytical phase of the study.

Quantification in plasma samples will be preceded by the preparation of sample extracts by combining 50 µL of ammonium hydroxide (14.5 M ammonia), 1 mL of a 1:1 acetonitrile/methanol solution, and 50 µL of internal standard with 50 µL of each plasma sample. The mixtures will be centrifuged to separate liquid supernatant from solid precipitate and supernatants will be dried at 40° C. under flowing nitrogen gas. The dried sample extracts will be reconstituted in 50 µL of a 1:1 water/methanol solution that contained 0.1% (v/v) trifluoroacetic acid. Plasma sample extracts will be analyzed by a liquid chromatography-mass spectrometry method that utilized an API 5000 (Applied Biosystems) instrument operated in positive ionization mode at a temperature of 500° C. using a multiple reaction monitoring mode of detection (MRM). The analytical column for liquid chromatography will be a Varian Metasil C18, 50 mm×2 mm and mobile phases A (0.1% formic acid in water) and B (0.1% formic acid in acetonitrile) will be pumped at a flow rate of 0.5 ml/min. Quantification in plasma extracts will be made by linear regression analysis employing a pure reference standard Stapled Peptide diluted in normal rat plasma to prepare eight calibration standards over the working concentration range of 20-10,000 ng/ml. The calibration standards will be extracted in identical fashion as sample extracts and analyzed before and after the sample extracts.

Pharmacokinetic parameters will be calculated using a non-compartmental model using the PK Functions add-in for Microsoft Excel. The terminal elimination half-life will be calculated as $\ln(2)/(\lambda z)$, where the rate constant ($\lambda z$) will be calculated as −1 times the estimated slope of the log-concentration versus time data over 2-12 hours. AUC values (hr*ng/ml) will be calculated by statistical moment and linear trapezoidal approximation methods over time points of 0-24 hours and 24 hour concentration values will be divided by ($\lambda z$) was added in order to extrapolate AUMC and AUC values to infinite time. Total body clearance (per kg body weight) will be calculated as dose divided by AUC. The volume of distribution at steady state (Vss) will be calculated as the product of clearance and mean residence time (MRT=AUC/AUMC).

An experiment will be also performed to compare different modes of administration. Subcutaneous injection of peptidomimetic macrocycle will be performed and compared to intravenous administration. Two groups of two animals each will be injected subcutaneously with a 3 mg/kg dose. Plasma will be collected at regular time points (e.g., 5, 20 minutes; 1, 2, 4, 8 12, and 48 hours) and the samples will be analyzed as indicated above.

Example 6—In Vitro Testing for Inhibition of Influenza Replication

An influenza antiviral evaluation assay was performed to examine the effects of peptidomimetic macrocycles at designated dose-response concentrations. See also Noah, J. W., W. Severson, D. L. Noah, L. Rasmussen, E. L. White, and C. B. Jonsson, *Antiviral Res,* 2007. 73(1): p. 50-9. Madin Darby canine kidney (MDCK) cells were used in the assay to test the efficacy of the compounds in preventing the cytopathic effect (CPE) induced by influenza infection. Either Ribavirin or Tamiflu were included in each run as a positive control compound. Subconfluent cultures of MDCK cells were plated into 96-well plates for the analysis of cell viability (cell cytotoxicity (CC)) and antiviral activity (CPE). Drugs were added to the cells 24 hours later. At a designated time, the CPE wells received 100 tissue culture infectious doses (100 $TCID_{50}$s) of titered influenza virus. 72 hours later the cell viability was determined. The effective compound concentrations which reduced viral-induced CPE by 25% ($IC_{25}$), 50% ($IC_{50}$), and 90% ($IC_{90}$) were calculated by regression analysis with semi-log curve fitting. Cell viability will be assessed using CellTiter-Glo (Promega). The toxic concentration of drug that reduced cell numbers by 50% and 90% ($TC_{50}$ and $TC_{90}$, respectively) were calculated as well. Selectivity (therapeutic) indices (SI=TC/IC) were also calculated. Cells were also used in a virus yield reduction (VYR) assay to determine antiviral efficacy of the compounds in reducing viral titers. Cells were plated and infected as described above and then incubated. Supernatants were then be harvested and viral titers were determined by plaque assay, TCID, or immunocytochemistry. Antiviral efficacy was calculated based on viral titer reduction compared to an untreated virus control and used to calculate $IC_{50}$. Results of the assays are shown below in Table 5, Table 6, Table 7, and Table 8.

TABLE 5

Cytopathic effect/toxicity (Visual)

| SP# | EC$_{50}$ (μM) H$_1$N$_1$ California/07/2009 | EC$_{50}$ (μM) H$_3$N$_2$ Perth/16/2009 |
|---|---|---|
| Ribavirin | ++++ | ++++ |
| 1 | + | ++ |
| 2 | + | +++ |
| 3 | + | ++ |
| 4 | + | ++ |
| 5 | ++ | +++ |
| 6 | +++ | ++ |
| 7 | +++ | ++ |
| 8 | +++ | ++ |
| 9 | +++ | ++ |
| 10 | ++ | ++ |
| 11 | ++++ | +++ |
| 12 | ++++ | +++ |
| 13 | ++ | + |
| 14 | ++++ | ++ |
| 15 | ++ | ++ |
| 16 | +++ | ++ |
| 17 | ++ | +++ |
| 18 | ++++ | ++ |
| 19 | ++++ | ++++ |
| 20 | +++ | ++++ |
| 21 | +++++ | +++++ |
| 22 | ++++ | +++++ |
| 23 | ++++ | ++++ |
| 24 | ++++ | ++++ |
| 25 | +++++ | +++++ |
| 26 | +++++ | +++ |
| 27 | +++++ | +++++ |

+ = >50 μM;
++ = >25-50 μM;
+++ = >10-25 μM;
++++ = >1.5-10 μM;
+++++ = ≤1.5 μM

TABLE 6

Cytopathic effect/toxicity (Neutral red)

| SP# | EC$_{50}$ (μM) H$_1$N$_1$ California/07/2009 | EC$_{50}$ (μM) H$_3$N$_2$ Perth/16/2009 |
|---|---|---|
| Ribavirin | +++ | +++ |
| 1 | ++ | ++ |
| 2 | + | ++ |
| 3 | + | + |
| 4 | + | ++ |
| 5 | ++ | +++ |
| 6 | +++ | ++ |
| 7 | +++ | ++ |
| 8 | +++ | ++ |
| 9 | +++ | ++ |
| 10 | ++ | ++ |
| 11 | ++++ | +++ |
| 12 | ++++ | +++ |
| 13 | ++ | + |
| 14 | ++++ | ++ |
| 15 | ++ | ++ |
| 16 | +++ | ++ |
| 17 | ++ | +++ |
| 18 | ++++ | ++ |
| 19 | ++++ | ++++ |
| 20 | ++ | ++++ |
| 21 | ++++ | ++++ |
| 22 | ++++ | +++++ |
| 23 | ++++ | ++++ |
| 24 | ++++ | ++++ |
| 25 | +++++ | +++++ |
| 26 | ++++ | +++ |
| 27 | +++++ | ++++ |

+ = >50 μM;
++ = >25-50 μM;
+++ = >10-25 μM;
++++ = >1.5-10 μM;
+++++ = ≤1.5 μM

As shown in Table 7, all peptides have a CC$_{50}$>100 μM against both H$_1$N$_1$ California/07/2009 and H$_3$N$_2$ Perth/16/2009 strains.

TABLE 7

Cell cytotoxicity (CC)

| SP# | CC$_{50}$ (μM) H$_1$N$_1$ California/07/2009 | CC$_{50}$ (μM) H$_3$N$_2$ Perth/16/2009 |
|---|---|---|
| Ribavirin | + | + |
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |
| 26 | + | + |
| 27 | + | + |

+ = >100 μM

As shown in Table 8, peptide SP-6 showed broad antiviral activity.

TABLE 8

Cytopathic effect/toxicity

| Influenza Strain | EC$_{50}$**** (μM) |
|---|---|
| H$_1$N$_1$ A/California/07/2009 (pandemic) | ND |
| H$_1$N$_1$ A/California/07/2009* | ++ |
| H$_1$N$_1$ A/California/07/2009** | ++++ |
| H$_1$N$_1$ A/HK/2369/09 (oseltamivir-resistant) | ND |
| H$_1$N$_1$ A/PR/8/34 | +++ |
| H$_1$N$_1$ A/Solomon Island/03/2006** | ++++ |
| H$_1$N$_1$ A/Solomon Island/03/2006*** | +++++ |
| H$_1$N$_1$ A/Brisbane/59/2007** | ++++ |
| H$_1$N$_1$ A/Brisbane/59/2007*** | ++++ |
| H$_3$N$_2$ A/Perth/16/2009* | ++++ |
| H$_3$N$_2$ A/Perth/16/2009** | ++++ |
| H$_5$N$_1$ A/Duck/MN/1525/81* | +++ |
| H$_5$N$_1$ A/Duck/MN/1525/81** | ++++ |

TABLE 8-continued

| Cytopathic effect/toxicity | |
|---|---|
| Influenza Strain | $EC_{50}$**** (μM) |
| $H_5N_1$ A/Hong Kong/213/2003** | + |
| $H_7N_9$ A/Anhui/1/2013** | + |
| Influenza B Florida/04/2006** | +++ |
| Influenza B Brisbane/60/2008** | ++++ |

*Assay conducted November 2013
**Assay conducted January 2014
***Assay conducted April 2014
****Cytopathic effect by Neutral Red Example 6—In Vitro Testing for Inhibition of Influenza Replication An influenza antiviral evaluation assay was performed to examine the effects of peptidomimetic macrocycles at designated dose-response concentrations against various viral strains. See also Noah, J. W., W. Severson, D. L. Noah, L. Rasmussen, E. L. White, and C. B. Jonsson, Antiviral Res, 2007. 73(1): p. 50-9. Madin Darby canine kidney (MDCK) cells were used in the assay to test the efficacy of the compounds in suppressing the cytopathic effect (CPE) induced by influenza infection. Ribavirin was included in each run as a positive control compound. Subconfluent cultures of MDCK cells were plated into 96-well plates to analyze cell viability (cell cytotoxicity (CC)) and antiviral activity (CPE). Drugs dissolved in DMSO were added to the cells after 24 hours.

At a designated time, the CPE wells also received 100 tissue culture infectious doses (100 $TCID_{50}s$) of titered influenza virus. 72 hours later, the cell viability was determined using visual and neutral red dye uptake methods. The effective compound concentrations that reduced viral replication by 50% ($EC_{50}$) and 90% ($EC_{90}$) were calculated by regression analysis with semi-log curve fitting. Cell viability was assessed using CellTiter-Glo™ (Promega). The compound concentrations that reduced cell viability by 50% ($CC_{50}$) and selectivity (therapeutic) indices ($SI_{50}=CC_{50}/EC_{50}$; $SI_{90}=CC_{90}/EC_{90}$) were also calculated. Cells were also used in a virus yield reduction (VYR) assay using quantitative polymerase chain reactions (qPCR) to determine antiviral efficacy of the compounds in reducing viral titers. Cells were plated and infected as described above and then incubated. The supernatants were then harvested, and viral titers were determined using a plaque assay, TCID, or immunocytochemistry. Antiviral efficacy levels were calculated based on viral titer reductions compared to an untreated virus control and used to calculate $EC_{50}$ values.

Table 9 details the concentration of the control (ribavirin), concentration of the peptidomimetic macrocycles SP 1-27, screened viruses, viral strains used for the assays, and the corresponding $EC_{50}$, $EC_{90}$, $CC_{50}$, $SI_{50}$ and $SI_{90}$ values. The data are presented in chronological order. The results show that the peptidomimetic macrocycles of the invention have sub-micromolar cellular activity against the viral strains tested.

TABLE 9

| SP# | Virus screened | Viral Strain | Drug Assay | $EC_{50}$ | $EC_{90}$ | $CC_{50}$ | $SI_{50}$ | $SI_{90}$ |
|---|---|---|---|---|---|---|---|---|
| Ribavirin | Influenza A $H_1N_1$ | California/07/2009 | Visual | 10 | | >320 | >32 | |
| Ribavirin | Influenza A $H_1N_1$ | California/07/2009 | Neutral Red | 10 | | >320 | >32 | |
| AP1 | Influenza A $H_1N_1$ | California/07/2009 | Visual | 28 | | >100 | >3.6 | |
| AP1 | Influenza A $H_1N_1$ | California/07/2009 | Neutral Red | 52 | | >100 | >1.9 | |
| SP6 | Influenza A $H_1N_1$ | California/07/2009 | Visual | 27 | | >100 | >3.7 | |
| SP6 | Influenza A $H_1N_1$ | California/07/2009 | Neutral Red | 31 | | >100 | >3.2 | |
| Ribavirin | Influenza A $H_3N_2$ | Perth/16/2009 | Visual | 10 | | >320 | >32 | |
| Ribavirin | Influenza A $H_3N_2$ | Perth/16/2009 | Neutral Red | 9 | | >320 | >36 | |
| AP1 | Influenza A $H_3N_2$ | Perth/16/2009 | Visual | 12 | | >100 | >8.3 | |
| AP1 | Influenza A $H_3N_2$ | Perth/16/2009 | Neutral Red | 12 | | >100 | >8.3 | |
| SP6 | Influenza A $H_3N_2$ | Perth/16/2009 | Visual | 3.8 | | >100 | >26 | |
| SP6 | Influenza A $H_3N_2$ | Perth/16/2009 | Neutral Red | 5.2 | | >100 | >19 | |
| Ribavirin | Influenza A $H_5N_1$ | Duck/MN/1525/81 | Visual | 10 | | >320 | >32 | |
| Ribavirin | Influenza A $H_5N_1$ | Duck/MN/1525/81 | Neutral Red | 9.6 | | >320 | >33 | |
| AP1 | Influenza A $H_5N_1$ | Duck/MN/1525/81 | Visual | 4 | | >100 | >25 | |
| AP1 | Influenza A $H_5N_1$ | Duck/MN/1525/81 | Neutral Red | 6.3 | | >100 | >16 | |
| SP6 | Influenza A $H_5N_1$ | Duck/MN/1525/81 | Visual | 12 | | >100 | >8.3 | |
| SP6 | Influenza A $H_5N_1$ | Duck/MN/1525/81 | Neutral Red | 15 | | >100 | >6.7 | |
| Ribavirin | Influenza A $H_1N_1$ | Solomon Is./03/2006 | Visual | 3.5 | | >320 | >91 | |
| Ribavirin | Influenza A $H_1N_1$ | Solomon Is./03/2006 | Neutral Red | 5 | | >320 | >64 | |
| AP1 | Influenza A $H_1N_1$ | Solomon Is./03/2006 | Visual | 1.1 | | >100 | >91 | |
| AP1 | Influenza A $H_1N_1$ | Solomon Is./03/2006 | Neutral Red | 3 | | >100 | >33 | |
| SP6 | Influenza A $H_1N_1$ | Solomon Is./03/2006 | Visual | 0.83 | | >100 | >120 | |
| SP6 | Influenza A $H_1N_1$ | Solomon Is./03/2006 | Neutral Red | 5.2 | | >100 | >19 | |
| Ribavirin | Influenza A $H_1N_1$ | Brisbane/59/2007 | Visual | 7.3 | | >320 | >44 | |
| Ribavirin | Influenza A $H_1N_1$ | Brisbane/59/2007 | Neutral Red | 7.2 | | >320 | >44 | |
| AP1 | Influenza A $H_1N_1$ | Brisbane/59/2007 | Visual | 6 | | >100 | >17 | |
| AP1 | Influenza A $H_1N_1$ | Brisbane/59/2007 | Neutral Red | 5.5 | | >100 | >18 | |
| SP6 | Influenza A $H_1N_1$ | Brisbane/59/2007 | Visual | 5.7 | | >100 | >18 | |
| SP6 | Influenza A $H_1N_1$ | Brisbane/59/2007 | Neutral Red | 5.6 | | >100 | >18 | |
| Ribavirin | Influenza A $H_1N_1$ | California/07/2009 | Visual | | 5.5 | >320 | | >58 |
| Ribavirin | Influenza A $H_1N_1$ | California/07/2009 | Neutral Red | 5.6 | | >320 | >57 | |
| AP1 | Influenza A $H_1N_1$ | California/07/2009 | Visual | | >65 | 65 | | 0 |
| AP1 | Influenza A $H_1N_1$ | California/07/2009 | Neutral Red | 18 | | 65 | 3.6 | |
| SP6 | Influenza A $H_1N_1$ | California/07/2009 | Visual | | >36 | 36 | | 0 |
| SP6 | Influenza A $H_1N_1$ | California/07/2009 | Neutral Red | 4.4 | | 36 | 8.2 | |
| Ribavirin | Influenza A $H_3N_2$ | Perth/16/2009 | Visual | | 5.5 | >320 | | >58 |
| Ribavirin | Influenza A $H_3N_2$ | Perth/16/2009 | Neutral Red | 5.6 | | >320 | >57 | |
| AP1 | Influenza A $H_3N_2$ | Perth/16/2009 | Visual | | 28 | >100 | | >3.6 |
| AP1 | Influenza A $H_3N_2$ | Perth/16/2009 | Neutral Red | 4.1 | | >100 | >24 | |

TABLE 9-continued

| SP# | Virus screened | Viral Strain | Drug Assay | EC$_{50}$ | EC$_{90}$ | CC$_{50}$ | SI$_{50}$ | SI$_{90}$ |
|---|---|---|---|---|---|---|---|---|
| SP6 | Influenza A H$_3$N$_2$ | Perth/16/2009 | Visual | | 22 | >100 | | >4.5 |
| SP6 | Influenza A H$_3$N$_2$ | Perth/16/2009 | Neutral Red | 3.8 | | >100 | >26 | |
| Ribavirin | Influenza A H$_5$N$_1$ | Duck/MN/1525/81 | Visual | | 9 | >320 | | >35 |
| Ribavirin | Influenza A H$_5$N$_1$ | Duck/MN/1525/81 | Neutral Red | 5.6 | | >320 | >57 | |
| AP1 | Influenza A H$_5$N$_1$ | Duck/MN/1525/81 | Visual | | 70 | >100 | | >1.4 |
| AP1 | Influenza A H$_5$N$_1$ | Duck/MN/1525/81 | Neutral Red | 6.4 | | >100 | >16 | |
| SP6 | Influenza A H$_5$N$_1$ | Duck/MN/1525/81 | Visual | | >70 | 70 | | 0 |
| SP6 | Influenza A H$_5$N$_1$ | Duck/MN/1525/81 | Neutral Red | 4.6 | | 70 | 15 | |
| Ribavirin | Influenza A H$_5$N$_1$ | Hong Kong/213/2003 | Visual | 43 | | >1000 | >23 | |
| Ribavirin | Influenza A H$_5$N$_1$ | Hong Kong/213/2003 | Neutral Red | 39 | | >1000 | >26 | |
| AP1 | Influenza A H$_5$N$_1$ | Hong Kong/213/2003 | Visual | >100 | | >100 | 0 | |
| AP1 | Influenza A H$_5$N$_1$ | Hong Kong/213/2003 | Neutral Red | >100 | | >100 | 0 | |
| SP6 | Influenza A H$_5$N$_1$ | Hong Kong/213/2003 | Visual | >100 | | >100 | 0 | |
| SP6 | Influenza A H$_5$N$_1$ | Hong Kong/213/2003 | Neutral Red | >100 | | >100 | 0 | |
| Ribavirin | Influenza A H$_7$H$_9$ | A/Anhui/1/2013 | Visual | 15 | | >1000 | >67 | |
| Ribavirin | Influenza A H$_7$H$_9$ | A/Anhui/1/2013 | Neutral Red | 18 | | >1000 | >56 | |
| AP1 | Influenza A H$_7$H$_9$ | A/Anhui/1/2013 | Visual | >100 | | >100 | 0 | |
| AP1 | Influenza A H$_7$H$_9$ | A/Anhui/1/2013 | Neutral Red | >100 | | >100 | 0 | |
| SP6 | Influenza A H$_7$H$_9$ | A/Anhui/1/2013 | Visual | >100 | | >100 | 0 | |
| SP6 | Influenza A H$_7$H$_9$ | A/Anhui/1/2013 | Neutral Red | >100 | | >100 | 0 | |
| Ribavirin | Influenza B | Florida/04/2006 | Visual | 3.4 | | >320 | >94 | |
| Ribavirin | Influenza B | Florida/04/2006 | Neutral Red | 4.8 | | >320 | >67 | |
| AP1 | Influenza B | Florida/04/2006 | Visual | 21 | | >100 | >4.8 | |
| AP1 | Influenza B | Florida/04/2006 | Neutral Red | 11 | | 86 | 7.8 | |
| SP6 | Influenza B | Florida/04/2006 | Visual | 14 | | >100 | >7.1 | |
| SP6 | Influenza B | Florida/04/2006 | Neutral Red | 18 | | 98 | 5.4 | |
| Ribavirin | Influenza B | Brisbane/60/2008 | Visual | 8.4 | | >320 | >38 | |
| Ribavirin | Influenza B | Brisbane/60/2008 | Neutral Red | 5.6 | | >320 | >57 | |
| AP1 | Influenza B | Brisbane/60/2008 | Visual | 2.4 | | >100 | >42 | |
| AP1 | Influenza B | Brisbane/60/2008 | Neutral Red | 6.9 | | >100 | >14 | |
| SP6 | Influenza B | Brisbane/60/2008 | Visual | 3.8 | | >100 | >26 | |
| SP6 | Influenza B | Brisbane/60/2008 | Neutral Red | 7.1 | | >100 | >14 | |
| Ribavirin | Influenza A H$_1$N$_1$ | Brisbane/59/2007 | Visual | | 5.2 | >320 | | >61 |
| Ribavirin | Influenza A H$_1$N$_1$ | Brisbane/59/2007 | Neutral Red | 5.6 | | >320 | >57 | |
| AP1 | Influenza A H$_1$N$_1$ | Brisbane/59/2007 | Visual | | >100 | >100 | | 0 |
| AP1 | Influenza A H$_1$N$_1$ | Brisbane/59/2007 | Neutral Red | 17 | | >100 | >5.9 | |
| SP6 | Influenza A H$_1$N$_1$ | Brisbane/59/2007 | Visual | | >100 | >100 | | 0 |
| SP6 | Influenza A H$_1$N$_1$ | Brisbane/59/2007 | Neutral Red | 5.5 | | >100 | >18 | |
| Ribavirin | Influenza A H$_1$N$_1$ | California/04/2009-M | Visual | 10 | | >320 | >32 | |
| Ribavirin | Influenza A H$_1$N$_1$ | California/04/2009-M | Neutral Red | 9.6 | | >320 | >33 | |
| AP1 | Influenza A H$_1$N$_1$ | California/04/2009-M | Visual | >100 | | >100 | 0 | |
| AP1 | Influenza A H$_1$N$_1$ | California/04/2009-M | Neutral Red | >100 | | >100 | 0 | |
| SP6 | Influenza A H$_1$N$_1$ | California/04/2009-M | Visual | 27 | | >100 | >3.7 | |
| SP6 | Influenza A H$_1$N$_1$ | California/04/2009-M | Neutral Red | 30 | | >100 | >3.3 | |
| Ribavirin | Influenza A H$_1$N$_1$ | Solomon Is./3/2006 | Visual | | 4.1 | >320 | | >78 |
| Ribavirin | Influenza A H$_1$N$_1$ | Solomon Is./3/2006 | Neutral Red | 1.9 | | >320 | >170 | |
| AP1 | Influenza A H$_1$N$_1$ | Solomon Is./3/2006 | Visual | | 3.7 | >100 | | >27 |
| AP1 | Influenza A H$_1$N$_1$ | Solomon Is./3/2006 | Neutral Red | 1.8 | | >100 | >56 | |
| SP6 | Influenza A H$_1$N$_1$ | Solomon Is./3/2006 | Visual | | 1.2 | >100 | | >83 |
| SP6 | Influenza A H$_1$N$_1$ | Solomon Is./3/2006 | Neutral Red | 0.65 | | >100 | >150 | |
| Ribavirin | Influenza A H$_1$N$_1$ | Solomon Is./3/2006-M | Visual | 10 | | >320 | >32 | |
| Ribavirin | Influenza A H$_1$N$_1$ | Solomon Is./3/2006-M | Neutral Red | 8.9 | | >320 | >36 | |
| AP1 | Influenza A H$_1$N$_1$ | Solomon Is./3/2006-M | Visual | 3.2 | | >100 | >31 | |
| AP1 | Influenza A H$_1$N$_1$ | Solomon Is./3/2006-M | Neutral Red | 3.1 | | >100 | >32 | |
| SP6 | Influenza A H$_1$N$_1$ | Solomon Is./3/2006-M | Visual | 3.2 | | >100 | >31 | |
| SP6 | Influenza A H$_1$N$_1$ | Solomon Is./3/2006-M | Neutral Red | 3.1 | | >100 | >32 | |
| Ribavirin | Influenza A H$_3$N$_2$ | Victoria/3/75-M | Visual | 10 | | >320 | >32 | |
| Ribavirin | Influenza A H$_3$N$_2$ | Victoria/3/75-M | Neutral Red | 9.8 | | >320 | >33 | |
| AP1 | Influenza A H$_3$N$_2$ | Victoria/3/75-M | Visual | 19 | | >100 | >5.3 | |
| AP1 | Influenza A H$_3$N$_2$ | Victoria/3/75-M | Neutral Red | 15 | | >100 | >6.7 | |
| SP6 | Influenza A H$_3$N$_2$ | Victoria/3/75-M | Visual | 24 | | >100 | >4.2 | |
| SP6 | Influenza A H$_3$N$_2$ | Victoria/3/75-M | Neutral Red | 24 | | >100 | >4.2 | |
| Ribavirin | Influenza B | Sichuan/379/99-M | Visual | 10 | | >320 | >32 | |
| Ribavirin | Influenza B | Sichuan/379/99-M | Neutral Red | 9.3 | | >320 | >34 | |
| AP1 | Influenza B | Sichuan/379/99-M | Visual | 36 | | >100 | >2.8 | |
| AP1 | Influenza B | Sichuan/379/99-M | Neutral Red | 30 | | >100 | >3.3 | |
| SP6 | Influenza B | Sichuan/379/99-M | Visual | 42 | | >100 | >2.4 | |
| SP6 | Influenza B | Sichuan/379/99-M | Neutral Red | 27 | | >100 | >3.7 | |
| Ribavirin | Influenza A H$_3$N$_2$ | Influenza A/Brisbane/10/2007 | CellTiter-Glo | 2.81 | 11.78 | >100 | >36 | >8 |
| Ribavirin | Influenza A H$_3$N$_2$ | Influenza A/Brisbane/10/2007 | qPCR/CellTiter-Glo | 1.18 | 7.63 | >100 | >85 | >13 |
| AP1 | Influenza A H$_3$N$_2$ | Influenza A/Brisbane/10/2007 | CellTiter-Glo | >100 | >100 | >100 | 1 | 1 |
| AP1 | Influenza A H$_3$N$_2$ | Influenza A/Brisbane/10/2007 | qPCR/CellTiter-Glo | <0.80 | >100 | >100 | 125 | 1 |
| SP6 | Influenza A H$_3$N$_2$ | Influenza A/Brisbane/10/2007 | CellTiter-Glo | >100 | >100 | >100 | 1 | 1 |

TABLE 9-continued

| SP# | Virus screened | Viral Strain | Drug Assay | $EC_{50}$ | $EC_{90}$ | $CC_{50}$ | $SI_{50}$ | $SI_{90}$ |
|---|---|---|---|---|---|---|---|---|
| SP6 | Influenza A $H_3N_2$ | Influenza A/Brisbane/10/2007 | qPCR/CellTiter-Glo | >100 | >100 | >100 | 1 | 1 |
| Ribavirin | Influenza A $H_1N_1$ | Influenza A/California/7/2009 | CellTiter-Glo | 6.53 | 16.21 | >100 | >15 | >6 |
| Ribavirin | Influenza A $H_1N_1$ | Influenza A/California/7/2009 | qPCR/CellTiter-Glo | 8.36 | 17.66 | >100 | >12 | >6 |
| AP1 | Influenza A $H_1N_1$ | Influenza A/California/7/2009 | CellTiter-Glo | >100 | >100 | >100 | 1 | 1 |
| AP1 | Influenza A $H_1N_1$ | Influenza A/California/7/2009 | qPCR/CellTiter-Glo | >100 | >100 | >100 | 1 | 1 |
| SP6 | Influenza A $H_1N_1$ | Influenza A/California/7/2009 | CellTiter-Glo | >100 | >100 | >100 | 1 | 1 |
| SP6 | Influenza A $H_1N_1$ | Influenza A/California/7/2009 | qPCR/CellTiter-Glo | >100 | >100 | >100 | 1 | 1 |
| Ribavirin | Influenza B | Influenza B/Brisbane/60/2008 | CellTiter-Glo | 66.17 | >100 | >100 | >2 | 1 |
| Ribavirin | Influenza B | Influenza B/Brisbane/60/2008 | qPCR/CellTiter-Glo | <0.8 | 2.00 | >100 | >125 | >50 |
| AP1 | Influenza B | Influenza B/Brisbane/60/2008 | CellTiter-Glo | >100 | >100 | >100 | 1 | 1 |
| AP1 | Influenza B | Influenza B/Brisbane/60/2008 | qPCR/CellTiter-Glo | >100 | >100 | >100 | 1 | 1 |
| SP6 | Influenza B | Influenza B/Brisbane/60/2008 | CellTiter-Glo | >100 | >100 | >100 | 1 | 1 |
| SP6 | Influenza B | Influenza B/Brisbane/60/2008 | qPCR/CellTiter-Glo | >100 | >100 | >100 | 1 | 1 |
| Ribavirin | Influenza A $H_1N_1$ | Influenza A/Texas/4/2009 | CellTiter-Glo | 14.64 | >100 | >100 | >1 | 1 |
| Ribavirin | Influenza A $H_1N_1$ | Influenza A/Texas/4/2009 | qPCR/CellTiter-Glo | 1.20 | >100 | >100 | >1 | 1 |
| AP1 | Influenza A $H_1N_1$ | Influenza A/Texas/4/2009 | CellTiter-Glo | >100 | >100 | >100 | 1 | 1 |
| AP1 | Influenza A $H_1N_1$ | Influenza A/Texas/4/2009 | qPCR/CellTiter-Glo | >100 | >100 | >100 | 1 | 1 |
| SP6 | Influenza A $H_1N_1$ | Influenza A/Texas/4/2009 | CellTiter-Glo | >100 | >100 | >100 | 1 | 1 |
| SP6 | Influenza A $H_1N_1$ | Influenza A/Texas/4/2009 | qPCR/CellTiter-Glo | >100 | >100 | >100 | 1 | 1 |
| Ribavirin | Influenza A $H_1N_1$ | California/07/2009 | Visual | 1.7 | | >320 | >190 | |
| Ribavirin | Influenza A $H_1N_1$ | California/07/2009 | Neutral Red | 11 | | >320 | >29 | |
| SP6 | Influenza A $H_1N_1$ | California/07/2009 | Visual | 12 | | >100 | >8.3 | |
| SP6 | Influenza A $H_1N_1$ | California/07/2009 | Neutral Red | 23 | | >100 | >4.3 | |
| SP7 | Influenza A $H_1N_1$ | California/07/2009 | Visual | 11 | | >100 | >9.1 | |
| SP7 | Influenza A $H_1N_1$ | California/07/2009 | Neutral Red | 11 | | >100 | >9.1 | |
| SP8 | Influenza A $H_1N_1$ | California/07/2009 | Visual | 19 | | >100 | >5.3 | |
| SP8 | Influenza A $H_1N_1$ | California/07/2009 | Neutral Red | 19 | | >100 | >5.3 | |
| SP9 | Influenza A $H_1N_1$ | California/07/2009 | Visual | 15 | | >100 | >6.7 | |
| SP9 | Influenza A $H_1N_1$ | California/07/2009 | Neutral Red | 22 | | >100 | >4.5 | |
| SP10 | Influenza A $H_1N_1$ | California/07/2009 | Visual | 32 | | >100 | >3.1 | |
| SP10 | Influenza A $H_1N_1$ | California/07/2009 | Neutral Red | 35 | | >100 | >2.9 | |
| SP11 | Influenza A $H_1N_1$ | California/07/2009 | Visual | 2.4 | | >100 | >42 | |
| SP11 | Influenza A $H_1N_1$ | California/07/2009 | Neutral Red | 4.1 | | >100 | >24 | |
| SP12 | Influenza A $H_1N_1$ | California/07/2009 | Visual | 3.2 | | >100 | >31 | |
| SP12 | Influenza A $H_1N_1$ | California/07/2009 | Neutral Red | 8 | | >100 | >12 | |
| SP13 | Influenza A $H_1N_1$ | California/07/2009 | Visual | 32 | | >100 | >3.1 | |
| SP13 | Influenza A $H_1N_1$ | California/07/2009 | Neutral Red | 31 | | >100 | >3.2 | |
| SP14 | Influenza A $H_1N_1$ | California/07/2009 | Visual | 3.2 | | >100 | >31 | |
| SP14 | Influenza A $H_1N_1$ | California/07/2009 | Neutral Red | 6.1 | | >100 | >16 | |
| SP15 | Influenza A $H_1N_1$ | California/07/2009 | Visual | 32 | | >100 | >3.1 | |
| SP15 | Influenza A $H_1N_1$ | California/07/2009 | Neutral Red | 28 | | >100 | >3.6 | |
| SP16 | Influenza A $H_1N_1$ | California/07/2009 | Visual | 18 | | >100 | >5.6 | |
| SP16 | Influenza A $H_1N_1$ | California/07/2009 | Neutral Red | 19 | | >100 | >5.3 | |
| SP17 | Influenza A $H_1N_1$ | California/07/2009 | Visual | 29 | | >100 | >3.4 | |
| SP17 | Influenza A $H_1N_1$ | California/07/2009 | Neutral Red | 30 | | >100 | >3.3 | |
| SP18 | Influenza A $H_1N_1$ | California/07/2009 | Visual | 6.8 | | >100 | >15 | |
| SP18 | Influenza A $H_1N_1$ | California/07/2009 | Neutral Red | 4.5 | | >100 | >22 | |
| SP1 | Influenza A $H_1N_1$ | California/07/2009 | Visual | 52 | | >100 | >1.9 | |
| SP1 | Influenza A $H_1N_1$ | California/07/2009 | Neutral Red | 36 | | >100 | >2.8 | |
| SP2 | Influenza A $H_1N_1$ | California/07/2009 | Visual | 68 | | >100 | >1.5 | |
| SP2 | Influenza A $H_1N_1$ | California/07/2009 | Neutral Red | 51 | | >100 | >2 | |
| SP3 | Influenza A $H_1N_1$ | California/07/2009 | Visual | >100 | | >100 | 0 | |
| SP3 | Influenza A $H_1N_1$ | California/07/2009 | Neutral Red | >100 | | >100 | 0 | |
| SP4 | Influenza A $H_1N_1$ | California/07/2009 | Visual | >100 | | >100 | 0 | |
| SP4 | Influenza A $H_1N_1$ | California/07/2009 | Neutral Red | >100 | | >100 | 0 | |
| SP5 | Influenza A $H_1N_1$ | California/07/2009 | Visual | 26 | | >100 | >3.8 | |
| SP5 | Influenza A $H_1N_1$ | California/07/2009 | Neutral Red | 34 | | >100 | >2.9 | |
| Ribavirin | Influenza A $H_3N_2$ | Perth/16/2009 | Visual | 10 | | >320 | >32 | |
| Ribavirin | Influenza A $H_3N_2$ | Perth/16/2009 | Neutral Red | 11 | | >320 | >27 | |

TABLE 9-continued

| SP# | Virus screened | Viral Strain | Drug Assay | $EC_{50}$ | $EC_{90}$ | $CC_{50}$ | $SI_{50}$ | $SI_{90}$ |
|---|---|---|---|---|---|---|---|---|
| SP6 | Influenza A $H_1N_1$ | California/07/2009 | Visual | 28 | | >100 | >3.6 | |
| SP6 | Influenza A $H_1N_1$ | California/07/2009 | Neutral Red | 28 | | >100 | >3.6 | |
| SP7 | Influenza A $H_1N_1$ | California/07/2009 | Visual | 32 | | >100 | >3.1 | |
| SP7 | Influenza A $H_1N_1$ | California/07/2009 | Neutral Red | 30 | | >100 | >3.3 | |
| SP8 | Influenza A $H_1N_1$ | California/07/2009 | Visual | 42 | | >100 | >2.4 | |
| SP8 | Influenza A $H_1N_1$ | California/07/2009 | Neutral Red | 38 | | >100 | >2.6 | |
| SP9 | Influenza A $H_1N_1$ | California/07/2009 | Visual | 40 | | >100 | >2.5 | |
| SP9 | Influenza A $H_1N_1$ | California/07/2009 | Neutral Red | 41 | | >100 | >2.4 | |
| SP10 | Influenza A $H_1N_1$ | California/07/2009 | Visual | 32 | | >100 | >3.1 | |
| SP10 | Influenza A $H_1N_1$ | California/07/2009 | Neutral Red | 32 | | >100 | >3.1 | |
| SP11 | Influenza A $H_1N_1$ | California/07/2009 | Visual | 21 | | >100 | >4.8 | |
| SP11 | Influenza A $H_1N_1$ | California/07/2009 | Neutral Red | 24 | | >100 | >4.2 | |
| SP12 | Influenza A $H_1N_1$ | California/07/2009 | Visual | 19 | | >100 | >5.3 | |
| SP12 | Influenza A $H_1N_1$ | California/07/2009 | Neutral Red | 24 | | >100 | >4.2 | |
| SP13 | Influenza A $H_1N_1$ | California/07/2009 | Visual | >100 | | >100 | 0 | |
| SP13 | Influenza A $H_1N_1$ | California/07/2009 | Neutral Red | >100 | | >100 | 0 | |
| SP14 | Influenza A $H_1N_1$ | California/07/2009 | Visual | 32 | | >100 | >3.1 | |
| SP14 | Influenza A $H_1N_1$ | California/07/2009 | Neutral Red | 30 | | >100 | >3.3 | |
| SP15 | Influenza A $H_1N_1$ | California/07/2009 | Visual | 32 | | >100 | >3.1 | |
| SP15 | Influenza A $H_1N_1$ | California/07/2009 | Neutral Red | 31 | | >100 | >3.2 | |
| SP16 | Influenza A $H_1N_1$ | California/07/2009 | Visual | 32 | | >100 | >3.1 | |
| SP16 | Influenza A $H_1N_1$ | California/07/2009 | Neutral Red | 31 | | >100 | >3.2 | |
| SP17 | Influenza A $H_1N_1$ | California/07/2009 | Visual | 24 | | >100 | >4.2 | |
| SP17 | Influenza A $H_1N_1$ | California/07/2009 | Neutral Red | 25 | | >100 | >4 | |
| SP18 | Influenza A $H_1N_1$ | California/07/2009 | Visual | 32 | | >100 | >3.1 | |
| SP18 | Influenza A $H_1N_1$ | California/07/2009 | Neutral Red | 31 | | >100 | >3.2 | |
| SP1 | Influenza A $H_1N_1$ | California/07/2009 | Visual | 32 | | >100 | >3.1 | |
| SP1 | Influenza A $H_1N_1$ | California/07/2009 | Neutral Red | 32 | | >100 | >3.1 | |
| SP2 | Influenza A $H_1N_1$ | California/07/2009 | Visual | 24 | | >100 | >4.2 | |
| SP2 | Influenza A $H_1N_1$ | California/07/2009 | Neutral Red | 32 | | >100 | >3.1 | |
| SP3 | Influenza A $H_1N_1$ | California/07/2009 | Visual | 38 | | >100 | >2.6 | |
| SP3 | Influenza A $H_1N_1$ | California/07/2009 | Neutral Red | 73 | | >100 | >1.4 | |
| SP4 | Influenza A $H_1N_1$ | California/07/2009 | Visual | 32 | | >100 | >3.1 | |
| SP4 | Influenza A $H_1N_1$ | California/07/2009 | Neutral Red | 32 | | >100 | >3.1 | |
| SP5 | Influenza A $H_1N_1$ | California/07/2009 | Visual | 12 | | >100 | >8.3 | |
| SP5 | Influenza A $H_1N_1$ | California/07/2009 | Neutral Red | 14 | | >100 | >7.1 | |
| Ribavirin | Influenza A $H_1N_1$ | California/07/2009 | VYR/Neutral Red | | 4.9 | >320 | | >65 |
| Ribavirin | Influenza A $H_1N_1$ | California/07/2009 | Neutral Red | 8.5 | | >320 | >38 | |
| SP6 | Influenza A $H_1N_1$ | California/07/2009 | VYR/Neutral Red | | 66 | >100 | | >1.5 |
| SP6 | Influenza A $H_1N_1$ | California/07/2009 | Neutral Red | 6.3 | | >100 | >16 | |
| SP11 | Influenza A $H_1N_1$ | California/07/2009 | VYR/Neutral Red | | 21 | >100 | | >4.8 |
| SP11 | Influenza A $H_1N_1$ | California/07/2009 | Neutral Red | 15 | | >100 | >6.7 | |
| SP12 | Influenza A $H_1N_1$ | California/07/2009 | VYR/Neutral Red | | 21 | >100 | | >4.8 |
| SP12 | Influenza A $H_1N_1$ | California/07/2009 | Neutral Red | 6.9 | | >100 | >14 | |
| SP14 | Influenza A $H_1N_1$ | California/07/2009 | VYR/Neutral Red | | 29 | >100 | | >3.4 |
| SP14 | Influenza A $H_1N_1$ | California/07/2009 | Neutral Red | 5.2 | | >100 | >19 | |
| SP18 | Influenza A $H_1N_1$ | California/07/2009 | VYR/Neutral Red | | 6.4 | >100 | | >16 |
| SP18 | Influenza A $H_1N_1$ | California/07/2009 | Neutral Red | 6.8 | | >100 | >15 | |
| Ribavirin | Influenza A $H_3N_2$ | Perth/16/2009 | VYR/Neutral Red | | 7.9 | >320 | | >41 |
| Ribavirin | Influenza A $H_3N_2$ | Perth/16/2009 | Neutral Red | 5.6 | | >320 | >57 | |
| SP6 | Influenza A $H_3N_2$ | Perth/16/2009 | VYR/Neutral Red | | 65 | >100 | | >1.5 |
| SP6 | Influenza A $H_3N_2$ | Perth/16/2009 | Neutral Red | 4.2 | | >100 | >24 | |
| SP11 | Influenza A $H_3N_2$ | Perth/16/2009 | VYR/Neutral Red | | 26 | >100 | | >3.8 |
| SP11 | Influenza A $H_3N_2$ | Perth/16/2009 | Neutral Red | 5.5 | | >100 | >18 | |
| SP12 | Influenza A $H_3N_2$ | Perth/16/2009 | VYR/Neutral Red | | 47 | >100 | | >2.1 |
| SP12 | Influenza A $H_3N_2$ | Perth/16/2009 | Neutral Red | 7.7 | | >100 | >13 | |
| SP14 | Influenza A $H_3N_2$ | Perth/16/2009 | VYR/Neutral Red | | 100 | >100 | | >1 |
| SP14 | Influenza A $H_3N_2$ | Perth/16/2009 | Neutral Red | 6.8 | | >100 | >15 | |
| SP18 | Influenza A $H_3N_2$ | Perth/16/2009 | VYR/Neutral Red | | >100 | >100 | | 0 |
| SP18 | Influenza A $H_3N_2$ | Perth/16/2009 | Neutral Red | 33 | | >100 | >3 | |
| Ribavirin | Influenza A $H_1N_1$ | California/07/2009 | Visual | 5.7 | | >320 | >56 | |
| Ribavirin | Influenza A $H_1N_1$ | California/07/2009 | Neutral Red | 6.8 | | >320 | >47 | |
| SP6 | Influenza A $H_1N_1$ | California/07/2009 | Visual | 5.4 | | >100 | >19 | |
| SP6 | Influenza A $H_1N_1$ | California/07/2009 | Neutral Red | 4.9 | | >100 | >20 | |
| SP18 | Influenza A $H_1N_1$ | California/07/2009 | Visual | 3.2 | | >100 | >31 | |
| SP18 | Influenza A $H_1N_1$ | California/07/2009 | Neutral Red | 3.8 | | >100 | >26 | |
| SP19 | Influenza A $H_1N_1$ | California/07/2009 | Visual | 4.1 | | >100 | >24 | |
| SP19 | Influenza A $H_1N_1$ | California/07/2009 | Neutral Red | 6 | | >100 | >17 | |
| SP20 | Influenza A $H_1N_1$ | California/07/2009 | Visual | 18 | | >100 | >5.6 | |
| SP20 | Influenza A $H_1N_1$ | California/07/2009 | Neutral Red | 26 | | >100 | >3.8 | |
| SP21 | Influenza A $H_1N_1$ | California/07/2009 | Visual | 1.3 | | >100 | >77 | |
| SP21 | Influenza A $H_1N_1$ | California/07/2009 | Neutral Red | 4.6 | | >100 | >22 | |
| SP22 | Influenza A $H_1N_1$ | California/07/2009 | Visual | 1.8 | | >100 | >56 | |
| SP22 | Influenza A $H_1N_1$ | California/07/2009 | Neutral Red | 2.6 | | >100 | >38 | |
| SP23 | Influenza A $H_1N_1$ | California/07/2009 | Visual | 4.3 | | >100 | >23 | |
| SP23 | Influenza A $H_1N_1$ | California/07/2009 | Neutral Red | 4.2 | | >100 | >24 | |
| SP24 | Influenza A $H_1N_1$ | California/07/2009 | Visual | 4.3 | | >100 | >23 | |
| SP24 | Influenza A $H_1N_1$ | California/07/2009 | Neutral Red | 6.9 | | >100 | >14 | |

TABLE 9-continued

| SP# | Virus screened | Viral Strain | Drug Assay | EC$_{50}$ | EC$_{90}$ | CC$_{50}$ | SI$_{50}$ | SI$_{90}$ |
|---|---|---|---|---|---|---|---|---|
| SP25 | Influenza A H$_1$N$_1$ | California/07/2009 | Visual | 0.57 | | >100 | >180 | |
| SP25 | Influenza A H$_1$N$_1$ | California/07/2009 | Neutral Red | 1.1 | | >100 | >91 | |
| SP26 | Influenza A H$_1$N$_1$ | California/07/2009 | Visual | 0.75 | | >100 | >130 | |
| SP26 | Influenza A H$_1$N$_1$ | California/07/2009 | Neutral Red | 2.1 | | >100 | >48 | |
| SP27 | Influenza A H$_1$N$_1$ | California/07/2009 | Visual | 0.57 | | >100 | >130 | |
| SP27 | Influenza A H$_1$N$_1$ | California/07/2009 | Neutral Red | 0.44 | | >100 | >230 | |
| Ribavirin | Influenza A H$_3$N$_2$ | Perth/16/2006 | Visual | 2.4 | | >320 | >130 | |
| Ribavirin | Influenza A H$_3$N$_2$ | Perth/16/2006 | Neutral Red | 4.6 | | >320 | >70 | |
| SP6 | Influenza A H$_3$N$_2$ | Perth/16/2006 | Visual | 4.3 | | >100 | >23 | |
| SP6 | Influenza A H$_3$N$_2$ | Perth/16/2006 | Neutral Red | 4.6 | | >100 | >22 | |
| SP18 | Influenza A H$_3$N$_2$ | Perth/16/2006 | Visual | 14 | | >100 | >7.1 | |
| SP18 | Influenza A H$_3$N$_2$ | Perth/16/2006 | Neutral Red | 22 | | >100 | >4.5 | |
| SP19 | Influenza A H$_3$N$_2$ | Perth/16/2006 | Visual | 5.7 | | >100 | >18 | |
| SP19 | Influenza A H$_3$N$_2$ | Perth/16/2006 | Neutral Red | 4.3 | | >100 | >23 | |
| SP20 | Influenza A H$_3$N$_2$ | Perth/16/2006 | Visual | 4.8 | | >100 | >21 | |
| SP20 | Influenza A H$_3$N$_2$ | Perth/16/2006 | Neutral Red | 3.7 | | >100 | >27 | |
| SP21 | Influenza A H$_3$N$_2$ | Perth/16/2006 | Visual | 0.54 | | >100 | >190 | |
| SP21 | Influenza A H$_3$N$_2$ | Perth/16/2006 | Neutral Red | 2.1 | | >100 | >48 | |
| SP22 | Influenza A H$_3$N$_2$ | Perth/16/2006 | Visual | 0.54 | | >100 | >190 | |
| SP22 | Influenza A H$_3$N$_2$ | Perth/16/2006 | Neutral Red | 0.83 | | >100 | >120 | |
| SP23 | Influenza A H$_3$N$_2$ | Perth/16/2006 | Visual | 5.7 | | >100 | >18 | |
| SP23 | Influenza A H$_3$N$_2$ | Perth/16/2006 | Neutral Red | 4.9 | | >100 | >20 | |
| SP24 | Influenza A H$_3$N$_2$ | Perth/16/2006 | Visual | 2.5 | | >100 | >40 | |
| SP24 | Influenza A H$_3$N$_2$ | Perth/16/2006 | Neutral Red | 3.4 | | >100 | >29 | |
| SP25 | Influenza A H$_3$N$_2$ | Perth/16/2006 | Visual | 0.34 | | >100 | >290 | |
| SP25 | Influenza A H$_3$N$_2$ | Perth/16/2006 | Neutral Red | 0.43 | | >100 | >230 | |
| SP26 | Influenza A H$_3$N$_2$ | Perth/16/2006 | Visual | 14 | | >100 | >7.1 | |
| SP26 | Influenza A H$_3$N$_2$ | Perth/16/2006 | Neutral Red | 23 | | >100 | >4.3 | |
| SP27 | Influenza A H$_3$N$_2$ | Perth/16/2006 | Visual | 0.32 | | >100 | >310 | |
| SP27 | Influenza A H$_3$N$_2$ | Perth/16/2006 | Neutral Red | 1.7 | | >100 | >59 | |
| Ribavirin | Influenza A H$_5$N$_1$ | A/Hong Kong/213/2003 | Visual | 4.2 | | >1000 | >238 | |
| Ribavirin | Influenza A H$_5$N$_1$ | A/Hong Kong/213/2003 | Neutral Red | 3.6 | | >1000 | >277 | |
| SP18 | Influenza A H$_5$N$_1$ | A/Hong Kong/213/2003 | Visual | >50 | | >50 | 0 | |
| SP18 | Influenza A H$_5$N$_1$ | A/Hong Kong/213/2003 | Neutral Red | >50 | | >50 | 0 | |
| SP21 | Influenza A H$_5$N$_1$ | A/Hong Kong/213/2003 | Visual | 34 | | >50 | >1.5 | |
| SP21 | Influenza A H$_5$N$_1$ | A/Hong Kong/213/2003 | Neutral Red | 39 | | >50 | >1.3 | |
| SP22 | Influenza A H$_5$N$_1$ | A/Hong Kong/213/2003 | Visual | >50 | | >50 | 0 | |
| SP22 | Influenza A H$_5$N$_1$ | A/Hong Kong/213/2003 | Neutral Red | >50 | | >50 | 0 | |
| SP25 | Influenza A H$_5$N$_1$ | A/Hong Kong/213/2003 | Visual | >50 | | >50 | 0 | |
| SP25 | Influenza A H$_5$N$_1$ | A/Hong Kong/213/2003 | Neutral Red | >50 | | >50 | 0 | |
| SP27 | Influenza A H$_5$N$_1$ | A/Hong Kong/213/2003 | Visual | >50 | | >50 | 0 | |
| SP27 | Influenza A H$_5$N$_1$ | A/Hong Kong/213/2003 | Neutral Red | >50 | | >50 | 0 | |
| Ribavirin | Influenza A H$_7$N$_9$ | A/Anhui/1/2013 | Visual | 3.2 | | >1000 | >313 | |
| Ribavirin | Influenza A H$_7$N$_9$ | A/Anhui/1/2013 | Neutral Red | 3 | | >1000 | >333 | |
| SP18 | Influenza A H$_7$N$_9$ | A/Anhui/1/2013 | Visual | >50 | | >50 | 0 | |
| SP18 | Influenza A H$_7$N$_9$ | A/Anhui/1/2013 | Neutral Red | >50 | | >50 | 0 | |
| SP21 | Influenza A H$_7$N$_9$ | A/Anhui/1/2013 | Visual | 16 | | >50 | >3.1 | |
| SP21 | Influenza A H$_7$N$_9$ | A/Anhui/1/2013 | Neutral Red | 17 | | >50 | >2.9 | |
| SP22 | Influenza A H$_7$N$_9$ | A/Anhui/1/2013 | Visual | 12 | | >50 | >4.2 | |
| SP22 | Influenza A H$_7$N$_9$ | A/Anhui/1/2013 | Neutral Red | 13 | | >50 | >3.8 | |
| SP25 | Influenza A H$_7$N$_9$ | A/Anhui/1/2013 | Visual | 23 | | >50 | >2.2 | |
| SP25 | Influenza A H$_7$N$_9$ | A/Anhui/1/2013 | Neutral Red | 33 | | >50 | >1.5 | |
| SP27 | Influenza A H$_7$N$_9$ | A/Anhui/1/2013 | Visual | 18 | | >50 | >2.8 | |
| SP27 | Influenza A H$_7$N$_9$ | A/Anhui/1/2013 | Neutral Red | 9.6 | | >50 | >5.2 | |
| Ribavirin | Influenza A H$_1$N$_1$ | A/Solomon Is./3/2006-M | Visual | 10 | | >320 | >32 | |
| Ribavirin | Influenza A H$_1$N$_1$ | A/Solomon Is./3/2006-M | Neutral Red | 10 | | >320 | >32 | |
| SP18 | Influenza A H$_1$N$_1$ | A/Solomon Is./3/2006-M | Visual | 13 | | >100 | >7.7 | |
| SP18 | Influenza A H$_1$N$_1$ | A/Solomon Is./3/2006-M | Neutral Red | 29 | | >100 | >3.4 | |
| SP21 | Influenza A H$_1$N$_1$ | A/Solomon Is./3/2006-M | Visual | 4.8 | | >100 | >21 | |
| SP21 | Influenza A H$_1$N$_1$ | A/Solomon Is./3/2006-M | Neutral Red | 5.3 | | >100 | >19 | |
| SP22 | Influenza A H$_1$N$_1$ | A/Solomon Is./3/2006-M | Visual | 12 | | >100 | >8.3 | |
| SP22 | Influenza A H$_1$N$_1$ | A/Solomon Is./3/2006-M | Neutral Red | 29 | | >100 | >3.4 | |
| SP25 | Influenza A H$_1$N$_1$ | A/Solomon Is./3/2006-M | Visual | 3.6 | | >100 | >28 | |
| SP25 | Influenza A H$_1$N$_1$ | A/Solomon Is./3/2006-M | Neutral Red | 6.5 | | >100 | >15 | |
| SP27 | Influenza A H$_1$N$_1$ | A/Solomon Is./3/2006-M | Visual | 32 | | >100 | >3.1 | |
| SP27 | Influenza A H$_1$N$_1$ | A/Solomon Is./3/2006-M | Neutral Red | 75 | | >100 | >1.3 | |
| Ribavirin | Influenza A H$_1$N$_1$ | California/07/20/09 | Visual/Neutral Red | | 2.7 | >320 | | >119 |
| Ribavirin | Influenza A H$_1$N$_1$ | California/07/20/09 | Neutral Red | 11 | | >320 | >29 | |
| SP18 | Influenza A H$_1$N$_1$ | California/07/20/09 | Visual/Neutral Red | | 4 | >100 | | >25 |
| SP18 | Influenza A H$_1$N$_1$ | California/07/20/09 | Neutral Red | 7 | | >100 | >14 | |
| SP21 | Influenza A H$_1$N$_1$ | California/07/20/09 | Visual/Neutral Red | | 9.6 | >100 | | >10 |
| SP21 | Influenza A H$_1$N$_1$ | California/07/20/09 | Neutral Red | 21 | | >100 | >4.8 | |
| SP22 | Influenza A H$_1$N$_1$ | California/07/20/09 | Visual/Neutral Red | | 6.5 | >100 | | >15 |
| SP22 | Influenza A H$_1$N$_1$ | California/07/20/09 | Neutral Red | 12 | | >100 | >8 | |

TABLE 9-continued

| SP# | Virus screened | Viral Strain | Drug Assay | $EC_{50}$ | $EC_{90}$ | $CC_{50}$ | $SI_{50}$ | $SI_{90}$ |
|---|---|---|---|---|---|---|---|---|
| SP25 | Influenza A $H_1N_1$ | California/07/20/09 | Visual/Neutral Red | | 8.2 | >100 | | >12 |
| SP25 | Influenza A $H_1N_1$ | California/07/20/09 | Neutral Red | 6.6 | | >100 | >15 | |
| SP27 | Influenza A $H_1N_1$ | California/07/20/09 | Visual/Neutral Red | | 8 | >100 | | >13 |
| SP27 | Influenza A $H_1N_1$ | California/07/20/09 | Neutral Red | 8.7 | | >100 | >11 | |
| Ribavirin | Influenza A $H_3N_2$ | Perth/16/2009 | Visual/Neutral Red | | 4.4 | >320 | | |
| Ribavirin | Influenza A $H_3N_2$ | Perth/16/2009 | Neutral Red | 5 | | >320 | >64 | >73 |
| SP18 | Influenza A $H_3N_2$ | Perth/16/2009 | Visual/Neutral Red | | >100 | >100 | | 0 |
| SP18 | Influenza A $H_3N_2$ | Perth/16/2009 | Neutral Red | >100 | | >100 | 0 | |
| SP21 | Influenza A $H_3N_2$ | Perth/16/2009 | Visual/Neutral Red | | 8 | >100 | | >13 |
| SP21 | Influenza A $H_3N_2$ | Perth/16/2009 | Neutral Red | 4.8 | | >100 | >21 | |
| SP22 | Influenza A $H_3N_2$ | Perth/16/2009 | Visual/Neutral Red | | 59 | >100 | | >1.7 |
| SP22 | Influenza A $H_3N_2$ | Perth/16/2009 | Neutral Red | 51 | | >100 | >2 | |
| SP25 | Influenza A $H_3N_2$ | Perth/16/2009 | Visual/Neutral Red | | 49 | >100 | | >2 |
| SP25 | Influenza A $H_3N_2$ | Perth/16/2009 | Neutral Red | 49 | | >100 | >2 | |
| SP27 | Influenza A $H_3N_2$ | Perth/16/2009 | Visual/Neutral Red | | 35 | >100 | | >2.9 |
| SP27 | Influenza A $H_3N_2$ | Perth/16/2009 | Neutral Red | 35 | | >100 | >2.9 | |

Example 7:—In Vivo Testing for Inhibition of Influenza Replication

This study evaluated the toxicity of two doses of a peptidomimetic macrocycle disclosed herein against an influenza A/CA/04/2009 (pandemic $H_1N_1$) virus infection in mice. In addition, antiviral activity in mice can be completed in parallel.

Animals:

Female 18-20 g BALB/c mice were obtained from Charles River Laboratories (Wilmington, Mass.) for this experiment. The mice were quarantined for 5 days before use and were maintained on Teklad Rodent Diet (Harlan Teklad) and tap water.

Virus:

Influenza A/CA/04/2009 (pandemic $H_1N_1$), an amantadine-resistant strain, were used as a representative of currently circulating influenza virus. Influenza A/CA/04/2009 ($H_1N_1$), strain designation 175190 were used. The viruses were adapted to replication in the lungs of BALB/c mice by 9 sequential passages in mice. Viruses were plaque-purified in MDCK cells and a virus stock is prepared by growth in embryonated chicken eggs and then MDCK cells.

Compound:

Peptidomimetic macrocycles were prepared in a PEG-based vehicle and then administered.

Experimental Design:

Animal numbers and study groups are described in Tables 10 and 11.

Maximum Tolerated Dose (Toxicity) Study (Table 10):

Groups of mice were treated by intravenous injection daily for 5 days with 5.0 or 10 mg/kg doses of peptidomimetic macrocycles. Five non-treated normal control mice were maintained for weight comparison. Mice were individually weighed prior to treatment and then every other day thereafter to assess the effects of treatment on weight loss through day 14 after beginning treatment.

Drug Dose-Range Finding (Efficacy) Study (Table 11):

Groups of mice were treated by intravenous injection daily for 5 days with 5.0 or 10.0 mg/kg doses of peptidomimetic macrocycles. Control groups included mice treated with 10 mg/kg/day oseltamivir twice per day at 12 hour intervals), or placebo (15 mice) treated with physiological sterile saline (PSS) according to the same dosing regimen. Five non-treated normal control mice were maintained for weight comparison. For influenza virus challenge, mice were anesthetized by i.p. injection of ketamine/xylazine (50 mg/kg//5 mg/kg) prior to challenge by the intranasal route with approximately $1\times10^5$ ($3\times LD_{50}$) cell culture infectious doses ($CCID_{50}$) of virus per mouse in a 90 µL inoculum volume.

Mice were weighed prior to treatment and then every other day thereafter to assess the effects of treatment on ameliorating weight loss due to virus infection. All mice group were observed for morbidity and mortality through day 21 post-infection.

Statistical Analysis:

Kaplan-Meier survival curves were generated and compared by the Log-rank (Mantel-Cox) test followed by pair-wise comparison using the Gehan-Breslow-Wilcoxon test in Prism 5.0f (GraphPad Softw Inc.). Mean body weights were analyzed by one-way analysis of variance (ANOVA) followed by Tukey's multiple comparison tests using Prism 5.0f.

This study determined the maximum dose of peptidomimetic macrocycles, which could be safely administered by the intravenous route to mice. Once daily treatment with each dose of peptidomimetic macrocycles at 5.0 or 10.0 mg/kg/day for 5 days were evaluated for weight loss and survival.

This study can also be used to determine whether treatment with peptidomimetic macrocycles increased survival against a lethal influenza A/CA/04/2009 (pandemic $H_1N_1$) virus challenge in mice. Parameters to evaluate following challenge infection include: percent survivors, mean day of death determinations, and individual body weight change to measure every other day following infection.

This study can also be used to determine the antiviral activity of peptidomimetic macrocycles at two doses against an influenza A/CA/04/2009 (pandemic $H_1N_1$) virus infection in mice. Once daily treatment with each compound at 5.0 or 10.0 mg/kg/day for 5 days were evaluated. All mice were observed for mortality and weight loss following virus challenge with influenza virus.

Experiments demonstrated that all mice survived at the SP-6 doses tested. Change in mean body weight of mice administered SP-6 at the indicated doses is exemplified in FIG. 1.

TABLE 10

Maximum Tolerated Dose Study Design

| Number/ Cage | Group No. | Infected | Compound | Dosage | Treatment Schedule |
|---|---|---|---|---|---|
| 5 | 2 | No | SP1-SP27 | 10.0 mg/kg/day | qd X 5 |
| 5 | 4 | No | SP1-SP27 | 5.0 mg/kg/day | |

TABLE 11

Drug Dose-Range Efficacy Study Design

| #/ Cage | Group # | Infected | Compound | Dosage | Treatment Schedule |
|---|---|---|---|---|---|
| 15 | 1 | Yes | *Placebo | — | qd X 5, |
| 10 | 3 | Yes | SP1-SP27 | 10.0 mg/kg/day | begin 4 hours |
| 10 | 5 | Yes | SP1-SP27 | 5.0 mg/kg/day | pre-virus |
| 10 | 7 | Yes | Oseltamivir | 10 mg/kg/day | |
| 5 | 8 | No | None (healthy controls) | — | bid X 5, begin 4 hours pre-virus, 12 hours apart |

*Placebo = Vehicle or PSS (physiological sterile saline)

Example 8—Testing for Inhibition of Influenza Replication in a Monkey

Figure 2:
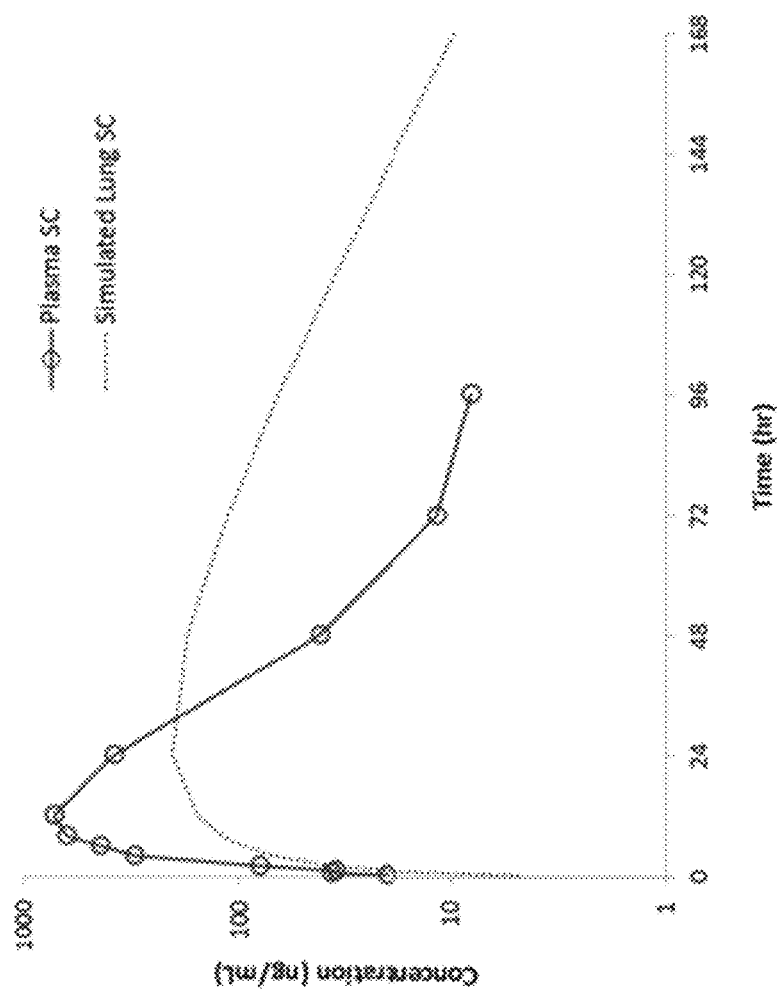
FIG. 2 exemplifies a graph of plasma PK and simulated lung PK in a cyno monkey administered a single subcutaneous dose of 2.25 mg/kg of Aileron peptide 1 (AP1).

A cyno-monkey with influenza was administered a single subcutaneous dose of 2.25 mg/kg of an exemplary stapled peptide. Results are shown in FIG. 2. Drug levels were measureable at 96 hours (4 days), the last time point assessed, with a 13 hour half-life and mean residence time of 21 hours. Simulated exposure in lung tissue indicate that a persistent, high levels of drug can be achieved following a single subcutaneous injection. Vd was estimated from monkey subcutaneous plasma pharmacokinetic parameters. Lung absorption rate (k01) was calculated from monkey subcutaneous plasma absorption rate and rat IV lung absorption rate. Lung elimination rate (k10) was scaled from mouse IV lung elimination rate.

Example 9—Dose-Range Determination Against an Influenza A Virus Infection in Mice A dose-range determination assay was used to evaluate the antiviral activity of Aileron peptide 1 (AP1) a peptidomimetic macrocycle of the invention, against an influenza A/Solomon Islands/3/2006 ($H_1N_1$) virus infection in mice.

Animals:

Female 18-20 g BALB/c mice were obtained from Charles River Laboratories (Wilmington, Mass.). The mice were quarantined for 72 hours before use and maintained on a Teklad Rodent Diet (Harlan Teklad) and tap water.

Virus:

Influenza A/Solomon Islands/3/2006 ($H_1H_1$) virus was obtained from the Centers for Disease Control and Prevention (Atlanta, Ga.). The virus was adapted to replicate in the lungs of BALB/c mice with 7 sequential passages in mice. The virus was plaque purified in MDCK cells, and a virus stock was prepared by growth in MDCK cells.

Compound:

Aileron peptide 1 was prepared in a PEG-based vehicle and then administered.

Experimental Design:

Animal numbers and study groups are described in Table 12. Groups of mice were treated by intravenous injection daily for 5 days with 2, 4, 8, and 12 mg/kg doses of Aileron peptide 1 beginning 4 hours pre-infection. Control groups included mice treated with 10 mg/kg/day of oseltamivir orally (by gavage) twice per day at 12 hours intervals, beginning 4 hours post-infection, or placebo (15 mice) treated with PSS administered intravenously for 5 days at 2.5 mL/kg. Five non-treated normal control mice were maintained for weight comparison. For the influenza virus challenge, mice were anesthetized by i.p. injection of ketamine/xylazine (50 mg/kg/5 mg/kg) prior to the challenge by the intranasal route with approximately $1 \times 10^5$ ($3 \times LD_{50}$) $CCID_{50}$ of virus per mouse in a 90 μL inoculum volume.

Mice were weighed prior to treatment and then every other day thereafter to assess the effects of treatment on ameliorating weight loss due to virus infection. All mice groups were observed for morbidity and mortality through day 21 post-infection.

Statistical Analysis:

Kaplan-Meier survival curves were generated and compared by the Log-rank (Mantel-Cox) test followed by pairwise comparison using the Gehan-Breslow-Wilcoxon test in Prism 6.0e (GraphPad Software, Inc.). Mean body weights were analyzed by one-way analysis of variance (ANOVA) followed by Tukey's multiple comparisons tests using Prism 6.0e.

TABLE 12

Experimental Design for Example 9

| Group # | Infected | Compound | Dosage | Treatment Schedule | Oservations |
|---|---|---|---|---|---|
| 1 | Yes | Placebo (Vehicle or PSS) | 2.5 mL/kg, i.v. | qd x 5, beg 4 hr pre-virus | Observed for weight los and mortality through day 21 |
| 3 | Yes | AP1 | 12 mg/kg/day, i.v. | | |
| 5 | Yes | AP1 | 8 mg/kg/day, i.v. | | |
| 7 | Yes | AP1 | 4 mg/kg/day, i.v. | | |
| 9 | Yes | AP1 | 2 mg/kg/day, i.v. | | |

TABLE 12-continued

| Experimental Design for Example 9 | | | | | |
|---|---|---|---|---|---|
| Group # | Infected | Compound | Dosage | Treatment Schedule | Oservations |
| 11 | Yes | Oseltamivir | 10 mg/kg/day, p.o. | Bid x 5, beg 4 hr pre-virus, 12 hr apart | |
| 10 | No | None (Normal control) | | Observed for normal weight gain | |

Figure 3A:
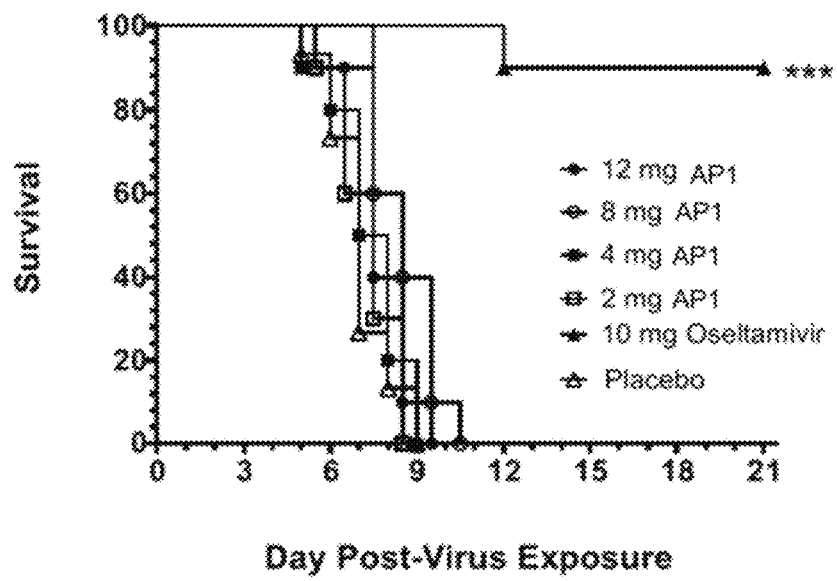
FIG. 3A exemplifies a graph of mouse survival over time after infection with influenza A virus and treatment with the indicated amounts of AP1 or Oseltamivir.
Figure 3B:
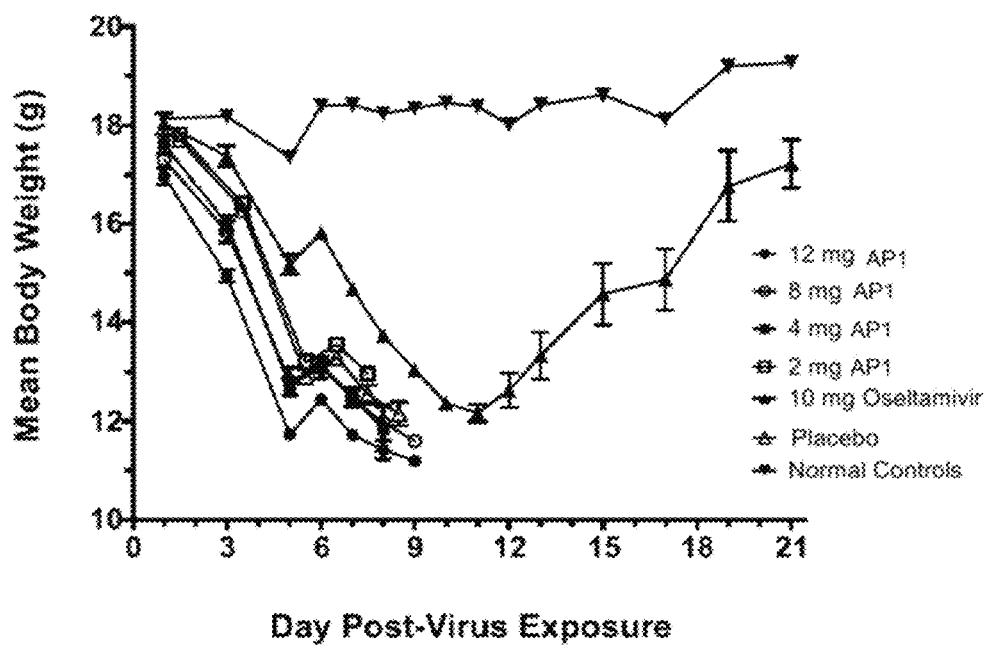
FIG. 3B exemplifies a graph of mouse mean body weight over time after infection with influenza A virus and treatment with the indicated amounts of AP1 or Oseltamivir.

Results are shown in FIG. 3A and FIG. 3B.

What is claimed is:

1. A peptidomimetic macrocycle or a pharmaceutically-acceptable salt thereof, wherein the peptidomimetic macrocycle: (i) comprises two non-natural amino acids connected by a macrocycle-forming linker; (ii) has an amino acid sequence Xaa0-Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-Xaa17-Xaa18; and (iii) has at least about 60% sequence identity to a sequence of Table 1b; wherein Xaa0 is —H or an N-terminal capping group;
each Xaa1-Xaa10 and Xaa12-Xaa15 is independently an amino acid;
Xaa11 is Ala;
each Xaa16 and Xaa17 is independently absent or an amino acid; and
Xaa18 is —NH$_2$, —OH, or a C-terminal capping group.

2. The peptidomimetic macrocycle or the pharmaceutically-acceptable salt of claim 1, wherein the macrocycle-forming linker connects amino acids Xaa5 and Xaa9.

3. The peptidomimetic macrocycle or the pharmaceutically-acceptable salt of claim 1, wherein the macrocycle-forming linker connects amino acids Xaa5 and Xaa12.

4. The peptidomimetic macrocycle or the pharmaceutically-acceptable salt of claim 1, wherein the peptidomimetic macrocycle is a compound of Formula (Ia):

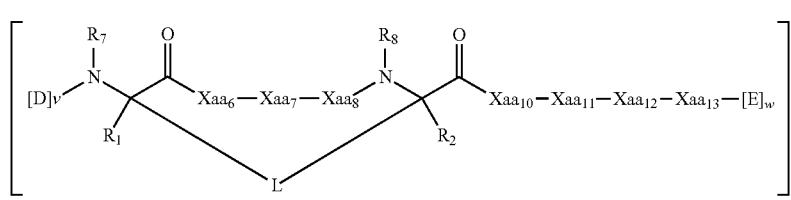

Formula (Ia)

wherein:
each of Xaa$_6$, Xaa$_7$, Xaa$_8$, Xaa$_{10}$, Xaa$_{11}$, Xaa$_{12}$, and Xaa$_{13}$ is independently an amino acid, wherein at least three, four, five, or each of Xaa$_6$, Xaa$_7$, Xaa$_8$, Xaa$_{10}$, Xaa$_{11}$, and Xaa$_{12}$, are the same amino acid as the amino acid at the corresponding position of the sequence X$_5$-Thr$_6$-Leu$_7$-Leu$_8$-X$_9$-Leu$_{10}$-Ala$_{11}$-Val$_{12}$/Ala$_{12}$, where each of X$_5$ and X$_9$ is independently an amino acid (SEQ ID NO: 1);
each D and E is independently an amino acid;

each R$_1$ and R$_2$ is independently —H, alkyl, alkenyl, alkynyl, arylalkyl, cycloalkyl, cycloalkylalkyl, heteroalkyl, or heterocycloalkyl, unsubstituted or substituted with halo-; or forms a macrocycle-forming linker L' connected to the α position of one of said D or E amino acids;
each L and L' is independently a macrocycle-forming linker;
each R$_3$ is independently —H, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;
each R$_6$ is independently —H, alkyl, alkenyl, alkynyl, arylalkyl, cycloalkylalkyl, heterocycloalkyl, a fluorescent moiety, a radioisotope or a therapeutic agent;
each R$_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;
each R$_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;
each v is independently is 4;
each w is independently 2, 3, or 4; and
u is 1.

5. The peptidomimetic macrocycle or the pharmaceutically-acceptable salt of claim 1, wherein the peptidomimetic macrocycle is a compound of Formula (Ib):

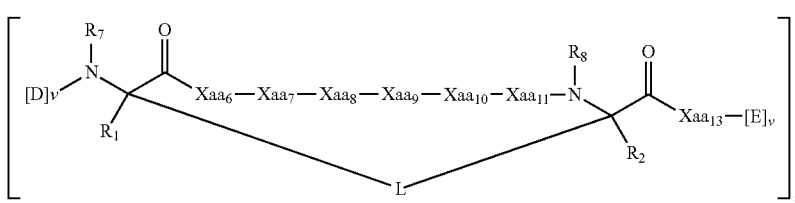

Formula (Ib)

wherein:
each of $Xaa_6$, $Xaa_7$, $Xaa_8$, $Xaa_9$, $Xaa_{10}$, $Xaa_{11}$ and $Xaa_{13}$ is independently an amino acid, wherein at least three, four, five, or each of $Xaa_6$, $Xaa_7$, $Xaa_8$, $Xaa_9$, $Xaa_{10}$, and $Xaa_{11}$ are the same amino acid as the amino acid at the corresponding position of the sequence $X_5$-$Thr_6$-$Leu_7$-$Leu_8$-$Phe_9$-$Leu_{10}$-$Ala_{11}$-$X_{12}$, where each of $X_5$ and $X_{12}$ is independently an amino acid (SEQ ID NO: 2);
each D and E is independently an amino acid;
each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-; or forms a macrocycle-forming linker L' connected to the α position of one of said D or E amino acids;
each L and L' is independently a macrocycle-forming linker;
each $R_3$ is independently —H, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;
each v is 4;
each w is 2, 3, or 4; and
u is 1.

6. The peptidomimetic macrocycle or the pharmaceutically-acceptable salt of claim 1, wherein the peptidomimetic macrocycle is a compound of Formula (I):

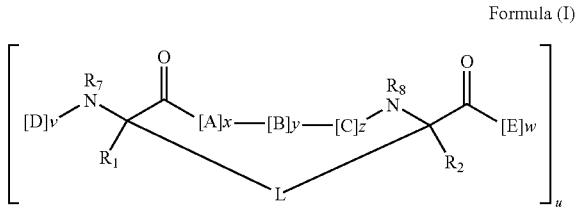

Formula (I)

wherein:
each A, B, C, D, and E is independently an amino acid;
each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-; or at least one of $R_1$ and $R_2$ forms a macrocycle-forming linker L' connected to the α position of one of said D or E amino acids;
each L and L' is independently a macrocycle-forming linker;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
each $R_7$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, optionally substituted with $R_5$, or part of a cyclic structure with an E residue;
each v and w is independently an integer from 0-1000;
u is an integer from 1-10; and
each x, y and z is independently an integer from 0-10.

7. The peptidomimetic macrocycle or the pharmaceutically-acceptable salt of claim 1, wherein the peptidomimetic macrocycle comprises an α,α-disubstituted amino acid.

8. The peptidomimetic macrocycle or the pharmaceutically-acceptable salt of claim 1, wherein each amino acid connected by the macrocycle-forming linker is an α,α-disubstituted amino acid.

9. The peptidomimetic macrocycle or the pharmaceutically-acceptable salt of claim 6, wherein u is 1.

10. The peptidomimetic macrocycle or the pharmaceutically-acceptable salt of claim 6, wherein x+y+z is 2, 3, 5 or 6.

11. The peptidomimetic macrocycle or the pharmaceutically-acceptable salt of claim 6, wherein each v is independently an integer from 0-10.

12. The peptidomimetic macrocycle or the pharmaceutically-acceptable salt of claim 6, wherein each v is 4.

13. The peptidomimetic macrocycle or the pharmaceutically-acceptable salt of claim 6, wherein $[D]_v$ is -$Asn_4$-$Val_3$-$Glu_2$-$Nle_1$ (SEQ ID NO: 4).

14. The peptidomimetic macrocycle or the pharmaceutically-acceptable salt of claim 6, wherein $[D]_v$ is -$Asn_4$-$Val_3$-$Glu_2$-$Phe_1$ (SEQ ID NO: 5).

15. The peptidomimetic macrocycle or the pharmaceutically-acceptable salt of claim 6, wherein each w is independently an integer from 0-10.

16. The peptidomimetic macrocycle or the pharmaceutically-acceptable salt of claim 6, wherein each w is 1, 2, 3, 4, 5, 6, or 8.

17. The peptidomimetic macrocycle or the pharmaceutically-acceptable salt of claim 6, wherein each of the first two amino acids represented by E comprises an uncharged side chain or a negatively charged side chain.

18. The peptidomimetic macrocycle or the pharmaceutically-acceptable salt of claim 6, wherein the first, second, third or fourth amino acid represented by E comprises a hydrophobic side chain.

19. The peptidomimetic macrocycle or the pharmaceutically-acceptable salt of claim 18, wherein the hydrophobic side chain is a small hydrophobic side chain.

20. The peptidomimetic macrocycle or the pharmaceutically-acceptable salt of claim 6, wherein each E is independently an amino acid selected from the group consisting of Ala, D-Ala, Aib, Lys, Leu, Ser, Glu, and Gln.

21. The peptidomimetic macrocycle or the pharmaceutically-acceptable salt of claim 6, wherein each L is independently alkylene, alkenylene, or alkynylene.

22. The peptidomimetic macrocycle of claim 6, wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo.

23. The peptidomimetic macrocycle or the pharmaceutically-acceptable salt of claim 6, wherein each $R_1$ and $R_2$ is independently alkyl.

24. The peptidomimetic macrocycle or the pharmaceutically-acceptable salt of claim 6, wherein each L and L' independently has a formula -$L_1$-$L_2$-, wherein
  each $L_1$ and $L_2$ is independently alkylene, alkenylene, alkynylene, heteroalkylene, cycloalkylene, heterocycloalkylene, arylene, heteroarylene, or [—$R_4$—K—$R_4$-]$_n$, each being optionally substituted with $R_5$;
  each $R_4$ is independently alkylene, alkenylene, alkynylene, heteroalkylene, cycloalkylene, heterocycloalkylene, arylene, or heteroarylene;
  each K is independently O, S, SO, $SO_2$, CO, $CO_2$ or $CONR_3$; and
  each n is independently an integer from 1-5.

25. The peptidomimetic macrocycle or the pharmaceutically-acceptable salt of claim 24, wherein each $L_1$ and $L_2$ is independently alkylene, alkenylene, alkynylene, heteroalkylene, cycloalkylene, heterocycloalkylene, arylene, or heteroarylene, each being optionally substituted with $R_5$.

26. The peptidomimetic macrocycle or the pharmaceutically-acceptable salt of claim 24, wherein each $L_1$ and $L_2$ is independently alkylene, alkenylene or alkynylene.

27. The peptidomimetic macrocycle of claim 24, wherein each $L_1$ and $L_2$ is independently alkylene or alkenylene.

28. A pharmaceutical composition comprising the peptidomimetic macrocycle or the pharmaceutically-acceptable salt of claim 1 and a pharmaceutically acceptable excipient.

29. A method of treating influenza infection in a subject comprising administering to the subject the peptidomimetic macrocycle or the pharmaceutically-acceptable salt of claim 1, wherein the peptidomimetic macrocycle has at least about 90% sequence identity to a sequence of Table 1b.

30. The method of claim 29, wherein the administering comprises administering subcutaneously or parenterally.

31. The method of claim 29, wherein the administering comprises administering a single dose of the peptidomimetic macrocycle.

32. A method of inhibiting the activity of the RNA-dependent RNA polymerase of an influenza virus in a subject comprising administering to the subject the peptidomimetic macrocycle or the pharmaceutically-acceptable salt of claim 1, wherein the peptidomimetic macrocycle has at least about 90% sequence identity to a sequence of Table 1 b.

* * * * *

```
                            SEQUENCE LISTING

<160> NUMBER OF SEQ ID NOS: 36

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Lys or Ala
<220> FEATURE:
<221> NAME/KEY: MOD_RES
<222> LOCATION: (8)..(8)
<223> OTHER INFORMATION: Val or Ala

<400> SEQUENCE: 1

Xaa Thr Leu Leu Xaa Leu Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Lys or Ala
<220> FEATURE:
<221> NAME/KEY: MOD_RES
<222> LOCATION: (8)..(8)
<223> OTHER INFORMATION: Any amino acid

<400> SEQUENCE: 2

Xaa Thr Leu Leu Phe Leu Xaa Xaa
1               5

<210> SEQ ID NO 3
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine or Phe

<400> SEQUENCE: 3

Xaa Glu Val Asn
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine

<400> SEQUENCE: 4

Xaa Glu Val Asn
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Glu Val Asn
1

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asp Val Asn Pro Thr Leu Leu Phe Leu Lys Val Pro Ala Gln
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Glu Arg Ile Lys Glu Leu Arg Asn Leu Met
1               5                   10

<210> SEQ ID NO 8
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 8

Leu Asp Val Asn Ala Thr Leu Leu Ala Leu Lys Val Xaa Ala Gln
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 9

Leu Asp Val Asn Ala Thr Leu Leu Ala Leu Lys Ala Xaa Ala Gln
```

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
     connected by an all-carbon crosslinker
     comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
     connected by an all-carbon crosslinker
     comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 10

Leu Asp Val Asn Ala Thr Leu Leu Ala Leu Lys Val Xaa Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
     connected by an all-carbon crosslinker
     comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
     connected by an all-carbon crosslinker
     comprising one double bond
<220> FEATURE:
<221> NAME/KEY: MOD_RES
<222> LOCATION: (14)..(14)
<223> OTHER INFORMATION: 2-aminoisobutyric acid
<220> FEATURE:

```
<223> OTHER INFORMATION: C-term NH2

<400> SEQUENCE: 11

Leu Asp Val Asn Ala Thr Leu Leu Ala Leu Lys Val Pro Xaa Gln
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 12

Phe Asp Val Asn Ala Thr Leu Leu Ala Leu Lys Val Xaa Ala Gln
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon crosslinker
      comprising one double bond
```

```
<220> FEATURE:
<221> NAME/KEY: MOD_RES
<222> LOCATION: (14)..(14)
<223> OTHER INFORMATION: 2-aminoisobutyric acid
<220> FEATURE:
<223> OTHER INFORMATION: C-term NH2

<400> SEQUENCE: 13

Ala Leu Asp Val Asn Ala Thr Leu Leu Ala Leu Ala Val Xaa Ala Gln
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 14

Leu Asp Val Asn Ala Thr Leu Leu Ala Leu Ala Val Xaa Ala Gln
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
```

```
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<223> OTHER INFORMATION: C-term NH2

<400> SEQUENCE: 15

Leu Asp Val Asn Ala Thr Leu Leu Ala Leu Ala Val Xaa Ala Gln Ala
1               5                   10                  15

Ala

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 16

Leu Asp Val Asn Ala Thr Leu Leu Ala Leu Ala Val Ala Ala Gln Ala
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
```

```
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 17

Leu Asp Val Asn Ala Thr Leu Leu Ala Leu Ala Val Ala Ala Ala Ala
1               5                   10                  15

Ala

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 18

Leu Asp Val Asn Ala Thr Leu Leu Ala Leu Ala Val Ser Ala Gln Ala
1               5                   10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
```

```
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 19

Leu Asp Val Asn Ala Thr Leu Leu Ala Leu Ala Val Gln Ala Gln Ala
1               5                   10                  15

Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 20

Leu Asp Val Asn Ala Thr Leu Leu Ala Leu Ala Val Glu Ala Gln Ala
1               5                   10                  15

Ala

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
``` connected by an all-carbon crosslinker
        comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon crosslinker
        comprising one double bond
<220> FEATURE:
<223> OTHER INFORMATION: C-term NH2

<400> SEQUENCE: 21

Leu Asp Val Asn Ala Thr Leu Leu Ala Leu Ala Val Ser Ala Ala Ala
1               5                   10                  15

Ala

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
        connected by an all-carbon crosslinker
        comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon crosslinker
        comprising one double bond
<220> FEATURE:
<223> OTHER INFORMATION: C-term NH2

<400> SEQUENCE: 22

Leu Asp Val Asn Ala Thr Leu Leu Ala Leu Ala Val Gln Ala Ala Ala
1               5                   10                  15

Ala

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)

```
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 23

Leu Asp Val Asn Ala Thr Leu Leu Ala Leu Ala Val Glu Ala Ala Ala
1               5                   10                  15
Ala

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<221> NAME/KEY: MOD_RES
<222> LOCATION: (17)..(17)
<223> OTHER INFORMATION: D-Ala
<220> FEATURE:
<223> OTHER INFORMATION: C-term NH2

<400> SEQUENCE: 24

Leu Asp Val Asn Ala Thr Leu Leu Ala Leu Ala Val Xaa Ala Gln Ala
1               5                   10                  15
Ala

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (13)..(13)
<223> OTHER INFORMATION: 2-aminoisobutyric acid
<220> FEATURE:
<221> NAME/KEY: MOD_RES
<222> LOCATION: (17)..(17)
<223> OTHER INFORMATION: D-Ala
<220> FEATURE:
<223> OTHER INFORMATION: C-term OH

<400> SEQUENCE: 25

Leu Asp Val Asn Ala Thr Leu Leu Ala Leu Ala Val Xaa Ala Gln Ala
1               5                   10                  15

Ala

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon crosslinker
      comprising one double bond
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 26

Leu Asp Val Asn Ala Thr Leu Leu Phe Leu Ala Ala Ala Ala Gln
1               5                   10                  15
```

```
<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (14)..(14)
<223> OTHER INFORMATION: 2-aminoisobutyric acid
<220> FEATURE:
<223> OTHER INFORMATION: C-term NH2

<400> SEQUENCE: 27

Leu Asp Val Asn Ala Thr Leu Leu Ala Leu Ala Val Gln Xaa Gln Ala
1               5                   10                  15

Ala

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (16)..(16)
<223> OTHER INFORMATION: 2-aminoisobutyric acid
<220> FEATURE:
<223> OTHER INFORMATION: C-term NH2
```

-continued

<400> SEQUENCE: 28

Leu Asp Val Asn Ala Thr Leu Leu Ala Leu Ala Val Gln Ala Gln Xaa
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (14)..(14)
<223> OTHER INFORMATION: 2-aminoisobutyric acid
<220> FEATURE:
<223> OTHER INFORMATION: C-term NH2

<400> SEQUENCE: 29

Leu Asp Val Asn Ala Thr Leu Leu Ala Leu Ala Val Gln Xaa Ala Ala
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)

```
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (16)..(16)
<223> OTHER INFORMATION: 2-aminoisobutyric acid
<220> FEATURE:
<223> OTHER INFORMATION: C-term NH2

<400> SEQUENCE: 30

Leu Asp Val Asn Ala Thr Leu Leu Ala Leu Ala Val Gln Ala Ala Xaa
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MISC_FEATURE
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon crosslinker
      comprising one double bond
<220> FEATURE:
<221> NAME/KEY: MOD_RES
<222> LOCATION: (15)..(15)
<223> OTHER INFORMATION: 2-aminoisobutyric acid
<220> FEATURE:
<223> OTHER INFORMATION: C-term NH2

<400> SEQUENCE: 31

Leu Asp Val Asn Ala Thr Leu Leu Ala Leu Ala Val Gln Ala Xaa Ala
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me R8-octenyl-alanine olefin amino acid
``` connected by an all-carbon crosslinker
    comprising one double bond
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
    connected by an all-carbon crosslinker
    comprising one double bond
<220> FEATURE:
<223> OTHER INFORMATION: C-term NH2

<400> SEQUENCE: 32

Leu Asp Val Asn Ala Thr Leu Leu Phe Leu Ala Ala Ala Ala Gln Ala
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me R8-octenyl-alanine olefin amino acid
    connected by an all-carbon crosslinker
    comprising one double bond
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
    connected by an all-carbon crosslinker
    comprising one double bond
<220> FEATURE:
<223> OTHER INFORMATION: C-term NH2

<400> SEQUENCE: 33

Leu Asp Val Asn Ala Thr Leu Leu Phe Leu Ala Ala Ala Ala Ala Ala
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)

```
<223> OTHER INFORMATION: Alpha-Me R8-octenyl-alanine olefin amino acid
      connected by an all-carbon crosslinker
      comprising one double bond
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 34

Leu Asp Val Asn Ala Thr Leu Leu Phe Leu Ala Ala Gln Ala Gln Ala
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon crosslinker
      comprising one double bond
<220> FEATURE:
<221> NAME/KEY: MISC_FEATURE
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon crosslinker
      comprising one double bond
<220> FEATURE:
<223> OTHER INFORMATION: C-term NH2

<400> SEQUENCE: 35

Leu Asp Val Asn Ala Thr Leu Leu Phe Leu Ala Ala Gln Ala Ala Ala
1               5                   10                  15

Ala

<210> SEQ ID NO 36
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or N-terminal capping group
<220> FEATURE:
<221> NAME/KEY: MOD_RES
<222> LOCATION: (1)..(100)
<223> OTHER INFORMATION: Any amino acid
<220> FEATURE:
<221> NAME/KEY: MISC_FEATURE
```

```
<222> LOCATION: (1)..(100)
<223> OTHER INFORMATION: This region may encompass 1-100 residues
<220> FEATURE:
<221> NAME/KEY: MOD_RES
<222> LOCATION: (101)..(101)
<223> OTHER INFORMATION: Norleucine or Phe
<220> FEATURE:
<221> NAME/KEY: MOD_RES
<222> LOCATION: (105)..(105)
<223> OTHER INFORMATION: Any crosslinked amino acid
<220> FEATURE:
<221> NAME/KEY: MOD_RES
<222> LOCATION: (109)..(109)
<223> OTHER INFORMATION: Phe or any crosslinked amino acid
<220> FEATURE:
<221> NAME/KEY: MOD_RES
<222> LOCATION: (111)..(111)
<223> OTHER INFORMATION: Lys or Ala
<220> FEATURE:
<221> NAME/KEY: MOD_RES
<222> LOCATION: (112)..(112)
<223> OTHER INFORMATION: Ala, Val or any crosslinked amino acid
<220> FEATURE:
<221> NAME/KEY: MOD_RES
<222> LOCATION: (113)..(113)
<223> OTHER INFORMATION: 2-aminoisobutyric acid, Ser, Ala, Glu, Gln or
      Pro
<220> FEATURE:
<221> NAME/KEY: MOD_RES
<222> LOCATION: (114)..(114)
<223> OTHER INFORMATION: 2-aminoisobutyric acid or Ala
<220> FEATURE:
<221> NAME/KEY: MOD_RES
<222> LOCATION: (115)..(115)
<223> OTHER INFORMATION: Gln, 2-aminoisobutyric acid or Ala
<220> FEATURE:
<221> NAME/KEY: MOD_RES
<222> LOCATION: (116)..(116)
<223> OTHER INFORMATION: 2-aminoisobutyric acid, Ala or absent
<220> FEATURE:
<221> NAME/KEY: MOD_RES
<222> LOCATION: (117)..(117)
<223> OTHER INFORMATION: D-Ala, Ala or absent
<220> FEATURE:
<221> NAME/KEY: MOD_RES
<222> LOCATION: (118)..(217)
<223> OTHER INFORMATION: Any amino acid
<220> FEATURE:
<221> NAME/KEY: MISC_FEATURE
<222> LOCATION: (118)..(217)
<223> OTHER INFORMATION: This region may encompass 1-100 residues
<220> FEATURE:
<223> OTHER INFORMATION: C-term NH2, OH or C-terminal capping group

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Asp Val Asn Xaa Thr Leu Leu Xaa Leu Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125
```

```
Xaa Xaa Xaa Xaa Xaa Xaa Xaa Xaa Xaa Xaa Xaa Xaa Xaa Xaa Xaa
        130             135             140

Xaa Xaa Xaa Xaa Xaa Xaa Xaa Xaa Xaa Xaa Xaa Xaa Xaa Xaa Xaa
145             150             155             160

Xaa Xaa Xaa Xaa Xaa Xaa Xaa Xaa Xaa Xaa Xaa Xaa Xaa Xaa Xaa
            165             170             175

Xaa Xaa Xaa Xaa Xaa Xaa Xaa Xaa Xaa Xaa Xaa Xaa Xaa Xaa Xaa
        180             185             190

Xaa Xaa Xaa Xaa Xaa Xaa Xaa Xaa Xaa Xaa Xaa Xaa Xaa Xaa Xaa
    195             200             205

Xaa Xaa Xaa Xaa Xaa Xaa Xaa Xaa Xaa
    210             215
```